United States Patent
Smith et al.

(10) Patent No.: US 12,097,250 B2
(45) Date of Patent: Sep. 24, 2024

(54) COMPOSITIONS COMPRISING *Streptococcus pneumoniae* POLYSACCHARIDE-PROTEIN CONJUGATES AND METHODS OF USE THEREOF

(71) Applicant: Merck Sharp & Dohme LLC, Rahway, NJ (US)

(72) Inventors: William J. Smith, Harleysville, PA (US); Patrick McHugh, Pipersville, PA (US); Michael Albert Winters, Doylestown, PA (US); Julie M. Skinner, Phoenixville, PA (US); Jian He, Blue Bell, PA (US); Luwy Musey, Blue Bell, PA (US); Chitrananda Abeygunawardana, Ambler, PA (US); Yadong Adam Cui, Norristown, PA (US); Michael J. Kosinski, Souderton, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 18/505,504

(22) Filed: Nov. 9, 2023

(65) Prior Publication Data

US 2024/0108711 A1    Apr. 4, 2024

Related U.S. Application Data

(60) Continuation of application No. 17/374,424, filed on Jul. 13, 2021, now Pat. No. 11,850,278, which is a division of application No. 16/208,778, filed on Dec. 4, 2018, now Pat. No. 11,116,828.

(60) Provisional application No. 62/595,388, filed on Dec. 6, 2017.

(51) Int. Cl.
| | | |
|---|---|---|
| *A61K 39/00* | (2006.01) | |
| *A61K 39/09* | (2006.01) | |
| *A61K 39/116* | (2006.01) | |
| *A61K 39/145* | (2006.01) | |
| *A61K 39/385* | (2006.01) | |
| *A61K 47/02* | (2006.01) | |
| *A61K 47/10* | (2017.01) | |
| *A61K 47/22* | (2006.01) | |
| *A61P 31/04* | (2006.01) | |
| *A61K 9/00* | (2006.01) | |

(52) U.S. Cl.
CPC .......... *A61K 39/092* (2013.01); *A61K 39/116* (2013.01); *A61K 39/145* (2013.01); *A61K 39/385* (2013.01); *A61K 47/02* (2013.01); *A61K 47/10* (2013.01); *A61K 47/22* (2013.01); *A61P 31/04* (2018.01); *A61K 9/0019* (2013.01); *A61K 2039/54* (2013.01); *A61K 2039/545* (2013.01); *A61K 2039/55* (2013.01); *A61K 2039/55516* (2013.01); *A61K 2039/6037* (2013.01); *A61K 2039/70* (2013.01)

(58) Field of Classification Search
CPC .................................................... A61K 39/092
See application file for complete search history.

(56) References Cited

U.S. PATENT DOCUMENTS

| | | |
|---|---|---|
| 4,365,170 A | 12/1982 | Okuhara |
| 4,673,574 A | 6/1987 | Anderson |
| 4,709,017 A | 11/1987 | Collier et al. |
| 4,902,506 A | 2/1990 | Anderson et al. |
| 4,912,094 A | 3/1990 | Myers et al. |
| 4,950,740 A | 8/1990 | Greenfield et al. |
| 5,057,540 A | 10/1991 | Kensil et al. |
| 5,623,057 A | 4/1997 | Marburg et al. |
| 5,843,711 A | 12/1998 | Collier et al. |
| 5,847,112 A | 12/1998 | Kniskern et al. |
| 5,917,017 A | 6/1999 | Collier et al. |
| 6,113,918 A | 9/2000 | Johnson et al. |
| 6,146,902 A | 11/2000 | McMaster |
| 6,207,646 B1 | 3/2001 | Krieg et al. |

(Continued)

FOREIGN PATENT DOCUMENTS

| | | |
|---|---|---|
| CN | 101180079 A | 5/2008 |
| CN | 101590224 A | 12/2009 |

(Continued)

OTHER PUBLICATIONS

Ada et al., Carbohydrate-Protein Conjugate Vaccines, Clin. Microbiology Infect., 2003, 79-85, 9.

(Continued)

*Primary Examiner* — Albert M Navarro
*Assistant Examiner* — Mark Navarro
(74) *Attorney, Agent, or Firm* — Matthew A. Leff; Alysia A. Finnegan

(57) ABSTRACT

The invention is related to multivalent immunogenic compositions comprising more than one *S. pneumoniae* polysaccharide protein conjugates, wherein each of the conjugates comprises a polysaccharide from an *S. pneumoniae* serotype conjugated to a carrier protein, wherein the serotypes of *S. pneumoniae* are as defined herein. Also provided are methods for inducing a protective immune response in a human patient comprising administering the multivalent immunogenic compositions of the invention to the patient. The multivalent immunogenic compositions are useful for providing protection against *S. pneumoniae* infection and diseases caused by *S. pneumoniae*. The compositions of the invention are also useful as part of treatment regimes that provide complementary protection for patients that have been vaccinated with a multivalent vaccine indicated for the prevention of pneumococcal disease.

9 Claims, 52 Drawing Sheets

Specification includes a Sequence Listing.

(56) References Cited

U.S. PATENT DOCUMENTS

| | | |
|---|---|---|
| 6,455,673 B1 | 9/2002 | Collier |
| 7,348,006 B2 | 3/2008 | Contorni |
| 7,709,001 B2 | 5/2010 | Hausdorff et al. |
| 7,812,006 B2 | 10/2010 | Mistretta |
| 7,935,787 B2 | 5/2011 | Khandke et al. |
| 8,192,746 B2 | 6/2012 | Caulfield et al. |
| 8,481,054 B2 | 7/2013 | Nahm |
| 8,562,999 B2 | 10/2013 | Khandke |
| 8,753,645 B2 | 6/2014 | Biemans |
| 8,808,707 B1 | 8/2014 | Siber |
| 8,808,708 B2 | 8/2014 | Hausdorff et al. |
| 8,895,024 B2 | 11/2014 | Hausdorff |
| 9,265,839 B2 | 2/2016 | Biemans |
| 9,265,840 B2 | 2/2016 | Biemans |
| 9,399,060 B2 | 7/2016 | Hausdorff |
| 9,422,345 B2 | 8/2016 | Blais |
| 9,492,559 B2 | 11/2016 | Emini |
| 9,669,084 B2 | 6/2017 | Siber |
| 9,778,266 B2 | 10/2017 | Nahm |
| 9,981,029 B2 | 5/2018 | Park et al. |
| 10,034,949 B2 | 7/2018 | Shin et al. |
| 10,058,607 B2 | 8/2018 | Shin et al. |
| 10,124,050 B2 | 11/2018 | Watson et al. |
| 10,406,220 B2 | 9/2019 | Siber et al. |
| 11,116,828 B2 * | 9/2021 | Smith .................. A61K 39/116 |
| 2003/0147922 A1 | 8/2003 | Capiau et al. |
| 2003/0180316 A1 | 9/2003 | Boutriau et al. |
| 2006/0228380 A1 | 10/2006 | Hausdorff et al. |
| 2007/0002063 A1 | 1/2007 | Kumagai et al. |
| 2007/0020631 A1 | 1/2007 | Kong |
| 2007/0184071 A1 | 8/2007 | Hausdorff et al. |
| 2007/0184072 A1 | 8/2007 | Wyeth |
| 2007/0231340 A1 | 10/2007 | Hausdorff et al. |
| 2008/0286838 A1 | 11/2008 | Yuan et al. |
| 2011/0195086 A1 | 8/2011 | Caulfield et al. |
| 2012/0321658 A1 | 12/2012 | Biemans et al. |
| 2012/0321660 A1 | 12/2012 | Biemans et al. |
| 2013/0344103 A1 | 12/2013 | Biemans et al. |
| 2015/0190520 A1 | 7/2015 | Shin et al. |
| 2015/0202309 A1 | 7/2015 | Emini et al. |
| 2015/0231270 A1 | 8/2015 | Prasad |
| 2015/0343076 A1 | 12/2015 | Park |
| 2017/0021006 A1 | 1/2017 | Watson et al. |
| 2018/0035359 A1 | 2/2018 | Ishii |
| 2018/0161445 A1 | 6/2018 | Dhere et al. |
| 2018/0207262 A1 | 7/2018 | Biemans et al. |
| 2018/0250389 A9 | 9/2018 | Biemans et al. |
| 2019/0240308 A1 | 8/2019 | Matur et al. |
| 2020/0197503 A1 | 6/2020 | Abeygunawardana et al. |
| 2020/0282040 A1 | 9/2020 | Porambo et al. |
| 2020/0282070 A1 | 9/2020 | Porambo et al. |
| 2020/0324701 A1 | 10/2020 | Usui |
| 2020/0360502 A1 | 11/2020 | An et al. |

FOREIGN PATENT DOCUMENTS

| | | |
|---|---|---|
| CN | 102068690 A | 5/2011 |
| CN | 103623401 A | 3/2014 |
| CN | 103656631 A | 3/2014 |
| CN | 104069488 A | 10/2014 |
| CN | 103656632 B | 1/2016 |
| CN | 105999254 A | 10/2016 |
| CN | 106102770 A | 11/2016 |
| CN | 107929728 A | 4/2018 |
| CN | 108144056 A | 6/2018 |
| CN | 108159408 A | 6/2018 |
| CN | 108245674 A | 7/2018 |
| CN | 108339115 A | 7/2018 |
| CN | 108524926 A | 9/2018 |
| CN | 108543066 A | 9/2018 |
| CN | 109091668 A | 12/2018 |
| CN | 109336989 A | 2/2019 |
| CN | 109771640 A | 5/2019 |
| CN | 110302375 A | 10/2019 |
| CN | 108079286 B | 7/2020 |
| CN | 111821432 A | 10/2020 |
| EP | 0378881 A1 | 7/1990 |
| EP | 0427347 A1 | 5/1991 |
| EP | 0471177 A2 | 2/1992 |
| EP | 0497524 A2 | 8/1992 |
| EP | 497525 B1 | 8/1992 |
| EP | 0594610 B1 | 5/1994 |
| EP | 497524 B1 | 7/1998 |
| EP | 2950815 B1 | 4/2018 |
| IN | 20140034913 A | 9/2015 |
| IN | 20140288913 A | 3/2016 |
| IN | 201623002962 A | 7/2017 |
| JP | 2013518891 A | 5/2013 |
| JP | 2017504661 A | 2/2017 |
| JP | 2017509656 A | 4/2017 |
| KR | 2018043122 A | 4/2018 |
| KR | 20180043122 A | 4/2018 |
| WO | 1990014837 A1 | 12/1990 |
| WO | 1991001146 A1 | 2/1991 |
| WO | 9315760 A1 | 8/1993 |
| WO | 1993017712 A2 | 9/1993 |
| WO | 1994003208 A1 | 2/1994 |
| WO | 9508348 A1 | 3/1995 |
| WO | 1996029094 A1 | 9/1996 |
| WO | 1996039182 A1 | 12/1996 |
| WO | 1998018930 A2 | 5/1998 |
| WO | 1998018931 A2 | 5/1998 |
| WO | 1998/033521 A1 | 8/1998 |
| WO | 1998058668 A2 | 12/1998 |
| WO | 2000061761 A1 | 10/2000 |
| WO | 2001072337 A1 | 10/2001 |
| WO | 2001098334 A2 | 12/2001 |
| WO | 2002053761 A2 | 7/2002 |
| WO | 2002083855 A2 | 10/2002 |
| WO | 2002091998 A2 | 11/2002 |
| WO | 2003009869 A1 | 2/2003 |
| WO | 2003051392 A2 | 6/2003 |
| WO | 2003054007 A2 | 7/2003 |
| WO | 2004071439 A2 | 8/2004 |
| WO | 2004081515 A2 | 9/2004 |
| WO | 2004083251 A2 | 9/2004 |
| WO | 2005120563 A2 | 12/2005 |
| WO | 2006065137 A2 | 6/2006 |
| WO | 2006110352 A2 | 10/2006 |
| WO | 2006110381 A1 | 10/2006 |
| WO | 2007071707 A2 | 6/2007 |
| WO | 2007071710 A2 | 6/2007 |
| WO | 2007071711 A2 | 6/2007 |
| WO | 2007127665 A2 | 11/2007 |
| WO | 2008021076 A2 | 2/2008 |
| WO | 2008045852 A2 | 4/2008 |
| WO | 2008079653 A1 | 7/2008 |
| WO | 2008079732 A2 | 7/2008 |
| WO | 2008118752 A2 | 10/2008 |
| WO | 2008143709 A2 | 11/2008 |
| WO | 2009000824 A2 | 12/2008 |
| WO | 2009000825 A2 | 12/2008 |
| WO | 2009009629 A1 | 1/2009 |
| WO | 2010080484 A1 | 7/2010 |
| WO | 2010080486 A2 | 7/2010 |
| WO | 2011031893 A1 | 3/2011 |
| WO | 2011100151 A1 | 8/2011 |
| WO | 2011110241 A1 | 9/2011 |
| WO | 2011151760 A2 | 12/2011 |
| WO | 2012078482 A1 | 6/2012 |
| WO | 2012158701 A1 | 11/2012 |
| WO | 2012173876 A1 | 12/2012 |
| WO | 2013191459 A1 | 12/2013 |
| WO | 2014092378 A1 | 6/2014 |
| WO | 2014097099 A2 | 6/2014 |
| WO | 2015110940 A2 | 7/2015 |
| WO | 2015110941 A2 | 7/2015 |
| WO | 2015110942 A2 | 7/2015 |
| WO | 2016113644 A1 | 7/2016 |
| WO | 2016178123 A1 | 11/2016 |
| WO | 2016199003 A1 | 12/2016 |
| WO | 2016207905 A2 | 12/2016 |
| WO | 2017011338 A1 | 1/2017 |
| WO | 2017013548 A1 | 1/2017 |

(56) References Cited

FOREIGN PATENT DOCUMENTS

| | | |
|---|---|---|
| WO | 2017067962 A1 | 4/2017 |
| WO | 2017085586 A1 | 5/2017 |
| WO | 2017085602 A1 | 5/2017 |
| WO | 2017173415 A2 | 10/2017 |
| WO | 2017220753 A1 | 12/2017 |
| WO | 2018009906 A1 | 1/2018 |
| WO | 2018027123 A1 | 2/2018 |
| WO | 2018027126 A1 | 2/2018 |
| WO | 2018048141 A1 | 3/2018 |
| WO | 2018064444 A1 | 4/2018 |
| WO | 2018080213 A1 | 5/2018 |
| WO | 2018134693 A1 | 7/2018 |
| WO | 2018144438 A1 | 8/2018 |
| WO | 2018144439 A1 | 8/2018 |
| WO | 2018156465 A1 | 8/2018 |
| WO | 2018156467 A1 | 8/2018 |
| WO | 2018156468 A1 | 8/2018 |
| WO | 2018156491 A1 | 8/2018 |
| WO | 2018169303 A1 | 9/2018 |
| WO | 2018227177 A1 | 12/2018 |
| WO | 2019036313 A1 | 2/2019 |
| WO | 2019050813 A1 | 3/2019 |
| WO | 2019050814 A1 | 3/2019 |
| WO | 2019050815 A1 | 3/2019 |
| WO | 2019050816 A1 | 3/2019 |
| WO | 2019050818 A1 | 3/2019 |
| WO | 2019070994 A1 | 4/2019 |
| WO | 2019083865 A1 | 5/2019 |
| WO | 2019131763 A1 | 7/2019 |
| WO | 2019152921 A1 | 8/2019 |
| WO | 2019152925 A1 | 8/2019 |
| WO | 2019170068 A1 | 9/2019 |
| WO | 2019203599 A1 | 10/2019 |
| WO | 2019212842 A1 | 11/2019 |
| WO | 2019212844 A1 | 11/2019 |
| WO | 2019212846 A1 | 11/2019 |
| WO | 2019217183 A1 | 11/2019 |
| WO | 2019220304 A1 | 11/2019 |
| WO | 2019236435 A1 | 12/2019 |
| WO | 2020009462 A1 | 1/2020 |
| WO | 2020021416 A1 | 1/2020 |
| WO | 2020058963 A1 | 3/2020 |
| WO | 2020075201 A1 | 4/2020 |
| WO | 2020121159 A1 | 6/2020 |
| WO | 2020152706 A1 | 7/2020 |
| WO | 2020157772 A1 | 8/2020 |
| WO | 2020208502 A1 | 10/2020 |
| WO | 2020247299 A1 | 12/2020 |
| WO | 2020247301 A1 | 12/2020 |
| WO | 2021010798 A1 | 1/2021 |
| WO | 2021021729 A1 | 2/2021 |

OTHER PUBLICATIONS

Andrews et al., Effectiveness of the 13-Valent Pneumococcal Conjugate Vaccine Against IPD in England and Wales, ISPPD-8, 2012, 179, Poster No. 148.
Andrews et al., Safety and immunogenicity of 15-valent pneumococcal conjugate vaccine (PCV15) compared to PCV13 in healthy older adults, Scientific Programme—Late Breakers, 2014, Abstract O-010, TP13 Special Session.
Andrews, Nick J. et al., Serotype-specific effectiveness and correlates of protection for the 13-valent pneumococcal conjugate vaccine: a postlicensure indirect cohort study, Lancet Infect. Dis., 2014, 839-846, 14.
Beall et al., Pre- and Postvaccination clonal Compositions of Invasive Pneumococcal Serotypes for Isolates Collected in the United States in 1999, 2001, and 2002, Journal of Clinical Microbiology, 2006, 999-1017, 44(3).
Bentley, S et al, Genetic Analysis of the Capsular Biosynthetic Locus from All 90 Pneumoccocal Serotypes, PLoS Genetics, 2006, 1-8, vol. 2, No. 3: e31.
Bentley, S et al., Capsule Biosynthesis Genes and Repeat-Unit Polysaccharide Structure for All 90 Serotypes of Genetic analysis of the capsular biosynthetic locus from all 90 pneumococcal serotypes, PLoS Genetics, 2006, 1, Fig. S1.
Bernatoniene, J. et al., Advances in Pneumococcal Vaccines Advantages for Infants and Children, Drugs, 2005, 229-255, 65(2).
Berry, David S. et al., Effect of O Acetylation of Neisseria meningitidis Serogroup A Capsular Polysaccharide on Development of Functional Immune Responses, Infection and Immunity, 2002, 3707-3713, 70(7).
Block et al., Pneumococcal Serotypes from Acute Otitis Mediate in Rural Kentucky, Pediatr. Infect. Dis. J., 2002, 859-865, 21.
Bo-Hyun Cho et al., Cost-effectiveness of administering 13-valent pneumococcal conjugate vaccine in addition to 23-valent pneumococcal polysaccharide vaccine to adults with immunocompromising conditions, Vaccine, 2013, 6011-6021, 31.
Bogaert, D. et al., *Streptococcus pneumoniae* colonisation: the key to pneumococcal disease, Lancet Infec. Dis., 2004, 144-154, 4.
Brady L. Spencer, The Pneumococcal Serotype 15C Capsule Is Partially O-Acetylated and Allows for Limited Evasion of 23-Valent Pneumococcal Polysaccharide Vaccine-Elicited Anti-Serotype 15B Antibodies, Clinical and Vaccine Immunology, Aug. 2017, 1-13, 24-8.
Brown, Paul W. et al., Characterization of Complex Prophylactic Vaccines with Protein and Glycoconjugate Components, Mass Spectrometry and Biophysical Characterization Group Analytical Research and Development, 2012, 1-34, 9th CASSS Symposium.
Bystricky, Slavomir et al., O-acetylation affects the binding properties of the carboxyl groups on the Vi bacterial polysaccharide, Biophysical Chemistry, 1994, 1-7, 51.
Chiayung Chu et al., Further Studies on the Immunogenicity of Haemophilus influenzae Type b and Pneumococcal Type 6A Polysaccharide-Protein Conjugates, Infection and Immunity, Apr. 1983, 245-256.
Choi, Eun Hwa et al., Capsular Polysaccharide (CPS) Release by Serotype 3 Pneumococcal Strains Reduces the Protective Effect of Anti-Type 3 CPS Antibodies, Clinical and Vaccine Immunology, 2016, 162-167, 23(2).
Cooper et al., The 13-valent pneumococcal conjugate vaccine (PCV13) elicts cross-functional opsoophagocytic killing responses in humans to *Streptococcus pneumoniae* serotypes 6C and 7A, Vaccine, 2011, 7207-7211, 29.
Dagan et al., Glycoconjugate Vaccines and Immune Interference: A Review, Vaccine, 2010, 5513-5523, 28.
Daniela Verthelyi, Adjuvant Properties of CpG Oligonucleotides in Primates, Methods Mol Med, 2006, 139-58, 127.
De La Pena, C. et al., Present and future of the pneumonia vaccination, Pediatrics, 2004, 47-55, 24(4).
Eskola, J. et al., Cross-Reactivity of Antibodies to Type 6B and 6A Polysaccharides of *Streptococcus pneumoniae*, Evoked by Pneumococcal Conjugate Vaccines, in Infants, Journal of Infectious Diseases, 2001, 789-793, 184.
Excerpt (Ex B) Summary of Product Characteristics for Prevenar 2005, 15 pages.
Fabiana Falugi et al., Rationally designed strings of promiscuous CD4 T cell epitopes provide help to Haemophilus influenzae type b oligosaccharide: a model for new conjugate vaccines, Eur. J. Immunol., 2001, 3816-3824, 31.
Fikri Y. Avci et al., A mechanism for glycoconjugate vaccine activation of the adaptive immune system and its implications for vaccine design, Nature Medicine, Dec. 2011, 1602-1610, 17-12.
Finn, Adam, Bacterial polysaccharide-protein conjugate vaccines, British Medical Bulletin, 2004, 1-14, 70.
Frasch, Carl E., Preparation of bacterial polysaccharide-protein conjugates: Analytical and manufacturing challenges, Vaccine, 2009, 6468-6470, 27.
Ganaie, Feroze et al., A New Pneumococcal Capsule Type, 10D, is the 100th Serotype and Has a Large cps Fragment from an Oral *Streptococcus*, mBio, 2020, 1-15, 11:e00937-20.
Geoffry S. Bethell et al., A Novel Method of Activation of Crosslinked Agaroses with 1, 1'-Carbonyldiimidazole Which Gives a

(56) References Cited

OTHER PUBLICATIONS

Matrix for Affinity Chromatography Devoid of Additional Charged Groups, The Journal of Biological Chemistry, 1979, 2572-2574, 254-8.

Ginsburg, A.S. et al., New Conjugate Vaccines for the Prevention of Pneumococcal Disease in Developing Countries, Drugs of Today, 2011, 207-214, 47(3).

Gowrisankar Rajam et al., Functional Antibodies to the O-Acetylated Pneumococcal Serotype 15B Capsular Polysaccharide Have Low Cross-Reactivities with Serotype 15C, Clinical and Vaccine Immunology, Sep. 2007, 1223-1227, 14-9.

Grabenstein, J.D. et al., A century of pneumococcal vaccination research in humans, Clinical Microbiology and Infection, 2012, 15-24, 18 (Suppl. 5).

Greene, Carolyn M. et al., Preventability of Invasive Pneumococcal Disease and Assessment of Current Polysaccharide Vaccine Recommendations for Adults: United States, 2001-2003, Clinical Infectious Diseases, 2006, 141-150, 43.

Hausdorff et al., Multinational Study of Pneumococcal Serotypes Causing Acute Otilitis Media in Children, Pediatr. Infect. Dis. J., 2002, 1008-1016, 21(11).

Hausdorff et al., The epidemiology of invasive pneumococcal disease: implications for conjugate vaccine development, The First International Symposium on Pneumococci and Pneumococcal Diseases (ISPPD-1), 1998, 27, 2-13:30, US.

Hausdorff et al., Which Pneumococcal Serogroups Cause the Most Invasive Disease Implications for Conjugate Vaccine Formation and Use, Part 1, Clinical Infectious Diseases, 2000, 100-121, 30.

Hausdorff, W.P. et al., Characteristics of Individual Pneumococcal Serotypes, The Fourth International Symposium on Pneumococci and Pneumococcal Diseases (ISPPD-4), 2004, 50, EPI-35.

Hausdorff, W.P. et al., Epidemiological differences among pneumococcal serotypes, Lancet Infectious Diseases, 2005, 83-93, 5.

Hausdorff, W.P. et al., Geographical differences in invasive pneumococcal disease rates and serotype frequency in young children, Lancet, 2001, 950-952, 357(9260).

Hausdorff, W.P. et al., Predicting the impact of new pneumococcal conjugate vaccines: serotype composition is not enough, Expert Review Vaccines, 2015, 413-428, 14(3).

Hausdorff, W.P. et al., The Contribution of Specific Pneumococcal Serogroups to Different Disease Manifestations: Implications for Conjugate Vaccine Formulation and Use, Part II, Clinical Infectious Diseases, 2000, 122-140, 30(1).

Hausdorff, W.P., Invasive pneumococcal disease in children: geographic and temporal variations in incidence and serotype distribution, European Journal of Pediatrics, 2002, S135-S139, 161 (Suppl. 2).

Henrichsen, Jorgen, Six Newly Recognized Types of *Streptococcus pneumoniae*, Journal of Clinical Microbiology, 1995, 2759-2762, 10.

Hevey, R. et al., Conjugation Strategies Used for the Preparation of Carbohydrate-Conjugate Vaccines, Chemistry of Bioconjugates: Synthesis, Characterization, and Biomedical Applications, First Edition, 2014, 387-413, Chapter 16.

Hicks et al., Incidence of Pneumococcal Disease Due to Non-Pneumococcal Conjugate Vaccine (PCV7) Serotypes in the US During the Era of Widespread PCV7 Vaccination, Journal of Infectious Diseases, 2007, 1346-1354, 196.

Ho, Mei M. et al., Physico-chemical and immunological examination of the thermal stability of tetanus toxoid conjugate vaccines, Vaccine, 2002, 3509-3522, 20.

Hsieh CL, Characterization of saccharide-CRM197 conjugate vaccines, Dev. Biol. (Basel), 2000, 93-104, 103.

Huebner, Robin E. et al., Long-term antibody levels and booster responses in South African children immunized with nonavalent pneumococcal conjugate vaccine, Vaccine, 2004, 2696-2700, 22.

International Search Report—Written Opinion of the International Search Authority for PCT/US2018/063709, 14 pages, Date Mailed Jul. 26, 2019.

Jakobsen et al., Pneumococcal serotype 19F conjugate vaccine induces cross-protective immunity to serotype 19A in a murine pneumococcal pneumoniae model, Infection and Immunity, 2003, 2956-2959, 71.

Joseph Kuo et al., Characterization of a Recombinant Pneumolysin and Its Use as a Protein Carrier for Pneumococcal Type 18C, Infection and Immunity, Jul. 1995, 2706-2713, 63-7.

Juan J. Calix et al., Biochemical, Genetic and Serological Characterization of Two Capsule Subtypes Among *Streptococcus pneumoniae* Serotype 20 Strains: Discovery of a New Pneumococcal Serotype, J. Biol. Chem, 2012, 27885-27894, 287-33.

K. Aaron Geno, Pneumococcal Capsules and Their Types: Past, Present, and Future, Clinical Microbiology Reviews, 2015, 871-899, 28.

Karin Baraldo et al., N19 Polyepitope as a Carrier for Enhanced Immunogenicity and Protective Efficacy of Meningococcal Conjugate Vaccines, Infection and Immunity, Aug. 2004, 4884-4887, 72-8.

Kei Yasuda et al., Role of Immunostimulatory DNA and TLR9 in Gene Therapy, Crit Rev Ther Drug Carrier Systems, 2006, 89-109, 23-2.

Kieninger, D.M., 48th Annual ICAAC/ISDA 46th Annual Meeting, Oct. 25-28, 2008.

Klugman, K.P. et al., Pneumococcal conjugate vaccine and pneumococcal common protein vaccines, Vaccines, 2013, 504-541, Chapter 25, 6th Edition.

Kyaw et al., Effect of Introduction of the Pneumococcal Conjugate Vaccine on Drug-Resistant *Streptococcus pneumoniae*, New England Journal of Medicine, 2006, 1455-1463, 354(14).

Lambrecht et al., Mechanism of action of clinically approved adjuvants, Current Opinion Immunology, 2009, pp. 23-29, vol. 21(1).

Lexau, C.A. et al., Changing Epidemiology of Invasive Pneumococcal Disease Among Older Adults in the Era of Pediatric Pneumococcal Conjugate Vaccine, The Journal of the American Medical Association, 2005, 2043-2051, 294(16).

Li, Hong et al., Validation of quantitative elisa for serum igg against pneumococcalcapsular polysaccharide of serotypes 2, 9N, 17F and 20, Chinese Journal of Biologicals, 2017, 751-755, 30(7).

MacNair, J.E. et al., Alignment of absolute and relative molecular size specifications for a polyvalent pneumococcal polysaccharide vaccine (PNEUMOVAX 23), Biologicals, 2005, 49-58, 33.

McFetridge, R. et al., Safety, tolerability, and immunogenicity of 15-valent pneumococcal conjugate vaccine in healthy adults, Vaccine, 2015, 2793-2799, 33.

McIntosh, E.D. et al., Global prevailing and emerging pediatric pneumococcal serotypes, Expert Review Vaccines, 2011, 109-129, 10(1).

Merck Sharp & Dohme Corp. (Petitioner), Pfizer Inc. (Patent Owner), Petition for Inter Partes Review, (AIA Review # IPR2017-02136), Case IPR2017-___, U.S. Pat. No. 9,492,559, dated Sep. 20, 2017, 81 pages.

Merck Sharp & Dohme Corp. (Petitioner), Pfizer Inc. (Patent Owner), Petition for Inter Partes Review, (AIA Review # IPR2017-02131), Case IPR2017-___, U.S. Pat. No. 9,492,559, dated Sep. 19, 2017, 82 pages.

Merck Sharp & Dohme Corp. (Petitioner), Pfizer Inc. (Patent Owner), Petition for Inter Partes Review, (AIA Review # IPR2017-02132), Case IPR2017-___, U.S. Pat. No. 9,492,559, dated Sep. 19, 2017, 85 pages.

Merck Sharp & Dohme Corp. (Petitioner), Pfizer Inc. (Patent Owner), Petition for Inter Partes Review, (AIA Review # IPR2017-02138), Case IPR2017-___, U.S. Pat. No. 9,492,559, dated Sep. 20, 2017, 82 pages.

Merck Sharp & Dohme Corp. (Petitioner), Wyeth LLC (Patent Owner), Petition for Inter Partes Review, (AIA Review # IPR2017-00378), Case IPR2016-___, U.S. Pat. No. 8,562,999, dated Dec. 1, 2016, 85 pages.

Merck Sharp & Dohme Corp. (Petitioner), Wyeth LLC (Patent Owner), Petition for Inter Partes Review, (AIA Review # IPR2017-00390), Case IPR2016-___, U.S. Pat. No. 8,562,999, dated Dec. 2, 2016, 83 pages.

(56) References Cited

OTHER PUBLICATIONS

Merck Sharp & Dohme Corp. (Petitioner), Wyeth LLC (Patent Owner), Petition for Inter Partes Review, (AIA Review # IPR2017-01194), Case IPR2017-___, U.S. Pat. No. 8,895,024, dated Mar. 29, 2017, 83 pages.
Merck Sharp & Dohme Corp. (Petitioner), Wyeth LLC (Patent Owner), Petition for Inter Partes Review, (AIA Review # IPR2017-01211), Case IPR2017-___, U.S. Pat. No. 9,399,060, dated Mar. 30, 2017, 71 pages.
Merck Sharp & Dohme Corp. (Petitioner), Wyeth LLC (Patent Owner), Petition for Inter Partes Review, (AIA Review # IPR2017-01215), Case IPR2017-___, U.S. Pat. No. 9,399,060, dated Mar. 30, 2017, 81 pages.
Merck Sharp & Dohme Corp. (Petitioner), Wyeth LLC (Patent Owner), Petition for Inter Partes Review, (AIA Review # IPR2017-01223), Case IPR2017-___, U.S. Pat. No. 9,399,060, dated Mar. 31, 2017, 60 pages.
Merck Sharp & Dohme Corp. (Petitioner), Wyeth LLC (Patent Owner), Petition for Post Grant Review, (AIA Review # PGR2017-00016), Case PGR2017-___, U.S. Pat. No. 9,399,060, dated Mar. 22, 2017, 105 pages.
Merck Sharp & Dohme Corp. (Petitioner), Wyeth LLC (Patent Owner), Petition for Post Grant Review, (AIA Review # PGR2017-00017), Case PGR2017-___, U.S. Pat. No. 9,399,060, dated Mar. 24, 2017, 98 pages.
Michael J. Gidley et al., Reductive methylation of proteins with sodium cyanoborohydride, Biochem, 1982, 331-334, 203.
Milton T. W. Hearn et al., Application of 1, 1'-Carbonyldiimidazole-activated Matrices for the purification of proteins, Journal of Chromatography, 1981, 509-518, 218.
MMWR, Direct and Indirect Effects of Routine Vaccination of Children with 7-Valent Pneumococcal Conjugate Vaccine on Incidence of Invasive Pneumococcal Disease, Centers for Disease Control and Prevention, 2005, 893-897, 54(36).
Morbidity and Mortality Weekly Report, Geographic Differences in HIV Infection Among Hispanics or Latinos—46 States and Puerto Rico, 2010, Centers for Disease Control and Prevention, 2012, 1-20, 61(40).
Neil Jentoft et al., Protein Labeling by Reductive Methylation with Sodium Cyanoborohydride: Effect of Cyanide and Metal Ions on the Reaction, Analytical Biochemistry, 1980, 186-190, 106.
O'Brien et al., Potential Impact of Conjugate Pneumococcal Vaccines of Pediatric Pneumococcal Diseases, Am. J. Epidemiol., 2004, 634-644, 159(7).
Obaro et al., Safety and Immunogenicity of Pneumococcal Conjugate Vaccine in Combination with Diphtheria, Tetanus Toxoid, Pertussis and Haemophilus Influenzae Type B Conjugate Vaccine, Pediatr. Infect. Dis. J., 2002, 940-946, 21(10).
Overturf et al., Pneumococcal Vaccination of Children, Seminars in Pediatric Infectious Diseases, 2002, 155-164, 13(3).
Paradiso, P., Essential criteria for evaluation of pneumococcal conjugate vaccine candidates, Vaccine, 2009, C15-C18, 27 (Suppl. 3).
Park et al., Differential Effects of pneumococcal vaccines against serotypes 6A and 6C, J Infect Dis, 2008, 1818-1822, 198.
Park, I.H. et al., Discovery of a New Capsular Serotype (6C) within Serogroup 6 of *Streptococcus pneumoniae*, Journal of Clinical Microbiology, 2007, 1225-1233, 45.
PDR, Prevnar, Physicians' Desk Reference, 2001, 1-9, 55 Edition.
Petitioner: *Merck Sharp & Dohme Corp.* v. Patent Owner: *GlaxoSmithKline Biologicals S.A.*, dated Jun. 11, 2018, 83 pages.
Petitioner: *Merck Sharp & Dohme Corp.* v. Patent Owner: *GlaxoSmithKline Biologicals S.A.*, dated Jun. 11, 2018, 84 pages.
Petitioner: *Merck Sharp & Dohme Corp.* v. Patent Owner: *GlaxoSmithKline Biologicals S.A.*, dated Jun. 11, 2018, 86 pages.
Petitioner: *Merck Sharp & Dohme Corp.* v. Patent Owner: *GlaxoSmithKline Biologicals S.A.*, dated Nov. 7, 2018, 83 pages.
Petitioner: *Merck Sharp & Dohme Corp.* v. Patent Owner: *GlaxoSmithKline Biologicals S.A.*, dated Nov. 7, 2018, 84 pages.
Pneumococcal Vaccine Polyvalent (Product Information), 2013, 6 pages.
Pollabauer, E.M. et al., The influence of carrier protein on the immunogenicity of simultaneously administered conjugate vaccines in infants, Vaccine, 2009, 1674-1679, 27.
Prymula et al., A Randomized Double-blind Efficacy Study, The Lancet, 2006, 740-748, 367.
Sanjiv Sur et al., Long Term Prevention of Allergic Lung Inflammation in a Mouse Model of Asthma by CpG Oligodeoxynucleotides, Journal of Immunology, 1999, 6284-6293, 162.
Sigurdardottir, Sigurveig T. et al., Immune response to octavalent diphtheria- and tetanus-conjugated pneumococcal vaccines is serotype- and carrier-specific: the choice for a mixed carrier vaccine, Pediatr Infect Dis J, 2002, 548-554, 21(6).
Sigurdardottir, Sigurveig TH. et al., Safety and immunogenicity of CRM197-conjugated pneumococcal-meningococcal C combination vaccine (9vPnC—MnCC) whether given in two or three primary doses, Vaccine, 2008, 4178-4186, 26.
Skinner et al., Pre-clinical Evaluation of a 15-Valent Pneumococcal Conjugate Vaccine (PCV15-CRM197) In an Infant-Rhesus Monkey Immunogenicity Model, Vaccine, 2011, 8870-8876, 29.
Smith, Edward J., Technical Report 12, Siliconization of Parenteral Drug Packaging Components, Journal of Parenteral Science and Technology, The Parenteral Drug Association, 1988, S4-S13, 42 (Suppl. 4).
Stacey, H.L. et al., Safety and immunogenicity of 15-valent pneumococcal conjugate vaccine (PCV-15) compared to PCV-13 in healthy older adults, Human Vaccines & Immunotherapeutics, 2019, 530-539, 15(3).
Su Wang et al., Adjuvant synergy in the response to hepatitis B vaccines, Science Direct, 2003, 4297-4306, 21.
T. Ben-Yedidia et al., Effect of pre-existing carrier immunity on the efficacy of synthetic influenza vaccine, Immunology Letters, 1998, 9-15, 64.
Traore et al., Incidence, Seasonality, Age Distribution, and Morality of Pneumococcal Meningitis in Burkina Faso and Togo, Clinical Infectious Disease, 2009, S181-S189, 48.
Tsuyoshi Uchida et al., Diphtheria Toxin and Related Proteins, J Biol Chem, 1973, 3838-3844, 218.
W. Nicklas, Aluminum salts, Research in Immunology, 1992, 489-493, 143.
Whitney et al., Decline in Invasive Pneumococcal Disease After the Introduction of Protein-Poloysacchairde Conjugate Vaccine, New England Journal of Medicine, 2003, 1737-1746, 348(18).
U.S. Appl. No. 17/374,424, filed Jul. 13, 2021.

\* cited by examiner

| Serotype | 2 μg v. 4 μg | 2 μg v. 1 μg | 2 μg v. 0.4 μg | 2 μg v. 0.08 μg | 2 μg v. 0.016 μg |
|---|---|---|---|---|---|
| 3 | 0.78 (0.26, 2.3) | 0.79 (0.27, 2.3) | 0.62 (0.21, 1.84) | 2.1 (0.7, 6.1) | 2.5 (0.85, 7.5) |
| 6C | 1.64 (0.3, 8.9) | 3.2 (0.6, 18) | 1.44 (0.27, 7.8) | 6.3 (1.15, 34) | 19 (3.5, 102) |
| 7F | 1.01 (0.22, 4.6) | 1.76 (0.39, 8) | 1.11 (0.24, 5.1) | 6.9 (1.52, 32) | 21 (4.5, 94) |
| 8 | 1.64 (0.36, 7.5) | 2.6 (0.57, 12) | 0.81 (0.18, 3.7) | 4.3 (0.94, 20) | 14 (3, 63) |
| 9N | 1.46 (0.35, 6) | 2.1 (0.52, 8.9) | 0.94 (0.23, 3.9) | 6.5 (1.58, 27) | 15 (3.5, 60) |
| 10A | 0.92 (0.24, 3.5) | 2.9 (0.75, 11) | 0.55 (0.14, 2.1) | 3.5 (0.9, 13) | 12 (3, 44) |
| 11A | 2.4 (0.51, 11) | 2.9 (0.62, 14) | 1.21 (0.26, 5.7) | 7.5 (1.61, 35) | 16 (3.5, 77) |
| 12F | 0.79 (0.18, 3.5) | 1.54 (0.35, 6.7) | 0.55 (0.13, 2.4) | 5 (1.14, 22) | 16 (3.7, 70) |
| 15A | 0.68 (0.14, 3.3) | 0.67 (0.14, 3.2) | 0.2 (0.041, 0.95) | 1.73 (0.36, 8.3) | 4.1 (0.86, 20) |
| 15B | 0.68 (0.15, 3.1) | 0.7 (0.15, 3.3) | 0.2 (0.043, 0.93) | 1.57 (0.34, 7.3) | 4.2 (0.89, 19) |
| 15C | 0.81 (0.18, 3.5) | 0.63 (0.14, 2.8) | 0.21 (0.049, 0.93) | 1.77 (0.4, 7.7) | 5.4 (1.24, 24) |
| 16F | 1.42 (0.28, 7.1) | 3.7 (0.73, 18) | 1.43 (0.29, 7.2) | 5.3 (1.05, 29) | 11 (2.3, 57) |
| 17F | 1.22 (0.24, 6.2) | 1.58 (0.31, 8.1) | 0.46 (0.09, 2.3) | 4.2 (0.82, 21) | 22 (4.3, 112) |
| 19A | 1.19 (0.42, 3.4) | 1.45 (0.51, 4.1) | 1.29 (0.45, 3.7) | 3 (1.05, 8.5) | 5 (1.74, 14) |
| 20A | 1.59 (0.37, 6.9) | 1.82 (0.42, 7.9) | 0.62 (0.14, 2.7) | 6.5 (1.52, 28) | 20 (4.7, 88) |
| 22F | 1.65 (0.31, 8.8) | 2.2 (0.41, 12) | 0.45 (0.084, 2.4) | 6.2 (1.17, 33) | 20 (3.7, 105) |
| 23A | 1.27 (0.27, 6) | 3.1 (0.65, 15) | 0.22 (0.046, 1.04) | 3.3 (0.7, 16) | 5.1 (1.08, 25) |
| 23B | 1.09 (0.18, 6.7) | 1.59 (0.26, 9.7) | 0.95 (0.16, 5.8) | 1.8 (0.29, 11) | 7.4 (1.21, 45) |
| 24F | 4.9 (1.1, 21) | 4.9 (1.11, 22) | 2.6 (0.58, 11) | 13 (3, 59) | 21 (4.7, 92) |
| 31 | 0.96 (0.23, 4.1) | 1.13 (0.27, 4.8) | 0.47 (0.11, 2) | 2.1 (0.66, 12) | 6.4 (1.51, 27) |
| 33F | 0.64 (0.18, 2.2) | 0.92 (0.26, 3.3) | 0.53 (0.15, 1.85) | 3.6 (1.03, 13) | 19 (5.5, 68) |
| 35B | 0.69 (0.25, 1.87) | 1.08 (0.4, 2.9) | 0.63 (0.23, 1.69) | 2.1 (0.77, 5.6) | 5.1 (1.9, 14) |

FIG. 19B

| Serotype | 2 μg v. 4 μg | 2 μg v. 1 μg | 2 μg v. 0.4 μg | 2 μg v. 0.08 μg | 2 μg v. 0.016 μg |
|---|---|---|---|---|---|
| 3 | 0.91 (0.34, 2.5) | 1.58 (0.59, 4.3) | 1.86 (0.69, 5.0) | 4.3 (1.59, 12.0) | 5.7 (2.1, 15.0) |
| 6C | 2.1 (0.39, 11.0) | 1.87 (0.35, 10) | 1.6 (0.3, 8.6) | 9.6 (1.79, 51) | 11 (1.98, 56) |
| 7F | 0.8 (0.23, 2.7) | 1.88 (0.55, 6.4) | 1.03 (0.3, 3.5) | 3.6 (1.05, 12) | 6.2 (1.83, 21) |
| 8 | 0.9 (0.3, 2.7) | 1.57 (0.53, 4.7) | 1.1 (0.37, 3.3) | 5.5 (1.84, 17) | 8.3 (2.8, 25) |
| 9N | 1.31 (0.4, 4.3) | 1.92 (0.58, 6.3) | 1.17 (0.36, 3.8) | 5.1 (1.56, 17) | 7.1 (2.2, 23) |
| 10A | 1.49 (0.26, 8.6) | 3 (0.53, 17) | 0.84 (0.15, 4.8) | 4.1 (0.71, 23) | 13 (2.2, 72) |
| 11A | 0.98 (0.2, 4.9) | 2.1 (0.42, 10) | 1.09 (0.22, 5.4) | 5.7 (1.15, 29) | 4.3 (0.86, 22) |
| 12F | 1.28 (0.31, 5.2) | 0.96 (0.24, 3.9) | 0.8 (0.2, 3.3) | 6.3 (1.53, 26) | 11 (2.7, 45) |
| 15A | 1.39 (0.36, 5.3) | 1.39 (0.36, 5.3) | 1.12 (0.29, 4.3) | 4.1 (1.06, 16) | 7.1 (1.85, 27) |
| 15B | 0.79 (0.19, 3.3) | 0.72 (0.17, 3) | 0.49 (0.12, 2.1) | 1.75 (0.41, 7.4) | 2.5 (0.6, 11) |
| 15C | 0.81 (0.21, 3.1) | 0.74 (0.19, 2.9) | 0.53 (0.14, 2) | 1.92 (0.5, 7.4) | 3.9 (1.03, 15) |
| 16F | 1.37 (0.33, 5.8) | 3.5 (0.83, 15) | 1.31 (0.31, 5.5) | 3.1 (0.73, 13) | 5.2 (1.24, 22) |
| 17F | 0.99 (0.31, 3.1) | 1.65 (0.52, 5.2) | 1.06 (0.33, 3.4) | 5.6 (1.76, 18) | 7.1 (2.3, 23) |
| 19A | 2.8 (0.51, 16) | 3.6 (0.65, 20) | 1.13 (0.21, 6.2) | 6.1 (1.0, 33) | 9.8 (1.78, 54) |
| 20A | 1.59 (0.37, 6.8) | 1.53 (0.36, 6.5) | 0.83 (0.19, 3.5) | 4.7 (1.1, 20) | 6.2 (1.45, 26) |
| 22F | 1.34 (0.32, 5.7) | 1.42 (0.34, 6) | 0.72 (0.17, 3) | 3.6 (0.84, 15) | 5.1 (1.2, 21) |
| 23A | 2.4 (0.48, 12) | 2.5 (0.51, 12) | 0.67 (0.14, 3.3) | 3.6 (0.74, 18) | 9.1 (1.84, 45) |
| 23B | 2.3 (0.28, 19) | 2.4 (0.29, 20) | 1.49 (0.18, 12) | 4 (0.48, 33) | 6.8 (0.82, 56) |
| 24F | 8.6 (0.9, 83) | 4.5 (0.46, 43) | 2.9 (0.3, 28) | 18 (1.85, 172) | 16 (1.61, 150) |
| 31 | 1.26 (0.33, 4.8) | 1.17 (0.45, 6.5) | 0.86 (0.23, 3.3) | 2.5 (0.64, 9.4) | 4.7 (1.22, 18) |
| 33F | 0.6 (0.18, 1.97) | 0.77 (0.23, 2.5) | 0.5 (0.15, 1.65) | 2.7 (0.81, 8.9) | 3.4 (1.02, 11) |
| 35B | 0.94 (0.43, 2.1) | 1.41 (0.64, 3.1) | 1.24 (0.56, 2.8) | 2.6 (1.18, 5.8) | 4.3 (1.94, 9.6) |

FIG. 20B

COMPOSITIONS COMPRISING *Streptococcus pneumoniae* POLYSACCHARIDE-PROTEIN CONJUGATES AND METHODS OF USE THEREOF

CROSS-REFERENCE TO RELATED APPLICATIONS

This application is a continuation application of U.S. application Ser. No. 17/374,424, filed Jul. 13, 2021, which is a divisional application of U.S. application Ser. No. 16/208,778, filed Dec. 4, 2018, which claims benefit of U.S. Provisional Application 62/595,388 filed Dec. 6, 2017, each of which are hereby incorporated by reference in their entirety.

REFERENCE TO SEQUENCE LISTING SUBMITTED ELECTRONICALLY

The instant application contains a Sequence Listing which has been submitted electronically in XML format and is hereby incorporated by reference in its entirety. The XML file, created on Oct. 4, 2023, is named 24534USCNT-SEQ_LISTING_ST26-04OCT2023.xml and is 3 KB in size. This sequence listing submitted via EFS-Web is part of the specification and is herein incorporated by reference in its entirety.

FIELD OF INVENTION

The present invention provides multivalent immunogenic compositions having distinct polysaccharide-protein conjugates. Each conjugate consists of a capsular polysaccharide prepared from a different serotype of *Streptococcus pneumoniae* conjugated to a carrier protein, preferably CRM197. The immunogenic compositions provide broad coverage against pneumococcal disease.

BACKGROUND OF THE INVENTION

*Streptococcus pneumoniae* is a Gram-positive bacterium and the most common cause of invasive bacterial disease (such as pneumonia, bacteraemia, meningitis and Otitis media) in infants and young children. Pneumococcus is encapsulated with a chemically linked polysaccharide which confers serotype specificity. There are over 90 known serotypes of pneumococci, and the capsule is the principle virulence determinant for pneumococci, as the capsule not only protects the inner surface of the bacteria from complement, but is itself poorly immunogenic. Polysaccharides are T-cell independent antigens, and, in most cases, can not be processed or presented on MHC molecules to interact with T-cells. They can however, stimulate the immune system through an alternate mechanism which involves cross-linking of surface receptors on B cells.

The multivalent pneumococcal polysaccharide vaccines that have been licensed for many years have proved valuable in preventing pneumococcal disease in adults, particularly, the elderly and those at high-risk. However, infants and young children respond poorly to unconjugated pneumococcal polysaccharides. The pneumococcal conjugate vaccine, Prevnar®, containing the 7 most frequently isolated serotypes (4, 6B, 9V, 14, 18C, 19F and 23F) causing invasive pneumococcal disease in young children and infants at the time, was first licensed in the United States in February 2000. Following universal use of Prevnar® in the United States, there has been a significant reduction in invasive pneumococcal disease in children due to the serotypes present in Prevnar®. See Centers for Disease Control and Prevention, MMWR Morb Mortal Wkly Rep 2005, 54(36): 893-7. However, there are limitations in serotype coverage with Prevnar® in certain regions of the world and some evidence of certain emerging serotypes in the United States (for example, 19A and others). See O'Brien et al., 2004, *Am J Epidemiol* 159:634-44; Whitney et al., 2003, *N Engl J Med* 348:1737-46; Kyaw et al., 2006, *N Engl J Med* 354:1455-63; Hicks et al., 2007, *J Infect Dis* 196:1346-54; Traore et al., 2009, *Clin Infect Dis* 48:S181-5189.

U.S. Patent Application Publication No. US 2006/0228380 describes a 13-valent pneumococcal polysaccharide-protein conjugate vaccine including serotypes 1, 3, 4, 5, 6A, 6B, 7F, 9V, 14, 18C, 19A, 19F and 23F. Chinese Patent Application Publication No. CN 101590224 A describes a 14-valent pneumococcal polysaccharide-protein conjugate vaccine including serotypes 1, 2, 4, 5, 6A, 6B, 7F, 9N, 9V, 14, 18C, 19A, 19F and 23F.

Other PCVs have covered 7, 10, 11, or 13 of the serotypes contained in PCV-15 (U.S Pub. No. 2011/0195086), but immune interference has been observed for some serotypes (e.g. lower protection for serotype 3 in GSK's PCV-11) and lower response rates to serotype 6B in Pfizer's PCV-13 (PREVNAR® 13). See Prymula et al., 2006, Lancet 367: 740-48 and Kieninger et al., Safety and Immunologic Non-inferiority of 13-valent Pneumococcal Conjugate Vaccine Compared to 7-valent Pneumococcal Conjugate Vaccine Given as a 4-Dose Series in Healthy Infants and Toddlers, presented at the 48$^{th}$ Annual ICAAC/ISDA 46$^{th}$ Annual Meeting, Washington DC, Oct. 25-28, 2008.

The current multivalent pneumococcal vaccines have been effective in reducing the incidence of pneumococcal disease associated with those serotypes present in the vaccines. However, the prevalence of the pneumococci expressing serotypes not present in the currently available vaccines has been increasing. Accordingly, there is a need for additional pneumococcal vaccine compositions which provide protection against different sets of pneumococcal serotypes and which can provide complementary protection against pneumococcal serotypes not present in currently available vaccines.

SUMMARY OF THE INVENTION

The invention provides multivalent immunogenic compositions comprising *S. pneumoniae* polysaccharide protein conjugates wherein each of the conjugates comprises a polysaccharide from an *S. pneumoniae* serotype conjugated to a carrier protein, wherein the serotypes of *S. pneumoniae* are as defined herein.

In particular embodiments of the invention, the serotypes of *S. pneumoniae* comprise a set of serotypes selected from the group consisting of:
  a) 15A, 16F, 23A, 23B, 24F, 31 and 35B;
  b) 15A, 16F, 23A, 23B, 24F, 31, 35B, 8, 9N, 10A, 11A, 12F, 15C, 17F, and 20; and
  c) 3, 7F, 19A, 22F, 33F, 15A, 16F, 23A, 23B, 24F, 31, 35B, 8, 9N, 10A, 11A, 12F, 15C, 17F, and 20.

In further particular embodiments of the invention, the serotypes of *S. pneumoniae* comprise a set of serotypes selected from the group consisting of:
  a) 15A, 16F, 23A, 23B, 24F, 31 and 35B;
  b) 15A, 16F, 23A, 23B, 24F, 31, 35B, 8, 9N, 10A, 11A, 12F, 15C, 17F, and 20A; and
  c) 3, 7F, 19A, 22F, 33F, 15A, 16F, 23A, 23B, 24F, 31, 35B, 8, 9N, 10A, 11A, 12F, 15C, 17F, and 20A.

In further particular embodiments of the invention, the serotypes of S. pneumoniae comprise a set of serotypes selected from the group consisting of:
a) 15A, 16F, 23A, 23B, 24F, 31 and 35B;
b) 15A, 16F, 23A, 23B, 24F, 31, 35B, 8, 9N, 10A, 11A, 12F, 15C, 17F, and 20B; and
c) 3, 7F, 19A, 22F, 33F, 15A, 16F, 23A, 23B, 24F, 31, 35B, 8, 9N, 10A, 11A, 12F, 15C, 17F, and 20B.

In some embodiments, the set of serotypes of S. pneumoniae listed in a), b) or c) further comprises: serotype 6C, serotype 6A, or serotypes 6A and 6B.

In some embodiments, at least one of the polysaccharide protein conjugates is formed by a conjugation reaction comprising an aprotic solvent, e.g. dimethylsulfoxide (DMSO). In specific embodiments, each of the polysaccharide protein conjugates is formed by a conjugation reaction comprising an aprotic solvent. As shown herein, the use of DMSO as a solvent during reductive amination of polysaccharide-protein conjugates results in unexpectedly superior stability and enhanced immunogenicity for those serotypes relative to the same conjugates prepared under aqueous conditions.

Also provided are methods for inducing a protective immune response in a human patient comprising administering the multivalent immunogenic compositions of the invention to the patient. In some embodiments of the methods of the invention, the patient was previously treated with a multivalent pneumococcal vaccine.

A multivalent immunogenic composition of the invention may be used as part of a treatment regimen with a different, complementary pneumococcal vaccine. Accordingly, the invention provides a method of inducing a protective immune response in a human patient comprising administering a multivalent immunogenic composition of the invention to the patient, further comprising administering a multivalent pneumococcal vaccine to the patient in any order. In particular embodiments, the multivalent pneumococcal vaccine is comprised of multiple S. pneumoniae polysaccharide protein conjugates wherein each of the conjugates comprises polysaccharide from an S. pneumoniae serotype conjugated to a carrier protein. In other embodiments, the multivalent pneumococcal vaccine is comprised of unconjugated capsular polysaccharides.

Also provided are methods for preparing a serotype 8 Streptococcus pneumoniae polysaccharide-protein conjugate utilizing a conjugation reaction in an aprotic solvent, wherein the conjugation reaction does not use cyanoborohydride.

The invention also provides multivalent immunogenic compositions comprising S. pneumoniae polysaccharide protein conjugates wherein each of the conjugates comprises a polysaccharide from an S. pneumoniae serotype conjugated to a carrier protein, wherein select serotypes of S. pneumoniae provide cross-reactivity to other select serotypes.

BRIEF DESCRIPTION OF THE DRAWINGS

FIG. 19B provides a PCV21 dose comparison PD1 GMT ratios (95% CI) corresponding to FIG. 19A GMT ratios whose lower 95% confidence bound exceed 1.0 are shaded light gray and GMT ratios whose upper 95% confidence bound are less than 1.0 are shaded dark gray. Serotype 15B data is included to evaluate cross protection.

FIG. 20B provides a PCV21 dose comparison PD2 GMT ratios (95% confidence interval) corresponding to FIG. 20A GMT ratios whose lower 95% confidence bound exceed 1.0 are shaded light gray. Serotype 15B data is included to evaluate cross protection.

FIG. 22G shows the impact of time and temperature (i.e. 7 Days at 4° C. or 37° C.) on stability of a 21-valent Pneumococcal Conjugate vaccine (PCV21 at 0.084 mg/mL PnPs), prepared with all drug substances conjugated in DMSO solvent, using intrinsic protein fluorescence spectroscopy with an excitation wavelength at 280 nm.

FIG. 31A and FIG. 31C show data for 8 common serotypes in all PCVs evaluated (6C, 15A, 16F, 23A, 23B, 24F, 31, 35B) and additional 8 common serotypes in PCV16, PCV21 and PCV31 (8, 9N, 10A, 11A, 12F, 15C, 17F, 20B). FIG. 31B and FIG. 31D show data for additional 16 serotypes not included in FIG. 31A and FIG. 31C. Five of them are also common serotypes in PCV21 and PCV31 (3, 7F, 19A, 22F, 33F), ten serotypes are contained exclusively in PCV31 (1, 4, 5, 6A, 6B, 9V, 14, 18C, 19F, 23F). Serotype 15B data is included to evaluate cross protection.

DETAILED DESCRIPTION OF THE INVENTION

Figure 1:
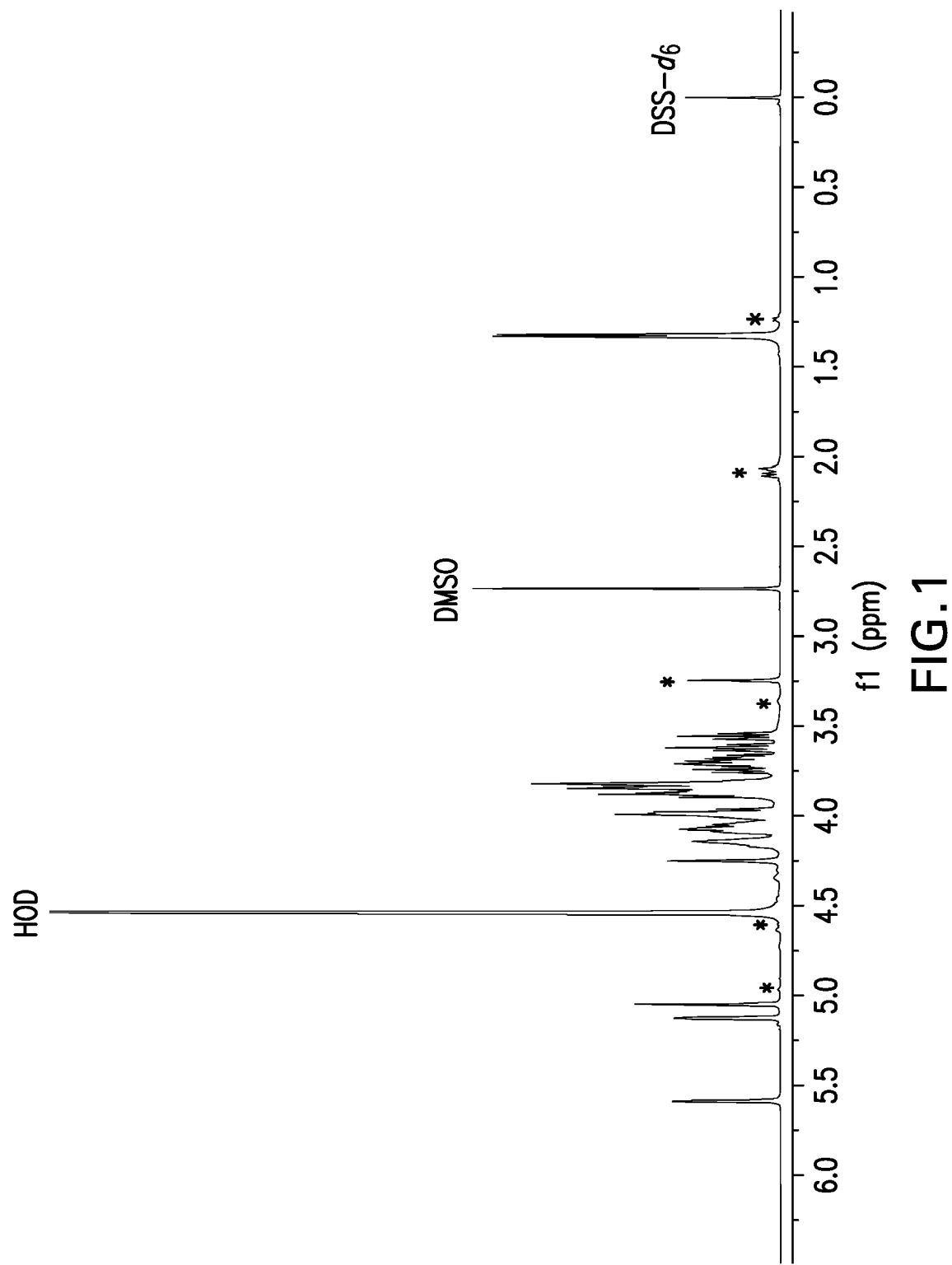
FIG. 1 depicts the 600 MHz one-dimensional $^1$H NMR spectrum of the capsular polysaccharide from S. pneumonia serotype 6C in deuterium oxide ($D_2O$) at 50° C. Signals arising from internal standards (DMSO and DSS-$d_6$) and residual water (HOD) are marked. Minor signals marked by * are due to S. pneumonia cell wall residuals such as C-polysaccharide and/or peptidoglycans.
Figure 2:
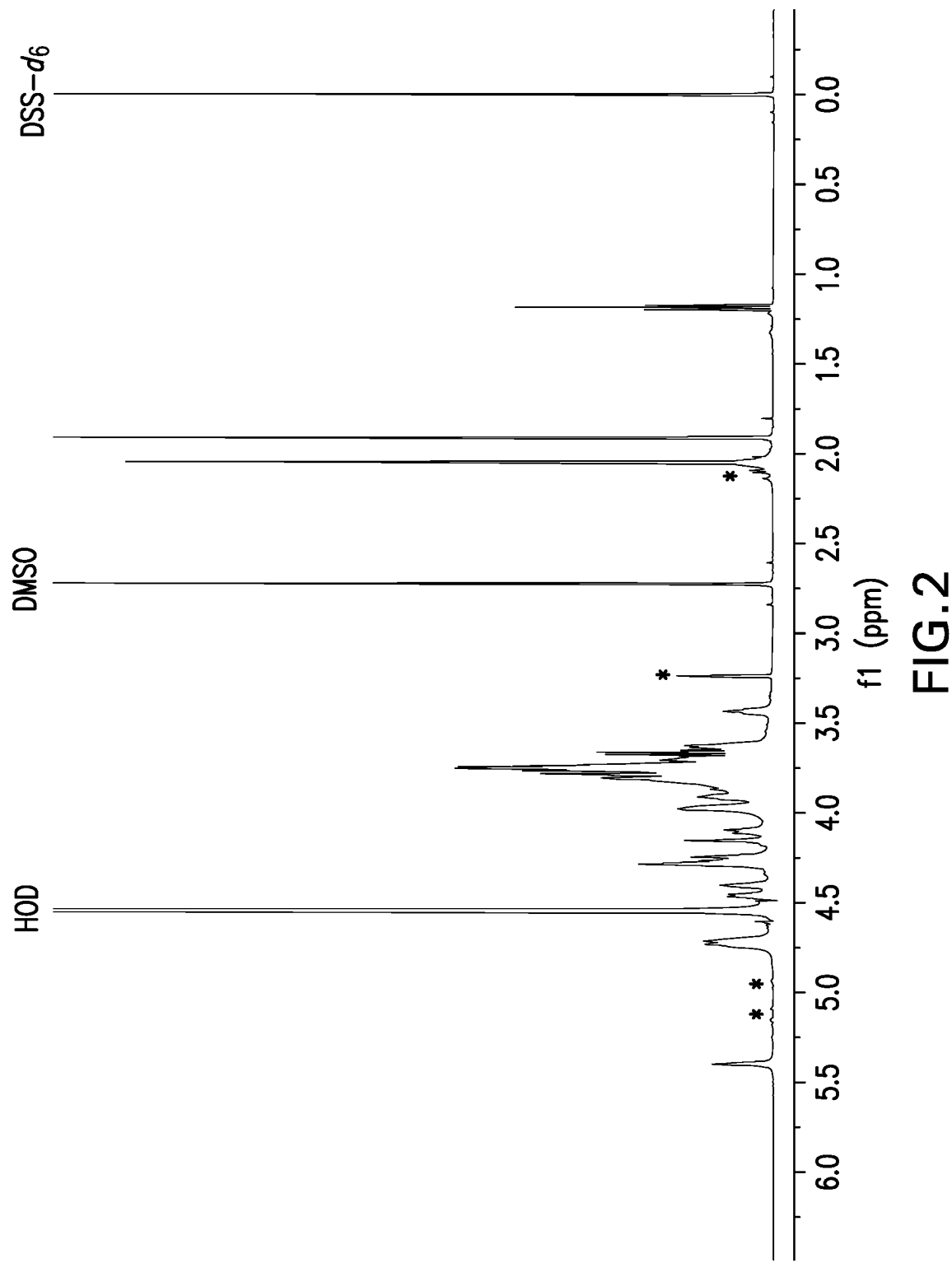
FIG. 2 depicts the 600 MHz one-dimensional $^1$H NMR spectrum of the capsular polysaccharide from S. pneumonia serotype 15A in deuterium oxide ($D_2O$) at 50° C. Signals arising from internal standards (DMSO and DSS-$d_6$) and residual water (HOD) are marked. Minor signals marked by * are due to S. pneumonia cell wall residuals such as C-polysaccharide and/or peptidoglycans.
Figure 3:
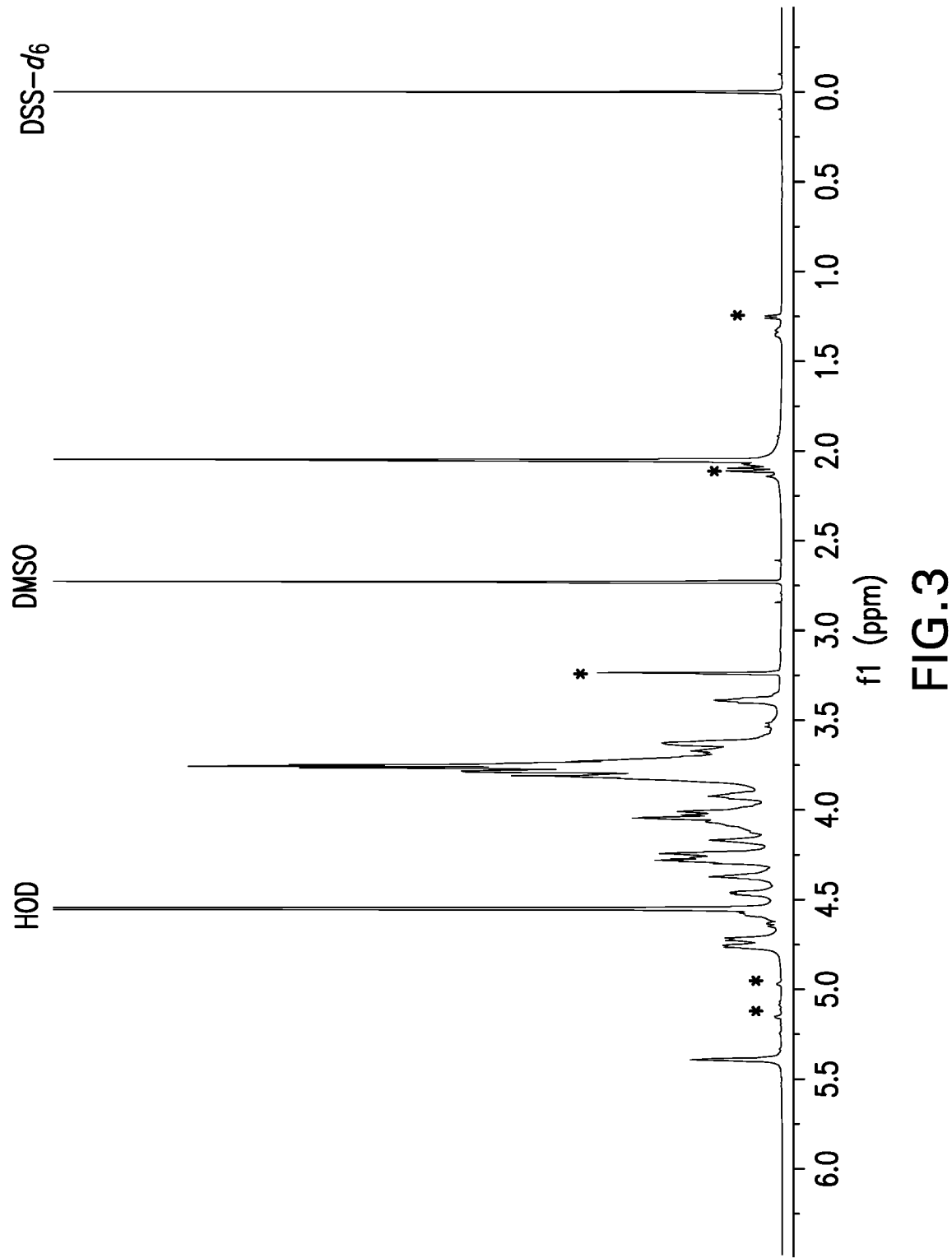
FIG. 3 depicts the 600 MHz one-dimensional $^1$H NMR spectrum of the capsular polysaccharide from S. pneumonia serotype de-O-acetylated 15B in deuterium oxide ($D_2O$) at 50° C. Signals arising from internal standards (DMSO and DSS-$d_6$) and residual water (HOD) are marked. Minor signals marked by * are due to S. pneumonia cell wall residuals such as C-polysaccharide and/or peptidoglycans.
Figure 4:
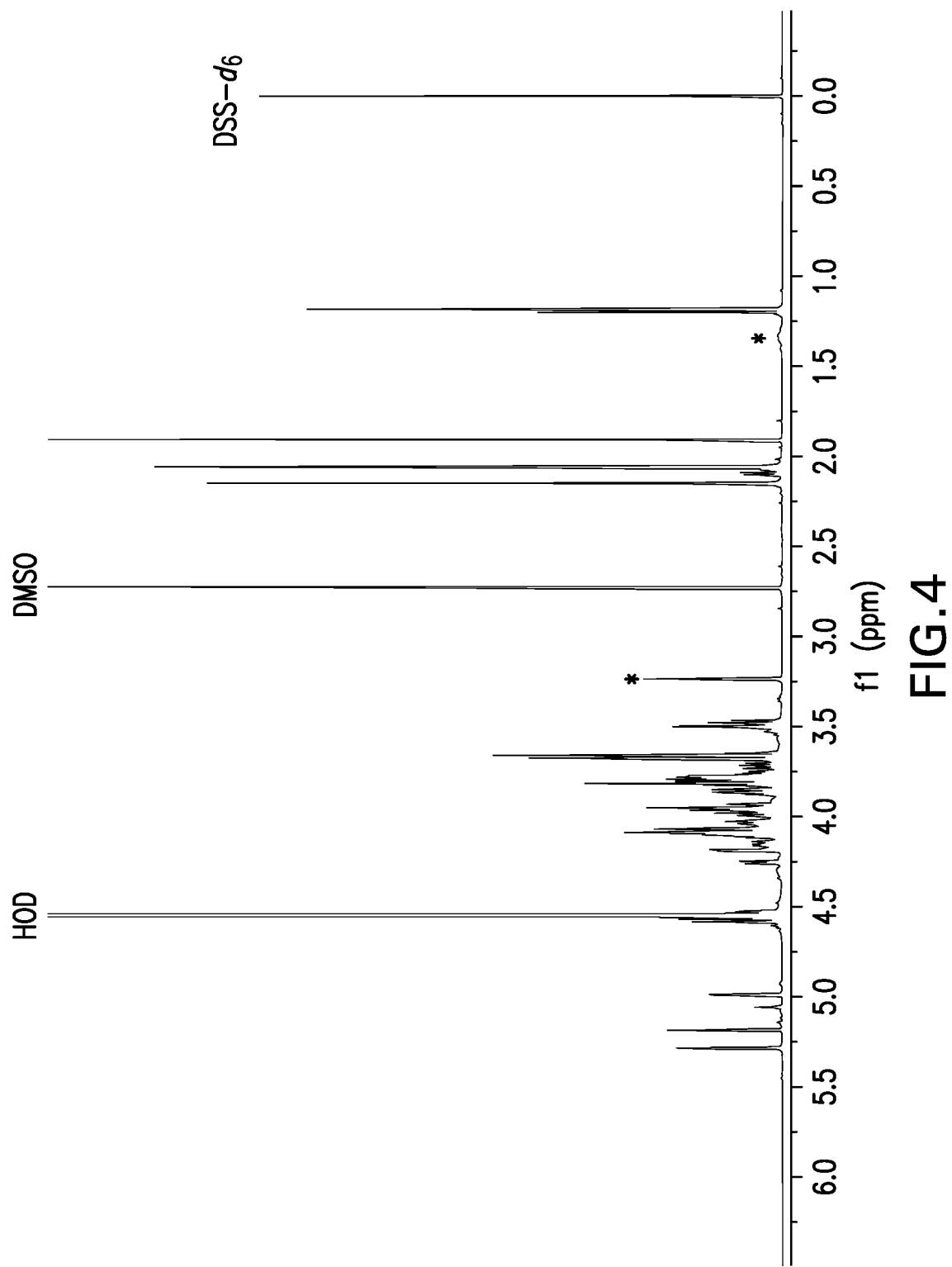
FIG. 4 depicts the 600 MHz one-dimensional $^1$H NMR spectrum of the capsular polysaccharide from S. pneumonia serotype 35B in $D_2O$ at 50° C. Signals arising from internal standards (DMSO and DSS-$d_6$) and residual water (HOD) are marked. Minor signals marked by * are due to S. pneumonia cell wall residuals such as C-polysaccharide and/or peptidoglycans.
Figure 5:
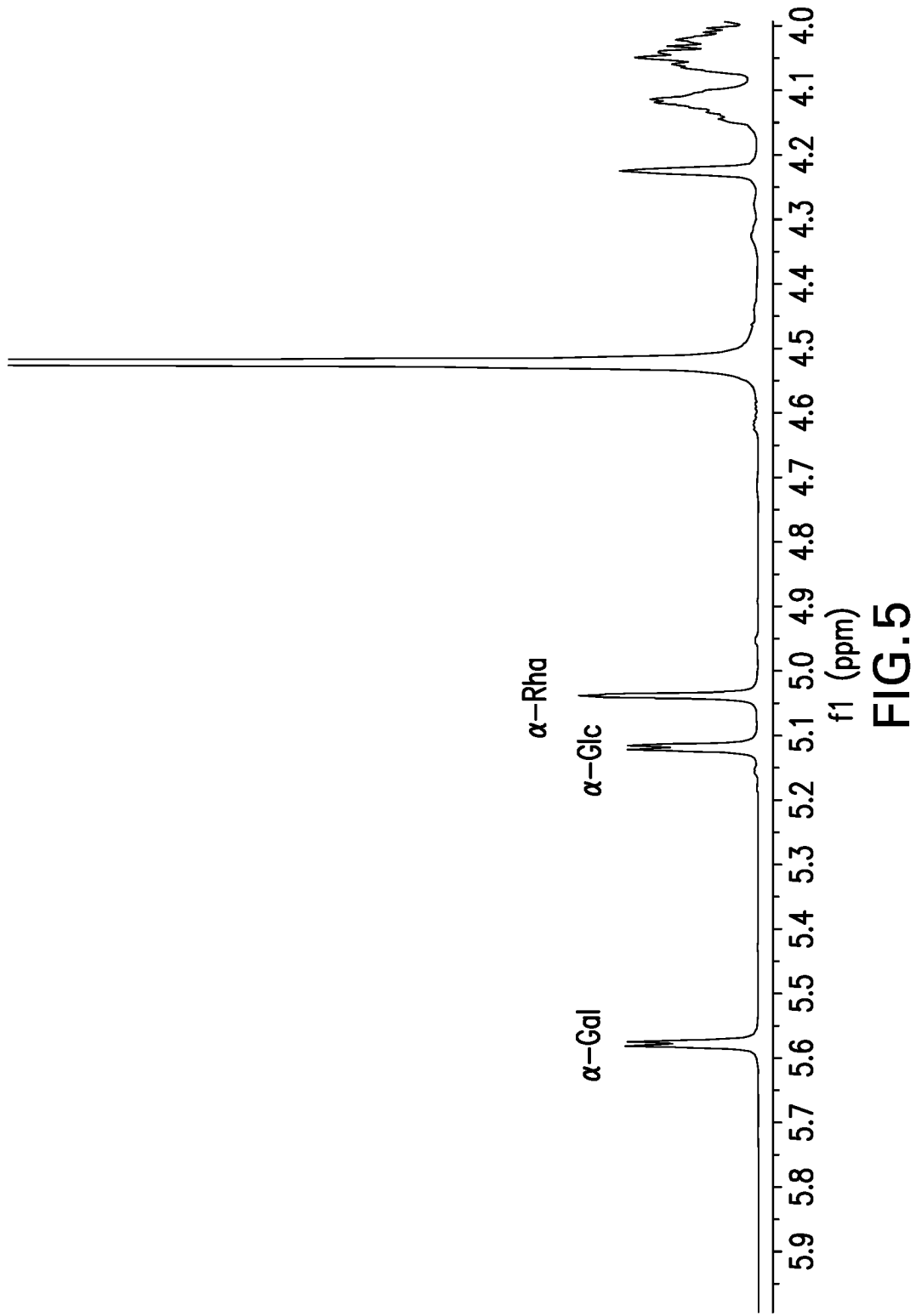
FIG. 5 depicts the $^1$H NMR identity region useful for serotype identification of S. pneumonia serotype 6C. Signal positions of each anomeric proton of the repeating unit from each monosaccharide residue are marked.
Figure 6:
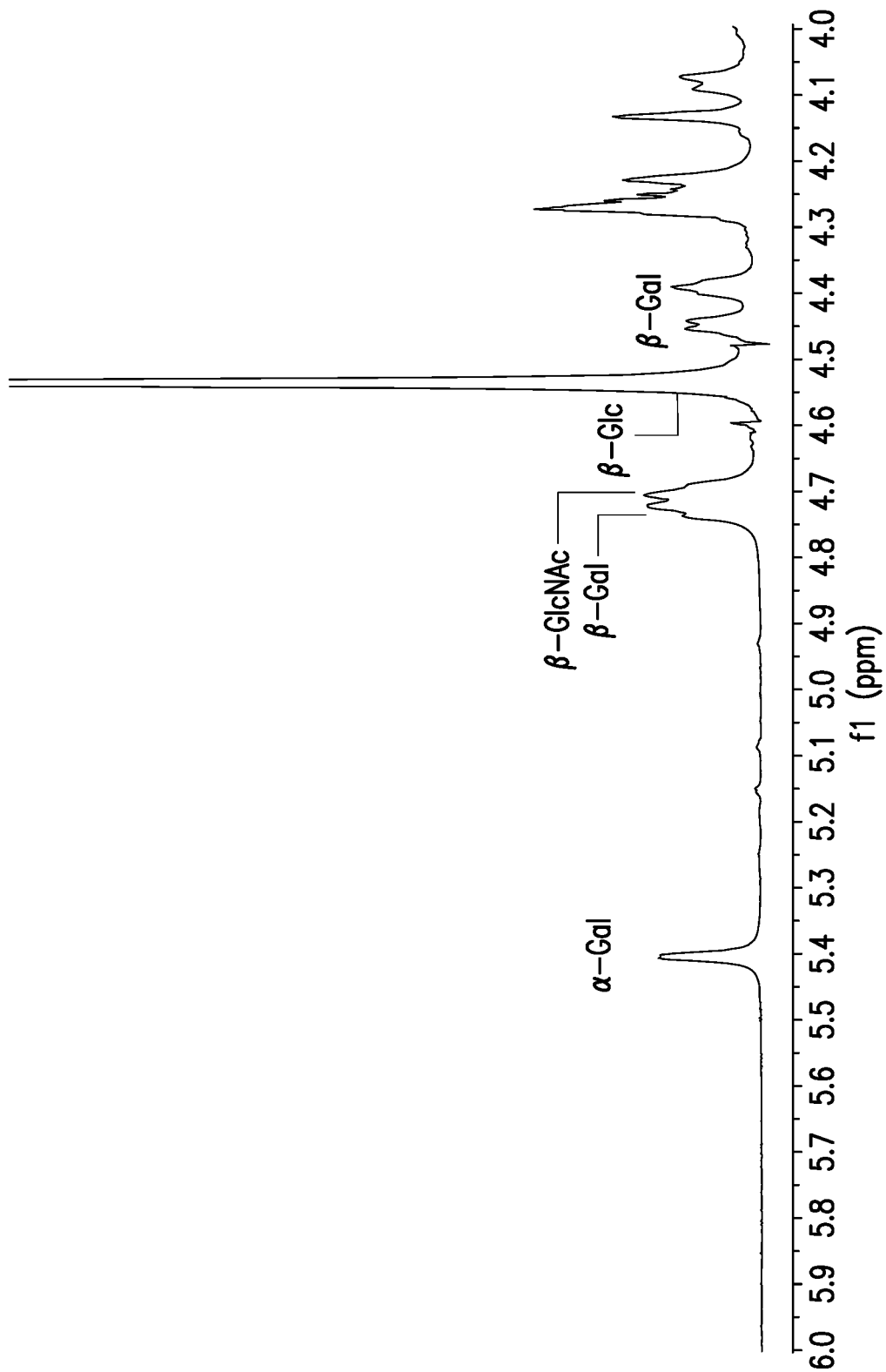
FIG. 6 depicts the $^1$H NMR identity region useful for serotype identification of S. pneumonia serotype 15A. Signal positions of each anomeric proton of the repeating unit from each monosaccharide residue are marked.
Figure 7:
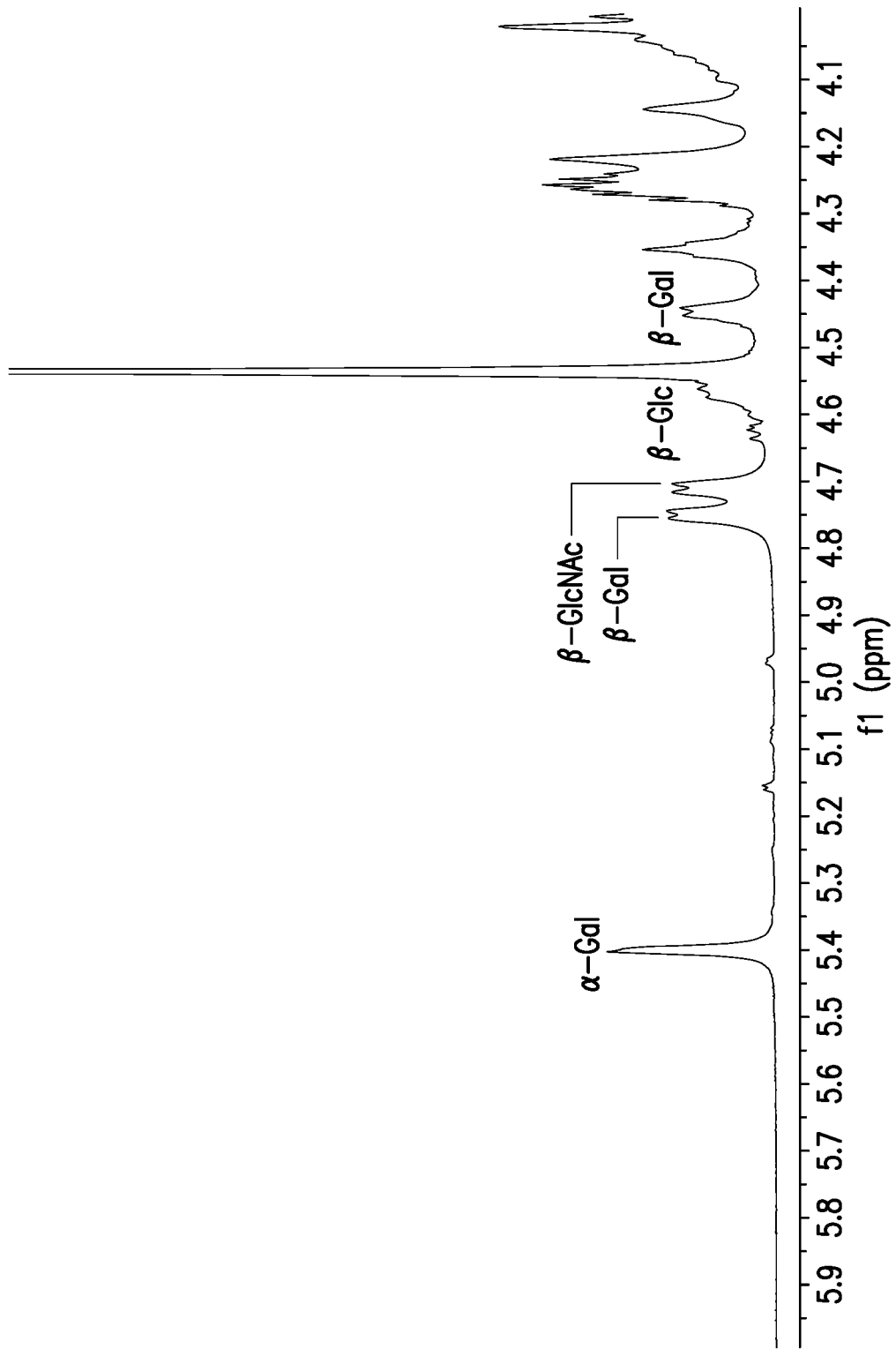
FIG. 7 depicts the $^1$H NMR identity region useful for serotype identification of S. pneumonia serotype de-O-acetylated 15B. Signal positions of each anomeric proton from each monosaccharide residue are marked.
Figure 8:
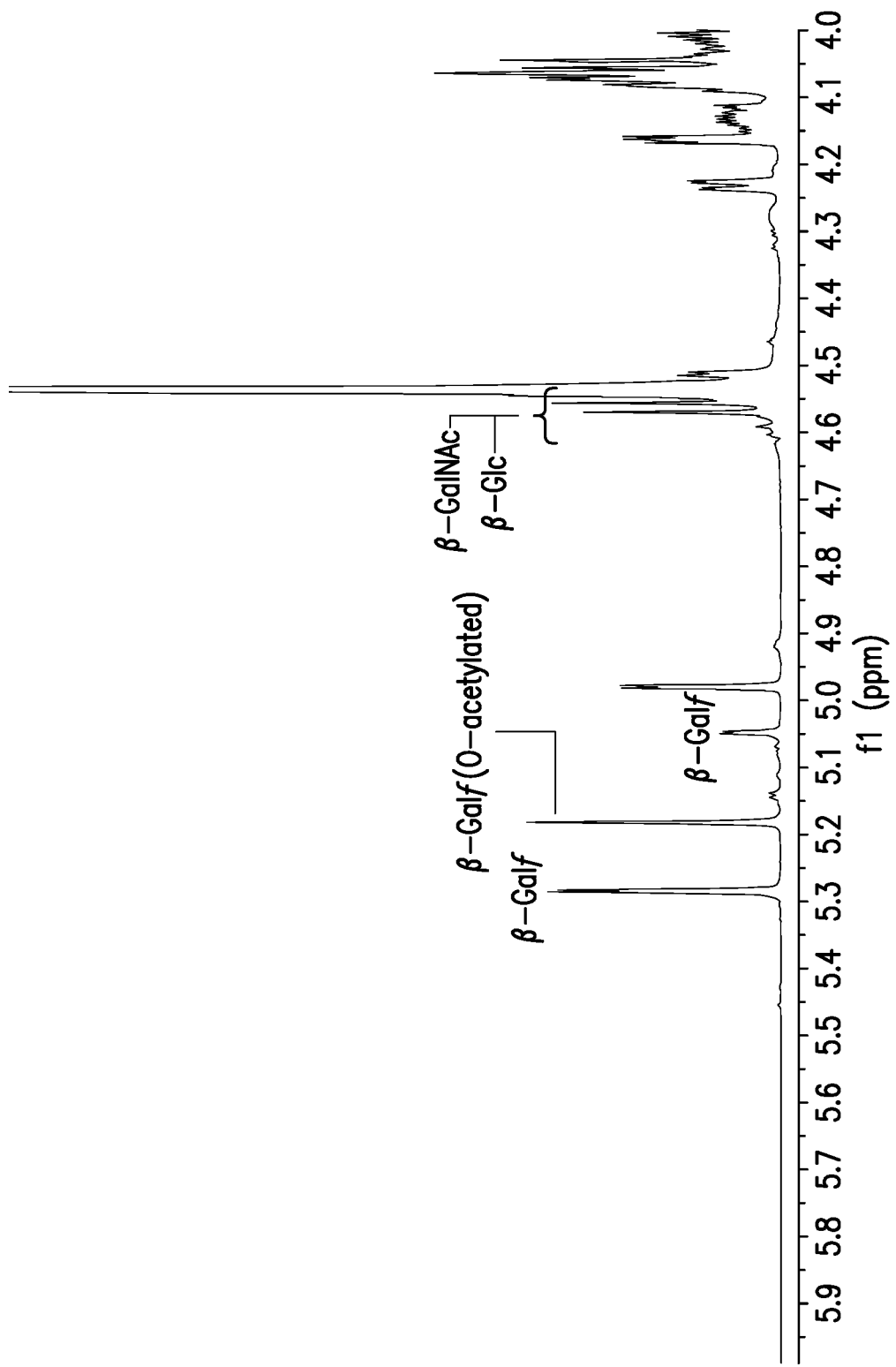
FIG. 8 depicts the $^1$H NMR identity region useful for serotype identification of S. pneumonia serotype 35B. Signal positions of each anomeric proton of the repeating unit from each monosaccharide residue are marked.
Figure 9A:
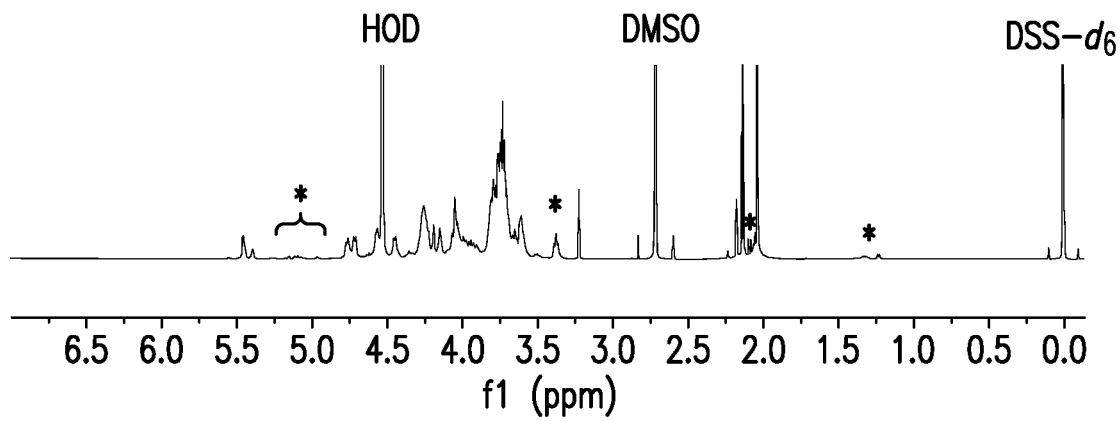
FIGS. 9A-9C depict the 600 MHz one-dimensional $^1$H NMR spectrum of native capsular polysaccharide from S. pneumonia serotype 15B (FIG. 9A), the de-O-acetylated capsular polysaccharide from S. pneumonia serotype 15B (FIG. 9B) and the capsular polysaccharide from S. pneumonia serotype 15C (FIG. 9C). Spectra were acquired in deuterium oxide ($D_2O$) at 50° C. Signals arising from internal standards (DMSO and DSS-d6) and residual water (HOD) are marked. Signals marked by * are due to S. pneumonia cell wall residuals such as C-polysaccharide and/or peptidoglycans.
Figure 9B:
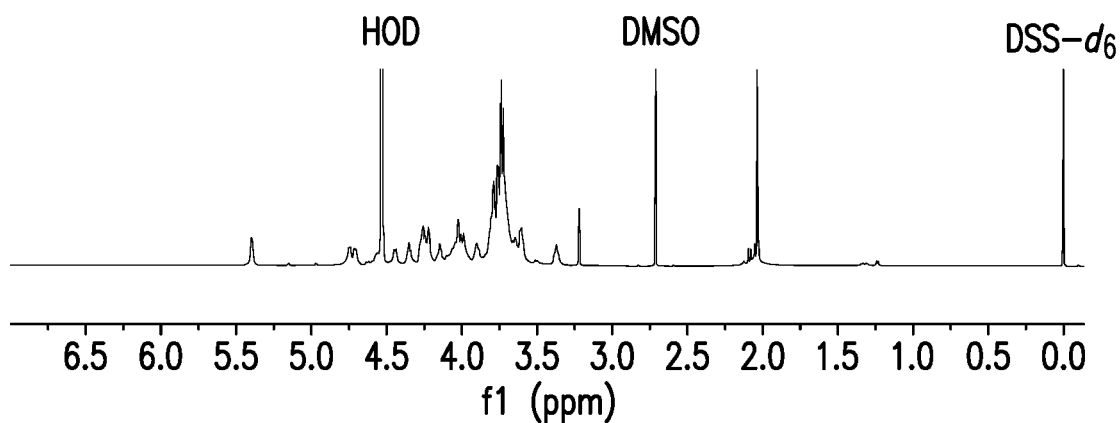
Figure 9C:
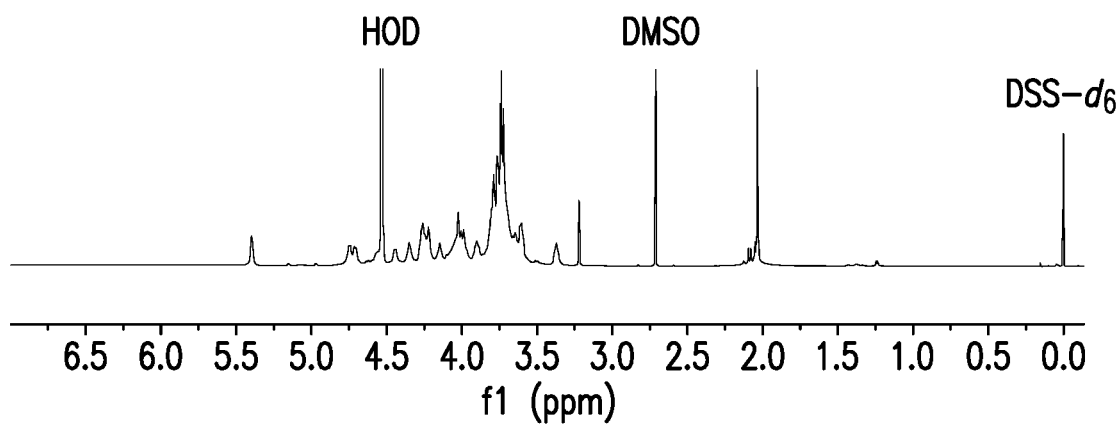
Figure 10A:
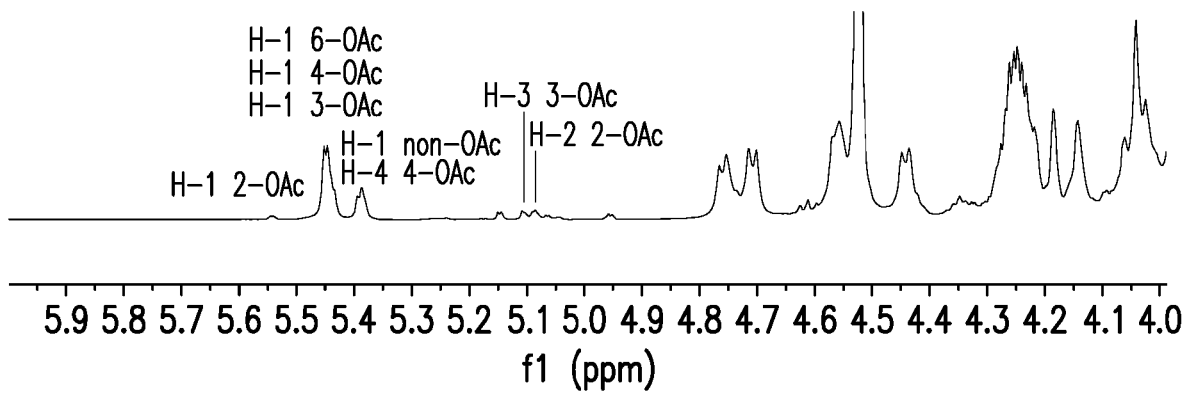
FIGS. 10A-10C show the anomeric region of the 600 MHz one-dimensional $^1$H NMR spectrum of native capsular polysaccharide from S. pneumonia serotype 15B (FIG. 10A), the de-O-acetylated capsular polysaccharide from S. pneumonia serotype 15B (FIG. 10B) and the capsular polysaccharide from S. pneumonia serotype 15C (FIG. 10C).
Figure 10B:
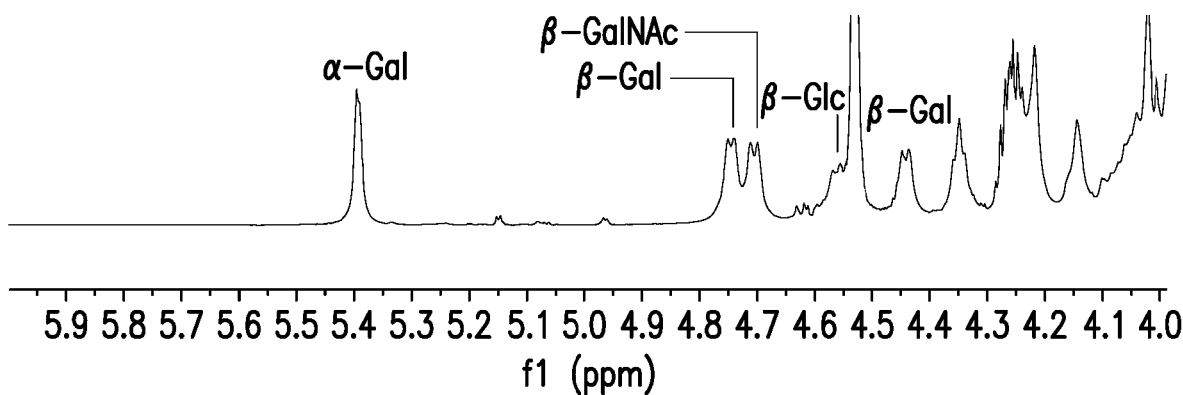
Figure 10C:
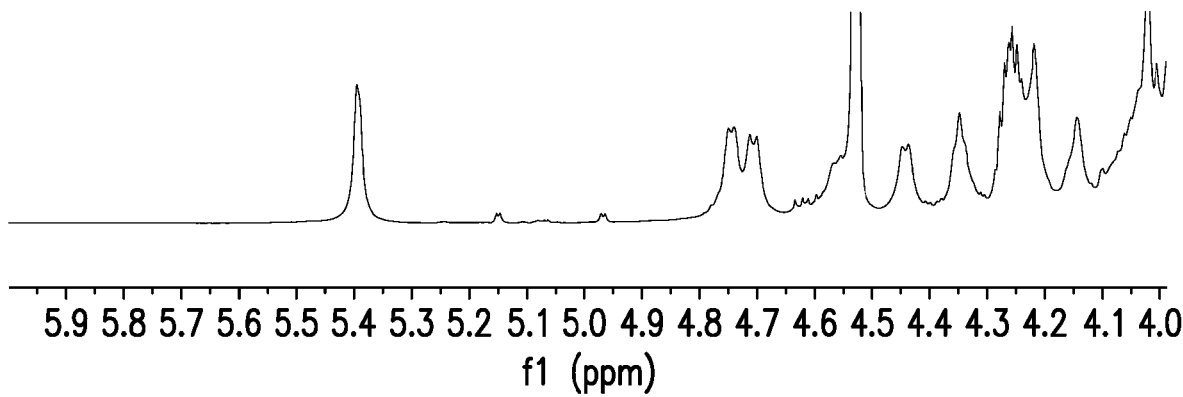
Figure 10D:
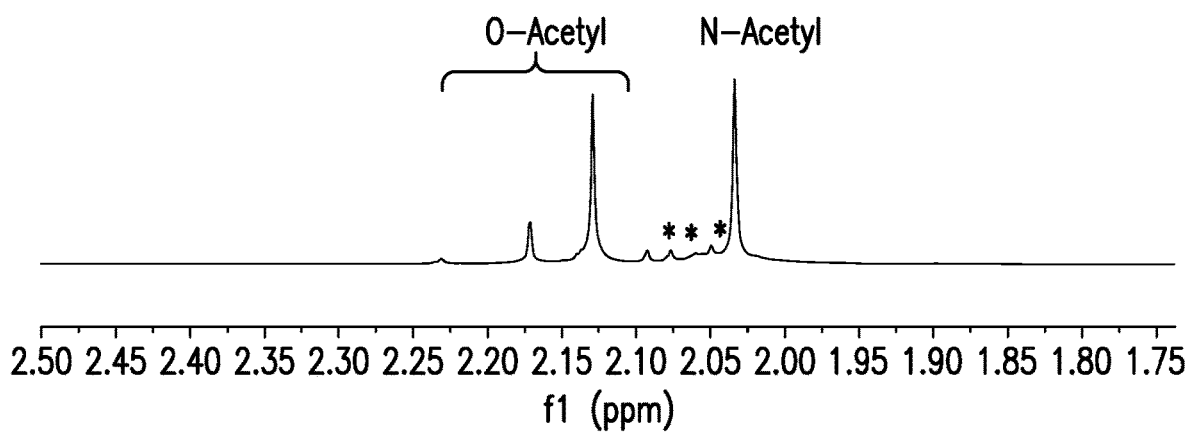
FIGS. 10D-10F show regions of the spectrum where the O-acetyl and N-acetyl methy signals of native capsular polysaccharide from S. pneumonia serotype 15B (FIG. 10D) the de-O-acetylated capsular polysaccharide from S. pneumonia serotype 15B (FIG. 10E) and the capsular polysaccharide from S. pneumonia serotype 15C (FIG. 10F).
Figure 10E:
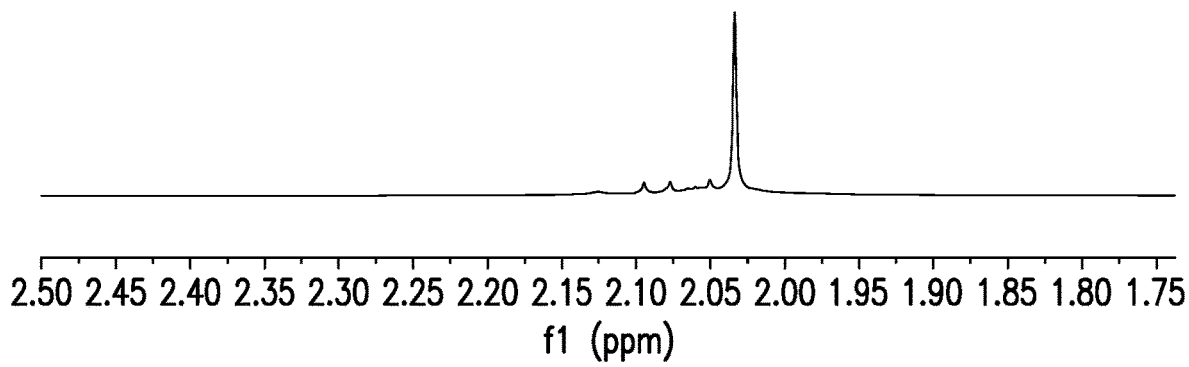
Figure 10F:
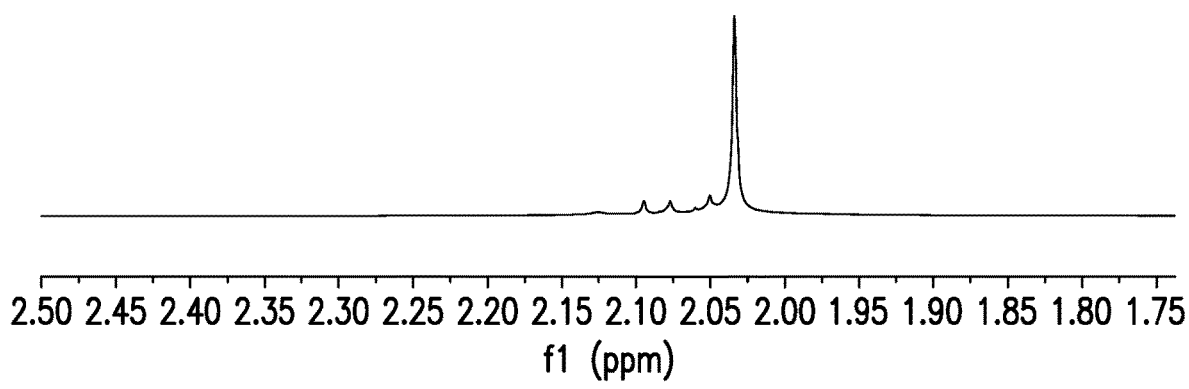

The present invention provides multivalent immunogenic compositions comprising pneumococcal polysaccharide-protein conjugates, wherein each of the conjugates comprises a polysaccharide from an *S. pneumoniae* serotype conjugated to a carrier protein, wherein the serotypes of *S. pneumoniae* are as defined herein. In some embodiments, the immunogenic composition comprises a set of pneomococcal serotypes selected from the group consisting of: (a) 15A, 16F, 23A, 23B, 24F, 31 and 35B; (b) 15A, 16F, 23A, 23B, 24F, 31, 35B, 8, 9N, 10A, 11A, 12F, 15C, 17F, and 20; and (c) 3, 7F, 19A, 22F, 33F, 15A, 16F, 23A, 23B, 24F, 31, 35B, 8, 9N, 10A, 11A, 12F, 15C, 17F, and 20. In some embodiments, the immunogenic composition comprises a set of pneomococcal serotypes selected from the group consisting of: (a) 15A, 16F, 23A, 23B, 24F, 31 and 35B; (b) 15A, 16F, 23A, 23B, 24F, 31, 35B, 8, 9N, 10A, 11A, 12F, 15C, 17F, and 20B; and (c) 3, 7F, 19A, 22F, 33F, 15A, 16F, 23A, 23B, 24F, 31, 35B, 8, 9N, 10A, 11A, 12F, 15C, 17F, and 20B. In other embodiments, the immunogenic composition comprises a set of pneomococcal serotypes selected from the group consisting of: (a) 15A, 16F, 23A, 23B, 24F, 31 and 35B; (b) 15A, 16F, 23A, 23B, 24F, 31, 35B, 8, 9N, 10A, 11A, 12F, 15C, 17F, and 20A; and (c) 3, 7F, 19A, 22F, 33F, 15A, 16F, 23A, 23B, 24F, 31, 35B, 8, 9N, 10A, 11A, 12F, 15C, 17F, and 20A. In further embodiments, the immunogenic composition comprises (i) serotype 6A; (ii) serotypes 6A and 6B; or (iii) serotype 6C. In a particular embodiment, the invention comprises multiple pneumococcal *S. pneumoniae* polysaccharide protein conjugates wherein each of the conjugates comprises a polysaccharide from an *S. pneumoniae* serotype conjugated to a carrier protein, wherein the serotypes of *S. pneumoniae* comprise serotypes 3, 6C, 7F, 8, 9N, 10A, 11A, 12F, 15A, 15C, 16F, 17F, 19A, 20A, 22F, 23A, 23B, 24F, 31, 33F and 35B. Said composition was found to be immunogenic in rabbits and generate functional antibody which killed vaccine-type bacterial strains at all doses tested (EXAMPLE 43). In another particular embodiment, the invention comprises multiple pneumococcal *S. pneumoniae* polysaccharide protein conjugates wherein each of the conjugates comprises a polysaccharide from an *S. pneumoniae* serotype conjugated to a carrier protein, wherein the serotypes of *S. pneumoniae* comprise serotypes 3, 7F, 19A, 22F, 33F, 8, 9N, 10A, 11A, 12F, 15C, 17F, 20, 6A, 15A, 15C, 16F, 23A, 23B, 24F, 31 and 35B. In another particular embodiment, the invention comprises multiple pneumococcal *S. pneumoniae* polysaccharide protein conjugates wherein each of the conjugates comprises a polysaccharide from an *S. pneumoniae* serotype conjugated to a carrier protein, wherein the serotypes of *S. pneumoniae* comprise serotypes 3, 7F, 19A, 22F, 33F, 8, 9N, 10A, 11A, 12F, 15C, 17F, 20B, 6A, 15A, 15C, 16F, 23A, 23B, 24F, 31 and 35B. In another particular embodiment, the invention comprises multiple pneumococcal *S. pneumoniae* polysaccharide protein conjugates wherein each of the conjugates comprises a polysaccharide from an *S. pneumoniae* serotype conjugated to a carrier protein, wherein the serotypes of *S. pneumoniae* comprise serotypes 3, 7F, 19A, 22F, 33F, 8, 9N, 10A, 11A, 12F, 15C, 17F, 20A, 6A, 15A, 15C, 16F, 23A, 23B, 24F, 31 and 35B.

The multivalent immunogenic compositions of the invention are useful for immunizing a patient against vaccine-type *S. pneumoniae* serotypes and as part of a treatment regimen with different, complementary pneumococcal vaccine(s). Accordingly, the invention provides a method of inducing a protective immune response in a human patient comprising administering a multivalent immunogenic composition of the invention to the patient, and further comprising administering a multivalent pneumococcal vaccine to the patient, in any order. In other embodiments, the multivalent immunogenic compositions of the invention are administered to a patient who had been previously immunized with a different multivalent pneumococcal vaccine.

In embodiments of the invention, conjugates from at least one pneumococcal serotype are prepared using reductive amination in an aprotic solvent such as DMSO. In further embodiments, the multivalent immunogenic composition comprises pneumococcal conjugates that were each prepared using reductive amination in an aprotic solvent. It is shown herein that PCV1, PCV7, PCV14, PCV16 and PCV21 (as defined, infra) drug products comprising drug substances that were each prepared using reductive amination in an aprotic solvent were stable against depolymerization or chemical degradation of the carbohydrate and stable against aggregation of the protein in the drug product formulation (see EXAMPLE 40 and EXAMPLE 45). The use of DMSO solvent enhances the covalent associations of polysaccharide to protein through direct consumption of lysine residues on the surface of the carrier protein. The increased covalent association has a direct benefit to increasing the stability of the polysaccharide protein conjugate of multivalent immunogenic compositions comprising polysaccharide antigens conjugated in DMSO.

I. Definitions and Abbreviations (1) As used throughout the specification and appended claims, the following abbreviations apply:

| | |
|---|---|
| APA | aluminum phosphate adjuvant |
| APC | antigen presenting cell |
| CI | confidence interval |
| DMSO | dimethylsulfoxide |
| DS | polysaccharide-protein Drug Substance |
| GMC | geometric mean concentraton |
| GMT | geometric mean titer |
| HPSEC | high performance size exclusion chromatography |
| IM | intra-muscular or intra-muscularly |
| LOS | lipo-oligosaccharide |
| LPS | lipopolysaccharide |
| MALS | multi-angle light scattering |
| MBC | monovalent bulk conjugate |
| MOPA | multiplexed opsonophagocytic assays |
| MW | molecular weight |
| NMWCO | nominal molecular weight cut off |
| NZWR | New Zealand White rabbit |
| OPA | opsonophagocytosis assay |
| PCV | pneumococcal conjugate vaccine |
| PD1 | post-dose 1 |
| PD2 | post-dose 2 |
| PnPs | Pneumoccal Polysaccharide |
| Ps | polysaccharide |
| PS-20 | polysorbate-20 |
| RI | refractive index |
| UV | ultraviolet |
| w/v | weight per volume |

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

(2) As used throughout the specification and in the appended claims, the singular forms "a," "an," and "the" include the plural reference unless the context clearly dictates otherwise.

(3) Reference to "or" indicates either or both possibilities unless the context clearly dictates one of the indicated possibilities. In some cases, "and/or" was employed to highlight either or both possibilities.

The terms "aqueous solvent" or "aqueous conditions" when used with conjugation, such as reductive amination, refers to use of water as the solvent for the conjugation reaction. The water may contain buffers and other components except that no organic solvent is present.

The terms "aprotic solvent", "DMSO solvent" or "DMSO conditions" when used with conjugation, such as reductive amination, refers to use of an aprotic solvent, or a combination of aprotic solvents, (or DMSO, as applicable) as the solvent for the conjugation reaction. The aprotic solvent may have some water present, for example, up to 1%, 2%, 5%, 10% or 20%.

The term "comprises" when used with the immunogenic composition of the invention refers to the inclusion of any other components, such as adjuvants and excipients, or the addition of one or more polysaccharide-protein conjugates that are not specifically enumerated. The term "consisting of" when used with the multivalent polysaccharide-protein conjugate mixture refers to a mixture having those particular S. pneumoniae polysaccharide protein conjugates and no other S. pneumoniae polysaccharide protein conjugates from a different serotype. "Consists essentially of" and variations such as "consist essentially of" or "consisting essentially of," indicate the inclusion of any recited elements or group of elements, and the optional inclusion of other elements, of similar or different nature than the recited elements, which do not materially change the basic or novel properties of the specified dosage regimen, method, or composition.

"Effective amount" of a composition of the invention refers to a dose required to elicit antibodies that significantly reduce the likelihood or severity of infectivitiy of a microbe, e.g., S. pneumonia, during a subsequent challenge.

As used herein, the phrase "indicated for the prevention of pneumococcal disease" means that a vaccine or immunogenic composition is approved by one or more regulatory authorities, such as the US Food and Drug Administration, for the prophylaxis of one or more diseases caused by any serotype of S. pneumoniae, including, but not limited to: pneumococcal disease generally, pneumococcal pneumonia, pneumococcal meningitis, pneumococcal bacteremia, invasive disease caused by S. pneumoniae, and otitis media caused by S. pneumoniae.

A "multivalent pneumococcal vaccine" is a pharmaceutical preparation comprising more than one active agent (e.g., pneumococcal capsular polysaccharide or pneumococcal polysaccharide protein conjugate) that provides active immunity to disease or pathological condition caused by more than one serotype of S. pneumoniae.

The term "polysaccharide" is meant to include any antigenic saccharide element (or antigenic unit) commonly used in the immunologic and bacterial vaccine arts, including, but not limited to, a "saccharide", an "oligosaccharide", a "polysaccharide", a "liposaccharide", a "lipo-oligosaccharide (LOS)", a "lipopolysaccharide (LPS)", a "glycosylate", a "glycoconjugate" and the like.

"PCV1," as used herein, refers to a 1-valent pneumococcal conjugate vaccine comprising one S. pneumoniae polysaccharide protein conjugate, comprising capsular polysaccharide from a S. pneumoniae serotype conjugated to a carrier protein, wherein the serotype of S. pneumoniae is 3 (as exemplified in Example 38 and 45). In specific embodiments, the carrier protein is CRM197.

"PCV7," as used herein, refers to a 7-valent pneumococcal conjugate vaccine comprising seven S. pneumoniae polysaccharide protein conjugates, each comprising capsular polysaccharides from a S. pneumoniae serotype conjugated to a carrier protein, wherein the serotypes of S.

*pneumoniae* are: 3, 8, 9N, 11A, 19A, 15A, and 10A. In specific embodiments, the carrier protein of one or more of the *S. pneumoniae* polysaccharide protein conjugates is CRM197. In further embodiments, the carrier protein of each of the *S. pneumoniae* polysaccharide protein conjugates is CRM197.

"PCV8," as used herein, refers to a 8-valent pneumococcal conjugate vaccine comprising eight *S. pneumoniae* polysaccharide protein conjugates, each comprising capsular polysaccharide from a *S. pneumoniae* serotype conjugated to a carrier protein, wherein the serotypes of *S. pneumoniae* are: 6C, 15A, 16F, 23A, 23B, 24F, 31, and 35B. In specific embodiments, the carrier protein of one or more of the *S. pneumoniae* polysaccharide protein conjugates is CRM197. In further embodiments, the carrier protein of each of the *S. pneumoniae* polysaccharide protein conjugates is CRM197.

"PCV14," as used herein, refers to a 14-valent pneumococcal conjugate vaccine comprising fourteen *S. pneumoniae* polysaccharide protein conjugates, each comprising capsular polysaccharides from a *S. pneumoniae* serotype conjugated to a carrier protein, wherein the serotypes of *S. pneumoniae* are: 3, 7F, 8, 9N, 10A, 11A, 12F, 15A, 16F, 17F, 19A, 20, 22F and 33F. In specific embodiments, the carrier protein of one or more of the *S. pneumoniae* polysaccharide protein conjugates is CRM197. In further embodiments, the carrier protein of each of the *S. pneumoniae* polysaccharide protein conjugates is CRM197.

"PCV15," as used herein, refers to a 15-valent pneumococcal conjugate vaccine comprising fifteen *S. pneumoniae* polysaccharide protein conjugates, each comprising capsular polysaccharides from a *S. pneumoniae* serotype conjugated to a carrier protein, wherein the serotypes of *S. pneumoniae* are: 1, 3, 4, 5, 6A, 6B, 7F, 9V, 14, 18C, 19A, 19F, 22F, 23F and 33F. In specific embodiments, the carrier protein of one or more of the *S. pneumoniae* polysaccharide protein conjugates is CRM197. In further embodiments, the carrier protein of each of the *S. pneumoniae* polysaccharide protein conjugates is CRM197.

"PCV16," as used herein, refers to a 16-valent pneumococcal conjugate vaccine comprising sixteen *S. pneumoniae* polysaccharide protein conjugates, each comprising capsular polysaccharide from a *S. pneumoniae* serotype conjugated to a carrier protein, wherein the serotypes of *S. pneumoniae* are: 6C, 8, 9N, 10A, 11A, 12F, 15A, 16F, 17F, 20A, 23A, 23B, 24F, 31, and 35B, and at least one of the following serogroup 15 serotypes: 15B, 15C, or de-O-acetylated-15B. In particular embodiments, the serogroup 15 serotype is serotype 15C or de-O-acetylated 15B. As shown herein (see EXAMPLE 3, infra), de-O-Acetyated serotype 15B pneumococcal polysaccharide is equivalent to serotype 15C pneumococcal polysaccharide and has an identical NMR spectra. In specific embodiments, the carrier protein of one or more of the *S. pneumoniae* polysaccharide protein conjugates is CRM197. In further embodiments, the carrier protein of each of the *S. pneumoniae* polysaccharide protein conjugates is CRM197.

"PCV21," as used herein, refers to a 21-valent pneumococcal conjugate vaccine comprising twenty-one *S. pneumoniae* polysaccharide protein conjugates, each comprising capsular polysaccharide from a *S. pneumoniae* serotype conjugated to a carrier protein, wherein the serotypes of *S. pneumoniae* are: 3, 6C, 7F, 8, 9N, 10A, 11A, 12F, 15A, 16F, 17F, 19A, 20, 22F, 23A, 23B, 24F, 31, 33F and 35B, and at least one of the following serogroup 15 serotypes: 15B, 15C or de-O-acetylated-15B. In particular embodiments, the serogroup 15 serotype is serotype 15C or de-O-acetylated 15B. In specific embodiments, the carrier protein of one or more of the *S. pneumoniae* polysaccharide protein conjugates is CRM197. In further embodiments, the carrier protein of each of the *S. pneumoniae* polysaccharide protein conjugates is CRM197.

*S. pneumoniae* serotypes 20A and 20B were identified (Calix, J. J. et al., J. Biol. Chem. (2012) 287(33): 27885-27894) within serogroup 20 in 2012 through genetic analysis. As discussed by Calix J. J., et al., conventional serotyping methods and commercially available antibodies were not able to distinguish these two serotypes previously and there is limited information today regarding serotyping efforts for serotypes 20A and 20B. Further, the disease prevalence of 20A or 20B within an identified disease caused by serogroup 20 is not well understood. As such, one of ordinary skill in the art might elect to include either or both of these two serotypes (20A and/or 20B) in a *S. pneumoniae* vaccine composition. It is also possible that a *S. pneumoniae* vaccine containing one serotype 20 polysaccharide antigen might cross protect against another (e.g., a vaccine including polysaccharide protein conjugates of *S. pneumoniae* serotype 20A, and not serotype 20B, may cross protect against infection with *S. pneumoniae* serotype 20B). Therefore, "serotype 20" as used herein may refer to a composition containing polysaccharide protein conjugates of serotype 20A and/or serotype 20B.

"CpG-containing nucleotide," "CpG-containing oligonucleotide," "CpG oligonucleotide," and similar terms refer to a nucleotide molecule of 6-50 nucleotides in length that contains an unmethylated CpG moiety. See, e.g., Wang et al., 2003, Vaccine 21:4297. CpG-containing oligonucleotides include modified oligonucleotides using any synthetic internucleoside linkages, modified base and/or modified sugar.

An "adjuvant," as defined herein, is a substance that serves to enhance the immunogenicity of an immunogenic composition of the invention. An immune adjuvant may enhance an immune response to an antigen that is weakly immunogenic when administered alone, e.g., inducing no or weak antibody titers or cell-mediated immune response, increase antibody titers to the antigen, and/or lowers the dose of the antigen effective to achieve an immune response in the individual. Thus, adjuvants are often given to boost the immune response and are well known to the skilled artisan.

A "patient" (alternatively referred to herein as a "subject") refers to a mammal capable of being infected with a *S. pneumoniae*. In preferred embodiments, the patient is a human. A patient can be treated prophylactically or therapeutically. Prophylactic treatment provides sufficient protective immunity to reduce the likelihood or severity of a pneomococcal infection or the effects thereof, e.g., pneumococcal pneumonia. Therapeutic treatment can be performed to reduce the severity or prevent recurrence of a *S. pneumoniae* infection or the clinical effects thereof. Prophylactic treatment can be performed using a multivalent immunogenic composition of the invention, as described herein. The composition of the invention can be administered to the general population or to those persons at an increased risk of pneumococcal infection, e.g. the elderly, or those who live with or care for the elderly.

Those "in need of treatment" include those previously exposed to or infected with *S. pneumoniae*, those who were previously vaccinated against *S. pneumoniae*, as well as those prone to have an infection or any person in which a reduction in the likelihood of infection is desired, e.g., the immunocompromised, the elderly, children, adults, or healthy individuals.

A "stable" multivalent immunogenic composition is a composition which has no significant changes observed at a refrigerated temperature (e.g., 2-8° C. or 4° C.) for at least 1 month, 2 months, 3 months, 6 months, 12 months and/or 24 months. Additionally, a "stable" composition includes one that exhibits desired features at temperatures including at 25° C. and 37° C. for periods including 1 month, 3 months, 6 months, 12 months, and/or 24 months. Typical acceptable criteria for stability are as follows: no more than about 5%, about 10%, about 15%, or about 20% variability in one or more of the following: (a) the number average molecular weight (Mn) of the S. pneumoniae polysaccharide protein conjugates in the composition, (b) weight average molecular weight (Mw) of the S. pneumoniae polysaccharide protein conjugates in the composition, (c) total polysaccharide concentration in the composition, (d) emission maximum of the composition measured using intrinsic protein fluorescence spectroscopy at a particular excitation wavelength, e.g. 280 nanometers, and (e) the fluorescence intensity of the composition measured using intrinsic protein fluorescence spectroscopy at a particular excitation wavelength. The term "stable" may also be used to refer to a particular pneumococcal conjugate within a multivalent immunogenic composition. In such use, the term refers to a conjugate that exhibits the desired properties over time, at a particular temperature, and such properties vary no more that about 5%, about 10%, about 15%, or about 20% over the time and temperature noted.

II. Multivalent Immunogenic Compositions

The invention provides multivalent immunogenic compositions comprising multiple S. pneumoniae polysaccharide protein conjugates wherein each of the conjugates comprises a polysaccharide from an S. pneumoniae serotype conjugated to a carrier protein. Different aspects and embodiments of the multivalent immunogenic compositions of the invention are described, infra.

In one embodiment (Embodiment E1), the invention provides a multivalent immunogenic composition comprising multiple S. pneumoniae polysaccharide protein conjugates, each comprising capsular polysaccharide from an S. pneumoniae serotype conjugated to a carrier protein, wherein the serotypes of S. pneumoniae comprise, consist, or consist essentially of:
(1) 15A
(2) 16F,
(3) one or more serogroup 23 serotypes selected from: (a) 23A and 23B, (b) 23A and 23F, (c) 23B and 23F, (d) 23A, (e) 23B, and (f) 23F,
(4) 24F,
(5) 31, and
(6) 35B.

In a sub-embodiment of Embodiment E1, the one or more serogroup 23 serotypes are 23A and 23B (i.e. and no other serogroup 23 serotypes are present). In a further sub-embodiment of Embodiment E1, the one or more serogroup 23 serotypes are 23A and 23F. In another sub-embodiment of Embodiment E1, the one or more serogroup 23 serotypes are 23B and 23F. In yet another sub-embodiment of Embodiment E1, 23A is the only serogroup 23 serotype. In a further sub-embodiment of Embodiment E1, 23B is the only serogroup 23 serotype. In a still further sub-embodiment of Embodiment E1, 23F is the only serogroup 23 serotype.

In a second embodiment (Embodiment E2), the invention provides a multivalent immunogenic composition comprising multiple S. pneumoniae polysaccharide protein conjugates comprising capsular polysaccharide from a S. pneumoniae serotype conjugated to a carrier protein, wherein the serotypes of S. pneumoniae comprise the serotypes set forth in Embodiment E1, or any sub-embodiment of Embodiment E1, and further comprise serotype: (1) 6C, (2) 6A, or (3) 6A and 6B.

In a sub-embodiment of Embodiment E2, the composition comprises serotype 6C. In a further sub-embodiment of Embodiment E2, the composition comprises serotypes 6A and 6B and does not comprise serotype 6C. In a another sub-embodiment of Embodiment E2, the composition comprises serotype 6A.

In a third embodiment (Embodiment E3), the invention provides a multivalent immunogenic composition comprising multiple S. pneumoniae polysaccharide protein conjugates comprising capsular polysaccharide from a S. pneumoniae serotype conjugated to a carrier protein, wherein the serotypes of S. pneumoniae comprise the serotypes set forth in Embodiments E1, or any sub-embodiments of Embodiment E1, or Embodiment E2, or any sub-embodiment of Embodiment E2, and further comprise serotypes:
(1) 8,
(2) 9N,
(3) 11A,
(4) 12F,
(5) 15B or 15C,
(6) 17F, and
(7) 20A and/or 20B.

In a fourth embodiment (Embodiment E4), the invention provides a multivalent immunogenic composition comprising multiple S. pneumoniae polysaccharide protein conjugates comprising capsular polysaccharide from a S. pneumoniae serotype conjugated to a carrier protein, wherein the serotypes of S. pneumoniae comprise the serotypes set forth in any of Embodiments E1-E3, or any sub-embodiments thereof, and further comprise serotypes: 10A or 39.

In a fifth embodiment (Embodiment E5), the invention provides a multivalent immunogenic composition comprising multiple S. pneumoniae polysaccharide protein conjugates as described above, wherein the S. pneumoniae serotypes comprise, consist, or consist essentially of: 8, 9N, 10A, 11A, 12F, 15C, 17F, 20A, 6C, 15A, 16F, 23A, 23B, 24F, 31, and 35B.

In a sixth embodiment (Embodiment E6), the invention provides a multivalent immunogenic composition comprising multiple S. pneumoniae polysaccharide protein conjugates as described above, wherein the S. pneumoniae serotypes comprise, consist, or consist essentially of: 8, 9N, 39, 11A, 12F, 15C, 17F, 20A, 6C, 15A, 16F, 23A, 23B, 24F, 31, and 35B.

In a seventh embodiment (Embodiment E7), the invention provides a multivalent immunogenic composition comprising multiple S. pneumoniae polysaccharide protein conjugates as described above, wherein the S. pneumoniae serotypes comprise, consist, or consist essentially of: 8, 9N, 10A, 11A, 12F, 15B, 17F, 20A, 6C, 15A, 16F, 23A, 23B, 24F, 31, and 35B.

In an eighth embodiment (Embodiment E8), the invention provides a multivalent immunogenic composition comprising multiple S. pneumoniae polysaccharide protein conjugates as described above, wherein the S. pneumoniae serotypes comprise, consist, or consist essentially of: 8, 9N, 39, 11A, 12F, 15B, 17F, 20A, 6C, 15A, 16F, 23A, 23B, 24F, 31, and 35B.

In a ninth embodiment (Embodiment E9), the invention provides a multivalent immunogenic composition comprising multiple S. pneumoniae polysaccharide protein conjugates as described above, wherein the *S. pneumoniae* serotypes comprise the serotypes set forth in any of Embodiments E1-E8 (or any sub-embodiment thereof), and further comprise serotypes: 3, 7F, and 19A.

In a tenth embodiment (Embodiment E10), the invention provides a multivalent immunogenic composition comprising multiple *S. pneumoniae* polysaccharide protein conjugates as described above, wherein the *S. pneumoniae* serotypes comprise the serotypes set forth in any of Embodiments E1-E9 (or any sub-embodiment thereof), and further comprise serotype 22F.

In an eleventh embodiment (Embodiment E11), the invention provides a multivalent immunogenic composition comprising multiple *S. pneumoniae* polysaccharide protein conjugates as described above, wherein the *S. pneumoniae* serotypes comprise the serotypes set forth in any of Embodiments E1-E10 (or any sub-embodiment thereof), and further comprise serotype 33F.

In a twelfth embodiment (Embodiment E12), the invention provides a multivalent immunogenic composition comprising multiple *S. pneumoniae* polysaccharide protein conjugates as described above, wherein the *S. pneumoniae* serotypes comprise, consist, or consist essentially of a set of *S. pneumoniae* serotypes selected from the group consisting of:
(1) 15A, 16F, 23A, 23B, 24F, 31, and 35B,
(2) 15A, 16F, 23F, 23B, 24F, 31, and 35B,
(3) 15A, 16F, 23A, 23F, 24F, 31, and 35B,
(4) 15A, 16F, 23A, 24F, 31, and 35B,
(5) 15A, 16F, 23B, 24F, 31, and 35B,
(6) 15A, 16F, 23F, 24F, 31, and 35B,
(7) 6C, 15A, 16F, 23A, 23B, 24F, 31, and 35B,
(8) 6C, 15A, 16F, 23F, 23B, 24F, 31, and 35B,
(9) 6C, 15A, 16F, 23A, 23F, 24F, 31, and 35B,
(10) 6C, 15A, 16F, 23A, 24F, 31, and 35B,
(11) 6C, 15A, 16F, 23B, 24F, 31, and 35B,
(12) 6C, 15A, 16F, 23F, 24F, 31, and 35B,
(13) 6A, 15A, 16F, 23A, 23B, 24F, 31, and 35B,
(14) 6A, 15A, 16F, 23F, 23B, 24F, 31, and 35B,
(15) 6A, 15A, 16F, 23A, 23F, 24F, 31, and 35B,
(16) 6A, 15A, 16F, 23A, 24F, 31, and 35B,
(17) 6A, 15A, 16F, 23B, 24F, 31, and 35B,
(18) 6A, 15A, 16F, 23F, 24F, 31, and 35B,
(19) 6A, 6B, 15A, 16F, 23A, 23B, 24F, 31, and 35B,
(20) 6A, 6B, 15A, 16F, 23F, 23B, 24F, 31, and 35B,
(21) 6A, 6B, 15A, 16F, 23A, 23F, 24F, 31, and 35B,
(22) 6A, 6B, 15A, 16F, 23A, 24F, 31, and 35B,
(23) 6A, 6B, 15A, 16F, 23B, 24F, 31, and 35B, and
(24) 6A, 6B, 15A, 16F, 23F, 24F, 31, and 35B.

In a thirteenth embodiment (Embodiment E13), the invention provides a multivalent immunogenic composition comprising multiple *S. pneumoniae* polysaccharide protein conjugates as described above, wherein the *S. pneumoniae* serotypes comprise, consist, or consist essentially of a set of *S. pneumoniae* serotypes selected from the group consisting of:
(1) 8, 9N, 10A, 11A, 12F, 15C, 17F, 20A, 6C, 15A, 16F, 23A, 23B, 24F, 31 and 35B,
(2) 8, 9N, 39, 11A, 12F, 15C, 17F, 20A, 6C, 15A, 16F, 23A, 23B, 24F, 31 and 35B,
(3) 8, 9N, 10A 11A 12F, 15B, 17F, 20A, 6C, 15A 16F, 23A, 23B, 24F, 31 and 35B,
(4) 8, 9N, 39, 11A, 12F, 15B, 17F, 20A, 6C, 15A, 16F, 23A, 23B, 24F, 31 and 35B,
(5) 8, 9N, 10A, 11A, 12F, 15C, 17F, 20A, 15A, 16F, 23A, 23B, 24F, 31 and 35B,
(6) 8, 9N, 10A, 11A, 12F, 15C, 17F, 20A, 6A, 6B, 15A, 16F, 23A, 23B, 24F, 31 and 35B,
(7) 8, 9N, 10A, 11A, 12F, 15C, 17F, 20A, 6A, 15A, 16F, 23A, 23B, 24F, 31 and 35B,
(8) 8, 9N, 39, 11A, 12F, 15C, 17F, 20A, 15A, 16F, 23A, 23B, 24F, 31 and 35B,
(9) 8, 9N, 39, 11A, 12F, 15C, 17F, 20A, 6A, 6B, 15A, 16F, 23A, 23B, 24F, 31 and 35B,
(10) 8, 9N, 39, 11A 12F, 15C, 17F, 20A, 6A, 15A 16F, 23A, 23B, 24F, 31 and 35B,
(11) 8, 9N, 10A, 11A, 12F, 15B, 17F, 20A, 15A, 16F, 23A, 23B, 24F, 31 and 35B,
(12) 8, 9N, 10A, 11A, 12F, 15B, 17F, 20A, 6A, 6B, 15A, 16F, 23A, 23B, 24F, 31 and 35B,
(13) 8, 9N, 10A, 11A, 12F, 15B, 17F, 20A, 6A, 15A, 16F, 23A, 23B, 24F, 31 and 35B,
(14) 8, 9N, 39, 11A, 12F, 15B, 17F, 20A, 15A, 16F, 23A, 23B, 24F, 31 and 35B,
(15) 8, 9N, 39, 11A, 12F, 15B, 17F, 20A, 6A, 6B, 15A, 16F, 23A, 23B, 24F, 31 and 35B,
(16) 8, 9N, 39, 11A, 12F, 15B, 17F, 20A, 6A, 15A, 16F, 23A, 23B, 24F, 31 and 35B,
(17) 8, 9N, 10A, 11A, 12F, 15C, 17F, 20A, 6C, 15A, 16F, 23F, 24F, 31 and 35B,
(18) 8, 9N, 39, 11A, 12F, 15C, 17F, 20A, 6C, 15A, 16F, 23F, 24F, 31 and 35B,
(19) 8, 9N, 10A, 11A, 12F, 15B, 17F, 20A, 6C, 15A, 16F, 23F, 24F, 31 and 35B,
(20) 8, 9N, 39, 11A, 12F, 15B, 17F, 20A, 6C, 15A, 16F, 23F, 24F, 31 and 35B,
(21) 8, 9N, 10A, 11A, 12F, 15C, 17F, 20A, 15A, 16F, 23F, 24F, 31 and 35B,
(22) 8, 9N, 10A, 11A, 12F, 15C, 17F, 20A, 6A, 6B, 15A, 16F, 23F, 24F, 31 and 35B,
(23) 8, 9N, 10A, 11A, 12F, 15C, 17F, 20A, 6A, 15A, 16F, 23F, 24F, 31 and 35B,
(24) 8, 9N, 39, 11A, 12F, 15C, 17F, 20A, 15A, 16F, 23F, 24F, 31 and 35B,
(25) 8, 9N, 39, 11A, 12F, 15C, 17F, 20A, 6A, 6B, 15A, 16F, 23F, 24F, 31 and 35B,
(26) 8, 9N, 39, 11A, 12F, 15C, 17F, 20A, 6A, 15A, 16F, 23F, 24F, 31 and 35B,
(27) 8, 9N, 10A, 11A, 12F, 15B, 17F, 20A, 15A, 16F, 23F, 24F, 31 and 35B,
(28) 8, 9N, 10A, 11A, 12F, 15B, 17F, 20A, 6A, 6B, 15A, 16F, 23F, 24F, 31 and 35B,
(29) 8, 9N, 10A, 11A, 12F, 15B, 17F, 20A, 6A, 15A, 16F, 23F, 24F, 31 and 35B,
(30) 8, 9N, 39, 11A, 12F, 15B, 17F, 20A, 15A, 16F, 23F, 24F, 31 and 35B,
(31) 8, 9N, 39, 11A, 12F, 15B, 17F, 20A, 6A, 6B, 15A, 16F, 23F, 24F, 31 and 35B, and
(32) 8, 9N, 39, 11A, 12F, 15B, 17F, 20A, 6A, 15A, 16F, 23F, 24F, 31 and 35B.

The thirteenth embodiment (Embodiment E13), further comprises the set of *S. pneumoniae* serotypes, rows (1) through (32) wherein serotype 20A in each set is substituted with either serotype 20 or serotype 20B.

In a fourteenth embodiment of the invention, (Embodiment E14), the invention provides a multivalent immunogenic composition comprising multiple *S. pneumoniae* polysaccharide protein conjugates as described above, wherein the *S. pneumoniae* serotypes comprise, consist, or consist essentially of a set of *S. pneumoniae* serotypes selected from any of the sets of serotypes set forth in Embodiment E13, rows (17) through (32), and further comprise serotypes 23A and/or 23B.

In a fifteenth embodiment (Embodiment E15), the invention provides a multivalent immunogenic composition comprising multiple S. pneumoniae polysaccharide protein conjugates as described above, wherein the S. pneumoniae serotypes comprise, consist, or consist essentially of a set of S. pneumoniae serotypes selected from the group consisting of:

(1) 3, 7F, 19A, 22F, 33F, 8, 9N, 10A, 11A, 12F, 15C, 17F, 20A, 6C, 15A, 16F, 23A, 23B, 24F, 31 and 35B,
(2) 3, 7F, 19A, 22F, 33F, 8, 9N, 39, 11A 12F, 15C, 17F, 20A, 6C, 15A 16F, 23A, 23B, 24F, 31 and 35B,
(3) 3, 7F, 19A, 22F, 33F, 8, 9N, 10A, 11A, 12F, 15B, 17F, 20A, 6C, 15A, 16F, 23A, 23B, 24F, 31 and 35B,
(4) 3, 7F, 19A, 22F, 33F, 8, 9N, 39, 11A, 12F, 15B, 17F, 20A, 6C, 15A, 16F, 23A, 23B, 24F, 31 and 35B,
(5) 3, 7F, 19A, 22F, 33F, 8, 9N, 10A, 11A, 12F, 15C, 17F, 20A 15A, 16F, 23A, 23B, 24F, 31 and 35B,
(6) 3, 7F, 19A, 22F, 33F, 8, 9N, 10A, 11A, 12F, 15C, 17F, 20A, 6A, 6B, 15A, 16F, 23A, 23B, 24F, 31 and 35B,
(7) 3, 7F, 19A, 22F, 33F, 8, 9N, 10A, 11A, 12F, 15C, 17F, 20A, 6A, 15A, 16F, 23A, 23B, 24F, 31 and 35B,
(8) 3, 7F, 19A, 22F, 33F, 8, 9N, 39, 11A, 12F, 15C, 17F, 20A 15A, 16F, 23A, 23B, 24F, 31 and 35B,
(9) 3, 7F, 19A, 22F, 33F, 8, 9N, 39, 11A 12F, 15C, 17F, 20A, 6A, 6B, 15A, 16F, 23A, 23B, 24F, 31 and 35B,
(10) 3, 7F, 19A, 22F, 33F, 8, 9N, 39, 11A, 12F, 15C, 17F, 20A, 6A, 15A, 16F, 23A, 23B, 24F, 31 and 35B,
(11) 3, 7F, 19A, 22F, 33F, 8, 9N, 10A, 11A, 12F, 15B, 17F, 20A 15A, 16F, 23A, 23B, 24F, 31 and 35B,
(12) 3, 7F, 19A, 22F, 33F, 8, 9N, 10A, 11A, 12F, 15B, 17F, 20A, 6A, 6B, 15A, 16F, 23A, 23B, 24F, 31 and 35B,
(13) 3, 7F, 19A, 22F, 33F, 8, 9N, 10A, 11A, 12F, 15B, 17F, 20A, 6A, 15A, 16F, 23A, 23B, 24F, 31 and 35B,
(14) 3, 7F, 19A, 22F, 33F, 8, 9N, 39, 11A, 12F, 15B, 17F, 20A 15A, 16F, 23A, 23B, 24F, 31 and 35B,
(15) 3, 7F, 19A, 22F, 33F, 8, 9N, 39, 11A, 12F, 15B, 17F, 20A, 6A, 6B, 15A, 16F, 23A, 23B, 24F, 31 and 35B,
(16) 3, 7F, 19A, 22F, 33F, 8, 9N, 39, 11A, 12F, 15B, 17F, 20A, 6A, 15A, 16F, 23A, 23B, 24F, 31 and 35B,
(17) 3, 7F, 19A, 22F, 33F, 8, 9N, 10A, 11A, 12F, 15C, 17F, 20A, 6C, 15A, 16F, 23F, 24F, 31 and 35B,
(18) 3, 7F, 19A, 22F, 33F, 8, 9N, 39, 11A, 12F, 15C, 17F, 20A, 6C, 15A, 16F, 23F, 24F, 31 and 35B,
(19) 3, 7F, 19A, 22F, 33F, 8, 9N, 10A 11A, 12F, 15B, 17F, 20A, 6C, 15A, 16F, 23F, 24F, 31 and 35B,
(20) 3, 7F, 19A, 22F, 33F, 8, 9N, 39, 11A, 12F, 15B, 17F, 20A, 6C, 15A, 16F, 23F, 24F, 31 and 35B,
(21) 3, 7F, 19A, 22F, 33F, 8, 9N, 10A, 11A, 12F, 15C, 17F, 20A, 15A, 16F, 23F, 24F, 31 and 35B,
(22) 3, 7F, 19A, 22F, 33F, 8, 9N, 10A, 11A, 12F, 15C, 17F, 20A, 6A, 6B, 15A, 16F, 23F, 24F, 31 and 35B,
(23) 3, 7F, 19A, 22F, 33F, 8, 9N, 10A, 11A, 12F, 15C, 17F, 20A, 6A, 15A, 16F, 23F, 24F, 31 and 35B,
(24) 3, 7F, 19A, 22F, 33F, 8, 9N, 39, 11A, 12F, 15C, 17F, 20A, 15A, 16F, 23F, 24F, 31 and 35B,
(25) 3, 7F, 19A, 22F, 33F, 8, 9N, 39, 11A, 12F, 15C, 17F, 20A, 6A, 6B, 15A, 16F, 23F, 24F, 31 and 35B,
(26) 3, 7F, 19A, 22F, 33F, 8, 9N, 39, 11A 12F, 15C, 17F, 20A, 6A, 15A 16F, 23F, 24F, 31 and 35B,
(27) 3, 7F, 19A, 22F, 33F, 8, 9N, 10A, 11A, 12F, 15B, 17F, 20A, 15A, 16F, 23F, 24F, 31 and 35B,
(28) 3, 7F, 19A, 22F, 33F, 8, 9N, 10A, 11A, 12F, 15B, 17F, 20A, 6A, 6B, 15A, 16F, 23F, 24F, 31 and 35B,
(29) 3, 7F, 19A, 22F, 33F, 8, 9N, 10A, 11A, 12F, 15B, 17F, 20A, 6A, 15A, 16F, 23F, 24F, 31 and 35B,
(30) 3, 7F, 19A, 22F, 33F, 8, 9N, 39, 11A, 12F, 15B, 17F, 20A, 15A, 16F, 23F, 24F, 31 and 35B,
(31) 3, 7F, 19A, 22F, 33F, 8, 9N, 39, 11A, 12F, 15B, 17F, 20A, 6A, 6B, 15A, 16F, 23F, 24F, 31 and 35B,
(32) 3, 7F, 19A, 22F, 33F, 8, 9N, 39, 11A, 12F, 15B, 17F, 20A, 6A, 15A, 16F, 23F, 24F, 31 and 35B,
(33) 3, 7F, 19A, 22F, 33F, 6C, 15A, 16F, 23A, 23B, 24F, 31, 35B, 8, 9N, 10A, 11A, 12F, 15C, 17F, and 20B,
(34) 3, 7F, 19A, 22F, 33F, 6C, 15A, 16F, 23A, 23B, 24B, 31, 35B, 8, 9N, 10A, 11A, 12F, 15C, 17F, and 20A,
(35) 3, 7F, 19A, 22F, 33F, 6C, 15A, 16F, 23A, 23B, 24B, 31, 35B, 8, 9N, 10A, 11A, 12F, 15C, 17F, and 20B,
(36) 3, 7F, 19A, 22F, 33F, 6A, 15A, 16F, 23A, 23B, 24F, 31, 35B, 8, 9N, 10A, 11A, 12F, 15C, 17F, and 20B,
(37) 3, 7F, 19A, 22F, 33F, 6A, 15A, 16F, 23A, 23B, 24B, 31, 35B, 8, 9N, 10A, 11A, 12F, 15C, 17F, and 20A,
(38) 3, 7F, 19A, 22F, 33F, 6A, 15A, 16F, 23A, 23B, 24B, 31, 35B, 8, 9N, 10A, 11A, 12F, 15C, 17F, and 20B,
(39) 3, 7F, 19A, 22F, 33F, 6C, 15A, 16F, 23A, 23B, 24F, 31, 35B, 8, 9N, 10A, 11A, 12F, 15C, 17F, and 20,
(40) 3, 7F, 19A, 22F, 33F, 6C, 15A, 16F, 23A, 23B, 24B, 31, 35B, 8, 9N, 10A, 11A, 12F, 15C, 17F, and 20,
(41) 3, 7F, 19A, 22F, 33F, 6C, 15A, 16F, 23A, 23B, 24B, 31, 35B, 8, 9N, 10A, 11A, 12F, 15C, 17F, and 20,
(42) 3, 7F, 19A, 22F, 33F, 6A, 15A, 16F, 23A, 23B, 24F, 31, 35B, 8, 9N, 10A, 11A, 12F, 15C, 17F, and 20,
(43) 3, 7F, 19A, 22F, 33F, 6A, 15A, 16F, 23A, 23B, 24B, 31, 35B, 8, 9N, 10A, 11A, 12F, 15C, 17F, and 20, and
(44) 3, 7F, 19A, 22F, 33F, 6A, 15A, 16F, 23A, 23B, 24B, 31, 35B, 8, 9N, 10A, 11A, 12F, 15C, 17F, and 20.

In a sixteenth embodiment of the invention, (Embodiment E16), the invention provides a multivalent immunogenic composition comprising multiple S. pneumoniae polysaccharide protein conjugates as described above, wherein the S. pneumoniae serotypes comprise, consist, or consist essentially of a set of S. pneumoniae serotypes selected from any of the sets of serotypes set forth in Embodiment E15, rows (17) through (32), and further comprise serotypes 23A and/or 23B.

In a seventeenth embodiment (Embodiment E17), the invention provides a multivalent immunogenic composition comprising multiple S. pneumoniae polysaccharide protein conjugates comprising capsular polysaccharide from a S. pneumoniae serotype conjugated to a carrier protein, wherein the serotypes of S. pneumoniae comprise a set of serotypes selected from the group consisting of:
  i. 6C, 15A, 16F, 23A, 23B, 24F, 31 and 35B,
  ii. 6C, 15A, 16F, 23A, 23B, 24F, 31, 35B, 8, 9N, 10A, 11A, 12F, 15C, 17F, and 20A, and
  iii. 3, 7F, 19A, 22F, 33F, 6C, 15A, 16F, 23A, 23B, 24F, 31, 35B, 8, 9N, 10A, 11A, 12F, 15C, 17F, and 20A;

In sub-embodiments of Embodiment E17, the immunogenic composition does not comprise any further S. pneumoniae polysaccharide protein conjugates.

In an eighteenth embodiment (Embodiment E18), the invention provides a multivalent immunogenic composition comprising multiple S. pneumoniae polysaccharide protein conjugates comprising capsular polysaccharide from a S. pneumoniae serotypes 6C, 15A, 16F, 23A, 23B, 24F, 31 and 35B. In sub-embodiments of Embodiment E18, the immunogenic composition does not comprise any further S. pneumoniae polysaccharide protein conjugates.

In a nineteenth embodiment (Embodiment E19), the invention provides a multivalent immunogenic composition comprising multiple S. pneumoniae polysaccharide protein conjugates comprising capsular polysaccharide from a S. pneumoniae serotypes 6C, 15A, 16F, 23A, 23B, 24F, 31, 35B, 8, 9N, 10A, 11A, 12F, 15C, 17F, and 20A. In sub-embodiments of Embodiment E19, the immunogenic composition does not comprise any further *S. pneumoniae* polysaccharide protein conjugates.

In a twentieth embodiment (Embodiment E20), the invention provides a multivalent immunogenic composition comprising multiple *S. pneumoniae* polysaccharide protein conjugates comprising capsular polysaccharide from a *S. pneumoniae* serotypes 3, 7F, 19A, 22F, 33F, 6C, 15A, 16F, 23A, 23B, 24F, 31, 35B, 8, 9N, 10A, 11A, 12F, 15C, 17F, and 20A. In sub-embodiments of Embodiment E20, the immunogenic composition does not comprise any further *S. pneumoniae* polysaccharide protein conjugates.

In another embodiment, the invention provides a multivalent immunogenic composition comprising multiple *S. pneumoniae* polysaccharide protein conjugates comprising capsular polysaccharide from a *S. pneumoniae* serotypes 3, 7F, 19A, 22F, 33F, 6A, 15A, 16F, 23A, 23B, 24F, 31, 35B, 8, 9N, 10A, 11A, 12F, 15C, 17F, and 20A. In sub-embodiments of this embodiment (i.e., 3, 7F, 19A, 22F, 33F, 6A, 15A, 16F, 23A, 23B, 24F, 31, 35B, 8, 9N, 10A, 11A, 12F, 15C, 17F, and 20A), the immunogenic composition does not comprise any further *S. pneumoniae* polysaccharide protein conjugates.

In another embodiment, the invention provides a multivalent immunogenic composition comprising multiple *S. pneumoniae* polysaccharide protein conjugates comprising capsular polysaccharide from a *S. pneumoniae* serotypes 3, 7F, 19A, 22F, 33F, 6A, 15A, 16F, 23A, 23B, 24F, 31, 35B, 8, 9N, 10A, 11A, 12F, 15C, 17F, and 20. In sub-embodiments of this embodiment (i.e., 3, 7F, 19A, 22F, 33F, 6A, 15A, 16F, 23A, 23B, 24F, 31, 35B, 8, 9N, 10A, 11A, 12F, 15C, 17F, and 20), the immunogenic composition does not comprise any further *S. pneumoniae* polysaccharide protein conjugates.

In another embodiment, the invention provides a multivalent immunogenic composition comprising multiple *S. pneumoniae* polysaccharide protein conjugates comprising capsular polysaccharide from a *S. pneumoniae* serotypes 3, 7F, 19A, 22F, 33F, 6A, 15A, 16F, 23A, 23B, 24F, 31, 35B, 8, 9N, 10A, 11A, 12F, 15C, 17F, and 20B. In sub-embodiments of this embodiment (i.e., 3, 7F, 19A, 22F, 33F, 6A, 15A, 16F, 23A, 23B, 24F, 31, 35B, 8, 9N, 10A, 11A, 12F, 15C, 17F, and 20B), the immunogenic composition does not comprise any further *S. pneumoniae* polysaccharide protein conjugates.

As shown herein (see EXAMPLE 3, infra), de-O-Acetylated serotype 15B pneumococcal polysaccharide is equivalent to serotype 15C pneumococcal polysaccharide and has an identical NMR spectra. De-O-Acetylated serotype 15B pneumococcal polysaccharide, as described and disclosed herein, is equivalent to serotype 15C pneumococcal polysaccharide and both may have an O-Acetyl content per repeating unit in the range of 0-5%, or in the range of 0-4%, or in the range of 0-3%, or in the range of 0-2%, or in the range of 0-1%, or in the range of 0-0.5%, or in the range of 0-0.1%, or no O-Acetyl content. In a report by Spencer B. L., et al., 15C may be slightly O-AO-Acetylated (Spencer, B. L. et al., *Clin. Vac. Immuno.* (2017) 24(8): 1-13). Thus, in any of the embodiments of the multivalent immunogenic compositions herein, de-O-acetylated serotype 15B can be used in place of serotype 15C. Processes for de-O-acetylation are known in the art, for example as described in Rajam et al., *Clinical and Vaccine Immunology*, 2007, 14(9):1223-1227.

In certain embodiments of any of the multivalent immunogenic compositions of the invention, including Embodiments E1 to E20 and any sub-embodiment thereof, the composition further comprises a pharmaceutically acceptable carrier.

Cross-Reactivity

In an embodiment the invention provides multivalent immunogenic compositions comprising *S. pneumoniae* polysaccharide protein conjugates wherein each of the conjugates comprises a polysaccharide from an *S. pneumoniae* serotype, including serotype 6C, conjugated to a carrier protein, wherein serotype 6C of *S. pneumoniae* provides cross-protection against serotypes 6A and 6B of *S. pneumoniae*.

In another embodiment the invention provides multivalent immunogenic compositions comprising *S. pneumoniae* polysaccharide protein conjugates as selected from Embodiments E1 to E20 wherein each of the conjugates comprises a polysaccharide from an *S. pneumoniae* serotype, including serotype 6C, conjugated to a carrier protein, wherein serotype 6C of *S. pneumoniae* provides cross-protection against serotypes 6A and 6B of *S. pneumoniae*.

In an embodiment the invention provides multivalent immunogenic compositions comprising *S. pneumoniae* polysaccharide protein conjugates wherein each of the conjugates comprises a polysaccharide from an *S. pneumoniae* serotype, including serotype 19A, conjugated to a carrier protein, wherein serotype 19A of *S. pneumoniae* provides cross-protection against serotype 19F of *S. pneumoniae*.

In another embodiment the invention provides multivalent immunogenic compositions comprising *S. pneumoniae* polysaccharide protein conjugates as selected from Embodiments E1 to E20 wherein each of the conjugates comprises a polysaccharide from an *S. pneumoniae* serotype, including serotype 19A, conjugated to a carrier protein, wherein serotype 19A of *S. pneumoniae* provides cross-protection against serotype 19F of *S. pneumoniae*.

In an embodiment the invention provides multivalent immunogenic compositions comprising *S. pneumoniae* polysaccharide protein conjugates wherein each of the conjugates comprises a polysaccharide from an *S. pneumoniae* serotype, including serotypes 23A and/or 23B, conjugated to a carrier protein, wherein serotypes 23A and/or 23B of *S. pneumoniae* provides cross-protection against serotype 23F of *S. pneumoniae*.

In another embodiment the invention provides multivalent immunogenic compositions comprising *S. pneumoniae* polysaccharide protein conjugates as selected from Embodiments E1 to E20 wherein each of the conjugates comprises a polysaccharide from an *S. pneumoniae* serotype, including serotypes 23A and/or 23B, conjugated to a carrier protein, wherein serotypes 23A and/or 23B of *S. pneumoniae* provides cross-protection against serotype 23F of *S. pneumoniae*.

In an embodiment the invention provides multivalent immunogenic compositions comprising *S. pneumoniae* polysaccharide protein conjugates wherein each of the conjugates comprises a polysaccharide from an *S. pneumoniae* serotype, including serotype 6A, conjugated to a carrier protein, wherein serotype 6A of *S. pneumoniae* provides cross-protection against serotypes 6B and/or 6C of *S. pneumoniae*.

In another embodiment the invention provides multivalent immunogenic compositions comprising *S. pneumoniae* polysaccharide protein conjugates as selected from Embodiments E1 to E20 wherein each of the conjugates comprises a polysaccharide from an *S. pneumoniae* serotype, including serotype 6A, conjugated to a carrier protein, wherein serotype 6A of *S. pneumoniae* provides cross-protection against serotypes 6B and/or 6C of *S. pneumoniae*.

In an embodiment the invention provides multivalent immunogenic compositions comprising *S. pneumoniae* polysaccharide protein conjugates wherein each of the conjugates comprises a polysaccharide from an *S. pneumoniae* serotype, including serotype 20A, conjugated to a carrier protein, wherein serotype 20A of *S. pneumoniae* provides cross-protection against serotype 20B of *S. pneumoniae*.

In another embodiment the invention provides multivalent immunogenic compositions comprising *S. pneumoniae* polysaccharide protein conjugates as selected from Embodiments E1 to E20 wherein each of the conjugates comprises a polysaccharide from an *S. pneumoniae* serotype, including serotype 20A, conjugated to a carrier protein, wherein serotype 20A of *S. pneumoniae* provides cross-protection against serotype 20B of *S. pneumoniae*.

In an embodiment the invention provides multivalent immunogenic compositions comprising *S. pneumoniae* polysaccharide protein conjugates wherein each of the conjugates comprises a polysaccharide from an *S. pneumoniae* serotype, including serotype 20B, conjugated to a carrier protein, wherein serotype 20B of *S. pneumoniae* provides cross-protection against serotype 20A of *S. pneumoniae*.

In another embodiment the invention provides multivalent immunogenic compositions comprising *S. pneumoniae* polysaccharide protein conjugates as selected from Embodiments E1 to E20 wherein each of the conjugates comprises a polysaccharide from an *S. pneumoniae* serotype, including serotype 20B, conjugated to a carrier protein, wherein serotype 20B of *S. pneumoniae* provides cross-protection against serotype 20A of *S. pneumoniae*.

In an embodiment the invention provides multivalent immunogenic compositions comprising *S. pneumoniae* polysaccharide protein conjugates wherein each of the conjugates comprises a polysaccharide from an *S. pneumoniae* serotype, including serotype 15C, conjugated to a carrier protein, wherein serotype 15C of *S. pneumoniae* provides cross-protection against serotype 15B of *S. pneumoniae*.

In another embodiment the invention provides multivalent immunogenic compositions comprising *S. pneumoniae* polysaccharide protein conjugates as selected from Embodiments E1 to E20 wherein each of the conjugates comprises a polysaccharide from an *S. pneumoniae* serotype, including serotype 15C, conjugated to a carrier protein, wherein serotype 15C of *S. pneumoniae* provides cross-protection against serotype 15B of *S. pneumoniae*.

Carrier Protein

In particular embodiments of the present invention, CRM197 is used as the carrier protein. CRM197 is a non-toxic variant (i.e., toxoid) of diphtheria toxin having the following sequence of amino acids:

```
                                              (SEQ ID NO: 1)
GADDVVDSSKSFVMENFSSYHGTKPGYVDSIQKGIQKPKSGTQGNYDDD

WKEFYSTDNKYDAAGYSVDNENPLSGKAGGVVKVTYPGLTKVLALKVDN

AETIKKELGLSLTEPLMEQVGTEEFIKRFGDGASRVVLSLPFAEGSSSV

EYINNWEQAKALSVELEINFETRGKRGQDAMYEYMAQACAGNRVRRSVG

SSLSCINLDWDVIRDKTKTKIESLKEHGPIKNKMSESPNKTVSEEKAKQ

YLEEFHQTALEHPELSELKTVTGTNPVFAGANYAAWAVNVAQVIDSETA

DNLEKTTAALSILPGIGSVMGIADGAVHHNTEEIVAQSIALSSLMVAQA

IPLVGELVDIGFAAYNFVESIINLFQVVHNSYNRPAYSPGHKTQPFLHD

GYAVSWNTVEDSIIRTGFQGESGHDIKITAENTPLPIAGVLLPTIPGKL

DVNKSKTHISVNGRKIRMRCRAIDGDVTFCRPKSPVYVGNGVHANLHVA

FHRSSSEKIHSNEISSDSIGVLGYQKTVDHTKVNSKLSLFFEIKS
```

In one embodiment, CRM197 is isolated from cultures of *Corynebacterium diphtheria* strain C7 (197) grown in casamino acids and yeast extract-based medium. In another embodiment, CRM197 is prepared recombinantly in accordance with the methods described in U.S. Pat. No. 5,614,382. Typically, CRM197 is purified through a combination of ultra-filtration, ammonium sulfate precipitation, and ion-exchange chromatography. In some embodiments, CRM197 is prepared in *Pseudomonas fluorescens* using Pfenex Expression Technology™ (Pfenex Inc., San Diego, CA).

Other suitable carrier proteins include additional inactivated bacterial toxins such as DT (Diphtheria toxoid) or fragment B of DT (DTFB), TT (tetanus toxid) or fragment C of TT, pertussis toxoid, cholera toxoid (e.g., as described in WO 2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumococcal surface protein A (PspA; See WO 02/091998), pneumococcal adhesin protein (PsaA), C5a peptidase from Group A or Group B *streptococcus*, or *Haemophilus influenzae* protein D, pneumococcal pneumolysin (Kuo et al., 1995, Infect Immun 63; 2706-13) including ply detoxified in some fashion for example dPLY-GMBS (See WO 04/081515) or dPLY-formol, PhtX, including PhtA, PhtB, PhtD, PhtE and fusions of Pht proteins for example PhtDE fusions, PhtBE fusions (See WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from *N. meningitidis*), PD (*Haemophilus influenzae* protein D; see, e.g., EP 0 594 610 B), or immunologically functional equivalents thereof, synthetic peptides (See EP0378881 and EP0427347), heat shock proteins (See WO 93/17712 and WO 94/03208), pertussis proteins (See WO 98/58668 and EP0471177), cytokines, lymphokines, growth factors or hormones (See WO 91/01146), artificial proteins comprising multiple human CD4+ T cell epitopes from various pathogen derived antigens (See Falugi et al., 2001, Eur J Immunol 31:3816-3824) such as N19 protein (See Baraldoi et al., 2004, *Infect Immun* 72:4884-7), iron uptake proteins (See WO 01/72337), toxin A or B of *C. difficile* (See WO 00/61761), and flagellin (See Ben-Yedidia et al., 1998, *Immunol Lett* 64:9) can also be used as carrier proteins.

Other DT mutants can be used as the carrier protein, such as $CRM_{176}$, $CRM_{228}$, $CRM_{45}$ (Uchida et al., 1973, *J Biol Chem* 218:3838-3844); $CRM_9$, $CRM_{45}$, $CRM_{102}$, $CRM_{103}$ and $CRM_{107}$ and other mutations described by Nicholls and Youle in *Genetically Engineered Toxins*, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711. Such DT mutants can also be used to make DTFB variants where the variants comprise the B fragment contain the epitope regions.

In certain embodiments, the carrier protein is selected from the group consisting of: Outer Membrane Protein Complex (OMPC), tetanus toxoid, diphtheria toxoid, protein D and CRM197.

In some embodiments of the invention, a second carrier can be used for one or more of the polysaccharide protein conjugates in the multivalent immunogenic composition. The second carrier protein is preferably a protein that is non-toxic and non-reactogenic and obtainable in sufficient amount and purity. The second carrier protein is also conjugated or joined with the *S. pneumoniae* polysaccharide to enhance immunogenicity of the antigen. Carrier proteins should be amenable to standard conjugation procedures. In one embodiment, each capsular polysaccharide not conjugated to the first carrier protein is conjugated to the same second carrier protein (e.g., each capsular polysaccharide molecule being conjugated to a single carrier protein). In another embodiment, the capsular polysaccharides not conjugated to the first carrier protein are conjugated to two or more carrier proteins (each capsular polysaccharide molecule being conjugated to a single carrier protein). In such embodiments, each capsular polysaccharide of the same serotype is typically conjugated to the same carrier protein.

In embodiments of the invention, including any of Embodiments E1-E20 and any sub-embodiments thereof, one or more (including 2, 3, 4, 5, 6, 7, 8, 9, 10, 11, 12, 13, 14, 15, 16, 17, 18, 19, 20, 21, where applicable) of the polysaccharide serotypes is conjugated to CRM197. In further embodiments of the invention, including any of Embodiments E1-E20 and any sub-embodiments thereof, each of the polysaccharide serotypes is conjugated to CRM197.

Formulation of the polysaccharide-protein conjugates of the present invention can be accomplished using art-recognized methods. For instance, individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In a preferred embodiment, the vaccine composition is formulated in L-histidine buffer with sodium chloride.

In some embodiments of the invention, the multivalent immunogenic composition comprises multiple *S. pneumoniae* polysaccharide protein conjugates comprising capsular polysaccharide from an *S. pneumoniae* serotype conjugated to a carrier protein and an adjuvant, wherein the *S. pneumoniae* serotypes are as described herein. Suitable adjuvants to enhance effectiveness of the composition include, but are not limited to:

(1) aluminum salts (alum), such as aluminum hydroxide, aluminum phosphate, aluminum sulfate, etc.;
(2) oil-in-water emulsion formulations (with or without other specific immunostimulating agents such as muramyl peptides (defined below) or bacterial cell wall components), such as, for example, (a) MF59 (International Patent Application Publication No. WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, MA), (b) SAF, containing 10% Squalene, 0.4% Tween 80, 5% pluronic-blocked polymer L121, and thr-MDP either microfluidized into a submicron emulsion or vortexed to generate a larger particle size emulsion, (c) Ribi™ adjuvant system (RAS), (Corixa, Hamilton, MT) containing 2% Squalene, 0.2% Tween 80, and one or more bacterial cell wall components from the group consisting of 3-O-deacylated monophosphorylipid A (MPL™) described in U.S. Pat. No. 4,912,094, trehalose dimycolate (TDM), and cell wall skeleton (CWS), preferably MPL+CWS (Detox™); and (d) a Montanide ISA;
(3) saponin adjuvants, such as Quil A or STIMULON™ QS-21 (Antigenics, Framingham, MA) (see, e.g., U.S. Pat. No. 5,057,540) may be used or particles generated therefrom such as ISCOM (immunostimulating complexes formed by the combination of cholesterol, saponin, phospholipid, and amphipathic proteins) and Iscomatrix® (having essentially the same structure as an ISCOM but without the protein);
(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyloxytetradecanoylamino]ethyl 2-Deoxy-4-O-phosphono-3-O-[(R)-3-tetradecanoyloxytetradecanoyl]-2-[(R)-3-tetradecanoyloxytetradecanoylamino]-b-D-glucopyranoside, which is also known as 529 (formerly known as RC529), which is formulated as an aqueous form or as a stable emulsion
(5) synthetic polynucleotides such as oligonucleotides containing CpG motif(s) (U.S. Pat. No. 6,207,646); and
(6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc; and
(7) complement, such as a trimer of complement component C3d.

In another embodiment, the adjuvant is a mixture of 2, 3, or more of the above adjuvants, e.g., SBAS2 (an oil-in-water emulsion also containing 3-deacylated monophosphoryl lipid A and QS21).

Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

In certain embodiments, the adjuvant is an aluminum salt. The aluminum salt adjuvant may be an alum-precipitated vaccine or an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493). The aluminum salt includes, but is not limited to, hydrated alumina, alumina hydrate, alumina trihydrate (ATH), aluminum hydrate, aluminum trihydrate, alhydrogel, Superfos, Amphogel, aluminum (III) hydroxide, aluminum hydroxyphosphate sulfate, Aluminum Phosphate Adjuvant (APA), amorphous alumina, trihydrated alumina, or trihydroxyaluminum.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a monodisperse particle size distribution. The product is then diafiltered against physiological saline and steam sterilized.

In certain embodiments, a commercially available Al(OH)$_3$ (e.g. Alhydrogel or Superfos of Denmark/Accurate Chemical and Scientific Co., Westbury, NY) is used to adsorb proteins in a ratio of 50-200 µg protein/mg aluminum hydroxide. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts may establish a depot of antigen that is released slowly over a period of 2-3 weeks, be involved in nonspecific activation of macrophages and complement activation, and/or stimulate innate immune mechanism (possibly through stimulation of uric acid). See, e.g., Lambrecht et al., 2009, Curr Opin Immunol 21:23.

Monovalent bulk aqueous conjugates are typically blended together and diluted to target 4 µg/mL for all serotypes except 6B, which will be diluted to target 8 µg/mL. Once diluted, the batch will be filter sterilized, and an equal volume of aluminum phosphate adjuvant added aseptically to target a final aluminum concentration of 250 µg/mL. The adjuvanted, formulated batch will be filled into single-use, 0.5 mL/dose vials.

In certain embodiments, the adjuvant is a CpG-containing nucleotide sequence, for example, a CpG-containing oligonucleotide, in particular, a CpG-containing oligodeoxynucleotide (CpG ODN). In another embodiment, the adjuvant is ODN 1826, which may be acquired from Coley Pharmaceutical Group.

Methods for use of CpG oligonucleotides are well known in the art and are described, for example, in Sur et al., 1999, J Immunol. 162:6284-93; Verthelyi, 2006, Methods Mol Med. 127:139-58; and Yasuda et al., 2006, Crit Rev Ther Drug Carrier Syst. 23:89-110.

In alternative embodiments, the immunogenic composition comprises multiple S. pneumoniae polysaccharide protein conjugates as described herein, for example in any of Embodiments E1-E20 or any sub-embodiment thereof, and does not comprise an adjuvant.

Formulations

The composition of the invention can be formulated as single dose vials, multi-dose vials or as pre-filled glass or plastic syringes.

In another embodiment, compositions of the present invention are administered orally, and are thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

Pharmaceutically acceptable carriers for liquid formulations are aqueous or non-aqueous solutions, suspensions, emulsions or oils. Examples of nonaqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

The pharmaceutical composition may be isotonic, hypotonic or hypertonic. However it is often preferred that a pharmaceutical composition for infusion or injection is essentially isotonic, when it is administrated. Hence, for storage the pharmaceutical composition may preferably be isotonic or hypertonic. If the pharmaceutical composition is hypertonic for storage, it may be diluted to become an isotonic solution prior to administration.

The isotonic agent may be an ionic isotonic agent such as a salt or a non-ionic isotonic agent such as a carbohydrate. Examples of ionic isotonic agents include but are not limited to NaCl, CaCl$_2$, KCl and MgCl$_2$. Examples of non-ionic isotonic agents include but are not limited to mannitol, sorbitol and glycerol.

It is also preferred that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8.

The buffer may, for example, be selected from the group consisting of TRIS, acetate, glutamate, lactate, maleate, tartrate, phosphate, citrate, carbonate, glycinate, histidine, glycine, succinate and triethanolamine buffer.

The buffer may be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic; dibasic acids such as aconitic, adipic, ascorbic, carbonic, glutamic, malic, succinic and tartaric, polybasic acids such as citric and phosphoric; and bases such as ammonia, diethanolamine, glycine, triethanolamine, and TRIS.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, Polysorbate 80 (PS-80), Polysorbate 20 (PS-20), and Poloxamer 188 (P188) are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The formulations of the invention may also contain a surfactant. Preferred surfactants include, but are not limited to: the polyoxyethylene sorbitan esters surfactants (commonly referred to as the Tweens), especially PS-20 and PS-80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. A preferred surfactant for including in the emulsion is PS-80.

Mixtures of surfactants can be used, e.g. PS-80/Span 85 mixtures. A combination of a polyoxyethylene sorbitan ester such as polyoxyethylene sorbitan monooleate (PS-80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as PS-80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

In certain embodiments, the composition consists essentially of histidine (20 mM), saline (150 mM) and 0.2% PS-20 or 0.04% PS-80 at a pH of 5.8 with 250 µg/mL of APA (Aluminum Phosphate Adjuvant). PS-20 can range from 0.005% to 0.3% (w/v) with the presence of PS-20 or PS-80 in formulation controlling aggregation during simulated manufacture and in shipping using primary packaging. In another embodiment, PS-20 can range from 0.025% to 0.8% (w/v). In another embodiment, PS-20 can range from 0.05% to 0.8% (w/v). In another embodiment, PS-20 can range from 0.05% to 0.2% (w/v). Process consists of combining a blend of up to 24 serotypes in histidine, saline, and PS-20 or PS-80, then combining this blended material with APA and saline with or without antimicrobial preservatives.

In particular embodiments, the multivalent immunogenic composition comprises S. pneumoniae polysaccharide protein conjugates wherein each of the conjugates comprises a polysaccharide from an S. pneumoniae serotype conjugated to a carrier protein, wherein the serotypes of S. pneumoniae in the polysaccharide protein conjugates comprise any of the sets of serotypes set forth herein, and further comprises 20-80 mM histidine pH 5.8 and 150 mM NaCl. In some embodiments, the multivalent immunogenic composition further comprises from 0.2% to 0.8% w/v polysorbate 20.

The choice of surfactant may need to be optimized for different drug products and drug substances. For multivalent vaccines having 15 or more serotypes, PS-20 and P188 are preferred. The choice of chemistry used to make conjugate can also play an important role in the stabilization of the formulation. In particular, when the conjugation reactions used to prepare different polysaccharide protein conjugates in a multivalent composition include both aqueous solvent and DMSO solvent, particular surfactant systems provide significant differences in stability. Improved stability of polysachharide protein conjugates was seen with polysorbate 20 alone or with poloxamer 188 in combination with a polyol.

The exact mechanism of how a specific detergent protects a biotherapeutic is poorly understood and cannot be predicted a priori. Possible stabilization mechanisms include preferential hydration, preferential exclusion, air/liquid interface competition between biotherapeutic and surface, surface tension, and/or direct association of the detergent with the biotherapeutics to mask hydrophobic patches which serve as seeds for aggregation.

Poloxamer may also be used in the compositions of the invention. A poloxamer is a nonionic triblock copolymer composed of a central hydrophobic chain of polyoxypropylene (poly(propylene oxide)) flanked by two hydrophilic chains of polyoxyethylene (poly(ethylene oxide)). Poloxamers are also known by the tradename Pluronic®. Because the lengths of the polymer blocks can be customized, many different poloxamers exist that have slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic® tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic® with a polyoxypropylene molecular mass of 1,800 g/mol and a 10% polyoxyethylene content). See U.S. Pat. No. 3,740,421.

Examples of poloxamers have the general formula: $HO(C_2H_4O)_a(C_3H_6O)_b(C_2H_4O)_aH$, wherein a and b blocks have the following values:

| Pluronic ® | Poloxamer | A | B | Molecular Weight |
| --- | --- | --- | --- | --- |
| L31 | | 2 | 16 | 1100 (average) |
| L35 | | | | 1900 (average) |
| L44NF | 124 | 12 | 20 | 2090 to 2360 |
| L64 | | | | 2900 (average) |
| L81 | | | | 2800 (average) |
| L121 | | | | 4400 (average) |
| P123 | | 20 | 70 | 5750 (average) |
| F68NF | 188 | 80 | 27 | 7680 to 9510 |
| F87NF | 237 | 64 | 37 | 6840 to 8830 |
| F108NF | 338 | 141 | 44 | 12700 to 17400 |
| F127NF | 407 | 101 | 56 | 9840 to 14600 |

Molecular weight units, as used herein, are in Dalton (Da) or g/mol.

Preferably, the poloxamer generally has a molecular weight in the range from 1100 to 17,400 Da, from 7,500 to 15,000 Da, or from 7,500 to 10,000 Da. The poloxamer can be selected from poloxamer 188 or poloxamer 407. The final concentration of the poloxamer in the formulations is from 0.001% to 5% weight/volume, or 0.025% to 1% weight/volume. In certain aspects, the polyol is propylene glycol and is at final concentration from 1% to 20% weight/volume. In certain aspects, the polyol is polyethylene glycol 400 and is at final concentration from 1% to 20% weight/volume.

Suitable polyols for the formulations of the invention are polymeric polyols, particularly polyether diols including, but are not limited to, propylene glycol and polyethylene glycol, Polyethylene glycol monomethyl ethers. Propylene glycol is available in a range of molecular weights of the monomer from ~425 to 2700. Polyethylene glycol and Polyethylene glycol monomethyl ether is also available in a range of molecular weights ranging from ~200 to ~35000 including but not limited to PEG200, PEG300, PEG400, PEG1000, PEG MME 550, PEG MME 600, PEG MME 2000, PEG MME 3350 and PEG MME 4000. A preferred polyethylene glycol is polyethylene glycol 400. The final concentration of the polyol in the formulations of the invention may be 1% to 20% weight/volume or 6% to 20% weight/volume.

The formulation also contains a pH-buffered saline solution. The buffer may, for example, be selected from the group consisting of TRIS, acetate, glutamate, lactate, maleate, tartrate, phosphate, citrate, carbonate, glycinate, histidine, glycine, succinate, HEPES (4-(2-hydroxyethyl)-1-piperazineethanesulfonic acid), MOPS (3-(N-morpholino)

propanesulfonic acid), MES (2-(N-morpholino)ethanesulfonic acid) and triethanolamine buffer. The buffer is capable of buffering a solution to a pH in the range of 4 to 10, 5.2 to 7.5, or 5.8 to 7.0. In certain aspect of the invention, the buffer is selected from the group consisting of phosphate, succinate, histidine, MES, MOPS, HEPES, acetate or citrate. The buffer may furthermore, for example, be selected from USP compatible buffers for parenteral use, in particular, when the pharmaceutical formulation is for parenteral use. The concentrations of buffer will range from 1 mM to 100 mM. The concentrations of buffer will range from 10 mM to 80 mM. The concentrations of buffer will range from 1 mM to 50 mM or 5 mM to 50 mM. In certain aspects, the buffer is histidine at a final concentration of 5 mM to 50 mM, or succinate at a final concentration of 1 mM to 10 mM. In certain aspects, the histidine is at a final concentration of 20 mM±2 mM.

While the saline solution (i.e., a solution containing NaCl) is preferred, other salts suitable for formulation include but are not limited to, $CaCl_2$, KCl and $MgCl_2$ and combinations thereof. Non-ionic isotonic agents including but not limited to sucrose, trehalose, mannitol, sorbitol and glycerol may be used in lieu of a salt. Suitable salt ranges include, but are not limited to 25 mM to 500 mM or 40 mM to 170 mM. In one aspect, the saline is NaCl, optionally present at a concentration from 20 mM to 170 mM.

In a preferred embodiment, the formulations comprise a L-histidine buffer with sodium chloride.

In another embodiment, the pharmaceutical composition is delivered in a controlled release system. For example, the agent can be administered using intravenous infusion, a transdermal patch, liposomes, or other modes of administration. In another embodiment, polymeric materials are used; e.g. in microspheres in or an implant.

The amount of conjugate in each vaccine dose is selected as an amount that induces an immunoprotective response without significant, adverse effects. Such amount can vary depending upon the pneumococcal serotype. Generally, for polysaccharide-based conjugates, each dose will comprise 0.08 to 100 g of each polysaccharide. In some embodiments of the invention, the dose of each polysaccharide conjugate is from 0.08 to 10 g. In further embodiments, the dose is from 1 to 5 g, from 0.4 to 4 g, from 0.4 to 3 g, from 0.4 to 2 g, or from 0.4 to 1 g. In some embodiments, the dose of one or more polysaccharide conjugates is 100, 150, 200, 250, 300, 400, 500, or 750 ng or 0.4, 0.5, 0.6, 0.7, 0.75, 0.8, 0.9, 1, 1.5, 2, 3, 4, 5, 6, 7, 7.5, 8, 9, 10, 11, 12, 13, 14, 15, 16, 18, 20, 22, 25, 30, 40, 50, 60, 70, 80, 90, or 100 g.

In some embodiments of the compositions of the invention, all of the polysaccharide conjugates are present in the composition in the same amount. In further embodiments, the polysaccharide conjugates are present in the composition in different amounts (i.e., at least one polysaccharide conjugate is present in an amount that is different than one or more of the other polysaccharide conjugates of the composition).

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

In one embodiment, the dose of the aluminum salt is 10, 15, 20, 25, 30, 50, 70, 100, 125, 150, 200, 300, 500, or 700 µg, or 1, 1.2, 1.5, 2, 3, 5 mg or more. In yet another embodiment, the dose of alum salt described above is per µg of recombinant protein.

The compositions of this invention may also include one or more proteins from *S. pneumoniae*. Examples of *S. pneumoniae* proteins suitable for inclusion include those identified in International Patent Application Publication Nos. WO 02/083855 and WO 02/053761.

In certain embodiments, the compositions of the invention are administered to a subject by one or more methods known to a person skilled in the art, such as parenterally, transmucosally, transdermally, intramuscularly, intravenously, intradermally, intra-nasally, subcutaneously, intra-peritonealy, and formulated accordingly. In one embodiment, compositions of the present invention are administered via epidermal injection, intramuscular injection, intravenous, intra-arterial, subcutaneous injection, or intra-respiratory mucosal injection of a liquid preparation. Liquid formulations for injection include solutions and the like.

III. Methods of Making

Capsular polysaccharides from *Streptococcus pneumoniae* can be prepared by standard techniques known to those skilled in the art. For example, polysaccharides can be isolated from bacteria and may be sized to some degree by known methods (see, e.g., European Patent Nos. EP497524 and EP497525); and preferably by microfluidisation accomplished using a homogenizer or by chemical hydrolysis. In one embodiment, each pneumococcal polysaccharide serotype is grown in a soy-based medium. The individual polysaccharides are then purified through standard steps including centrifugation, precipitation, and ultra-filtration. See, e.g., U.S. Patent Application Publication No. 2008/0286838 and U.S. Pat. No. 5,847,112. Polysaccharides can be sized in order to reduce viscosity in polysaccharide samples and/or to improve filterability for conjugated products using techniques such as mechanical or chemical sizing. Chemical hydrolysis may be conducted using acetic acid. Mechanical sizing may be conducted using High Pressure Homogenization Shearing.

The purified polysaccharides can be chemically activated to make the saccharides capable of reacting with the carrier protein. The purified polysaccharides can be connected to a linker. Once activated or connected to a linker, each capsular polysaccharide is separately conjugated to a carrier protein to form a glycoconjugate. The polysaccharide conjugates may be prepared by known coupling techniques.

The polysaccharide can be coupled to a linker to form a polysaccharide-linker intermediate in which the free terminus of the linker is an ester group. The linker is therefore one in which at least one terminus is an ester group. The other terminus is selected so that it can react with the polysaccharide to form the polysaccharide-linker intermediate.

The polysaccharide can be coupled to a linker using a primary amine group in the polysaccharide. In this case, the linker typically has an ester group at both termini. This allows the coupling to take place by reacting one of the ester groups with the primary amine group in the polysaccharide by nucleophilic acyl substitution. The reaction results in a polysaccharide-linker intermediate in which the polysaccharide is coupled to the linker via an amide linkage. The linker is therefore a bifunctional linker that provides a first ester group for reacting with the primary amine group in the polysaccharide and a second ester group for reacting with the primary amine group in the carrier molecule. A typical linker is adipic acid N-hydroxysuccinimide diester (SIDEA).

The coupling can also take place indirectly, i.e. with an additional linker that is used to derivatise the polysaccharide prior to coupling to the linker.

The polysaccharide is coupled to the additional linker using a carbonyl group at the reducing terminus of the polysaccharide. This coupling comprises two steps: (a1) reacting the carbonyl group with the additional linker; and (a2) reacting the free terminus of the additional linker with the linker. In these embodiments, the additional linker typically has a primary amine group at both termini, thereby allowing step (a1) to take place by reacting one of the primary amine groups with the carbonyl group in the polysaccharide by reductive amination. A primary amine group is used that is reactive with the carbonyl group in the polysaccharide. Hydrazide or hydroxylamino groups are suitable. The same primary amine group is typically present at both termini of the additional linker. The reaction results in a polysaccharide-additional linker intermediate in which the polysaccharide is coupled to the additional linker via a C—N linkage.

The polysaccharide can be coupled to the additional linker using a different group in the polysaccharide, particularly a carboxyl group. This coupling comprises two steps: (a1) reacting the group with the additional linker; and (a2) reacting the free terminus of the additional linker with the linker. In this case, the additional linker typically has a primary amine group at both termini, thereby allowing step (a1) to take place by reacting one of the primary amine groups with the carboxyl group in the polysaccharide by EDAC activation. A primary amine group is used that is reactive with the EDAC-activated carboxyl group in the polysaccharide. A hydrazide group is suitable. The same primary amine group is typically present at both termini of the additional linker. The reaction results in a polysaccharide-additional linker intermediate in which the polysaccharide is coupled to the additional linker via an amide linkage.

In one embodiment, the chemical activation of the polysaccharides and subsequent conjugation to the carrier protein by reductive amination can be achieved by means described in U.S. Pat. Nos. 4,365,170, 4,673,574 and 4,902,506, U.S. Patent Application Publication Nos. 2006/0228380, 2007/184072, 2007/0231340 and 2007/0184071, and WO2006/110381, WO2008/079653, and WO2008/143709). The chemistry may include the activation of pneumococcal polysaccharide by reaction with any oxidizing agent which oxidizes a terminal hydroxyl group to an aldehyde, such as periodate (including sodium periodate, potassium periodate, or periodic acid). The reaction leads to a random oxidative cleavage of vicinal hydroxyl groups of the carbohydrates with the formation of reactive aldehyde groups.

Coupling to the carrier protein is by reductive amination via direct amination to the lysyl groups of the protein. For example, conjugation can be carried out by reacting a mixture of the activated polysaccharide and carrier protein with a reducing agent such as sodium cyanoborohydride in the presence of nickel. The conjugation reaction may take place under aqueous solution or in the presence of DMSO. See, e.g., US2015/0231270, US2011/0195086 and EP 0471 177 B1. Unreacted aldehydes are then capped with the addition of a strong reducing agent, such as sodium borohydride.

Reductive amination involves two steps, (1) oxidation of the polysaccharide to form reactive aldehydes, (2) reduction of the imine (Schiff base) formed between activated polysaccharide and a carrier protein to form a stable amine conjugate bond. Before oxidation, the polysaccharide is optionally size reduced. Mechanical methods (e.g. homogenization) or chemical hydrolysis may be employed. Chemical hydrolysis may be conducted using acetic acid. The oxidation step may involve reaction with periodate. For the purpose of the present invention, the term "periodate" includes both periodate and periodic acid; the term also includes both metaperiodate ($IO_4^-$) and orthoperiodate ($IO_6^-$) and includes the various salts of periodate (e.g., sodium periodate and potassium periodate). In an embodiment the capsular polysaccharide is oxidized in the presence of metaperiodate, preferably in the presence of sodium periodate ($NaIO_4$). In another embodiment the capsular polysaccharide is oxydized in the presence of orthoperiodate, preferably in the presence of periodic acid.

In one embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls (as described in WO 2014/097099). In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof. In an aspect, said oxidant is a molecule bearing a N-halo moiety. In an aspect, said oxidant is selected from the group consisting of N-Chlorosuccinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

In certain aspects, the oxidizing agent is 2,2,6,6-Tetramethyl-1-piperidinyloxy (TEMPO) free radical and N-Chlorosuccinimide (NCS) as the cooxidant (as described in WO 2014/097099). Therefore in one aspect, the glycoconjugates from S. pneumoniae are obtainable by a method comprising the steps of: a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups (said method is designated "TEMPO/NCS-reductive amination" thereafter).

Optionally the oxidation reaction is quenched by addition of a quenching agent. The quenching agent may be selected from vicinal diols, 1-,2-aminoalcohols, amino acids, glutathione, sulfite, bisulfate, dithionite, metabisulfite, thiosulfate, phosphites, hypophosphites or phosphorous acid (such as glycerol, ethylene glycol, propan-1-,2-diol, butan-1,2-diol or butan-2,3-diol, ascorbic acid).

In certain embodiments, the instant invention provides a method for preparing a serotype 8 *Streptococcus pneumoniae* polysaccharide-protein conjugate utilizing a conjugation reaction in an aprotic solvent, wherein the conjugation reaction does not use cyanoborohydride. In further embodiments, the conjugation reaction is a Schiff base reduction or reductive amination. In further embodiments, the protein is tetanus toxoid, diphtheria toxoid, or CRM197. In still further embodiments the protein is CRM197. In further embodiments, the conjugation reaction is reductive amination. In further embodiments, the reductive amination is performed in dimethylsulfoxide (DMSO).

In some embodiments, the oxidized polysaccharides before conjugation have a molecular weight of between 30 kDa and 1,000 kDa. Molecular weight can be calculated by size exclusion chromatography (SEC) combined with multiangle light scattering detector (MALS) and refractive index detector (RI). In some embodiments, the polysaccharide has a molecular weight of between 50 kDa and 300 kDa. In some embodiments, the polysaccharide has a molecular weight of between 50 kDa and 1,000 kDa. In additional embodiments, the polysaccharide has a molecular weight of between 70 kDa and 900 kDa. In other embodiments, the polysaccharide has a molecular weight of between 100 kDa and 800 kDa. In other embodiments, the polysaccharide has a molecular weight of between 200 kDa and 600 kDa. In further embodiments, the polysaccharide has a molecular weight of 100 kDa to 1,000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; 500 kDa to 600 kDa.

The second step of the conjugation process is the reduction of the imine (Schiff base) bond between activated polysaccharide and a carrier protein to form a stable conjugate bond (so-called reductive amination), using a reducing agent. Reducing agents which are suitable include the cyanoborohydrides (such as sodium cyanoborohydride or sodium borohydride). In one embodiment the reducing agent is sodium cyanoborohydride.

In certain embodiments, the reductive amination reaction is carried out in aprotic solvent (or a mixture of aprotic solvents). In one embodiment, the reduction reaction is carried out in DMSO or in DMF (dimethylformamide) solvent. The DMSO or DMF solvent may be used to reconstitute the activated polysaccharide and carrier protein, if lyophilized. In one embodiment, the aprotic solvent is DMSO.

At the end of the reduction reaction, there may be unreacted aldehyde groups remaining in the conjugates, which may be capped using a suitable capping agent. In one embodiment this capping agent is sodium borohydride ($NaBH_4$). Suitable alternatives include sodium triacetoxyborohydride or sodium or zinc borohydride in the presence of Bronsted or Lewis acids), amine boranes such as pyridine borane, 2-Picoline Borane, 2,6-diborane-methanol, dimethylamine-borane, t-BuMe'PrN—$BH_3$, benzylamine-$BH_3$ or 5-ethyl-2-methylpyridine borane (PEMB) or borohydride exchange resin. Following the conjugation (the reduction reaction and optionally the capping), the glycoconjugates may be purified (enriched with respect to the amount of polysaccharide-protein conjugate) by a variety of techniques known to the skilled person. These techniques include dialysis, concentration/diafiltration operations, tangential flow filtration, precipitation/elution, column chromatography (ion exchange chromatography, multimodal ion exchange chromatography, DEAE, or hydrophobic interaction chromatography), and depth filtration. In an embodiment, the glycoconjugates are purified by diafiltration or ion exchange chromatography or size exclusion chromatography.

Glycoconjugates prepared using reductive amination in an aprotic solvent are generally used in multivalent pneumococcal conjugate vaccines. Thus, in certain embodiments for multivalent compositions where not all the serotypes are prepared in an aprotic solvent, the reduction reaction for the remaining serotypes is carried out in aqueous solvent (e.g., selected from PBS (phosphate buffered saline), MES (2-(N-morpholino)ethanesulfonic acid), HEPES (4-(2-hydroxyethyl)-1-piperazineethanesulfonic acid), Bis-tris, ADA (N-(2-Acetamido)iminodiacetic acid), PIPES (piperazine-N,N'-bis(2-ethanesulfonic acid)), MOPSO (3-Morpholino-2-hydroxypropanesulfonic acid), BES (N,N-bis(2-hydroxyethyl)-2-aminoethanesulfonic acid), MOPS (3-(N-morpholino)propanesulfonic acid), DIPSO (3-Bis(2-hydroxyethyl) amino-2-hydroxypropane-1-sulfonic acid), MOBS (4-(N-morpholino)butanesulfonic acid), HEPPSO (N-(2-Hydroxyethyl)piperazine-N-(2-hydroxypropanesulfonic acid)), POPSO (Piperazine-1,4-bis(2-hydroxy-3-propanesulfonic acid)), TEA (triethanolamine), EPPS (4-(2-Hydroxyethyl)piperazine-1-propanesulfonic acid), Bicine at a pH between 6.0 and 8.5, 7.0 and 8.0, or 7.0 and 7.5).

*S. pneumonia* capsular polysaccharide-protein conjugates that can be prepared using reductive amination in an aprotic solvent, include, but are not limited to, serotypes: 3, 6A, 6B, 6C, 7F, 8, 9N, 10A, 11A, 12F, 15A, 15B, 15C, 16F, 17F, 19A, 20A, 22F, 23A, 23B, 23F, 24F, 31, 33F, 35B, and 39. *S. pneumonia* capsular polysaccharide-protein conjugates that can be prepared using reductive amination in an aprotic solvent, include, but are not limited to, serotypes: 3, 6A, 6B, 6C, 7F, 8, 9N, 10A, 11A, 12F, 15A, 15B, 15C, 16F, 17F, 19A, 20, 22F, 23A, 23B, 23F, 24F, 31, 33F, 35B, and 39. *S. pneumonia* capsular polysaccharide-protein conjugates that can be prepared using reductive amination in an aprotic solvent, include, but are not limited to, serotypes: 3, 6A, 6B, 6C, 7F, 8, 9N, 10A, 11A, 12F, 15A, 15B, 15C, 16F, 17F, 19A, 20B, 22F, 23A, 23B, 23F, 24F, 31, 33F, 35B, and 39. The polysaccharides may be used in the form of oligosaccharides. These are conveniently formed by fragmentation of purified polysaccharide (e.g. by hydrolysis), which will usually be followed by purification of the fragments of the desired size.

In certain embodiments, pneumococcal polysaccharide-protein conjugates of one or more of serotypes 3, 6A, 6B, 6C, 7F, 8, 9N, 10A, 11A, 12F, 15A, 15B, 15C, 16F, 17F, 19A, 20A, 22F, 23A, 23B, 23F, 24F, 31, 33F, 35B, and 39 are prepared using reductive amination in an aprotic solvent. In certain embodiments, pneumococcal polysaccharide-protein conjugates of one or more of serotypes 3, 6A, 6B, 6C, 7F, 8, 9N, 10A, 11A, 12F, 15A, 15B, 15C, 16F, 17F, 19A, 20, 22F, 23A, 23B, 23F, 24F, 31, 33F, 35B, and 39 are prepared using reductive amination in an aprotic solvent. In certain embodiments, pneumococcal polysaccharide-protein conjugates of one or more of serotypes 3, 6A, 6B, 6C, 7F, 8, 9N, 10A, 11A, 12F, 15A, 15B, 15C, 16F, 17F, 19A, 20B, 22F, 23A, 23B, 23F, 24F, 31, 33F, 35B, and 39 are prepared using reductive amination in an aprotic solvent. In certain embodiments, each of the serotypes in the multivalent immunogenic composition is prepared using reductive amination in an aprotic solvent. In certain embodiments, polysaccharides of one or more serotypes in a multivalent composition are conjugated using reductive amination in an aprotic solvent and polysaccharides of one or more serotypes are conjugated using reductive amination in an aqueous solvent. In certain embodiments, polysaccharides of two or more serotypes in a multivalent composition are conjugated using reductive amination in an aprotic solvent. In other embodiments, polysaccharides of three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, or twenty-one or more serotypes in a multivalent composition are conjugated using reductive amination in an aprotic solvent. In certain embodiments, polysaccharides from one or more serotypes in a multivalent composition are conjugated using other chemistries which may be in an aprotic solvent or in an aqueous solvent.

Thus, the invention relates to a multivalent immunogenic composition comprising multiple S. pneumoniae polysaccharide protein conjugates, each comprising capsular polysaccharide from an S. pneumoniae serotype conjugated to a carrier protein, wherein the serotypes of S. pneumoniae are as described herein (i.e. in Section II, "Multivalent Immunogenic Compositions"), wherein the conjugation reaction whereby the polysaccharide from one or more of the polysaccharide protein conjugates is conjugated to the carrier protein is in an aprotic solvent. In certain embodiments, at least 30, 35, 40, 45, 50, 55, 60, 65, 70, 75, 80, 85, 90, 95, or 100% of the serotypes in a multivalent composition are prepared in an aprotic solvent. The remainder of the serotypes are prepared using an alternative chemistry and/or in an aqueous solvent.

It was determined that the use of DMSO as a solvent during reductive amination of polysaccharide-protein conjugates results in the unexpectedly superior stability and enhanced immunogenicity for those serotypes relative to the same conjugates prepared under aqueous conditions (See U.S. application Ser. Nos. 62/463,216 and 62/555,444). As shown herein (see EXAMPLE 40), drug product formulations containing the pneumococcal conjugates of the invention prepared using reductive amination in an aprotic solvent (e.g. DMSO) resulted in superior physical and chemical stability as compared to a vaccine utilizing drug substances prepared using a protic (i.e. aqueous) solvent during reductive amination in the conjugation process. Thus, in some embodiments, all of the pneumococcal polysaccharide conjugates in the multivalent composition are prepared in an aprotic solvent.

In certain embodiments of the invention the total polysaccharide concentration in the composition is from about 0.02 to about 0.175 mg/mL. In certain embodiments of the invention the total polysaccharide concentration in the composition is from about 0.03 to about 0.175 mg/mL. In certain embodiments of the invention the total polysaccharide concentration in the composition is from about 0.04 to about 0.175 mg/mL. In other embodiments, the total polysaccharide concentration in the composition is from about 0.065 to about 0.085 mg/mL, about 0.070 to about 0.080 mg/mL, about 0.065 to about 0.080 mg/mL, about 0.070 to about 0.085 mg/mL, about 0.110 to about 0.128 mg/mL, about 0.110 to about 0.175 mg/mL, about 0.10 to about 0.175 mg/mL, about 0.110 to about 0.170 mg/mL, about 0.115 to about 0.15 mg/mL, about 0.110 to about 0.15 mg/mL, about 0.110 to about 0.125 mg/mL, about 0.150 to about 0.170 mg/mL, about 0.150 to about 0.165 mg/mL, about 0.140 to about 0.170 mg/mL, about 0.130 to about 0.170 mg/mL, about 0.150 to about 0.175 mg/mL, about 0.070 to about 0.170 mg/mL, about 0.065 to about 0.175 mg/mL, or about 0.065 to about 0.180 mg/mL.

In embodiments of the invention wherein one or more, or all, of the polysaccharide-protein conjugates in the multivalent immunogenic compositions are prepared in an aprotic solvent, the total polysaccharide concentration in the composition is stable for 4 weeks or more at 37° C., 4 weeks or more at 25° C., and 12 weeks or more at 4° C.

In certain embodiments of the invention wherein one or more, or all, of the polysaccharide-protein conjugates in the multivalent immunogenic compositions are prepared in an aprotic solvent, the weight average molecular weight (Mw) of all of the S. pneumoniae polysaccharide protein conjugates in the composition (average of all conjugates in the composition) is from about 3,500 to about 4,700 kDa, from about 3,500 to about 4,600 kDa, from about 3,500 to about 4,500 kDa, from about 3,500 to about 4,400 kDa, from about 3,500 to about 4,300 kDa, from about 3,500 to about 4,200 kDa, from about 3,600 to about 4,700 kDa, from about 3,600 to about 4,600 kDa, from about 3,600 to about 4,500 kDa, from about 3,600 to about 4,400 kDa, from about 3,600 to about 4,300 kDa, from about 3,600 to about 4,200 kDa, from about 3,700 to about 4,700 kDa, from about 3,700 to about 4,600 kDa, from about 3,700 to about 4,500 kDa, from about 3,700 to about 4,400 kDa, from about 3,700 to about 4,300 kDa, from about 3,700 to about 4,200 kDa, from about 3,800 to about 4,700 kDa, from about 3,800 to about 4,600 kDa, from about 3,800 to about 4,500 kDa, from about 3,800 to about 4,400 kDa, from about 3,800 to about 4,300 kDa, from about 3,800 to about 4,200 kDa, from about 3,900 to about 4,700 kDa, from about 3,900 to about 4,600 kDa, from about 3,900 to about 4,500 kDa, from about 3,900 to about 4,400 kDa, from about 3,900 to about 4,300 kDa, or from about 3,900 to about 4,200 kDa.

In certain embodiments of the invention wherein the polysaccharide-protein conjugates in the multivalent immunogenic compositions are prepared in an aprotic solvent, the Mw of each of the S. pneumoniae polysaccharide protein conjugates in the composition (for a single serotype) is from about 1,000 to about 10,000 kDa, from about 1,500 to about 5,500 kDa, from about 1,500 to about 5,600 kDa, from about 1,500 to about 5,700 kDa, from about 1,500 to about 5,800 kDa, from about 1,500 to about 5,900 kDa, from about 1,500 to about 6,000 kDa, from about 1,000 to about 5,500 kDa, from about 1,000 to about 5,000 kDa, from about 1,000 to about 4,000 kDa, from about 1,000 to about 4,500 kDa, from about 1,000 to about 4,000 kDa, or from about 1,000 to about 3,500 kDa. In other embodiments, the Mw of a conjugate from a single serotype within the composition is about 1,000 kDa, about 1,100 kDa, about 1,200 kDa, about 1,300 kDa, about 1,400 kDa, about 1,500 kDa, about 1,600 kDa, about 1,700 kDa, about 1,800 kDa, about 1,900 kDa, about 2,000 kDa, about 2,100 kDa, about 2,200 kDa, about 2,300 kDa, about 2,400 kDa, about 2,500 kDa, about 2,600 kDa, about 2,700 kDa, about 2,800 kDa, about 2,900 kDa, about 3,000 kDa, about 3,100 kDa, about 3,200 kDa, about 3,300 kDa, about 3,400 kDa, about 3,500 kDa, about 3,600 kDa, about 3,700 kDa, about 3,800 kDa, about 3,900 kDa, about 4,000 kDa, about 4,100 kDa, about 4,200 kDa, about 4,300 kDa, about 4,400 kDa, about 4,500 kDa, about 4,600 kDa, about 4,700 kDa, about 4,800 kDa, about 4,900 kDa, about 5,000 kDa, about 5,100 kDa, about 5,200 kDa, about 5,300 kDa, about 5,400 kDa, or about 5,500 kDa.

In certain embodiments of the invention the polysaccharide-protein conjugates in the multivalent immunogenic compositions are prepared in an aprotic solvent. Compositions containing higher percentages of S. pneumoniae polysaccharides conjugated to a carrier protein in an aprotic solvent (as opposed to being prepared in a protic solvent)

may be preferred. In certain embodiments, the percentage (as calculated by the number of polysaccharide serotypes prepared in an aprotic solvent divided by the total number of polysaccharide serotypes, where total number includes those prepared in an aprotic solvent or a protic solvent) of S. pneumoniae serotype specific conjugates prepared in an aprotic solvent may be greater than 50%, or greater than 60%, or greater than 70%, or greater than 80%, or greater than 90% or are 100%.

In certain embodiments of the invention, the serotype 3 polysaccharide-protein conjugate in the composition is prepared in an aprotic solvent and the Mw of said conjugate is from about 1,000 to about 5,000 kDa, or from about 1,000 to about 4,000 kDa, or from about 1,000 to about 3,000 kDa, or from about 1,000 to about 2,500 kDa, or from about 1,000 to about 2,000 kDa.

In certain embodiments of the invention wherein one or more, or all, of the polysaccharide-protein conjugates in the multivalent immunogenic compositions are prepared in an aprotic solvent, the number average molecular weight (Mn) of the S. pneumoniae polysaccharide protein conjugates in the composition (average of all conjugates in the composition) is from about 900 to about 3,000 kDa, from about 1,000 to about 3,000 kDa, from about 1,000 to about 2,500 kDa, from about 1,500 to about 2,500 kDa, from about 1,800 to about 2,500 kDa, from about 1,900 to about 2,500 kDa, or from about 2,000 to about 2,500 kDa.

In certain embodiments of the invention wherein one or more, or all, of the polysaccharide-protein conjugates in the multivalent immunogenic compositions are prepared in an aprotic solvent, the Mn of each of the S. pneumoniae polysaccharide protein conjugates in the composition (for a single serotype) is from about 700 to about 7,000 kDa, from about 1,000 to about 6,000 kDa, from about 1,000 to about 5,000 kDa, from about 1,000 to about 4,000 kDa, from about 1,000 to about 3,000 kDa, from about 900 to about 5,500 kDa, from about 900 to about 5,000 kDa, from about 900 to about 4,500 kDa, from about 900 to about 4,000 kDa, from about 900 to about 3,500 kDa, or from about 900 to about 3,000 kDa.

In embodiments of the invention, the Mw and/or Mn of the S. pneumoniae polysaccharide protein conjugates in the composition is stable for 4 weeks or more at 37° C., 4 weeks or more at 25° C., and/or 12 weeks or more at 4° C.

In embodiments of the invention, the polysaccharide concentration, Mw, and/or Mn are determined using HPSEC UV/MALS/RI.

In some embodiment of the invention, wherein one or more, or all, of the polysaccharide-protein conjugates in the multivalent immunogenic compositions are prepared in an aprotic solvent, the emission maximum of the composition measured using intrinsic protein fluorescence spectroscopy with an excitation wavelength at 280 nanometers (nm) is from about 335 nm to about 342 nm. In some embodiments, the emission maximum remains from about 335 nm to about 342 nm and the fluorescence intensity is stable for at least 1 week at 37° C. In some embodiments, the emission maximum remains from about 335 nm to about 342 nm and the fluorescence intensity is stable for 1 week at 37° C.

In some embodiments, all of the pneumococcal polysaccharide conjugates in the multivalent composition are prepared using reductive amination in DMSO. In certain sub-embodiments, the multivalent composition comprising polysaccharide conjugates which were all prepared using DMSO does not comprise an adjuvant.

Without being bound by any theory, one possible mechanism for the enhanced immunogenicity observed with glycoconjugates prepared in DMSO include an increased number of linkages between the carbohydrate (capsular polysaccharide) and lysine residues on the surface of the carrier protein which would result in additional attachment points between the protein and polysaccharide to impart stability and counter chemical depolymerization or breakdown of the peptide carbohydrate bond. See, e.g., Hsieh, Characterization of Saccharide-CRM197 Conjugate Vaccines in Brown F, Corbel M, Griffiths E (eds): Physico-Chemical Procedures for the Characterization of Vaccines. Dev. Biol. Basel, Karger, 2000, vol 103, pp. 93-104. An additional benefit of the increased polysaccharide-protein linkages that are created during conjugation in the DMSO solvent could be additional opportunities for successful presentation of peptide-carbohydrate to T-cells. It can be appreciated that due to the genetic variability in the human population resulting in varying abilities and sensitivity of loading or associating with specific peptide sequences conjugated to carbohydrate antigens, that additional points of attachment on the carrier protein would allow for increased chances for successful antigen presentation at the surface of an antigen presenting cell (APC) to allow for a T-cell dependent response to an otherwise T-cell independent antigen. Another possible mechanism of enhanced immunogenicity observed by conjugation in the DMSO solvent could be due to the denaturation of CRM197 in organic solvent, which exposes additional lysines for polysaccharide linkages giving increased chances for glycopeptide presentation at the surface of an APC for T-cell dependent response to different peptide epitopes. See Avci et al., 2011, Nature Medicine 17: 1602-1610.

Yet another benefit of conjugation in an organic solvent generating denatured CRM197 in the conjugates could be reduced immunological interference of antibodies against native CRM197 epitopes. A further benefit of the increased polysaccharide-protein linkages that are created during conjugation in the DMSO solvent could be the formation of larger sized polysaccharide protein conjugates resulting in enhanced immunogenicity. The compositions of the invention are believed to provide significant advantages in eliciting a human response.

In certain embodiments, the conjugation reaction is performed by reductive amination wherein nickel is used for greater conjugation reaction efficiency and to aid in free cyanide removal. Transition metals are known to form stable complexes with cyanide and are known to improve reductive methylation of protein amino groups and formaldehyde with sodium cyanoborohydride (S Gidley et al., *Biochem J.* 1982, 203: 331-334; Jentoft et al. *Anal Biochem.* 1980, 106: 186-190). By complexing residual, inhibitory cyanide, the addition of nickel increases the consumption of protein during the conjugation and leads to formation of larger, potentially more immunogenic conjugates.

Differences in starting cyanide levels in sodium cyanoborohydride reagent lots also lead to inconsistent conjugation performance, resulting in variable product attributes, such as conjugate size and conjugate Ps-to-CRM197 ratio. The addition of nickel reduced conjugation inconsistency by complexing cyanide, eliminating differences in sodium cyanoborohydride lots.

Suitable alternative chemistries include the activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g. EDAC or EDC) chemistry via a carboxyl group on the protein carrier. Such conjugates are described in International Patent Application Publication Nos. WO 93/15760, WO 95/08348 and WO 96/29094; and Chu et al., 1983, Infect. Immunity 40:245-256.

Other suitable techniques use carbodiimides, hydrazides, active esters, norborane, p-nitrobenzoic acid, N-hydroxysuccinimide, S—NHS, EDC, TSTU. Many are described in International Patent Application Publication No. WO 98/42721. Conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18) followed by reaction of with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

After conjugation of the capsular polysaccharide to the carrier protein, the polysaccharide-protein conjugates are purified (enriched with respect to the amount of polysaccharide-protein conjugate) by one or more of a variety of techniques. Examples of these techniques are well known to the skilled artisan and include concentration/diafiltration operations, ultrafiltration, precipitation/elution, column chromatography, and depth filtration. See, e.g., U.S. Pat. No. 6,146,902.

After the individual glycoconjugates are purified, they are compounded to formulate the immunogenic composition of the present invention. These pneumococcal conjugates are prepared by separate processes and bulk formulated into a single dosage formulation.

An alternative method for characterizing the glycoconjugates of the invention is by the number of lysine residues in the carrier protein (e.g., CRM197) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In a preferred embodiment, the degree of conjugation of the glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the glycoconjugate of the invention is about 2, about 3, about 4, about 5, about 6, about 7, about 8, about 9, about 10, about 11, about 12, about 13, about 14 or about 15. In a preferred embodiment, the degree of conjugation of the glycoconjugate of the invention is between 4 and 7. In some such embodiments, the carrier protein is CRM197.

The glycoconjugates of the compositions of the invention may also be characterized by the ratio (weight/weight) of saccharide to carrier protein (Ps:Pr). In some embodiments, the ratio of polysaccharide to carrier protein of the glycoconjugates (w/w) in the composition is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.5, between 0.5 and 1.5, between 0.8 and 2.5, between 0.5 and 1.0, between 1.0 and 1.5, between 1.0 and 2.0, between 0.8 and 2.4, between 0.8 and 2.3, between 0.8 and 2.2, between 0.8 and 2.1, between 0.8 and 2.0, between 0.8 and 1.9, between 0.8 and 1.8, between 0.8 and 1.7, between 0.8 and 1.6, between 0.8 and 1.5, between 0.8 and 1.4, between 0.8 and 1.3, between 0.9 and 2.4, between 0.9 and 2.3, between 0.9 and 2.2, between 0.9 and 2.1, between 0.9 and 2.0, between 0.9 and 1.9, between 0.9 and 1.8, between 0.9 and 1.7, between 0.9 and 1.6, between 0.9 and 1.5, between 0.9 and 1.4, between 0.9 and 1.3, between 0.9 and 1.2, between 1.0 and 2.4, between 1.0 and 2.3, between 1.0 and 2.2, between 1.0 and 2.1, between 1.0 and 2.0, between 1.0 and 1.9, between 1.0 and 1.8, between 1.0 and 1.7, between 1.0 and 1.6, between 1.0 and 1.5, between 1.0 and 1.4, between 1.0 and 1.3 or between 1.0 and 1.2. In further embodiments, the saccharide to carrier protein ratio (w/w) is between 0.8 and 1.2. In some such embodiments, the carrier protein is CRM197. The glycoconjugates and immunogenic compositions of the invention may contain free saccharide that is not covalently conjugated to the carrier protein, but is nevertheless present in the glycoconjugate composition. The free saccharide may be non-covalently associated with (i.e., non-covalently bound to, adsorbed to, or entrapped in or with) the glycoconjugate.

In specific embodiments, the saccharide to carrier protein ratio (w/w) for the serotype 15A conjugate is from about 1.0 to about 2.0, from about 1.25 to about 1.75, or from about 1.3 to about 1.7. In other embodiments, the saccharide to carrier protein ratio (w/w) for serotype 15A is about 1.1, 1.2, 1.3, 1.4, 1.5, 1.6, 1.7, or 1.8.

In specific embodiments, the saccharide to carrier protein ratio (w/w) for the serotype 15C conjugate is from about 1.0 to about 2.0, from about 1.25 to about 1.75, or from about 1.3 to about 1.7. In other embodiments, the saccharide to carrier protein ratio (w/w) for serotype 15C is about 1.1, 1.2, 1.3, 1.4, 1.5, 1.6, 1.7, or 1.8.

In specific embodiments, the saccharide to carrier protein ratio (w/w) for the serotype 33F conjugate is from about 1.0 to about 2.0, from about 1.25 to about 1.75, or from about 1.3 to about 1.7. In other embodiments, the saccharide to carrier protein ratio (w/w) for serotype 33F is about 1.1, 1.2, 1.3, 1.4, 1.5, 1.6, 1.7, or 1.8.

In specific embodiments, the saccharide to carrier protein ratio (w/w) for the serotype 35B conjugate is from about 1.25 to about 2.25, from about 1.25 to about 2.0, or from about 1.3 to about 1.8. In other embodiments, the saccharide to carrier protein ratio (w/w) for serotype 33B is about 1.2, 1.3, 1.3, 1.5, 1.6, 1.7, 1.8, 1.9, or 2.0.

In specific embodiments, the saccharide to carrier protein ratio (w/w) for the serotype 24F conjugate is from about 0.5 to about 1.5, from about 0.75 to about 1.25, or from about 0.8 to about 1.0. In other embodiments, the saccharide to carrier protein ratio (w/w) for serotype 24F is about 0.5, 0.6, 0.7, 0.8, 0.9, or 1.0.

In a preferred embodiment, the glycoconjugate comprises less than about 50%, 45%, 40%, 35%, 30%, 25%, 20% or 15% of free polysaccharide compared to the total amount of polysaccharide. In a preferred embodiment the glycoconjugate comprises less than about 25% of free polysaccharide compared to the total amount of polysaccharide. In a preferred embodiment the glycoconjugate comprises less than about 20% of free polysaccharide compared to the total amount of polysaccharide. In a preferred embodiment the glycoconjugate comprises less than about 15% of free polysaccharide compared to the total amount of polysaccharide.

IV. METHODS OF USE

Embodiments of the invention also include one or more of the multivalent immunogenic compositions described herein (i) for use in, (ii) for use as a medicament or composition for, or (iii) for use in the preparation of a medicament for: (a) therapy (e.g., of the human body); (b) medicine; (c) inhibition of infection with *Streptococcus pneumoniae*; (d) induction of an immune response or a protective immune response against *S. pneumoniae*; (e) prophylaxis of infection by *S. pneumoniae*; (f) prevention of recurrence of *S. pneumoniae* infection; (g) reduction of the progression, onset or severity of pathological symptoms associated with *S. pneumoniae* infection including the prevention of associated complications such as brain damage, hearing loss, and seizures, (h) reduction of the likelihood of a *S. pneumoniae* infection or, (i) treatment, prophylaxis of, or delay in the onset, severity, or progression of pneumococcal disease(s), including, but not limited to: pneumococcal pneumonia, pneumococcal bacteremia, pneumococcal meningitis, otits media and sinusitis. In these uses, the multivalent pneumococcal polysaccharide-conjugate compositions of the invention can optionally be employed in combination with one or more adjuvants, or without an adjuvant.

Accordingly, the invention provides methods for the prophylactic treatment of (i.e. protection against) *S. pneumoniae* infection or pneumococcal disease comprising administering one or more of the multivalent immunogenic pneumococcal polysaccharide-protein conjugate compositions of the invention to a patient in need of treatment.

The compositions and formulations of the present invention can be used to protect or treat a human susceptible to infection, e.g., a pneumococcal infection, by means of administering a composition of the invention via a systemic or mucosal route.

In one embodiment, the invention provides a method of inducing an immune response to *S. pneumoniae*, comprising administering to a patient an immunologically effective amount of a multivalent immunogenic composition of the invention. In another embodiment, the invention provides a method of vaccinating a human against a pneumococcal infection, comprising the step of administering to the human an immunogically effective amount of a multivalent immunogenic composition of the invention.

Thus, in one aspect, the invention provides a method for (1) inducing an immune response in a human patient, (2) inducing a protective immune response in a human patient, (3) vaccinating a human patient against an infection with *S. pneumoniae*, or (4) reducing the likelihood of a *S. pneumoniae* infection in a human patient, the method comprising administering a multivalent immunogenic composition of the invention to the patient (i.e. any multivalent immunogenic composition described herein, such as the multivalent immunogenic compositions described in Section II, entitled "Multivalent Immunogenic Compositions," supra).

In one embodiment, the invention provides a method for the prevention of pneumococcal *pneumoniae* and invasive disease in adults 18 years of age and older. In another embodiment, the invention provides a method for the prevention of pneumococcal *pneumoniae* and invasive disease caused by the 24 *Streptococcus pneumoniae* strains (3, 6A, 6C, 7F, 8, 9N, 10A, 11A 12F, 15A, 15B, 15C, 16F, 17F, 19A, 20A, 20B, 22F, 23A, 23B, 24F, 31, 33F, and 35B).

In one embodiment of the methods above, the composition comprises multiple *S. pneumoniae* polysaccharide protein conjugates wherein each of the conjugates comprises a polysaccharide from an *S. pneumoniae* serotype conjugated to a carrier protein, wherein the serotypes of *S. pneumoniae* comprise the set of serotypes: 3, 7F, 19A, 22F, 33F, 15A, 16F, 23A, 23B, 24F, 31, 35B, 8, 9N, 10A, 11A, 12F, 15C, 17F, and 20A. In one embodiment of the methods above, the composition comprises multiple *S. pneumoniae* polysaccharide protein conjugates wherein each of the conjugates comprises a polysaccharide from an *S. pneumoniae* serotype conjugated to a carrier protein, wherein the serotypes of *S. pneumoniae* comprise the set of serotypes: 3, 7F, 19A, 22F, 33F, 15A, 16F, 23A, 23B, 24F, 31, 35B, 8, 9N, 10A, 11A, 12F, 15C, 17F, and 20. In one embodiment of the methods above, the composition comprises multiple *S. pneumoniae* polysaccharide protein conjugates wherein each of the conjugates comprises a polysaccharide from an *S. pneumoniae* serotype conjugated to a carrier protein, wherein the serotypes of *S. pneumoniae* comprise the set of serotypes: 3, 7F, 19A, 22F, 33F, 15A, 16F, 23A, 23B, 24F, 31, 35B, 8, 9N, 10A, 11A, 12F, 15C, 17F, and 20B. In another embodiment of the methods above, the composition further comprises a *S. pneumoniae* polysaccharide protein conjugate of serotype 6A or 6C.

It has been shown that a pneumococcal conjugate vaccine comprising serotype 6A may provide some cross-protection against serotype 6C (Cooper et al., Vaccine 29 (2011) 7207-7211). Therefore, in some embodiments of the methods above, the invention also provides use of multivalent immunogenic compositions that do not comprise serotype 6C, but instead comprise serotype 6A or serotypes 6A and 6B. In other embodiments, the immunogenic composition comprises pneumococcal conjugates of serotypes 6A, 6B, and 6C. In particular embodiments of the methods above, the serotypes of *S. pneumoniae* comprise a set of serotypes selected from the group consisting of:

I-a) 3, 7F, 19A, 22F, 33F, 15A, 16F, 23A, 23B, 24F, 31, 35B, 8, 9N, 10A, 11A, 12F, 15C, 17F, and 20A;
I-b) 3, 7F, 19A, 22F, 33F, 6A, 15A, 16F, 23A, 23B, 24F, 31, 35B, 8, 9N, 10A, 11A, 12F, 15C, 17F, and 20A;
I-c) 3, 7F, 19A, 22F, 33F, 6A, 6B, 15A, 16F, 23A, 23B, 24F, 31, 35B, 8, 9N, 10A, 11A, 12F, 15C, 17F, and 20A; and
I-d) 3, 7F, 19A, 22F, 33F, 6C, 15A, 16F, 23A, 23B, 24F, 31, 35B, 8, 9N, 10A, 11A, 12F, 15C, 17F, and 20A.

In particular embodiments of the set of serotypes above (I-a to I-d), serotype 20 or 20B may be substituted for serotype 20A.

In further embodiments of the methods above, the serotypes of *S. pneumoniae* comprise a set of serotypes selected from the group consisting of:

II-a) 15A, 16F, 23A, 23B, 24F, 31 and 35B;
II-b) 6A, 15A, 16F, 23A, 23B, 24F, 31 and 35B;
II-c) 6A, 6B, 15A, 16F, 23A, 23B, 24F, 31 and 35B;

II-d) 6C, 15A, 16F, 23A, 23B, 24F, 31 and 35B;
II-e) 15A, 16F, 23A, 23B, 24F, 31, 35B, 8, 9N, 10A, 11A, 12F, 15C, 17F, and 20A;
II-f) 6A, 15A, 16F, 23A, 23B, 24F, 31, 35B, 8, 9N, 10A, 11A, 12F, 15C, 17F, and 20A;
II-g) 6A, 6B, 15A, 16F, 23A, 23B, 24F, 31, 35B, 8, 9N, 10A, 11A, 12F, 15C, 17F, and 20A; and
II-h) 6C, 15A, 16F, 23A, 23B, 24F, 31, 35B, 8, 9N, 10A, 11A, 12F, 15C, 17F, and 20A.

In particular embodiments of the set of serotypes above (II-e to IIh), serotype 20 or 20B may be substituted for serotype 20A.

In further embodiments of the methods above, the serotypes of S. pneumoniae comprise a set of serotypes as set forth in any of embodiments I-a), II-a) or II-e) and further comprise serotypes 6A, 6B, and 6C.

It has also been shown that a pneumococcal conjugate vaccine comprising serotype 10A may provide some cross-protection against serotype 39 (see WO 2017/085586). Therefore, in some embodiments of the methods above, the invention also provides use of multivalent immunogenic compositions that do not comprise serotype 10A, but instead comprise serotype 39. In other embodiments, the immunogenic composition comprises pneumococcal conjugates of serotypes 10A and 39. In particular embodiments of the methods above, the serotypes of S. pneumoniae comprise a set of serotypes selected from the group consisting of:

III-a) 3, 7F, 19A, 22F, 33F, 15A, 16F, 23A, 23B, 24F, 31, 35B, 8, 9N, 39, 11A, 12F, 15C, 17F, and 20A;
III-b) 3, 7F, 19A, 22F, 33F, 6A, 15A, 16F, 23A, 23B, 24F, 31, 35B, 8, 9N, 39, 11A, 12F, 15C, 17F, and 20A;
III-c) 3, 7F, 19A, 22F, 33F, 6A, 6B, 15A, 16F, 23A, 23B, 24F, 31, 35B, 8, 9N, 39, 11A, 12F, 15C, 17F, and 20A;
III-d) 3, 7F, 19A, 22F, 33F, 6C, 15A, 16F, 23A, 23B, 24F, 31, 35B, 8, 9N, 39, 11A, 12F, 15C, 17F, and 20A;
III-e) 15A, 16F, 23A, 23B, 24F, 31, 35B, 8, 9N, 39, 11A, 12F, 15C, 17F, and 20A;
III-f) 6A, 15A, 16F, 23A, 23B, 24F, 31, 35B, 8, 9N, 39, 11A, 12F, 15C, 17F, and 20A;
III-g) 6A, 6B, 15A, 16F, 23A, 23B, 24F, 31, 35B, 8, 9N, 39, 11A, 12F, 15C, 17F, and 20A; and
III-h) 6C, 15A, 16F, 23A, 23B, 24F, 31, 35B, 8, 9N, 39, 11A, 12F, 15C, 17F, and 20A.

In particular embodiments of the set of serotypes above (II-a to III-h), serotype 20 or 20B may be substituted for serotype 20A.

In further embodiments of the methods above, the serotypes of S. pneumoniae comprise a set of serotypes as set forth in any of embodiments III-a) to III-h) and further comprise serotype 10A.

It has also been shown that immunogenic conjugates comprising S. pneumoniae serotype 15B capsular polysaccharide covalently linked to a carrier protein may provide some cross-protection against serotype 15C and/or serotype 15A (see WO 2015/110942). Therefore, in some embodiments of the methods above, the invention also provides use of multivalent immunogenic compositions that do not comprise serotype 15C (or de-O-acetylated 15B), but instead comprise serotype 15B (i.e. the serotype 15B polysaccharide is not de-O-acetylated). In other embodiments, the immunogenic composition comprises pneumococcal conjugates of serotypes 15B and 15C (or de-O-acetylated 15B). In particular embodiments of the methods above, the serotypes of S. pneumoniae comprise a set of serotypes selected from the group consisting of:

IV-a) 3, 7F, 19A, 22F, 33F, 15A, 16F, 23A, 23B, 24F, 31, 35B, 8, 9N, 10A, 11A, 12F, 15B, 17F, and 20A;
IV-b) 3, 7F, 19A, 22F, 33F, 6A, 15A, 16F, 23A, 23B, 24F, 31, 35B, 8, 9N, 10A, 11A, 12F, 15B, 17F, and 20A,
IV-c) 3, 7F, 19A, 22F, 33F, 6A, 6B, 15A, 16F, 23A, 23B, 24F, 31, 35B, 8, 9N, 10A, 11A, 12F, 15B, 17F, and 20A;
IV-d) 3, 7F, 19A, 22F, 33F, 6C, 15A, 16F, 23A, 23B, 24F, 31, 35B, 8, 9N, 10A, 11A, 12F, 15B, 17F, and 20A,
IV-e) 15A, 16F, 23A, 23B, 24F, 31, 35B, 8, 9N, 10A 11A, 12F, 15B, 17F, and 20A;
IV-f) 6A, 15A, 16F, 23A, 23B, 24F, 31, 35B, 8, 9N, 10A, 11A, 12F, 15B, 17F, and 20A;
IV-g) 6A, 6B, 15A, 16F, 23A, 23B, 24F, 31, 35B, 8, 9N, 10A, 11A, 12F, 15B, 17F, and 20A;
IV-h) 6C, 15A, 16F, 23A, 23B, 24F, 31, 35B, 8, 9N, 10A, 11A, 12F, 15B, 17F, and 20A;

In particular embodiments of the set of serotypes above (IVa to IVh), serotype 20 or 20B may be substituted for serotype 20A.

In further embodiments of the methods above, the serotypes of S. pneumoniae comprise a set of serotypes as set forth in any of embodiments IV-a) to IV-h) and further comprise serotype 15C (and/or de-O-acetylated 15B).

The compositions of the invention are useful in methods for providing complementary protection against S. pneumoniae in patients who had previously received a multivalent pneumococcal vaccine. In this use, the compositions of the invention can provide protection against particular S. pneumoniae serotypes that a patient had not been previously vaccinated against, can provide additional protection against S. pneumoniae serotypes that a patient had been previously vaccinated against, or can provide protection against both S. pneumoniae serotypes that a patient had not been previously vaccinated against and S. pneumoniae serotypes that a patient had been previously vaccinated against.

Thus, the invention provides a method of inducing an immune response, vaccinating, or inducing a protective immune response against S. pneumoniae in a patient, comprising administering a multivalent immunogenic composition to the patient, the composition comprising multiple S. pneumoniae polysaccharide protein conjugates, wherein the polysaccharide protein conjugates comprise capsular polysaccharide from a S. pneumoniae serotype conjugated to a carrier protein, wherein the patient had previously been vaccinated against S. pneumoniae. In embodiments of this aspect of the invention, the multivalent immunogenic composition can be any multivalent immunogenic composition described herein. In particular embodiments of the methods of the invention, the multivalent immunogenic composition is administered to a patient who was previously treated with a multivalent pneumococcal vaccine. The multivalent immunogenic vaccine may be any vaccine that is indicated for the prevention of pneumococcal disease caused by more than one serotype of S. pneumoniae.

In specific embodiments of the method above, the patient was previously treated with a multivalent pneumococcal vaccine that is indicated for the prevention of pneumococcal disease caused by S. pneumoniae serotypes selected from the group consisting of:
a) 4, 6B, 9V, 14, 18C, 19F and 23F;
b) 4, 6B, 9V, 14, 18C, 19F, 23F, 1, 3, 5, 6A, 7F, and 19A;
c) 1, 4, 5, 6B, 7F, 9V, 14, 18C, 19F and 23F;
d) 4, 6B, 9V, 14, 18C, 19F, 23F, 1, 3, 5, 6A, 7F, 19A, 22F, and 33F;
e) 4, 6B, 9V, 14, 18C, 19F, 23F, 1, 3, 5, 7F, 19A, 22F, 33F, 2, 8, 9N, 10A, 11A, 12F, 15B, 17F, and 20; and
f) 4, 6B, 9V, 14, 18C, 19F, 23F, 1, 3, 5, 6A, 7F, 19A, 22F, 33F, 8, 10A, 11A, 12F and 15B.

In specific embodiments of the method above, the multivalent pneumococcal vaccine comprises capsular polysaccharides of *S. pneumoniae* serotypes 4, 6B, 9V, 14, 18C, 19F, 23F, 1, 3, 5, 7F, 19A, 22F, 33F, 2, 8, 9N, 10A, 11A, 12F, 15B, 17F, and 20A. In specific embodiments of the method above, the multivalent pneumococcal vaccine comprises capsular polysaccharides of *S. pneumoniae* serotypes 4, 6B, 9V, 14, 18C, 19F, 23F, 1, 3, 5, 7F, 19A, 22F, 33F, 2, 8, 9N, 10A, 11A, 12F, 15B, 17F, and 20. In specific embodiments of the method above, the multivalent pneumococcal vaccine comprises capsular polysaccharides of *S. pneumoniae* serotypes 4, 6B, 9V, 14, 18C, 19F, 23F, 1, 3, 5, 7F, 19A, 22F, 33F, 2, 8, 9N, 10A, 11A, 12F, 15B, 17F, and 20B.

In specific embodiments of the method above, the multivalent pneumococcal vaccine comprises multiple polysaccharide protein conjugates, wherein the polysaccharide protein conjugates comprise polysaccharide from a *S. pneumoniae* serotype conjugated to a carrier protein. In other embodiments, the multivalent pneumococcal vaccine comprises multiple *S. pneumoniae* capsular polysaccharides that are not conjugated to a carrier protein.

In additional embodiments of the method above, the patient was previously treated with PREVNAR® 13 (Pneumococcal 13-valent Conjugate Vaccine [Diphtheria CRM197 Protein], Pfizer, Inc., Philadelphia, PA, USA).

In further embodiments of the method above, the patient was previously treated with PNEUMOVAX® 23 (Pneomoccoal Vaccine Polyvalent, Merck & Co., Inc., Kenilworth, NJ, USA).

In still further embodiments of the method above, the patient was previously treated with SYNFLORIX™ (Pneumococcal polysaccharide conjugate vaccine (adsorbed), GlaxoSmithKline Biologicals s.a., Rixensart, Belgium).

In embodiments of the method above, the multivalent immunogenic composition of the invention is administered to a patient at any time after the patient has received a multivalent pneumococcal vaccine, according to the treatment regimen provided by the medical professional, e.g. a physician. In particular embodiments, the multivalent immunogenic composition of the invention is administered to a patient from 1 month to 5 years after the patient has received the multivalent pneumococcal vaccine, alternatively, from 1 month to 1 year, from 1 month to 2 years, from 1 month to 3 years, from 1 month to 4 years, from 1 month to 6 months, from 2 months to 6 months, from 2 months to 1 year, from 1 year to 5 years, from 6 months to 5 years, from 6 months to 4 years, from 6 months to 3 years, from 6 months to 2 years, from 6 months to 1 year, from 1 year to 4 years, from 1 year to 3 years, or from 1 year to 2 years, after the patient has received the multivalent pneumococcal vaccine. In further embodiments, the multivalent immunogenic composition is administered to the patient about 1 month, about 2 months, about 3 months, about 4 months, about 5 months, about 6 months, about 7 months, about 8 months, about 9 months, about 10 months, about 11 months, about 1 year, about 1.25 years, about 1.5 years, about 1.75 years, about 2 years, about 2.25 years, about 2.5 years, about 2.75 years, about 3 years, about 3.25 years, about 3.5 years, about 3.75 years, about 4 years, about 4.25 years, about 4.5 years, about 4.75 years, or about 5 years after the patient has received the multivalent pneumococcal vaccine.

In further embodiments, the invention provides a method for (1) inducing an immune response in a human patient, (2) inducing a protective immune response in a human patient, (3) vaccinating a human patient against an infection with *S. pneumoniae*, or (4) reducing the likelihood of a *S. pneumoniae* infection in a human patient, the method comprising administering a multivalent immunogenic composition of the invention and administering a multivalent pneumococcal vaccine to the patient, in any order. The multivalent pneumococcal vaccine may be any vaccine indicated for the prevention of pneumococcal disease caused by more than one serotype of *S. pneumoniae*.

In specific embodiments of the method above, the patient is treated with a multivalent immunogenic composition of the invention and a multivalent pneumococcal vaccine that is indicated for the prevention of pneumococcal disease caused by *S. pneumoniae* serotypes selected from the group consisting of:
a) 4, 6B, 9V, 14, 18C, 19F and 23F;
b) 4, 6B, 9V, 14, 18C, 19F, 23F, 1, 3, 5, 6A, 7F, and 19A;
c) 1, 4, 5, 6B, 7F, 9V, 14, 18C, 19F and 23F;
d) 4, 6B, 9V, 14, 18C, 19F, 23F, 1, 3, 5, 6A, 7F, 19A, 22F, and 33F;
e) 4, 6B, 9V, 14, 18C, 19F, 23F, 1, 3, 5, 7F, 19A, 22F, 33F, 2, 8, 9N, 10A, 11A, 12F, 15B, 17F, and 20; and
f) 4, 6B, 9V, 14, 18C, 19F, 23F, 1, 3, 5, 6A, 7F, 19A, 22F, 33F, 8, 10A, 11A, 12F and 15B.

In specific embodiments of the method above, the multivalent pneumococcal vaccine comprises capsular polysaccharides of *S. pneumoniae* serotypes 4, 6B, 9V, 14, 18C, 19F, 23F, 1, 3, 5, 7F, 19A, 22F, 33F, 2, 8, 9N, 10A, 11A, 12F, 15B, 17F, and 20A.

In specific embodiments of the method above, the multivalent pneumococcal vaccine comprises multiple polysaccharide protein conjugates, wherein the polysaccharide protein conjugates comprise polysaccharide from a *S. pneumoniae* serotype conjugated to a carrier protein. In other embodiments, the multivalent pneumococcal vaccine comprises multiple *S. pneumoniae* capsular polysaccharides that are not conjugated to a carrier protein.

In additional embodiments of the method above, the patient is treated with a multivalent immunogenic composition of the invention and is treated with PREVNAR® 13 (Pneumococcal 13-valent Conjugate Vaccine [Diphtheria CRM197 Protein], Pfizer, Inc., Philadelphia, PA, USA), in any order. In one embodiment, the patient is administered PREVNAR® 13 first and the patient is administered a multivalent immunogenic composition of the invention second. In alternative embodiments, the patient is administered a multivalent immunogenic composition of the invention first and is administered PREVNAR® 13 second.

In further embodiments of the method above, the patient is treated with a multivalent immunogenic composition of the invention and is treated with PNEUMOVAX® 23 (pneomoccoal vaccine polyvalent, Merck & Co., Inc., Kenilworth, NJ, USA), in any order. In one embodiment, the patient is administered PNEUMOVAX® 23 first and the patient is administered a multivalent immunogenic composition of the invention second. In alternative embodiments, the patient is administered a multivalent immunogenic composition of the invention first and is administered PNEUMOVAX® 23 second.

In still further embodiments of the method above, the patient is treated with a multivalent immunogenic composition of the invention and is treated with SYNFLORIX™ (Pneumococcal polysaccharide conjugate vaccine (adsorbed), GlaxoSmithKline Biologicals s.a., Rixensart, Belgium), in any order. In one embodiment, the patient is administered SYNFLORIX™ first and the patient is administered a multivalent immunogenic composition of the invention second. In alternative embodiment, the patient is administered a multivalent immunogenic composition of the invention first and is administered SYNFLORIX™ second.

In some embodiments of the method above, the multivalent immunogenic composition and the multivalent pneumococcal vaccine are administered concurrently. As used herein, "concurrent administration" is not limited to dosing of two compositions at the same time, but includes administration one right after the other in any order. In some embodiments, the multivalent immunogenic composition and the multivalent pneumococcal vaccine are administered via intramuscular or subcutaneous administration into separate anatomical sites, e.g. two different arms.

In some embodiments of the method above, the amount of time between administration of the multivalent immunogenic composition of the invention and the multivalent pneumococcal vaccine is from about 4 weeks to about 1 year. In alternative embodiments, the amount of time is from about 1 month to about 5 years.

In one embodiment, the patient is administered the multivalent pneumococcal vaccine first and the multivalent immunogenic composition of the invention second. In alternative embodiments, the patient is administered a multivalent immunogenic composition of the invention first and is administered the multivalent pneumococcal vaccine second.

Also provided is a method of inducing an immune response, vaccinating or inducing a protective immune response against S. pneumoniae in a patient, comprising:
(1) administering a multivalent immunogenic composition to the patient, the composition comprising multiple S. pneumoniae polysaccharide protein conjugates, wherein each of the polysaccharide protein conjugates comprise capsular polysaccharide from a S. pneumoniae serotype conjugated to a carrier protein,
(2) waiting for a pre-determined amount of time to pass, and
(3) administering a multivalent pneumococcal vaccine to the patient.

In this method, the multivalent immunogenic composition can comprise any combination of S. pneumoniae polysaccharide protein conjugates set forth herein and the multivalent pneumococcal vaccine can be any vaccine indicated for the prevention of disease caused by more than one serotype of S. pneumoniae.

Also provided by the invention is a method of inducing an immune response, vaccinating or inducing a protective immune response against S. pneumoniae in a patient, comprising:
(1) administering a multivalent pneumococcal vaccine to the patient,
(2) waiting for a pre-determined amount of time to pass, and
(3) administering a multivalent immunogenic composition to the patient, the composition comprising multiple S. pneumoniae polysaccharide protein conjugates, wherein each of the polysaccharide protein conjugates comprise capsular polysaccharide from a S. pneumoniae serotype conjugated to a carrier protein.

In this method, the multivalent immunogenic composition can comprise any combination of S. pneumoniae polysaccharide protein conjugates set forth herein and the multivalent pneumococcal vaccine can be any vaccine indicated for the prevention of disease caused by more than one serotype of S. pneumoniae.

In some embodiments of the methods above, the multivalent pneumococcal vaccine comprises multiple S. pneumoniae polysaccharide protein conjugates, wherein the polysaccharide protein conjugates comprise capsular polysaccharide from a S. pneumoniae serotype conjugated to a carrier protein. In alternative embodiments, the multivalent pneumococcal vaccine comprises S. pneumoniae capsular polysaccharides that are not conjugated to a carrier protein.

In any embodiments of the methods of the invention (i.e. any of the methods described herein), the method may further comprise administering one or more additional doses of a multivalent immunogenic composition of the invention to the patient. In such methods, the patient may have already received a multivalent pneumococcal vaccine prior to receiving a first dose of a multivalent immunogenic composition of the invention, supra, or may not have been vaccinated against S. pneumoniae prior to receiving a multivalent immunogenic composition of the invention. Thus, in one embodiment, a patient who had received a multivalent pneumococcal vaccine indicated for the prevention of pneumococcal disease caused by S. pneumoniae is administered two or more doses of a multivalent immunogenic composition of the invention. In alternative embodiments, a patient who had not been previously treated with any vaccine indicated for the prevention of pneumococcal disease, is administered two or more doses of a multivalent immunogenic composition of the invention.

In embodiments of the method above, the two or more doses are of the same multivalent immunogenic composition of the invention. In alternative embodiments, the two or more doses are of different multivalent immunogenic compositions of the invention.

In specific embodiments of any of these methods, the patient is administered two, three, or four doses of a multivalent immunogenic composition of the invention. In particular embodiments, the patient is immunocompromised (e.g., on an immunosuppressive regimen following a stem cell transplant) and the number of doses is three.

In some embodiments, the amount of time between administration of each dose of multivalent immunogenic composition of the invention is from about 4 weeks to about 1 year. In alternative embodiment, the amount of time between administration of each dose of multivalent immunogenic composition of the invention is from about 1 month to about 5 years.

In embodiments of any of the methods of the invention, the patient to be treated with the composition(s) of the invention is a human. In certain embodiments, the human patient is a toddler (approximately 12 to 24 months), or young child (approximately 2 to 5 years). The compositions of this invention are also suitable for use with older children, adolescents and adults (e.g., aged 18 to 45 years, aged 18 to 50 years, aged 18 to 55 years, aged 18 to 60 years or 18 to 65 years). In other embodiments of any of the methods of the invention, the patient is from about 2 to about 18 years of age. In further embodiments of any of the methods of the invention, the patient is 18 years of age or older.

In further embodiments of the methods of the invention, the human patient is elderly. In some embodiments of any of the methods of the invention, the patient is 50 years of age or older. In some embodiments of any of the methods of the invention, the patient is 55 years of age or older. In some embodiments of any of the methods of the invention, the patient is 60 years of age or older. In still further embodiments of any of the methods of the invention, the patient is 65 years of age or older. In additional embodiments of any of the methods of the invention, the patient is 70 years of age or older.

In some embodiments of any of the methods of the invention, the patient to be treated with an immunogenic composition of the invention is immunocompromised.

In some embodiments of any of the methods of the invention, the multivalent immunogenic composition is administered concomitantly with a vaccine against influenza. In certain embodiments, the influenza vaccine is a "senior flu vaccine," a high dose flu vaccine indicated for the elderly, e.g. persons aged 65 and older.

The invention provides a method for inducing a protective immune response in a patient against a pneomococcal infection comprising the step of administering to the patient an immunologically effective amount of any of the multivalent immunogenic pneumococcal polysaccharide-protein conjugate compositions described herein. Optimal amounts of components for a particular vaccine (i.e. multivalent immunogenic composition) can be ascertained by standard studies involving observation of appropriate immune responses in subjects. For example, in another embodiment, the dosage for human vaccination is determined by extrapolation from animal studies to human data. In another embodiment, the dosage is determined empirically.

The methods of the invention can be used for the prevention and/or reduction of primary clinical syndromes caused by microbes, e.g., *S. pneumonia*, including both invasive infections (meningitis, pneumonia, and bacteremia), and noninvasive infections (acute otitis media, and sinusitis).

Administration of the compositions of the invention can include one or more of: injection via the intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage). In specific embodiments, the compositions of the invention are administered to the patient via intramuscular or subcutaneous administration.

ADDITIONAL EMBODIMENTS OF THE INSTANT INVENTION (1) A multivalent immunogenic composition comprising *S. pneumoniae* polysaccharide protein conjugates wherein each of the conjugates comprises a polysaccharide from an *S. pneumoniae* serotype conjugated to a carrier protein, wherein the serotypes of *S. pneumoniae* in the polysaccharide protein conjugates comprise a set of serotypes selected from the group consisting of:
  a) 15A, 16F, 23A, 23B, 24F, 31 and 35B;
  b) 15A, 16F, 23A, 23B, 24F, 31, 35B, 8, 9N, 10A, 11A, 12F, 15C, 17F, and 20; and
  c) 3, 7F, 19A, 22F, 33F, 15A, 16F, 23A, 23B, 24F, 31, 35B, 8, 9N, 10A, 11A, 12F, 15C, 17F, and 20.
(2) The multivalent immunogenic composition of embodiment 1, wherein the set of serotypes of *S. pneumoniae* listed in a), b) or c) further comprises:
  (i) serotype 6C,
  (ii) serotype 6A, or
  (iii) serotypes 6A and 6B.
(3) The multivalent immunogenic composition of embodiment 1, wherein the serotypes of *S. pneumoniae* comprise a set of serotypes selected from the group consisting of:
  a) 6C, 15A, 16F, 23A, 23B, 24F, 31, 35B, 8, 9N, 10A, 11A, 12F, 15C, 17F, and 20;
  b) 6A, 15A, 16F, 23A, 23B, 24F, 31, 35B, 8, 9N, 10A, 11A, 12F, 15C, 17F, and 20; and
  c) 6A, 6B, 15A, 16F, 23A, 23B, 24F, 31, 35B, 8, 9N, 10A, 11A, 12F, 15C, 17F, and 20
wherein serotype 20 in sets a) to c) may be optionally substituted with either serotype 20A or serotype 20B.
(4) The multivalent immunogenic composition of embodiment 1, wherein the serotypes of *S. pneumoniae* comprise a set of serotypes selected from the group consisting of:
  a) 3, 7F, 19A, 22F, 33F, 6C, 15A, 16F, 23A, 23B, 24F, 31, 35B, 8, 9N, 10A, 11A, 12F, 15C, 17F, and 20A;
  b) 3, 7F, 19A, 22F, 33F, 6A, 15A, 16F, 23A, 23B, 24F, 31, 35B, 8, 9N, 10A, 11A, 12F, 15C, 17F, and 20A; and
  c) 3, 7F, 19A, 22F, 33F, 6A, 6B, 15A, 16F, 23A, 23B, 24F, 31, 35B, 8, 9N, 10A, 11A, 12F, 15C, 17F, and 20A.
(5) The multivalent immunogenic composition of embodiment 1 wherein the serotypes of *S. pneumoniae* comprise serotypes selected from the group consisting of 3, 7F, 19A, 22F, 33F, 6C, 15A, 16F, 23A, 23B, 24F, 31, 35B, 8, 9N, 10A, 11A, 12F, 15C, 17F, and 20A.
(6) The multivalent immunogenic composition of embodiment 1 wherein the serotypes of *S. pneumoniae* comprise serotypes selected from the group consisting of 3, 7F, 19A, 22F, 33F, 6A, 15A, 16F, 23A, 23B, 24F, 31, 35B, 8, 9N, 10A, 11A, 12F, 15C, 17F, and 20A.
(7) The multivalent immunogenic composition of any of embodiments 1 to 6, wherein the immunogenic composition does not comprise any further *S. pneumoniae* polysaccharide protein conjugates.
(8) The multivalent immunogenic composition of any of embodiments 1 to 7, wherein at least one of the polysaccharide protein conjugates is formed by a conjugation reaction comprising an aprotic solvent.
(9) The multivalent immunogenic composition of any of embodiments 1 to 8, wherein each of the polysaccharide protein conjugates is formed by a conjugation reaction comprising an aprotic solvent.
(10) The multivalent immunogenic composition of embodiments 1 to 9, wherein the total polysaccharide concentration in the composition is from about 0.02 to about 0.175 mg/mL.
(11) The multivalent immunogenic composition of any of embodiments 1 to 10, wherein the weight average molecular weight (Mw) of the *S. pneumoniae* polysaccharide protein conjugates in the composition is from about 1,000 to about 6,000 kDa.
(12) The multivalent immunogenic composition of any of embodiments 1 to 11, wherein the number average molecular weight (Mn) of the *S. pneumoniae* polysaccharide protein conjugates in the composition is from about 500 to about 4,000 kDa.
(13) The multivalent immunogenic composition of any of embodiments 1 to 12, wherein the composition is stable for up to 4 weeks or more at 37° C.
(14) The multivalent immunogenic composition of any of embodiments 1 to 12, wherein the composition is stable for up to 12 weeks or more at 4° C.
(15) The multivalent immunogenic composition of embodiment 13 or 14, wherein stability is determined using HPSEC UV/MALS/RI.
(16) The multivalent immunogenic composition of any of embodiments 1 to 15, wherein the emission maximum of the composition measured using intrinsic protein fluorescence spectroscopy with an excitation wavelength at 280 nanometers (nm) is from about 335 nm to about 342 nm.
(17) The multivalent immunogenic composition of embodiment 16, wherein the emission maximum remains from about 335 nm to about 342 nm and the fluorescence intensity is stable for at least 1 week at 37° C.

(18) The multivalent immunogenic composition of any of embodiments 8-17, wherein the aprotic solvent is dimethylsulfoxide (DMSO).

(19) The multivalent immunogenic composition of embodiment 8 or 9, wherein the conjugation reaction is reductive amination.

(20) The multivalent immunogenic composition of any one of embodiments 1 to 19, wherein the carrier protein is selected from the group consisting of Outer Membrane Protein Complex (OMPC), tetanus toxoid, diphtheria toxoid, protein D and CRM197.

(21) The multivalent immunogenic composition of any one of embodiments 1 to 20, wherein the carrier protein is CRM197.

(22) The multivalent immunogenic composition of any one of embodiments 1 to 21, wherein the composition further comprises an adjuvant.

(23) The multivalent immunogenic composition of any one of embodiments 1 to 21, wherein the composition does not comprise an adjuvant.

(24) The multivalent immunogenic composition of any one of embodiments 1 to 23, further comprising 10-80 mM histidine pH 5.8 and 150 mM NaCl.

(25) The multivalent immunogenic composition of embodiment 24, further comprising from 0.025% to 0.8% w/v polysorbate 20.

(26) A multivalent immunogenic composition comprising S. pneumoniae polysaccharide protein conjugates, wherein each of the conjugates comprises a polysaccharide from an S. pneumoniae serotype conjugated to CRM197, wherein the serotypes of S. pneumoniae in the polysaccharide protein conjugates consist of a set of serotypes selected from the group consisting of:
  a) 15A, 16F, 23A, 23B, 24F, 31 and 35B;
  b) 6A, 6B, 15A, 16F, 23A, 23B, 24F, 31 and 35B;
  c) 6A, 15A, 16F, 23A, 23B, 24F, 31 and 35B;
  d) 6C, 15A, 16F, 23A, 23B, 24F, 31 and 35B;
  e) 15A, 16F, 23A, 23B, 24F, 31, 35B, 8, 9N, 10A, 11A, 12F, 15C, 17F, and 20A;
  f) 6A, 15A, 16F, 23A, 23B, 24F, 31, 35B, 8, 9N, 10A, 11A, 12F, 15C, 17F, and 20A;
  g) 6A, 6B, 15A, 16F, 23A, 23B, 24F, 31, 35B, 8, 9N, 10A, 11A, 12F, 15C, 17F, and 20A;
  h) 6C, 15A, 16F, 23A, 23B, 24F, 31, 35B, 8, 9N, 10A, 11A, 12F, 15C, 17F, and 20A;
  i) 3, 7F, 19A, 22F, 33F, 15A, 16F, 23A, 23B, 24F, 31, 35B, 8, 9N, 10A, 11A, 12F, 15C, 17F, and 20A;
  j) 3, 7F, 19A, 22F, 33F, 6A, 15A, 16F, 23A, 23B, 24F, 31, 35B, 8, 9N, 10A, 11A, 12F, 15C, 17F, and 20A;
  k) 3, 7F, 19A, 22F, 33F, 6A, 6B, 15A, 16F, 23A, 23B, 24F, 31, 35B, 8, 9N, 10A, 11A, 12F, 15C, 17F, and 20A; and
  l) 3, 7F, 19A, 22F, 33F, 6C, 15A, 16F, 23A, 23B, 24F, 31, 35B, 8, 9N, 10A, 11A, 12F, 15C, 17F, and 20A;
wherein serotype 20A in sets e) to l) may be optionally substituted with either serotype 20 or serotype 20B; wherein each of the polysaccharide protein conjugates is formed by a conjugation reaction comprising an aprotic solvent and wherein the composition does not comprise an adjuvant.

(27) A multivalent immunogenic composition of embodiment 26 comprising S. pneumoniae polysaccharide protein conjugates, wherein each of the conjugates comprises a polysaccharide from an S. pneumoniae serotype conjugated to CRM197, wherein the serotypes of S. pneumoniae in the polysaccharide protein conjugates consist of serotypes selected from 3, 7F, 19A, 22F, 33F, 6C, 15A, 16F, 23A, 23B, 24F, 31, 35B, 8, 9N, 10A, 11A, 12F, 15C, 17F, and 20A; wherein serotype 20A may be optionally substituted with either serotype 20 or serotype 20B; wherein each of the polysaccharide protein conjugates is formed by a conjugation reaction comprising an aprotic solvent and wherein the composition does not comprise an adjuvant.

(28) A multivalent immunogenic composition of embodiment 26 comprising S. pneumoniae polysaccharide protein conjugates, wherein each of the conjugates comprises a polysaccharide from an S. pneumoniae serotype conjugated to CRM197, wherein the serotypes of S. pneumoniae in the polysaccharide protein conjugates consist of serotypes selected from 3, 7F, 19A, 22F, 33F, 6A, 15A, 16F, 23A, 23B, 24F, 31, 35B, 8, 9N, 10A, 11A, 12F, 15C, 17F, and 20A; wherein serotype 20A may be optionally substituted with either serotype 20 or serotype 20B; wherein each of the polysaccharide protein conjugates is formed by a conjugation reaction comprising an aprotic solvent and wherein the composition does not comprise an adjuvant.

(29) A method for inducing a protective immune response in a human patient comprising administering the multivalent immunogenic composition of any one of embodiments 1 to 28 to the patient.

(30) The method of embodiment 29, wherein the serotypes of S. pneumoniae comprise a set of serotypes selected from the group consisting of:
  a) 3, 7F, 19A, 22F, 33F, 15A, 16F, 23A, 23B, 24F, 31, 35B, 8, 9N, 10A, 11A, 12F, 15C, 17F, and 20A;
  b) 3, 7F, 19A, 22F, 33F, 6A, 15A, 16F, 23A, 23B, 24F, 31, 35B, 8, 9N, 10A, 11A, 12F, 15C, 17F, and 20A;
  c) 3, 7F, 19A, 22F, 33F, 6A, 6B, 15A, 16F, 23A, 23B, 24F, 31, 35B, 8, 9N, 10A, 11A, 12F, 15C, 17F, and 20A; and
  d) 3, 7F, 19A, 22F, 33F, 6C, 15A, 16F, 23A, 23B, 24F, 31, 35B, 8, 9N, 10A, 11A, 12F, 15C, 17F, and 20A;
wherein serotype 20A in sets a) to d) may be optionally substituted with either serotype 20 or serotype 20B.

(31) The method of embodiment 29, wherein the serotypes of S. pneumoniae comprise a set of serotypes selected from the group consisting of:
  a) 15A, 16F, 23A, 23B, 24F, 31 and 35B;
  b) 6A, 15A, 16F, 23A, 23B, 24F, 31 and 35B 6A, 6B, 15A, 16F, 23A, 23B, 24F, 31 and 35B;
  c) 6C, 15A, 16F, 23A, 23B, 24F, 31 and 35B;
  d) 15A, 16F, 23A, 23B, 24F, 31, 35B, 8, 9N, 10A, 11A, 12F, 15C, 17F, and 20A;
  e) 6A, 15A, 16F, 23A, 23B, 24F, 31, 35B, 8, 9N, 10A, 11A, 12F, 15C, 17F, and 20A;
  f) 6A, 6B, 15A, 16F, 23A, 23B, 24F, 31, 35B, 8, 9N, 10A, 11A, 12F, 15C, 17F, and 20A; and
  g) 6C, 15A, 16F, 23A, 23B, 24F, 31, 35B, 8, 9N, 10A, 11A, 12F, 15C, 17F, and 20A;
wherein serotype 20A in sets d) to g) may be optionally substituted with either serotype 20 or serotype 20B.

(32) The method of embodiment 30, wherein the serotypes of S. pneumoniae comprise serotypes selected from 3, 7F, 19A, 22F, 33F, 6C, 15A, 16F, 23A, 23B, 24F, 31, 35B, 8, 9N, 10A, 11A, 12F, 15C, 17F, and 20A.

(33) The method of embodiment 30, wherein the serotypes of S. pneumoniae comprise serotypes selected from 3, 7F, 19A, 22F, 33F, 6A, 15A, 16F, 23A, 23B, 24F, 31, 35B, 8, 9N, 10A, 11A, 12F, 15C, 17F, and 20A.
(34) The method of any of embodiments 29 to 33, wherein the patient was previously treated with a multivalent pneumococcal vaccine.
(35) The method of embodiment 34, wherein the multivalent pneumococcal vaccine is indicated for the prevention of pneumococcal disease caused by serotypes selected from the group consisting of:
  a) 4, 6B, 9V, 14, 18C, 19F and 23F;
  b) 4, 6B, 9V, 14, 18C, 19F, 23F, 1, 3, 5, 6A, 7F, and 19A;
  c) 1, 4, 5, 6B, 7F, 9V, 14, 18C, 19F and 23F;
  d) 4, 6B, 9V, 14, 18C, 19F, 23F, 1, 3, 5, 6A, 7F, 19A, 22F, and 33F;
  e) 4, 6B, 9V, 14, 18C, 19F, 23F, 1, 3, 5, 7F, 19A, 22F, 33F, 2, 8, 9N, 10A, 11A, 12F, 15B, 17F, and 20;
  f) 4, 6B, 9V, 14, 18C, 19F, 23F, 1, 3, 5, 6A, 7F, 19A, 22F, 33F, 8, 10A, 11A, 12F and 15B; and
  g) 4, 6B, 9V, 14, 18C, 19F, 23F, 1, 3, 5, 6A, 6C, 7F, 19A, 22F, 33F, 8, 10A, 11A, 12F and 15B
(36) The method of embodiment 34 or 35, wherein the multivalent pneumococcal vaccine comprises multiple polysaccharide protein conjugates, wherein the polysaccharide protein conjugates comprise polysaccharide from a *S. pneumoniae* serotype conjugated to a carrier protein.
(37) The method of any of embodiments 31 to 36, further comprising administering one or more additional doses of the multivalent immunogenic composition to the patient.
(38) The method of embodiment 37, wherein the amount of time between doses is from about 4 weeks to about 1 year.
(39) The method of embodiment 37 or embodiment 38, wherein two additional doses are administered to the patient and the patient is immunocompromised.
(40) The method of any of embodiments 31 to 33, further comprising administering a multivalent pneumococcal vaccine to the patient in any order, wherein the multivalent immunogenic composition and the multivalent pneumococcal vaccine are not the same.
(41) The method of embodiment 40, wherein the multivalent pneumococcal vaccine is indicated for the prevention of pneumococcal disease caused by *S. pneumoniae* serotypes selected from the group consisting of:
  a) 4, 6B, 9V, 14, 18C, 19F and 23F;
  b) 4, 6B, 9V, 14, 18C, 19F, 23F, 1, 3, 5, 6A, 7F, and 19A;
  c) 1, 4, 5, 6B, 7F, 9V, 14, 18C, 19F and 23F;
  d) 4, 6B, 9V, 14, 18C, 19F, 23F, 1, 3, 5, 6A, 7F, 19A, 22F, and 33F;
  e) 4, 6B, 9V, 14, 18C, 19F, 23F, 1, 3, 5, 7F, 19A, 22F, 33F, 2, 8, 9N, 10A, 11A, 12F, 15B, 17F, and 20;
  f) 4, 6B, 9V, 14, 18C, 19F, 23F, 1, 3, 5, 6A, 7F, 19A, 22F, 33F, 8, 10A, 11A, 12F and 15B; and
  g) 4, 6B, 9V, 14, 18C, 19F, 23F, 1, 3, 5, 6A, 6C, 7F, 19A, 22F, 33F, 8, 10A, 11A, 12F and 15B.
(42) The method of embodiment 41, wherein the multivalent pneumococcal vaccine is comprised of multiple *S. pneumoniae* polysaccharide protein conjugates wherein each of the conjugates comprises polysaccharide from an *S. pneumoniae* serotype conjugated to a carrier protein.
(43) The method of any of embodiments 40-42, wherein the multivalent immunogenic composition and the multivalent pneumococcal vaccine are administered concurrently.
(44) The method of any of embodiments 40-42, wherein the amount of time between administration of the multivalent immunogenic composition and the multivalent pneumococcal vaccine is from about 4 weeks to about 1 year.
(45) The method of any of embodiments 40-42 or 44, wherein the multivalent immunogenic composition is administered before the multivalent pneumococcal vaccine.
(46) The method of any of embodiments 40-42 or 44, wherein the multivalent pneumococcal vaccine is administered before the multivalent immunogenic composition.
(47) The method of any of embodiments 31 to 46, wherein the patient is 50 years of age or older.
(48) The method of any of embodiments 31 to 46, wherein the patient is between 2 and 18 years of age.
(49) The method of any of embodiments 31 to 46, wherein the patient is 18 years of age or older.
(50) The method of any of embodiments 31 to 46, wherein the patient is 65 years of age or older.
(51) The method of any of embodiments 31 to 50, wherein the patient is immunocompromised.
(52) The method of any of embodiments 31 to 51, wherein the immunogenic composition is administered by subcutaneous or intramuscular injection.
(53) The method of any of embodiments 31 to 52, wherein the immunogenic composition is administered concomitantly with a vaccine against influenza.
(54) A method for preparing a serotype 8 *Streptococcus pneumoniae* polysaccharide-protein conjugate utilizing a conjugation reaction in an aprotic solvent, wherein the conjugation reaction does not use cyanoborohydride.
(55) The method of embodiment 54, wherein the conjugation reaction is a Schiff base reduction or reductive amination.
(56) The method of embodiments 54 and 55, wherein the protein is tetanus toxoid, diphtheria toxoid, or CRM197.
(57) The method of embodiment 56, wherein the protein is CRM197.
(58) The method of any one of embodiments 54 to 57, wherein the conjugation reaction is reductive amination.
(59) The method of any of embodiments 54 to 48, wherein the reductive amination is performed in dimethylsulfoxide (DMSO).
(60) A method for inducing a protective immune response in a human patient comprising administering the multivalent immunogenic composition of embodiments 1 to 28 to the human patient, wherein the polysaccharide dose of each serotype is from about 0.4 to about 4 μg.
(61) A multivalent immunogenic composition comprising *S. pneumoniae* polysaccharide protein conjugates, wherein each of the conjugates comprises a polysaccharide from a *S. pneumoniae* serotype conjugated to a carrier protein, and wherein the polysaccharide protein conjugates include polysaccharides of *S. pneumoniae* serotypes selected from the group consisting of:
  I) 3, 7F, 19A, 22F, 33F, 6A, 15A, 16F, 23A, 23B, 24F, 31, 35B, 8, 9N, 10A, 11A, 12F, 15C, 17F, and 20;
  II) 3, 7F, 19A, 22F, 33F, 6A, 15A, 16F, 23A, 23B, 24F, 31, 35B, 8, 9N, 10A, 11A, 12F, 15C, 17F, and 20A;

III) 3, 7F, 19A, 22F, 33F, 6A, 15A, 16F, 23A, 23B, 24F, 31, 35B, 8, 9N, 10A, 11A, 12F, 15C, 17F, and 20B;

IV) 3, 7F, 19A, 22F, 33F, 6C, 15A, 16F, 23A, 23B, 24F, 31, 35B, 8, 9N, 10A, 11A, 12F, 15C, 17F, and 20;

V) 3, 7F, 19A, 22F, 33F, 6C, 15A, 16F, 23A, 23B, 24F, 31, 35B, 8, 9N, 10A, 11A, 12F, 15C, 17F, and 20A; and VI) 3, 7F, 19A, 22F, 33F, 6C, 15A, 16F, 23A, 23B, 24F, 31, 35B, 8, 9N, 10A, 11A, 12F, 15C, 17F, and 20B.

(62) The multivalent immunogenic composition of embodiment 61, wherein the immunogenic composition does not comprise polysaccharide protein conjugates having polysaccharides from any further *S. pneumoniae* serotypes.

(63) The multivalent immunogenic composition of any of embodiments 61 or 62, wherein at least one of the polysaccharide protein conjugates is formed by a conjugation reaction comprising an aprotic solvent.

(64) The multivalent immunogenic composition of any of embodiments 61 to 63, wherein each of the polysaccharide protein conjugates is formed by a conjugation reaction comprising an aprotic solvent.

(65) The multivalent immunogenic composition of any of embodiments 63 to 64, wherein the aprotic solvent is dimethylsulfoxide (DMSO).

(66) The multivalent immunogenic composition of any of embodiments 61 to 65, wherein the carrier protein is selected from the group consisting of Outer Membrane Protein Complex (OMPC), tetanus toxoid, diphtheria toxoid, protein D and CRM197.

(67) The multivalent immunogenic composition of any of embodiments 61 to 66, wherein the carrier protein is CRM197.

(68) The multivalent immunogenic composition of any of embodiments 61 to 67, wherein the composition further comprises an adjuvant.

(69) The multivalent immunogenic composition of any of embodiments 61 to 67, wherein the composition does not comprise an adjuvant.

(70) A method for inducing a protective immune response in a human patient comprising administering the multivalent immunogenic composition of any of embodiments 61 to 69 to a patient.

(71) The method of embodiment 70, wherein the patient was previously treated with a multivalent pneumococcal vaccine.

(72) The method of any of embodiments 70 to 71, further comprising administering one or more additional doses of the multivalent immunogenic composition to the patient.

(73) The method of any of embodiments 70 to 72, wherein the amount of time between doses is from about 4 weeks to about 1 year.

(74) The method of any of embodiments 70 to 73, wherein two additional doses are administered to the patient and the patient is immunocompromised.

(75) The method of any of embodiments 70 to 74, further comprising administering a multivalent pneumococcal vaccine to the patient in any order, wherein the multivalent immunogenic composition and the multivalent pneumococcal vaccine are not the same.

(76) The method of embodiment 75, wherein the multivalent pneumococcal vaccine is comprised of multiple *S. pneumonia* polysaccharide protein conjugates wherein each of the conjugates comprises polysaccharide from a *S. pneumoniae* serotype conjugated to a carrier protein.

(77) The method of any of embodiments 75 to 76, wherein the multivalent immunogenic composition and the multivalent pneumococcal vaccine are administered concurrently.

(78) The method of any of embodiments 75 to 77, wherein the amount of time between administration of the multivalent immunogenic composition and the multivalent pneumococcal vaccine is from about 4 weeks to about 1 year.

(79) The method of any of embodiments 75 to 78, wherein the multivalent immunogenic composition is administered before the multivalent pneumococcal vaccine.

(80) The method of any of embodiments 75 to 78, wherein the multivalent pneumococcal vaccine is administered before the multivalent immunogenic composition.

(81) The method of any of embodiments 70 to 80, wherein the patient is 50 years of age or older.

(82) The method of any of embodiments 70 to 81, wherein the patient is between 2 and 18 years of age.

(83) The method of any of embodiments 70 to 82, wherein the patient is 18 years of age or older.

(84) The method of any of embodiments 70 to 83, wherein the patient is 65 years of age or older.

(85) The method of any of embodiments 70 to 84, wherein the patient is immunocompromised.

(86) The method of any of embodiments 70 to 85, wherein the immunogenic composition is administered by subcutaneous or intramuscular injection.

(87) The method of any of embodiments 70 to 86, wherein the immunogenic composition is administered concomitantly with a vaccine against influenza.

(88) A method for the prevention of pneumococcal *pneumoniae* and invasive disease in adults 18 years of age and older comprising administering the multivalent immunogenic composition of embodiment 62 to a patient.

(89) A method for the prevention of pneumococcal *pneumoniae* and invasive disease caused by the 24 *Streptococcus pneumoniae* strains (3, 6A, 6C, 7F, 8, 9N, 10A, 11A, 12F, 15A, 15B, 15C, 16F, 17F, 19A, 20A, 20B, 22F, 23A, 23B, 24F, 31, 33F, and 35B) comprising administering the multivalent immunogenic composition of embodiment 62 to a patient.

(90) A multivalent immunogenic composition comprising 21 distinct polysaccharide protein conjugates, wherein each of the conjugates comprises a capsular polysaccharide from a *S. pneumoniae* serotype conjugated to a carrier protein, wherein the polysaccharide are prepared from *S. pneumoniae* serotypes 3, 7F, 19A, 22F, 33F, 6A, 15A, 16F, 23A, 23B, 24F, 31, 35B, 8, 9N, 10A, 11A, 12F, 15C, 17F, and 20A and wherein the carrier protein is CRM197.

(91) The multivalent immunogenic composition of embodiment 90, wherein the immunogenic composition does not comprise polysaccharide protein conjugates prepared from any other *S. pneumoniae* serotypes.

(92) The multivalent immunogenic composition of embodiment 90, wherein each of the polysaccharide protein conjugates is formed by a conjugation reaction comprising an aprotic solvent, wherein the aprotic solvent is dimethylsulfoxide (DMSO).

(93) The multivalent immunogenic composition of embodiment 90, wherein the composition does not comprise an adjuvant.

(4) All publications mentioned herein are incorporated by reference for the purpose of describing and disclosing methodologies and materials that might be used in connection with the present invention.

(5) Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

(6)

Example 1

Preparation of S. Pneumoniae Capsular Polysaccharides

Methods of culturing pneumococci are well known in the art. See, e.g., Chase, 1967, Methods of Immunology and Immunochemistry 1:52. Methods of preparing pneumococcal capsular polysaccharides are also well known in the art. See, e.g., European Patent No. EP 0 497 524 B1. The process described below generally follows the method described in European Patent No. EP 0 497 524 B1 and is generally applicable to all pneumococcal serotypes.

Isolates of pneumococcal strains for serotypes 6C, 23B, and 31 were obtained from Centers for Disease Control and Prevention (Atlanta, GA). Strains for serotypes 3, 8, 10A, 11A, 12F, 15B, 22F, and 33F were obtained from the University of Pennsylvania (Dr. Robert Austrian). Strains for serotypes 17F and 19A were obtained from the FDA Office of Biologics (Dr. John Robbins). Serotype 7F was obtained from the State University of New York, Downstate Medical Center (Dr. Gerald Schiffman). Isolates of pneumococcal serotypes not listed above were obtained from the American Type Culture Collection (Manassas, VA). Where needed, subtypes were differentiated on the basis of Quellung reaction using specific antisera. See, e.g., U.S. Pat. No. 5,847,112. The obtained isolates were further clonally isolated by plating serially in two stages on agar plates consisting of an animal-component free medium containing soy peptone, yeast extract, and glucose without hemin. For serotype 7F, the agar plates used also contained hemin. Clonal isolates for each serotype were further expanded in liquid culture using animal-component free media containing soy peptone, yeast extract, HEPES, sodium chloride, sodium bicarbonate, potassium phosphate, glucose, and glycerol to prepare the pre-master cell banks.

The production of each serotype of pneumococcal polysaccharide consisted of a cell expansion and batch production fermentation followed by chemical inactivation prior to downstream purification. A thawed cell bank vial from each serotype was expanded using a shake flask or culture bottle containing a pre-sterilized animal-component free growth media containing soy peptone or soy peptone ultrafiltrate, yeast extract or yeast extract ultrafiltrate, HEPES, sodium chloride, sodium bicarbonate, potassium phosphate, and glucose. The cell expansion culture was grown in a sealed shake flask or bottle to minimize gas exchange with temperature and agitation control. For serotypes 3, 7F, 8, 9N, 10A, 11A, 12F, 15B, 17F, 19A, 20, 22F, and 33F, a thawed cell bank vial was expanded using a fermentor containing the same media. During the cell expansion of these serotypes, temperature, pH, pressure, and agitation were controlled. Airflow overlay was also controlled as sparging was not used. After achieving a specified culture density, as measured by optical density at 600 nm, a portion of the cell expansion culture was transferred to a production fermentor containing pre-sterilized animal-component free growth media containing soy peptone or soy peptone ultrafiltrate, yeast extract or yeast extract ultrafiltrate, sodium chloride, potassium phosphate, and glucose. Temperature, pH, pressure, and agitation were controlled. Airflow overlay was also controlled as sparging was not used.

The batch fermentation was terminated via the addition of a chemical inactivating agent, phenol, when glucose was nearly exhausted. Pure phenol was added to a final concentration of 0.8-1.2% to inactivate the cells and liberate the capsular polysaccharide from the cell wall. Primary inactivation occurs for a specified time within the fermentor where temperature and agitation continue to be controlled. After primary inactivation, the batch was transferred to another vessel where it was held for an additional specified time at controlled temperature and agitation for complete inactivation. This was confirmed by either microbial plating techniques or by verification of the phenol concentration and specified time. The inactivated broth was then purified.

Example 2

Purification of Pneumococcal Polysaccharides

The purification process for the pneumococcal polysaccharides consisted of several centrifugation, depth filtration, concentration/diafiltration operations, and precipitation steps. All procedures were performed at room temperature unless otherwise specified.

Inactivated broth from the fermentor cultures of S. pneumoniae were flocculated with a cationic polymer (such as BPA-1000, TRETOLITE® (Baker Hughes Inc., Houston, TX), Spectrum 8160, poly(ethyleneimine), and Millipore pDADMAC). The cationic polymers binded to the impurity proteins, nucleic acids and cell debris. Following the flocculation step and an aging period, flocculated solids were removed via centrifugation and multiple depth filtration steps. Clarified broth was concentrated and diafiltered using a 100 kDa to 500 kDa MWCO (molecular weight cutoff) filter. Diafiltration was accomplished using Tris, $MgCl_2$ buffer and sodium phosphate buffer. Diafiltration removed residual nucleic acid and protein.

Removal of further impurities was accomplished by reprecipitation of the polysaccharide in sodium acetate and phenol with denatured alcohol and/or isopropanol. During the phenol precipitation step, sodium acetate in sodium phosphate saline buffer and phenol (liquefied phenols or solid phenols) were charged to the diafiltered retentate. Alcohol fractionation of the polysaccharide was then conducted in two stages. In the first stage a low percent alcohol was added to the preparation to precipitate cellular debris and other unwanted impurities, while the crude polysaccharide remained in solution. The impurities were removed via centrifugation followed by a depth filtration step. The polysaccharide was then recovered from the solution by adding additional isopropanol or denatured alcohol to the batch. The precipitated polysaccharide pellet was recovered by centrifugation, triturated and dried as a powder and stored frozen at −70° C.

Example 3

Structure Identity Analysis of Certain Pneumococcal Serotypes by NMR Testing

Samples for NMR analysis were prepared by dissolving polysaccharide powder at 5 mg powder/mL solution in deuterium oxide ($D_2O$) containing 0.01% dimethyl sulfoxide (DMSO) and 0.01% 2,2-Dimethyl-2-silapentane-5-sulfonate-$d_6$ sodium salt (DSS-$d_6$). DMSO is an internal standard that was used for quantitative analysis and DSS-$d_6$ was used to set the chemical shift scale to 0 ppm. A one-dimensional proton NMR data set was acquired at 50° C. and a portion of spectrum containing the anomeric resonances as then selectively written as x, y coordinates to an ASCII file for analysis using a Microsoft Excel workbook. The Y coordinates (i.e., spectral profile) were then compared to spectral profiles of capsular bacterial polysaccharides in a reference database. The reference profiles were generated in a similar manner on selected preparations of each serotype thereafter designated as the reference lot. A pairwise comparison was made of the y-values from the sample and the reference spectra to produce a correlation coefficient ($\rho_{x,y}$) as a measure of similarity between the spectra. A p-value of ≥0.95 with any of the reference spectra was taken as positive identification of the polysaccharide structure.

FIGS. 1-4 provide the 600 MHz one-dimensional $^1$H NMR spectra of capsular polysaccharides from S. pneumonia serotypes 6C, 15A, de-O-acetylated 15B and 35B, respectively. The $^1$H NMR identity regions used for serotype identification of S. pneumonia serotypes 6C, 15A, de-O-acetylated 15B and 35B are provided in FIGS. 5-8, respectively.

Structure of Capsular Polysaccharides from S. pneumonia Serotypes De-O-Acetylated 15B and 15C Immunogenicity studies were conducted using PCV21 in New Zealand White rabbits (see EXAMPLE 43, infra). In these studies, de-O-acetylated polysaccharide serotype 15B was used in the polyvalent composition in place of serotype 15C. NMR studies were conducted to confirm that de-O-acetylated 15B polysaccharide was equivalent to serotype 15C polysaccharide.

Structural differences between capsular polysaccharide serotypes show up as chemical shift differences in the NMR spectrum. The anomeric region (approximately 4.4 ppm to 6.0 ppm) is sensitive to every structural feature in the repeat unit of the polysaccharide. Differences in stereochemistry, monosaccharide composition, O-acetylation and glyosidic linkage impacts the chemical shifts of the anomeric signals leaving this region of the spectrum unique to each serotype. For de-O-acetylated serotype 15B polysaccharide, the complete $^1$H NMR spectrum is identical to the $^1$H NMR spectrum of serotype 15C polysaccharide, indicating the repeat unit of both polysaccharides consists of the same monosaccharide substituents and glyosidic linkage sites (see FIGS. 9B-9C and 10B-10C). It is also clearly shown that de-O-Acetylation step removed the O-AO-Acetate group present in the 15B polysaccharide, and that there are essentially no observed O-Acetate groups left (see FIGS. 10A-10F).

Example 4

Preparation of Serotype 3 Conjugate for Polyvalent Study Using DMSO Conjugation

Polysaccharide was dissolved, sized to a target molecular mass, chemically activated and buffer-exchanged by ultrafiltration. Activated polysaccharide and purified CRM197 were individually lyophilized and redissolved in dimethylsulfoxide (DMSO). Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 380 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.25 moles of sodium metaperiodate per mole of polysaccharide repeating unit to achieve a target level of polysaccharide activation (moles aldehyde per mole of polysaccharide repeating unit). The oxidation reaction proceeded for 12 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in Pseudomonas fluorescens as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 2 mg Ps/mL with sucrose concentration of 10% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 1.0 g Ps/L and a polysaccharide to CRM197 mass ratio of 1.3. The mass ratio was selected to control the polysaccharide to CRM197 ratio in the resulting conjugate. Sodium cyanoborohydride (1 mole per mole of polysaccharide repeating unit) was added, and conjugation proceeded for 1 hour at 22° C.

Reduction with Sodium Borohydride

Sodium borohydride (2 moles per mole of polysaccharide repeating unit) was added following the conjugation reaction and incubated for 1.6 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 1

Attributes of serotype 3 conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 186/253 kD | 862/1468 kD | 1.16 | 8.2 | <1% | <1% |

Example 5

Preparation of Serotype 6C for Conjugate Monovalent Study Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Oxidation

Purified pneumococcal capsular Ps powder was dissolved in water and 0.45-micron filtered. Filtered dissolved polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.10 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.2 g Ps/L and a polysaccharide to CRM197 mass ratio of 1.4. The mass ratio was selected to control the polysaccharide to CRM197 ratio in the resulting conjugate. Sodium cyanoborohydride (1 mole per mole of polysaccharide repeating unit) was added, and conjugation proceeded for 15 hours at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 2

Attributes of serotype 6C conjugate for monovalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 144/229 kD | 2038/4182 kD | 1.20 | 9.2 | 3.1% | 5.8% |

Example 6

Preparation of Serotype 6C Conjugate for Polyvalent Study Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Oxidation

Purified pneumococcal capsular Ps powder was dissolved in water and 0.45-micron filtered. Filtered dissolved polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.10 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 1.9 g Ps/L and a polysaccharide to CRM197 mass ratio of 1.4. The mass ratio was selected to control the polysaccharide to CRM197 ratio in the resulting conjugate. Sodium cyanoborohydride (1 mole per mole of polysaccharide repeating unit) was added, and conjugation proceeded for 15 hours at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 3

Attributes of serotype 6C conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 144/229 kD | 2104/5006 kD | 1.11 | 8.4 | 4.9% | 2.2% |

Preparation of Serotype 6A Conjugate for Monovalent Studies Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes. Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.10 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 1.5 g Ps/L and a polysaccharide to CRM197 mass ratio of 1.4. The mass ratio was selected to control the polysaccharide to CRM197 ratio in the resulting conjugate. Sodium cyanoborohydride (1 mole per mole of polysaccharide repeating unit) was added, and conjugation proceeded for 15 hour at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 3

Attributes of serotype 6A conjugate for monovalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 238/ 278 kD | 2565/ 6310 kD | 1.021 | 9.2 | 3% | 5% |

Example 7

Preparation of Serotype 7F Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 150 bar/7 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.24 moles of sodium metaperiodate per mole of polysaccharide repeating unit to achieve a target level of polysaccharide activation (moles aldehyde per mole of polysaccharide repeating unit). The oxidation reaction proceeded for 4 hours at 4° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.6 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 4 hours at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 4

Attributes of serotype 7F conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 76/118 kD | 1817/ 4026 kD | 1.55 | 6.7 | <1% | 3.2% |

Example 8

Preparation of Serotype 8 Conjugate for Polyvalent Study Using DMSO Conjugation

Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 600 bar/5 passes.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.18 moles of sodium metaperiodate per mole of polysaccharide repeating unit to achieve a target level of polysaccharide activation (moles aldehyde per mole of polysaccharide repeating unit). The oxidation reaction proceeded for 4 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 4.0 g Ps/L and a polysaccharide to CRM197 mass ratio of 1.5. The mass ratio was selected to control the polysaccharide to CRM197 ratio in the resulting conjugate. After the blend, the conjugation reaction proceeded for 2 hours at 22° C. Sodium cyanoborohydride was not added to the conjugation reaction because it was observed that sodium cyanoborohydride addition could result in irreversible precipitation during the conjugation reaction for serotype 8. Omitting sodium cyanoborohydride from the reaction avoided precipitation without significantly impacting conjugate attributes.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 5

Attributes of serotype 8 conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 110/ 128 kD | 1479/ 2196 kD | 1.17 | 10.3 | 3.7% | <1% |

Example 9

Preparation of Serotype 9N Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 250 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.16 moles of sodium metaperiodate per mole of polysaccharide repeating unit to achieve a target level of polysaccharide activation (moles aldehyde per mole of polysaccharide repeating unit). The oxidation reaction proceeded for 4 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.25 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 1 hour at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 6

Attributes of serotype 9N conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 195/ 226 kD | 1407/ 3134 kD | 1.33 | 10.1 | 1.9% | <1% |

Example 10

Preparation of Serotype 10A Conjugate for Monovalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes followed by 600 bar/5 passes to achieve a target molecular mass.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.15 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 5.0 g Ps/L and a polysaccharide to CRM197 mass ratio of 2.0. The mass ratio was selected to control the polysaccharide to CRM197 ratio in the resulting conjugate. Sodium cyanoborohydride (1 mole per mole of polysaccharide repeating unit) was added, and conjugation proceeded for 4 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 7

Attributes of serotype 10A conjugate for monovalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 76/ 111 kD | 5137/ 7061 kD | 1.13 | 5.1 | <1% | 15% |

Example 11

Preparation of Serotype 10A Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 600 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.16 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 4.0 g Ps/L and a polysaccharide to CRM197 mass ratio of 1.75. The mass ratio was selected to control the polysaccharide to CRM197 ratio in the resulting conjugate. Sodium cyanoborohydride (1 mole per mole of polysaccharide repeating unit) was added, and conjugation proceeded for 4 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 8

Attributes of serotype 10A conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 94/ 130 kD | 1540/ 3000 kD | 1.54 | 7.7 | 8.5% | <1% |

Example 12

Preparation of Serotype 11A Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 92° C. for 75 minutes, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.13 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO containing 25 mM sodium chloride. The polysaccharide and CRM197 solutions were blended to achieve a polysaccharide concentration of 3.5 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 4 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 9

Attributes of serotype 11A conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 63/96 kD | 1584/ 2804 kD | 0.89 | 7.4 | 2.2% | 2.8% |

Example 13

Preparation of Serotype 12F Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 90° C. for 45 minutes, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.26 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO containing 25 mM sodium chloride. The polysaccharide and CRM197 solutions were blended to achieve a polysaccharide concentration of 3.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 4 hours at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 10

Attributes of serotype 12F conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 54/73 kD | 1766/ 3119 kD | 1.20 | 9.6 | 1.3% | 1.5% |

Example 14

Preparation of Serotype 15A Conjugate for Monovalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 1.75 moles of sodium metaperiodate per mole of polysaccharide repeating unit to achieve a target level of polysaccharide activation (moles aldehyde per mole of polysaccharide repeating unit). The oxidation reaction proceeded for 20 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO containing 25 mM sodium chloride. The polysaccharide and CRM197 solutions were blended to achieve a polysaccharide concentration of 6.0 g Ps/L and a polysaccharide to CRM197 mass ratio of 2.0. The mass ratio was selected to control the polysaccharide to CRM197 ratio in the resulting conjugate. Sodium cyanoborohydride (1 mole per mole of polysaccharide repeating unit) was added, and conjugation proceeded for 2.5 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 11

Attributes of serotype 15A conjugate for monovalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 158/ 200 kD | 6949/ 9235 kD | 1.05 | 9.7 | 10% | 5.0% |

Example 15

Preparation of Serotype 15A Conjugate for 15A/B/C Cross Protection Study Using Aqueous Conjugation Polysaccharide was dissolved, size reduced, chemically activated and buffer-exchanged by ultrafiltration. Purified CRM197 was then conjugated to the activated polysaccharide utilizing nickel chloride in the aqueous reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water and 0.45-micron filtered. Dissolved polysaccharide was homogenized to reduce the molecular mass. Homogenization pressure and number of passes through the homogenizer were controlled to 200 bar/5 passes to achieve a target molecular mass. Size-reduced polysaccharide was then concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.45 moles of sodium metaperiodate per mole of polysaccharide repeating unit. The oxidation reaction proceeded for 20 hours at 22° C. The activated product was diafiltered against 10 mM potassium phosphate, pH 6.4 using a 10 kDa NMWCO tangential flow ultrafiltration membrane. Ultrafiltration was conducted at 2-8° C. Further activation was achieved by adjusting the ultrafiltered product to 22° C. and pH 5. Activation was conducted with the addition of 100 mM sodium metaperiodate solution with a charge of 2.0 moles of sodium metaperiodate per mole of polysaccharide repeating unit to achieve a target level of polysaccharide activation (moles aldehyde per mole of polysaccharide repeating unit). The oxidation reaction proceeded for 20 hours at 22° C. The second activated product was diafiltered against 10 mM potassium phosphate, pH 6.4 using a 10 kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 6.0. The buffer pH selected was to improve the stability of activated polysaccharide during the conjugation reaction. Purified CRM197, obtained through expression in *Pseudomonas fluorescens* as previously described (WO 2012/173876 A1), was 0.2-micron filtered and combined with the buffered polysaccharide solution at a polysaccharide to CRM197 mass ratio of 0.6. The mass ratio was selected to control the polysaccharide to CRM197 ratio in the resulting conjugate. The polysaccharide and phosphate concentrations were 9.75 g/L and 100 mM respectively. The polysaccharide concentration was selected to control the size of the resulting conjugate. Nickel chloride was added to approximately 2 mM using a 100 mM nickel chloride solution. Sodium cyanoborohydride (2 moles per mole of polysaccharide repeating unit) was added. Conjugation proceeded for 148 hours at 10° C. to maximize consumption of polysaccharide and protein.

Reduction with Sodium Borohydride

Following the conjugation reaction, the batch was diluted to a polysaccharide concentration of approximately 3.0 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. Polysorbate 20 was added to the retentate batch to a concentration of 0.05% (w/v) then the batch was 0.2 micron filtered (with 0.5 micron prefilter).

The batch was adjusted to a polysaccharide concentration of 1.0 g/L with additional 10 mM L-histidine in 150 mM sodium chloride, pH 7.0 buffer with 0.03% (w/v) polysorbate 20. The batch was dispensed into aliquots and frozen at ≤−60° C.

TABLE 12

Attributes of serotype 15A conjugate for 15A/B/C cross protection study from aqueous conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 118/ 154 kD | 465/ 695 kD | 0.99 | 4.5 | 9.6% | <1% |

Example 16

Preparation of Serotype 15A Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 1.75 moles of sodium metaperiodate per mole of polysaccharide repeating unit to achieve a target level of polysaccharide activation (moles aldehyde per mole of polysaccharide repeating unit). The oxidation reaction proceeded for 20 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO which was pre-heated to 34° C. The polysaccharide solution was spiked with sodium chloride to a concentration of 50 mM. The polysaccharide and CRM197 solutions were blended to achieve a polysaccharide concentration of 5.0 g Ps/L and a polysaccharide to CRM197 mass ratio of 2.0. The mass ratio was selected to control the polysaccharide to CRM197 ratio in the resulting conjugate. Sodium cyanoborohydride (1 mole per mole of polysaccharide repeating unit) was added, and conjugation proceeded for 2 hours at 34° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 13

Attributes of serotype 15A conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 214/ 231 kD | 1628/ 3518 kD | 1.57 | 7.3 | 17% | 7.8% |

Example 17

Preparation of Serotype 15B Conjugate for 15A/B/C Cross Protection Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 300 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.20 moles of sodium metaperiodate per mole of polysaccharide repeating unit to achieve a target level of polysaccharide activation (moles aldehyde per mole of polysaccharide repeating unit). The oxidation reaction proceeded for 4 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.0 g Ps/L and a polysaccharide to CRM197 mass ratio of 2.0. The mass ratio was selected to control the polysaccharide to CRM197 ratio in the resulting conjugate. Sodium cyanoborohydride (1 mole per mole of polysaccharide repeating unit) was added, and conjugation proceeded for 5 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 14

Attributes of serotype 15B conjugate for 15A/B/C cross protection study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 203/ 252 kD | 2329/ 3881 kD | 1.67 | 7.9 | 3.6% | 4.4% |

Example 18

Preparation of Serotype 15C Conjugate for Monovalent Study and 15A/B/C Cross Protection Study Using DMSO Conjugation Polysaccharide derived from *Streptococcus pneumoniae* serotype 15B was dissolved, sized to a target molecular mass, subjected to mild base hydrolysis to release O-Acetyl groups, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction, Base Hydrolysis and Oxidation

Purified serotype 15B pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 300 bar/5 passes.

Size-reduced polysaccharide was concentrated and diafiltered against water using a 10 kDa NMWCO tangential flow ultrafiltration membrane.

The polysaccharide solution was heated to 60° C. and sodium bicarbonate pH 9 buffer was added to a final concentration 50 mM. The batch was incubated with mixing for 13 hours at 60° C. to release OO-Acetyl groups. Potassium phosphate pH 6 buffer was added to a final concentration of 136 mM to neutralize pH and the solution was cooled to ambient temperature. The solution was then concentrated and diafiltered against water using a 10 kDa NMWCO tangential flow ultrafiltration membrane.

The polysaccharide solution was adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.20 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.0 g Ps/L and a polysaccharide to CRM197 mass ratio of 2.0. The mass ratio was selected to control the polysaccharide to CRM197 ratio in the resulting conjugate. Sodium cyanoborohydride (1 mole per mole of polysaccharide repeating unit) was added, and conjugation proceeded for 4 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 15

Attributes of serotype 15C conjugate for monovalent study and 15A/B/C cross protection study from DMSO conjugation

| O-acetyl/Ps | Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|---|
| None detected | 182/246 kD | 1962/4019 kD | 1.31 | 4.8 | 3.8% | 13% |

Example 19

Preparation of Serotype 15C Conjugate for Polyvalent Study Using DMSO Conjugation Polysaccharide derived from *Streptococcus pneumoniae* serotype 15B was dissolved, sized to a target molecular mass, subjected to mild base hydrolysis to release O-Acetyl groups, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction, Base Hydrolysis and Oxidation

Purified serotype 15B pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 300 bar/5 passes.

Size-reduced polysaccharide was concentrated and diafiltered against water using a 10 kDa NMWCO tangential flow ultrafiltration membrane.

The polysaccharide solution was heated to 60° C. and sodium bicarbonate pH 9 buffer was added to a final concentration 50 mM. The batch was incubated with mixing for 13 hours at 60° C. to release O-Acetyl groups. Potassium phosphate pH 6 buffer was added to a final concentration of 136 mM to neutralize pH and the solution was cooled to ambient temperature. The solution was then concentrated and diafiltered against water using a 10 kDa NMWCO tangential flow ultrafiltration membrane.

The polysaccharide solution was adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.20 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.0 g Ps/L and a polysaccharide to CRM197 mass ratio of 1.75. The mass ratio was selected to control the polysaccharide to CRM197 ratio in the resulting conjugate. Sodium cyanoborohydride (1 mole per mole of polysaccharide repeating unit) was added, and conjugation proceeded for 8 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤-60° C.

TABLE 16

Attributes of serotype 15C conjugate for polyvalent study rom DMSO conjugation

| O-acetyl/Ps | Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|---|
| None detected | 182/246 kD | 1540/3230 kD | 1.34 | 6.6 | 9.2% | 5.7% |

Example 20

Preparation of Serotype 16F Conjugate for Monovalent Study Using Aqueous Conjugation Polysaccharide was dissolved, size reduced, chemically activated and buffer-exchanged by ultrafiltration. Purified CRM197 was then conjugated to the activated polysaccharide utilizing nickel chloride in the aqueous reaction mixture, and the resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular polysaccharide powder was dissolved in water, and 0.45-micron filtered. Dissolved polysaccharide was homogenized to reduce the molecular mass. Homogenization pressure and number of passes through the homogenizer were controlled to 200 bar/5 passes followed by 500 bar/5 passes to achieve a target molecular mass. Size-reduced polysaccharide was then concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.15 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 using a 10 kDa NMWCO tangential flow ultrafiltration membrane. Ultrafiltration was conducted at 2-8° C.

Polysaccharide Conjugation to CRM197

Oxidized polysaccharide solution was mixed with water and 1.5 M potassium phosphate pH 7.0. The buffer pH selected was to improve the stability of activated polysaccharide during the conjugation reaction. Purified CRM197, obtained through expression in *Pseudomonas fluorescens* as previously described (WO 2012/173876 A1), was 0.2-micron filtered and combined with the buffered polysaccharide solution at a polysaccharide to CRM197 mass ratio of 0.7. The mass ratio was selected to control the polysaccharide to CRM197 ratio in the resulting conjugate. The polysaccharide and phosphate concentrations were 7.5 g/L and 100 mM respectively. The polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for 122 hours at 22° C. to maximize consumption of polysaccharide and protein.

Reduction with Sodium Borohydride

Following the conjugation reaction, the batch was diluted to a polysaccharide concentration of approximately 3.0 g/L, cooled to 2-8° C., and 1.2-micron filtered. The batch was diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

Final Filtration and Product Storage

The batch was then concentrated and diafiltered against 10 mM L-histidine in 150 mM sodium chloride, pH 7.0 at 4° C. using a 300 kDa NMWCO tangential flow ultrafiltration membrane. Polysorbate 20 was added to the retentate batch to a concentration of 0.05% (w/v) then the batch was 0.2 micron filtered (with 0.5 micron prefilter).

The batch was adjusted to a polysaccharide concentration of 1.0 g/L with additional 10 mM L-histidine in 150 mM sodium chloride, pH 7.0 buffer with 0.03% (w/v) polysorbate 20. The batch was dispensed into aliquots and frozen at ≤−60° C.

TABLE 17

Attributes of serotype 16F conjugate for monovalent study from aqueous conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 90/ 139 kD | 1860/ 5539 kD | 1.10 | 3.3 | 7.0% | <1% |

Example 21

Preparation of Serotype 16F Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 1000 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.15 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a concentration of 50 mM. The polysaccharide and CRM197 solutions were blended to achieve a polysaccharide concentration of 2.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 2 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 18

Attributes of serotype 16F conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 91/ 177 kD | 2075/ 3966 kD | 1.29 | 11.0 | <1% | <1% |

Example 22

Preparation of Serotype 17F Conjugate for Monovalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.11 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a concentration of 50 mM. The polysaccharide and CRM197 solutions were blended to achieve a polysaccharide concentration of 2.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 2 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 19

Attributes of serotype 17F conjugate for monovalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 179/ 216 kD | 2630/ 4632 kD | 1.20 | 8.0 | 1.9% | 4.5% |

Example 23

Preparation of Serotype 17F Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.11 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a concentration of 20 mM. The polysaccharide and CRM197 solutions were blended to achieve a polysaccharide concentration of 2.1 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 2 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 20

Attributes of serotype 17F conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 150/212 kD | 2650/ 4110 kD | 1.10 | 7.7 | 2.8% | 1.5% |

Example 24

Preparation of Serotype 19A Conjugate for Polyvalent Study Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Oxidation

Purified pneumococcal capsular Ps powder was dissolved in water and 0.45-micron filtered. The polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The amount of sodium metaperiodate added was 0.26 moles of sodium metaperiodate per mole of polysaccharide repeating unit to achieve a target level of polysaccharide activation (moles aldehyde per mole of polysaccharide repeating unit). The oxidation reaction proceeded for 20 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.8 g Ps/L and a polysaccharide to CRM197 mass ratio of 1.33. The mass ratio was selected to control the polysaccharide to CRM197 ratio in the resulting conjugate. Sodium cyanoborohydride (1 mole per mole of polysaccharide repeating unit) was added, and conjugation proceeded for 1.5 hours at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kDa NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 21

Attributes of serotype 19A conjugate for polyvalent study from DMSO conjugation

| Oxidized Ps Mn/ Mw | Conjugate Mn/Mw | Ps:Pr | Lysine Consumption (mol/mol CRM197) | Free Ps/ Total Ps | Free Protein/ Total Protein |
|---|---|---|---|---|---|
| 96/186 kD | 1714/ 3585 kD | 1.22 | 9.1 | 7.0% | 1.4% |

Example 25

Preparation of Serotype 20A Conjugate for Monovalent Study Using DMSO Conjugation Polysaccharide previously determined to be serotype 20A (Calix et al., Biochemical, Genetic, and Serological Characterization of Two Capsule Subtypes among *Streptococcus pneumoniae* Serotype 20 Strains, *J. Biol. Chem.* 287(33): 27885-27894, (2012)) was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 200 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. Sodium metaperiodate added at 0.11 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 2.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 6 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 22

Attributes of serotype 20A conjugate for monovalent study from DMSO conjugation

| Oxidized Ps Mn/ Mw | Conjugate Mn/Mw | Ps:Pr | Lysine Consumption (mol/mol CRM197) | Free Ps/ Total Ps | Free Protein/ Total Protein |
|---|---|---|---|---|---|
| 165/215 kD | 5159/ 7778 kD | 1.17 | 6.1 | <1% | 6.5% |

Example 26

Preparation of Serotype 20A Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 220 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. Sodium metaperiodate added at 0.16 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a concentration of 20 mM. The polysaccharide and CRM197 solutions were blended to achieve a polysaccharide concentration of 1.4 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 4 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 23

Attributes of serotype 20A conjugate for polyvalent study from DMSO conjugation

| Oxidized Ps Mn/Mw | Conjugate Mn/Mw | Ps:Pr | Lysine Consumption (mol/mol CRM197) | Free Ps/Total Ps | Free Protein/Total Protein |
|---|---|---|---|---|---|
| 178/215 kD | 2478/3863 kD | 1.10 | 8.3 | 1.0% | 1.0% |

Example 27

Preparation of Serotype 22F Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 400 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. Sodium metaperiodate added at 0.12 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 1.8 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 1 hour at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 24

Attributes of serotype 22F conjugate for polyvalent study from DMSO conjugation

| Oxidized Ps Mn/Mw | Conjugate Mn/Mw | Ps:Pr | Lysine Consumption (mol/mol CRM197) | Free Ps/Total Ps | Free Protein/Total Protein |
|---|---|---|---|---|---|
| 170/196 kD | 1800/3970 kD | 1.13 | 7.0 | <1% | 1.1% |

Example 28

Preparation of Serotype 23A Conjugate for Monovalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 90° C. for 1.5 hours, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The sodium metaperiodate added was 0.20 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a concentration of 50 mM. The polysaccharide and CRM197 solutions were blended to achieve a polysaccharide concentration of 3.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added and conjugation proceeded for 2 hours at 22° C.

Reduction with Sodium Borohydride

Sodium borohydride (2 moles per mole of polysaccharide repeating unit) was added following the conjugation reaction and incubated for 3 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 25

Attributes of serotype 23A conjugate for monovalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 70/97 kD | 2183/ 3837 kD | 1.20 | 11.8 | <1% | <1% |

Example 29

Preparation of Serotype 23A Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 90° C. for 1.5 hours, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The sodium metaperiodate added was 0.20 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 3.5 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added and conjugation proceeded for 2 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 26

Attributes of serotype 23A conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 116/175 kD | 2156/ 4933 kD | 1.12 | 6.3 | 3.3% | 2.1% |

Example 30

Preparation of Serotype 23B Conjugate for Monovalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 400 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. Sodium metaperiodate added at 0.10 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a final concentration of 50 mM. The polysaccharide and CRM197 solutions were blended to achieve a polysaccharide concentration of 5.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 2 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 27

Attributes of serotype 23B conjugate for monovalent study from DMSO conjugation

| Oxidized Ps Mn/Mw | Conjugate Mn/Mw | Ps:Pr | Lysine Consumption (mol/mol CRM197) | Free Ps/Total Ps | Free Protein/Total Protein |
|---|---|---|---|---|---|
| 155/179 kD | 1322/3299 kD | 1.28 | 6.2 | 13% | 5.1% |

Example 31

Preparation of Serotype 23B Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 400 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. Sodium metaperiodate added at 0.13 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 5.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 4 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 28

Attributes of serotype 23B conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 172/197 kD | 1076/ 2514 kD | 1.26 | 7.4 | 12% | 3.2% |

Example 32

Preparation of Serotype 24F Conjugate for Monovalent and Polyvalent Studies Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 92° C. for 50 minutes, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The sodium metaperiodate added was 0.18 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 2 mg Ps/mL with sucrose concentration of 10% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a final concentration of 50 mM. The polysaccharide and CRM197 solutions were blended to achieve a polysaccharide concentration of 1.5 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 2 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 29

Attributes of serotype 24F conjugate for monovalent and polyvalent studies from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 56/100 kD | 2233/ 4875 kD | 0.94 | 7.3 | 4.4% | 1.4% |

Example 33

Preparation of Serotype 31 Conjugate for Monovalent Study Using DMSO Conjugation

Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was size-reduced by acid hydrolysis by adding acetic acid to 200 mM, incubating at 90° C. for 30 minutes, then neutralizing by adding cold potassium phosphate pH 7 buffer to 400 mM.

Size-reduced polysaccharide was concentrated and diafiltered against water using a 5 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The sodium metaperiodate added was 0.16 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 4.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added and conjugation proceeded for 1 hour at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 30

Attributes of serotype 31 conjugate for monovalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 96/119 kD | 1818/ 2999 kD | 1.15 | 9.5 | <1% | <1% |

Example 34

Preparation of Serotype 31 Conjugate for Polyvalent Study Using DMSO Conjugation

Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 400 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. Sodium metaperiodate added at 0.12 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a final concentration of 50 mM. The polysaccharide and CRM197 solutions were blended to achieve a polysaccharide concentration of 3.5 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 1 hour at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

TABLE 31

Attributes of serotype 31 conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 149/186 kD | 2354/ 5971 kD | 1.26 | 8.9 | <1% | <1.8% |

Example 35

Preparation of Serotype 33F Conjugate for Polyvalent Study Using DMSO Conjugation Polysaccharide was dissolved, sized to a target molecular mass, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 350 bar/4 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. Sodium metaperiodate was added at 0.12 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide and CRM197 solutions were blended to achieve a polysaccharide concentration of 1.8 g Ps/L and a polysaccharide to CRM197 mass ratio of 1.75. The mass ratio was selected to control the polysaccharide to CRM197 ratio in the resulting conjugate. Sodium cyanoborohydride (1 mole per mole of polysaccharide repeating unit) was added, and conjugation proceeded for 4 hours at 22° C.

Reduction with Sodium Borohydride

Sodium borohydride (2 moles per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 32

Attributes of serotype 33F conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 186/220 kD | 1630/ 2470 kD | 1.28 | 8.4 | 1.3% | 5.4% |

Example 36

Preparation of Serotype 35B Conjugate for Monovalent Study Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Oxidation

Purified pneumococcal capsular Ps powder was dissolved in water and 0.45-micron filtered. Dissolved polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The sodium metaperiodate added was 0.05 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 were redissolved individually in equal volumes of DMSO containing 25 mM sodium chloride. The polysaccharide and CRM197 solutions were blended to achieve a polysaccharide concentration of 10 g Ps/L and a polysaccharide to CRM197 mass ratio of 4.0. The mass ratio was selected to control the polysaccharide to CRM197 ratio in the resulting conjugate. Conjugation proceeded for 2.5 hours at 22° C. Sodium borohydride (0.025 moles per mole of polysaccharide repeating unit) was added over two spikes during the conjugation incubation.

Reduction with Sodium Borohydride

Sodium borohydride (2 moles per mole of polysaccharide repeating unit) was added following the conjugation reaction and incubated for 1.5 hours at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 33

Attributes of serotype 35B conjugate for monovalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 48/82 kD | 5494/ 7385 kD | 1.26 | 4.5 | 1.8% | 11% |

Example 37

Preparation of Serotype 35B Conjugate for Polyvalent Study Using DMSO Conjugation Polysaccharide was dissolved, chemically activated and buffer-exchanged by ultrafiltration. Activated polysaccharide and purified CRM197 were individually lyophilized and redissolved in DMSO. Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Oxidation

Purified pneumococcal capsular Ps powder was dissolved in water and 0.45-micron filtered. Dissolved polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The sodium metaperiodate added was 0.05 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.2 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps was redissolved in DMSO containing 50 mM sodium chloride. Lyophilized CRM197 was redissolved in an equal volume of DMSO. The polysaccharide and CRM197 solutions were blended to achieve a polysaccharide concentration of 5.25 g Ps/L and a polysaccharide to CRM197 mass ratio of 3.5. The mass ratio was selected to control the polysaccharide to CRM197 ratio in the resulting conjugate. Conjugation proceeded for 3 hours at 34° C. Sodium borohydride (0.0375 moles per mole of polysaccharide repeating unit) was added over three spikes during the conjugation incubation.

Reduction with Sodium Borohydride

Sodium borohydride (2 moles per mole of polysaccharide repeating unit) was added following the conjugation reaction and incubated for 1 hour at 34° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered (with 0.5 micron prefilter) then diluted with additional 10 mM histidine in 150 mM sodium chloride, pH 7.0 with 0.015% (w/v) polysorbate 20, dispensed into aliquots and frozen at ≤−60° C.

TABLE 34

Attributes of serotype 35B conjugate for polyvalent study from DMSO conjugation

| Oxidized Ps Mn/Mw | Conjugate Mn/Mw | Ps:Pr | Lysine Consumption (mol/mol CRM197) | Free Ps/ Total Ps | Free Protein/ Total Protein |
|---|---|---|---|---|---|
| 48/82 kD | 1287/ 2585 kD | 2.1 | 6.9 | 7.8% | 4.6% |

Some aqueous conjugation methods were not described for all serotypes in Examples 38-51. For those aqueous conjugation methods not described herein, similar methods can be found in WO2018/156491.

Example 38

Formulation of Pneumococcal Conjugate Vaccines

Individual pneumococcal polysaccharide-protein conjugates prepared utilizing different chemistries as described in the Examples, supra, were used for the formulation of 1-, 7-, 8-, 14-, 15-, 16-, 21- and 31-valent pneumococcal conjugate vaccines referred to as PCV1, PCV7, PCV8, PCV14, PCV15, PCV16, PCV21, and PCV31, respectively.

The PCV1 vaccine drug product formulation contained serotype 3 conjugated either using reductive amination in a protic (aqueous) solvent or an aprotic (DMSO) solvent and formulated in 20 mM L-Histidine pH 5.8, 150 mM NaCl and 0.1% (w/v) PS-20 for a target final concentration of 84 µg/mL (w/v) Pneumococcal Polysaccharide (PnPs) in the vaccine.

The PCV7 vaccine drug product formulation contained serotypes 3, 8, 9N, 10A, 11A, 15A and 19A, conjugated either using reductive amination in a protic (aqueous) solvent or an aprotic (e.g. DMSO) and formulated in 20 mM L-Histidine pH 5.8, 150 mM NaCl and 0.1% (w/v) PS-20. Each polysaccharide-protein conjugate in PCV7 was formulated at 12 µg/mL (w/v) Pneumococcal Polysaccharide (PnPs) for a target final concentration of 84 µg/mL PnPs in the vaccine.

The PCV8 vaccine drug product contained serotypes 6C, 15A, 16F, 23A, 23B, 24F, 31 and 35B conjugated either using reductive amination in an aprotic solvent (e.g DMSO) and formulated in 20 mM L-Histidine pH 5.8, 150 mM NaCl and 0.2% (w/v) PS-20. Each polysaccharide-protein conjugate in PCV8 was formlulated at 4 µg/mL (w/v) Pneumococcal Polysaccharide (PnPs) for a target final concentration of 32 µg/mL PnPs in the vaccine.

The PCV14 vaccine drug product contained serotypes 3, 7F, 8, 9N, 10A, 11A, 12F, 15A, 16F, 17F, 19A, 20A, 22F and 33F conjugated either using reductive amination in a protic (aqueous) solvent or an aprotic (e.g. DMSO) and formulated in 20 mM L-Histidine pH 5.8, 150 mM NaCl and 0.1% (w/v) PS-20. Each polysaccharide-protein conjugate in PCV14 was formulated at 6 µg/mL (w/v) Pneumococcal Polysaccharide (PnPs) for a target final concentration of 84 µg/mL PnPs in the vaccine.

The PCV15 vaccine drug product contained serotypes 1, 3, 4, 5, 6A, 6B, 7F, 9V, 14, 18C, 19A, 19F, 22F, 23F and 33F conjugated in a protic (aqueous) solvent and formulated in 20 mM L-Histidine pH 5.8, 150 mM NaCl and 0.2% (w/v) PS-20. Each polysaccharide-protein conjugate was formulated at 4 µg/mL (w/v) Pneumococcal Polysaccharide (PnPs), except for 6B, which was formulated at 8 µg/mL, for a target final concentration of 64 µg/mL PnPs in the vaccine.

The PCV16 vaccine drug product contained serotypes 6C, 8, 9N, 10A, 11A, 12F, 15A, 15C, 16F, 17F, 20A, 23A, 23B, 24F, 31, and 35B, conjugated using reductive amination in an aprotic solvent (e.g. DMSO) and formulated in 20 mM L-Histidine pH 5.8 150 mM NaCl and 0.2% (w/v) PS-20. Each polysaccharide-protein conjugate was formulated at 4 µg/mL (w/v) or 8 µg/mL (w/v) Pneumococcal Polysaccharide (PnPs) for a target final concentration of 64 µg/mL or 128 µg/mL PnPs in the vaccine.

The PCV21 vaccine drug product contained serotypes 3, 6C, 7F, 8, 9N, 10A, 11A, 12F, 15A, 15C, 16F, 17F, 19A, 20A, 22F, 23A, 23B, 24F, 31, 33F and 35B, conjugated using reductive amination in an aprotic solvent (e.g. DMSO) and formulated in 20 mM L-Histidine pH 5.8 150 mM NaCl and various concentration of PS-20 as defined in each example. Each polysaccharide-protein conjugate was formulated at 4 µg/mL (w/v) or 8 µg/mL (w/v) Pneumococcal Polysaccharide (PnPs) for a target final concentration of 84 µg/mL or 168 µg/mL PnPs in the vaccine. In some examples, PCV21 was formulated with 250 µg [Al]/mL in the form of Aluminum Phosphate.

The PCV31 vaccine drug product contained serotypes 1, 3, 4, 5, 6A, 6B, 6C, 7F, 8, 9N, 9V, 10A, 11A, 12F, 14, 15A, 15C, 16F, 17F, 18C, 19A, 19F, 20A, 22F, 23A, 23B, 23F, 24F, 31, 33F and 35B conjugated using reductive amination in a protic solvent (aqueous) or an aprotic solvent (e.g. DMSO) and formulated in 20 mM L-Histidine pH 5.8 150 mM NaCl and 0.2% PS-20. Each polysaccharide-protein conjugate was formulated at 4 µg/mL (w/v) Pneumococcal Polysaccharide (PnPs), except for 6B, which was formulated at 8 µg/mL PnPs, for a target final concentration of 128 µg/mL PnPs in the vaccine. In some examples, PCV31 was formulated with 250 µg [Al]/mL in the form of Aluminum Phosphate.

Additional monovalent PCV drug product formulations were prepared utilizing pneumococcal polysaccharide-protein conjugate serotypes 6A, 6B, 6C, 10A, 15A, 15B, 15C, 16F, 17F, 20A, 23A, 23B, 24F, 31 or 35B. Additional details are described in the specific examples for these formulations.

To prepare the PCV drug product formulation, the required volumes of bulk conjugates needed to obtain the indicated final concentration of (w/v) Pneumococcal Polysaccharide (also referred to as PnPs) were calculated based on the batch volume and the bulk polysaccharide concentration.

The formulation process consisted of a conjugate bulk blend preparation at 1× to 4× of final concentration of PnPs blends in 10-80 mM Histidine, 0.0-0.8% (w/v) PS-20, and 150 mM sodium chloride, pH 5.8.

Histidine pH 5.8, PS-20 (if utilized) and 150 mM sodium chloride solutions were prepared and added to the formulation vessel. The individual pneumococcal polysaccharide-protein conjugates, stored frozen, were thawed at 2-8° C. and then added to the formulation vessel. During the addition of polysaccharide-protein conjugate to the formulation buffer (conjugate blend), the vessel was mixed to ensure homogeneity using a magnetic sir bar or magnetic impeller. After all additions were made and the solution was stirred, the conjugate blend was passed through sterilizing filters and collected in a vessel with or without Aluminum phosphate adjuvant. In some cases, the sterilizing filters were chased with 150 mM sodium chloride to adjust the batch to target concentration.

The formulations were filled into plastic syringes, glass syringes, or vials.

Example 39

Stability Assessment of Pneumococcal Conjugate Vaccines

The PCV16 (128 µg/mL PnPs) or two PCV21 pneumococcal conjugate vaccine drug products (84 µg/mL or 168 µg/mL PnPs) were filled in syringes or vials. The polysaccharide protein conjugates were made via reductive amination in an aprotic solvent (e.g. DMSO) and were formulated in 20 mM L-Histidine, pH 5.8, 150 mM NaCl, and 0.2% (w/v) PS-20. These drug products were placed at 25° C. or 37° C. for up to four weeks and at 4° C. for up to twelve weeks. In some cases, the syringes were placed on a horizontal rotation platform and shaken for up to 18 hours after storage for 1 week at 4° C., 25° C. or 37° C. This was done to simulate the shipping and handling stresses that may accompany drug product manufacture and distribution. To assess stability of the PCV16 or PCV21 drug products, HPSEC UV/MALS/RI was used. High Performance Size Exclusion Chromatography (HPSEC), using two Shodex columns (803 and 806), coupled together in series and Ultraviolet (UV) multi-angle light scattering (MALS) and refractive index (RI) detection to measure concentration and molar mass of PCV drug product formulations during storage. The concentration is calculated for each time interval across the peak and is then integrated at all intervals to achieve the final concentration value. Light scattering is proportional to the product of the molecular mass and the concentration of the analyte. Molar masses or Molecular weight at each interval is calculated from the detector signals. The weighted average (Mw) or number average (Mn) molecular mass is calculated across all intervals for the peak and reported as average molecular weight.

Storage may result in damage to protein and/or carbohydrate of a conjugate vaccine. Carbohydrate antigens that possess phosphodiester main-chain bonds or other instabilities in the repeat unit of the polysaccharide may be susceptible to depolymerization through hydrolysis upon storage for extended time and temperature. Furthermore, the carrier protein or carbohydrate that is used in the conjugate vaccine may be susceptible to aggregation upon storage and physical stresses.

Figure 11A:
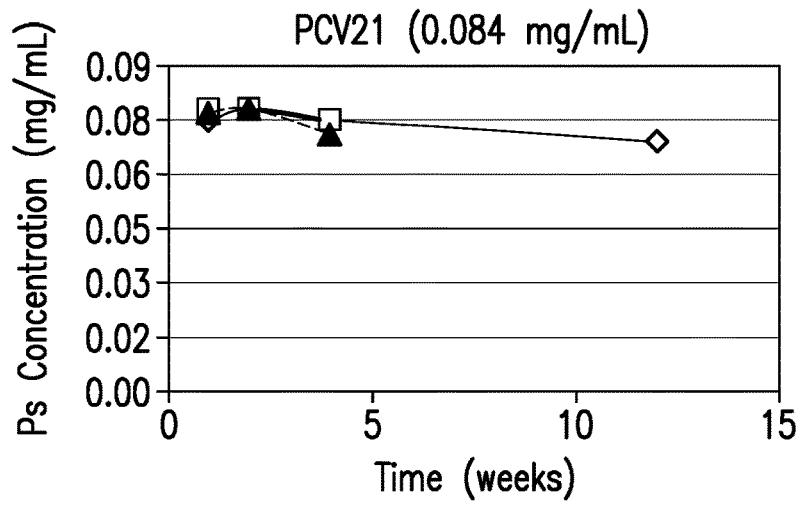
FIGS. 11A-11C show the impact of time and temperature (up to 12 weeks at 4° C.-diamonds, up to 4 weeks at 25° C.-squares, up to 4 weeks at 37° C.-triangles) on the polysaccharide concentration of a PCV16 (0.128 mg/mL [FIG. 11B]) or PCV21 (0.084 mg/mL [FIG. 11A] or 0.169 mg/mL [FIG. 11C]) drug products using HPSEC-UV/MALS/RI (see EXAMPLE 39).
Figure 11B:
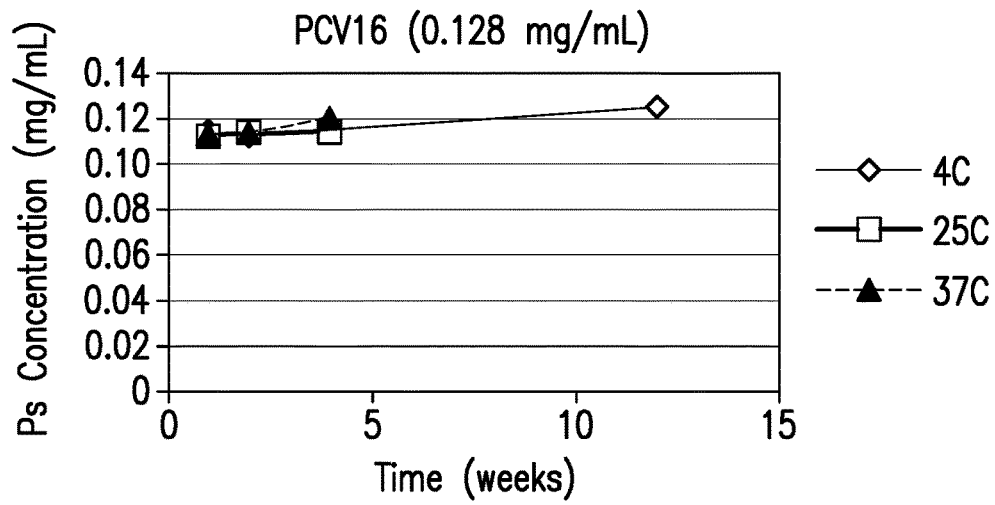
Figure 11C:
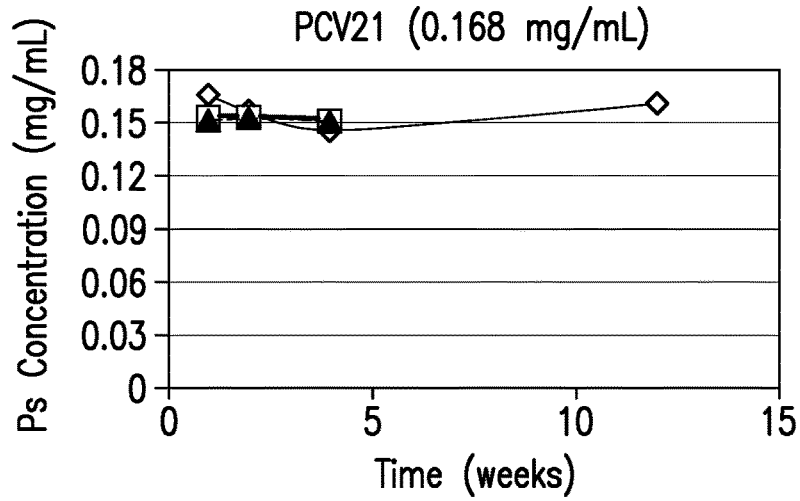
Figure 12A:
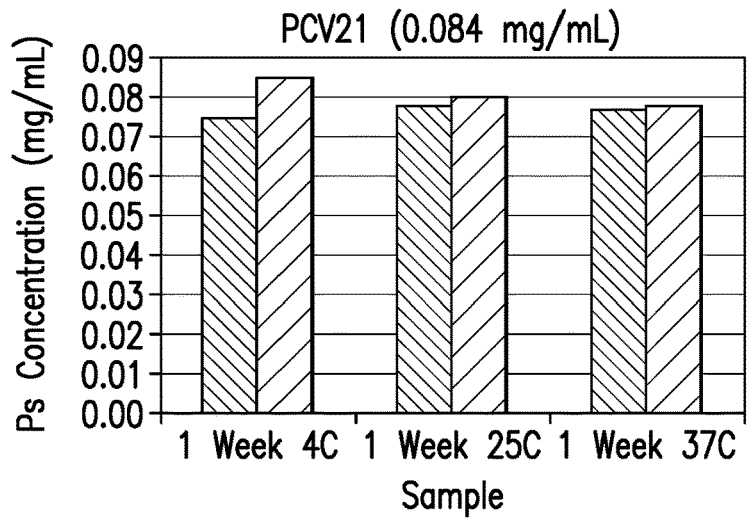
FIGS. 12A-12C show the impact of horizontal rotation agitation and temperature (1 week at either 4° C., 25° C., or 37° C.) on polysaccharide concentration of a PCV16 (0.128 mg/mL [FIG. 12B]) or PCV21 (0.084 mg/mL [FIG. 12A] or 0.169 mg/mL [FIG. 12C]) drug products dispensed in prefilled syringes (see EXAMPLE 39).
Figure 12B:
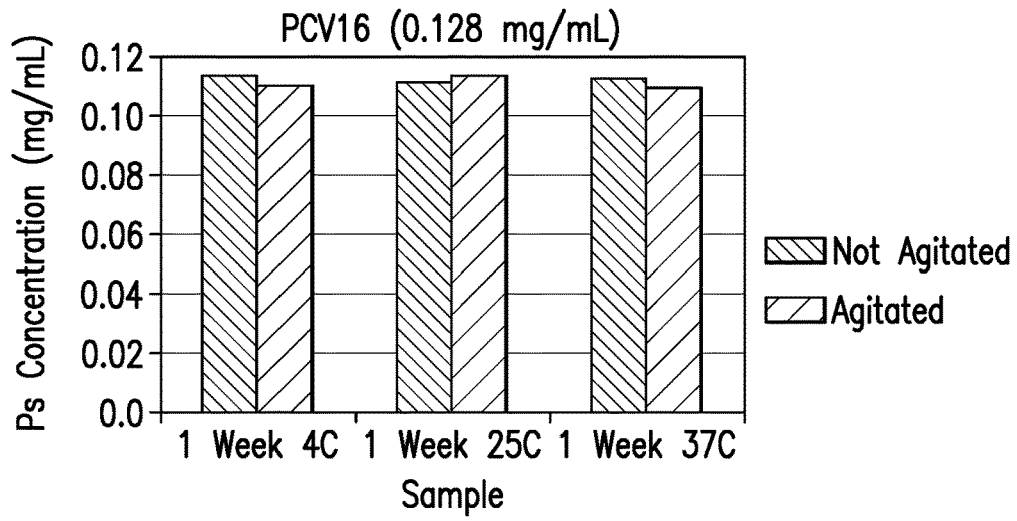
Figure 12C:
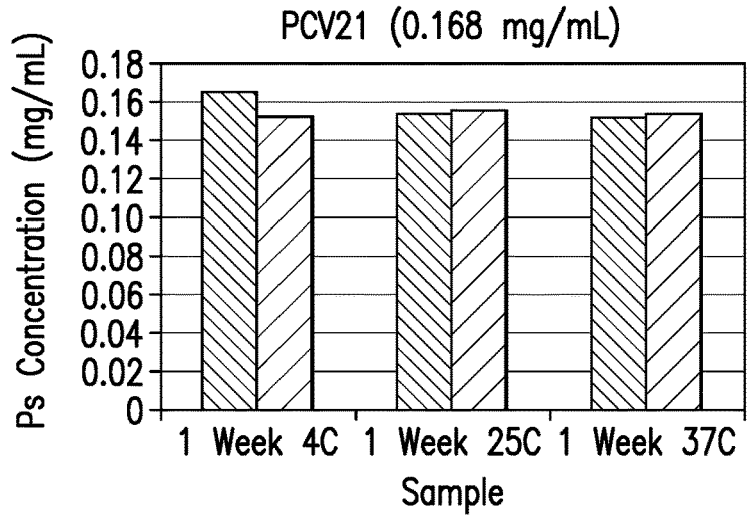

As shown in FIGS. 11A-11C, the PCV16 and PCV21 drug products were stable through 4 weeks at 25° C. and 37° C. and up to 12 wks at 4° C. regardless of polysaccharide concentration. Moreover, upon horizontal agitation after thermal stress, the PCV16 and PCV21 drug products were shown to be stable. No loss of antigen quantity due to non-specific adsorption to the side of the containers or vessels was observed under these thermal and physical stresses. Additionally, no aggregation of the drug product was observed which would impact its performance on the column (e.g. irreversible binding to the column or unable to enter/exit the resolving columns) in estimating total dose of the vaccine (FIGS. 12A-12C).

Figure 13A:
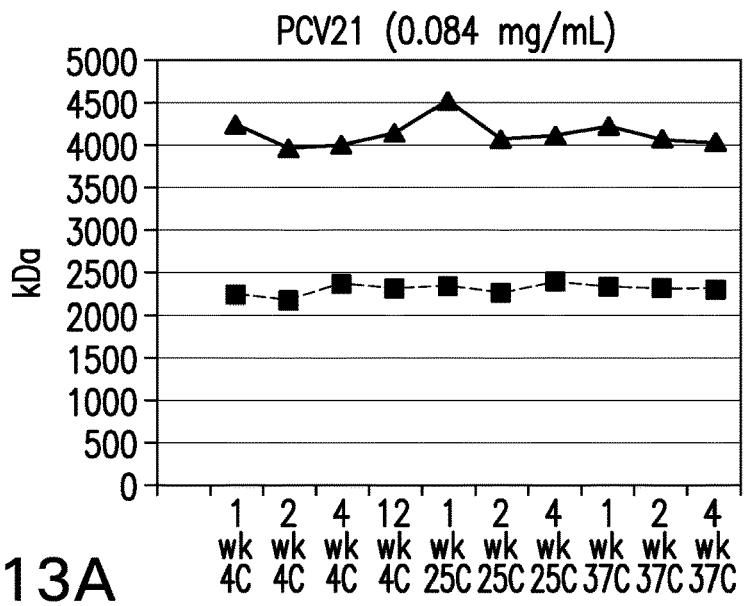
FIGS. 13A-13C show the impact of PS concentration over time and temperature (up to 4 weeks at either 4° C., 25° C., or 37° C.) on the average molecular weight (Mw and Mn) of PCV16 (0.128 mg/mL [FIG. 12B]) or PCV21 (0.084 mg/mL [FIG. 12A] or 0.169 mg/mL [FIG. 12C]) drug products using HPSEC-UV/MALS/RI.
Figure 13B:
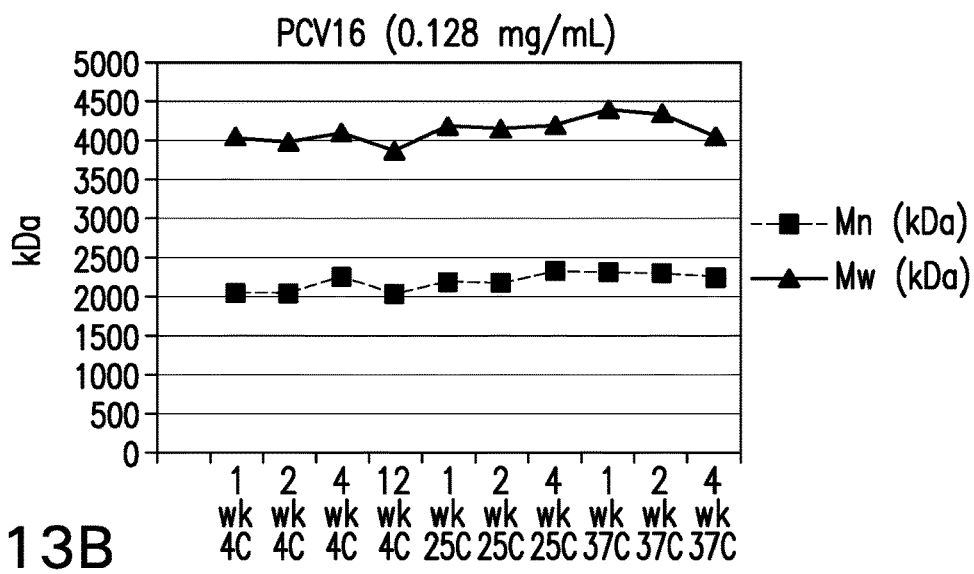
Figure 13C:
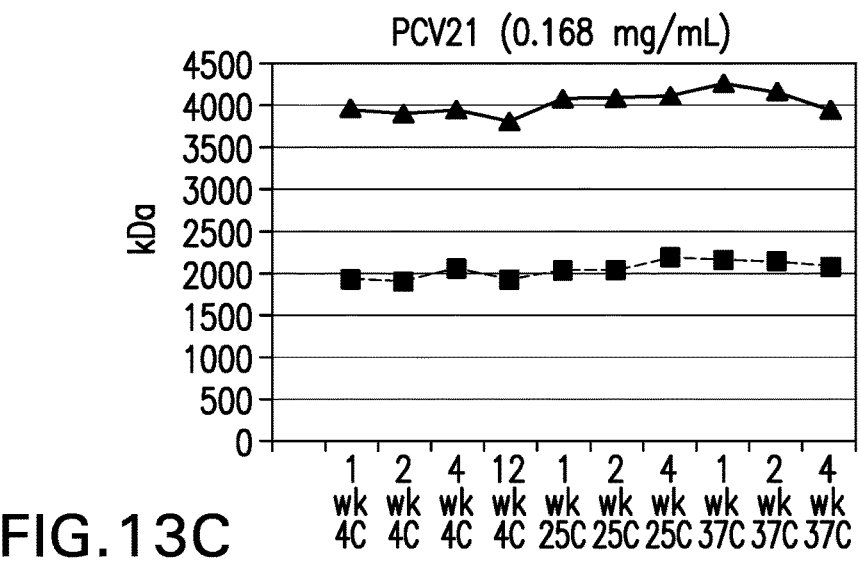

HPSEC UV/MALs/RI was used to measure the molecular weight of a polysaccharide-protein conjugate. If the polysaccharide-protein conjugates in the drug product were degrading or depolymerizing, a decrease in molecular weight would be evident and if aggregation of the drug product was occurring, an increase in molecular weight would occur. This measurement provides additional characterization on the quality of the vaccine drug product or intermediate. As shown in FIGS. 13A-13C, the PCV16 and PCV21 drug products comprising drug substances that were each prepared using reductive amination in an aprotic solvent (e.g. DMSO) were stable against depolymerization or chemical degradation of the carbohydrate and stable against aggregation of the protein in the drug product formulation. This indicates that the PCV16 and PCV21 drug products using polysaccharide protein conjugates prepared using reductive amination in an aprotic solvent, such as DMSO, are stable through elevated temperature and physical stresses. The formulations demonstrate excellent stability in terms of both quantity and quality. The formulation does not lose total dose due to non-specific adsorption to the side of the containers or other surfaces and the formulation does not degrade or aggregate as indicated by the stable molecular weight of the vaccine drug product (weight averaged molecular weight (Mw) and number averaged molecular weight (Mn)).

Example 40

Impact of Conjugation Chemistry on Stability of a Pneumococcal Conjugate Vaccine Individual pneumococcal polysaccharide-protein conjugates prepared utilizing different chemistries as described in the Examples, supra, were used for the formulation of 15- and a 16-valent pneumococcal conjugate vaccines referred to as PCV15 and PCV16 at 64 µg/mL. The PCV15 vaccine drug product contained serotypes 1, 3, 4, 5, 6A, 6B, 7F, 9V, 14, 18C, 19A, 19F, 22F, 23F and 33F, conjugated using reductive amination in a protic solvent (all aqueous) and formulated in 20 mM L-Histidine pH 5.8, 150 mM NaCl and 0.2% w/v PS-20 (see EXAMPLE 38). The PCV16 drug product contained serotypes 6C, 8, 9N, 10A, 11A, 12F, 15A, 15C, 16F, 17F, 20A, 23A, 23B, 24F, 31, and 35B, conjugated using reductive amination in an aprotic solvent (e.g. all DMSO) and formulated in 20 mM L-Histidine, pH 5.8, 150 mM NaCl, and 0.2% (w/v) PS-20 (see EXAMPLE 38). Each polysaccharide-protein conjugate was formulated at 4 µg/mL (w/v) Pneumococcal Polysaccharide (PnPs) except for 6B in PCV15, which was formulated at 8 µg/mL, for a final concentration of 64 µg/mL PnPs in each vaccine.

The vaccine-filled containers were placed at 4° C. or 37° C. for up to 1 week. Intrinsic Protein Fluorescence Spectroscopy (IPFS) was used to assess the stability of pneumococcal polysaccharide-conjugated carrier protein, CRM197, in the PCV15 or PCV16 compositions upon storage for up to 1 week at 4° C. and 37° C. Fluorescence emission spectra (Em 290-400 nm) of undiluted samples were collected using a Jasco FP-6500 Spectrofluorometer at ambient room temperature in a 1 cm path length quartz cuvette. An Excitation wavelength of 280 nm was used with a scan speed of 100 nm/min and excitation and emission bandpass of 3 nm.

Figure 14A:
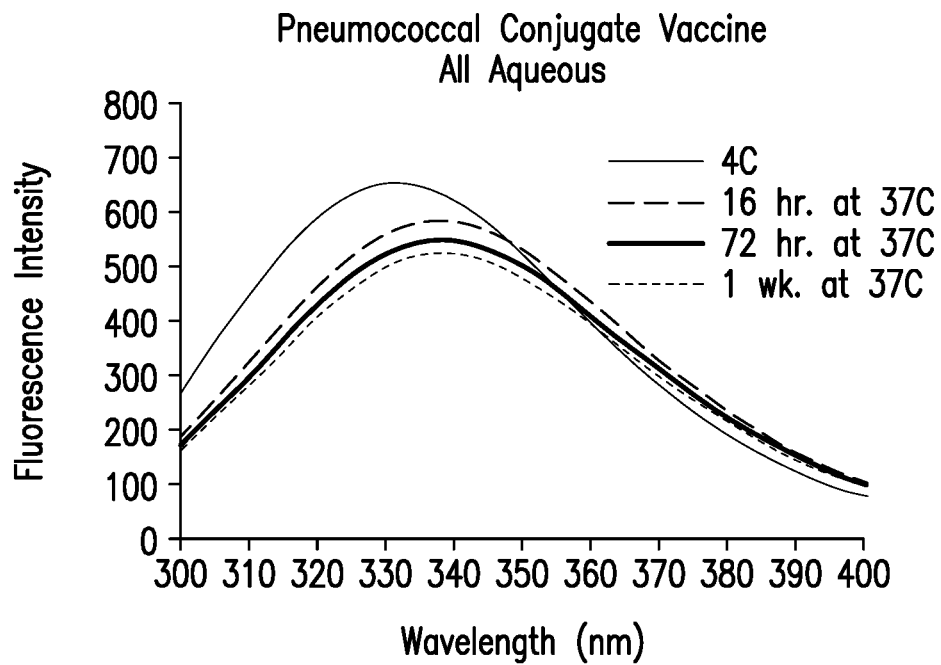
FIGS. 14A and 14B show the impact of time and temperature (up to 1 wk at 4° C. or 37° C.) on stability of a Pneumococcal Conjugate vaccine (PCV15 or PCV16) prepared with drug substances conjugated in FIG. 14A) a protic solvent (PCV15 formulated using all aqueous conjugation) or FIG. 14B) an aprotic solvent (PCV16 formulated using all DMSO conjugation at 0.064 mg/mL PnPs) using intrinsic protein fluorescence spectroscopy with an excitation wavelength at 280 nm (EXAMPLE 40).
Figure 14B:
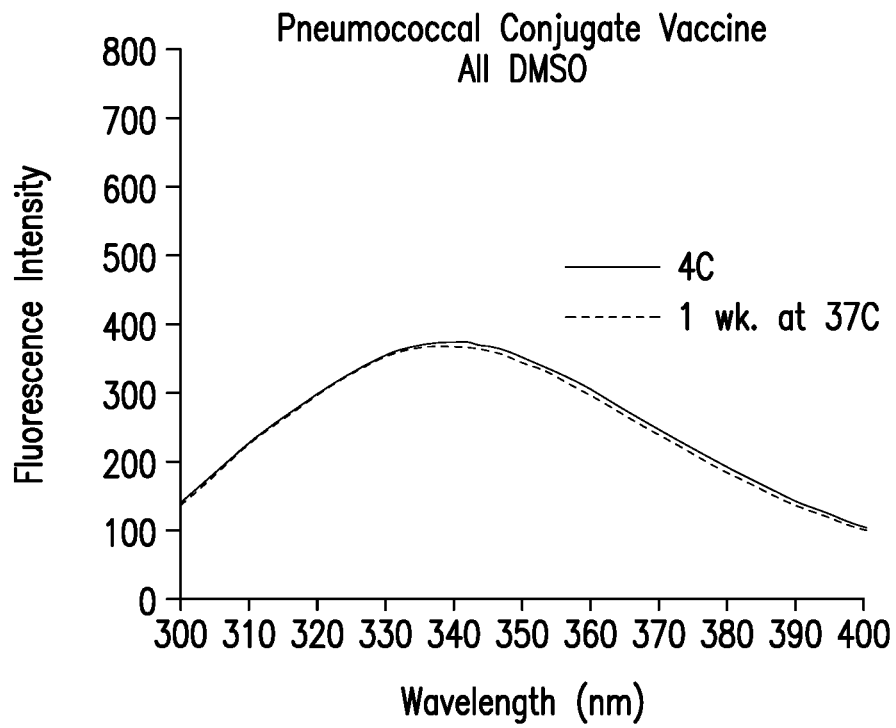

As shown in FIGS. 14A-14B, the drug product formulation containing drug substances prepared using reductive amination in an aprotic solvent (e.g. all DMSO) resulted in superior physical and chemical stability as compared to a vaccine utilizing drug substances prepared using a protic solvent during reductive amination in the conjugation process (all aqueous conjugation). In as little as 16 hours at 37° C., the fluorescence intensity of the PCV15 drug product, at 64 µg/mL PnPs, prepared using reductive amination in a protic solvent (all aqueous) for the conjugation process was reduced and the emission maximum of the vaccine shifted from 332 nm to 338 nm. The PCV16 vaccine drug product, at 64 µg/mL PnPs, utilizing drug substances prepared with reductive amination chemistry in an aprotic solvent (e.g. all DMSO) did not show a change in fluorescence intensity or emission maximum 338 nm. It should be understood that the resulting signal intensity and emission maximum acquired from the IPFS measurement is due to the collective stability of the individual drug substances in a multivalent complex drug product. We have shown that a vaccine drug product utilizing all drug substances prepared in an aprotic solvent is stable while a vaccine drug product utilizing all drug substances prepared in an a protic solvent is not stable.

Without being bound to any particular theory, this stability could be due to conjugation in DMSO resulting in unfolding and denaturing the carrier protein. Conjugation to the denatured carrier protein would lock the conformation in a denatured state post conjugation. If so, this study would also suggest the final conformation is stable under the stress study evaluated here. It is therefore preferred to use a vaccine with conjugate mostly prepared with aprotic solvents to provide a consistent and stable vaccine drug product.

If a vaccine drug product composition included a mixture of drug substances, glycoconjugates or polysaccharide protein conjugates utilizing different reductive amination solvents (aqueous or DMSO) in the conjugation processes, the average emission maximum or intensity measured from the drug product formulation would be weighted due to the contribution of each aqueous polysaccharide protein conjugate emission at 332 nm and each non-aqueous polysaccharide protein conjugate emission at 338 nm. It would be expected that a change would occur, in either intensity or emission maxima, upon elevated temperature for such a mixture that does not use all polysaccharide protein conjugates, prepared using reductive amination in an aprotic solvent, in the multivalent drug product formulation. It is therefore preferred to use a vaccine with conjugate mostly prepared with aprotic solvents to provide a consistent and stable vaccine drug product.

Example 41

Compiled Monovalent Rabbit Immunogenicity Studies for Selected Serotypes

Adult New Zealand White rabbits (NZWR, n=3/group) were intramuscularly (IM) immunized with 0.25 ml or 0.5 mL (for 15C only) of respective monovalent conjugate vaccine on day 0 and day 14 (alternating sides). Monovalent pneumococcal vaccines, formulated in 20 mM L-Histidine, pH 5.8, 150 mM NaCl, and 0.2% (w/v) PS-20 and formulation process described in Example 38, were dosed as follows: (1) 1 µg PnPs (6C, 10A, 15A, 16F, 17F, 20A, 23A, 23B, 24F, 31 or 35B, each conjugated to CRM197) with 62.5 µg aluminum phosphate adjuvant (APA) per immunization, or (2) 2 µg PnPs (15C-CRM197 with 125 µg APA per immunization. Sera were collected prior to study start (pre-immune) and on days 14 (post-dose 1, PD1) and 28 (post-dose 2, PD2). NZWRs were observed at least daily by trained animal care staff for any signs of illness or distress. The vaccine formulations in NZWRs were deemed to be safe and well tolerated, as no vaccine-related adverse events were noted. All animal experiments were performed in strict accordance with the recommendations in the Guide for Care and Use of Laboratory Animals of the National Institutes of Health. The NZWR experimental protocol was approved by the Institutional Animal Care and Use Committees at both Merck & Co., Inc. (Kenilworth, NJ) and Covance (Denver, PA).

NZWR sera were tested in ELISA assays to evaluate IgG immunogenicity using a 1-2 mg/mL respective PnPs coating concentration. Functional antibody was determined through opsonophagocytosis assays (OPA) based on previously described protocols available online at the Bacterial Respiratory Pathogen Reference Laboratory at the University of Alabama at Birmingham using Opsotiter® 3 software (UAB Research Foundation, Caro-Aguilar et al. Immunogenicity differences of a 15-valent pneumococcal polysaccharide conjugate vaccine (PCV15) based on vaccine dose, route of immunization and mouse strain. Vaccine 35(6):865-72 (2017); Burton et al. Development and validation of a fourfold multiplexed opsonization assay (MOPA4) for pneumococcal antibodies. *Clin Vaccine Immunol* 13(9):1004-9 (2006)).

Figure 15:
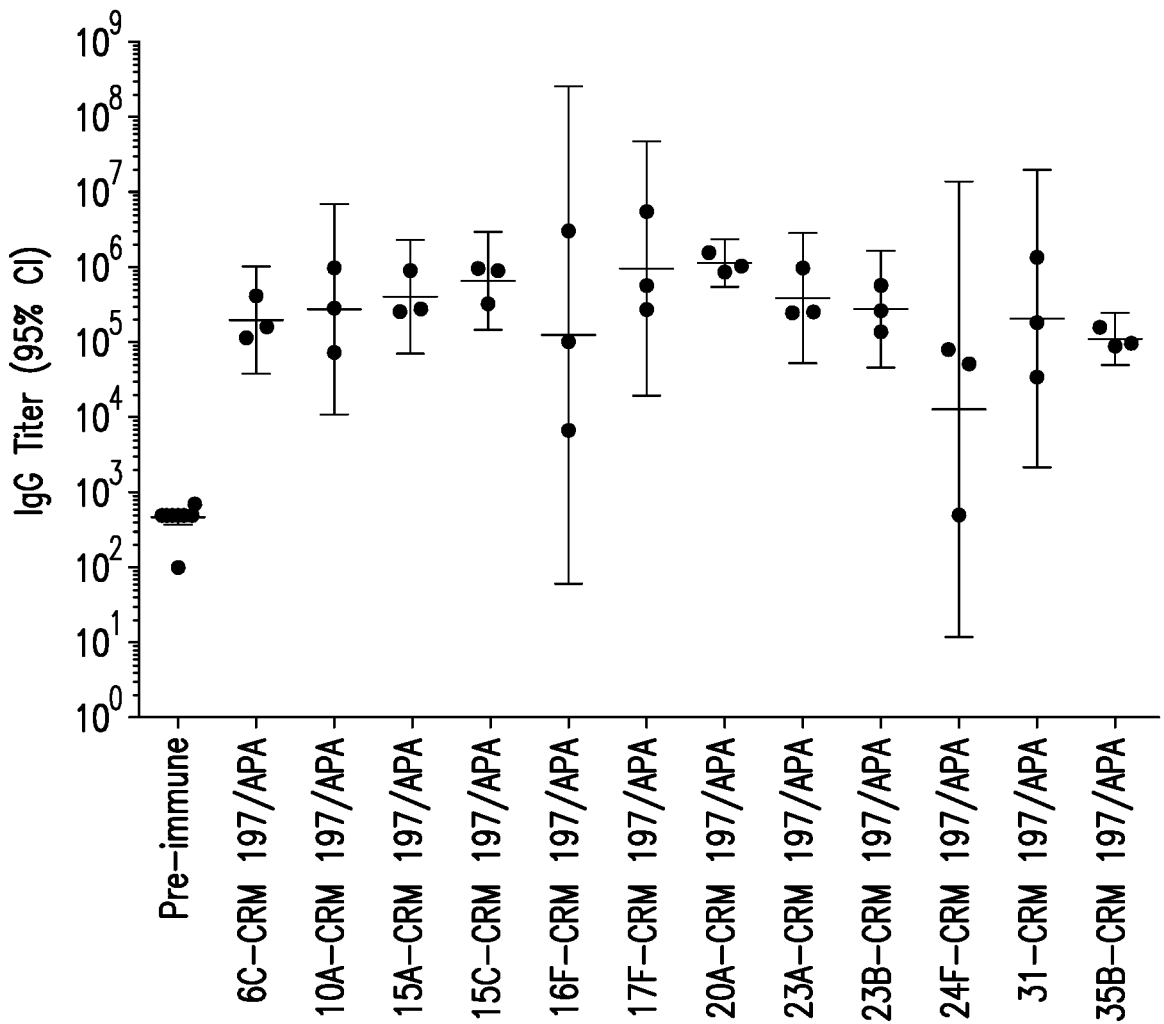
FIG. 15 shows ELISA IgG antibody dilution titers (post-dose 2) for rabbits immunized with S. pneumoniae monovalent serotypes conjugated to CRM197 and formulated with aluminum phosphate adjuvant (APA). Symbols indicate the individual titers and error bars represent the 95% confidence intervals (CIs) of the geometric mean titers (GMTs).
Figure 16:
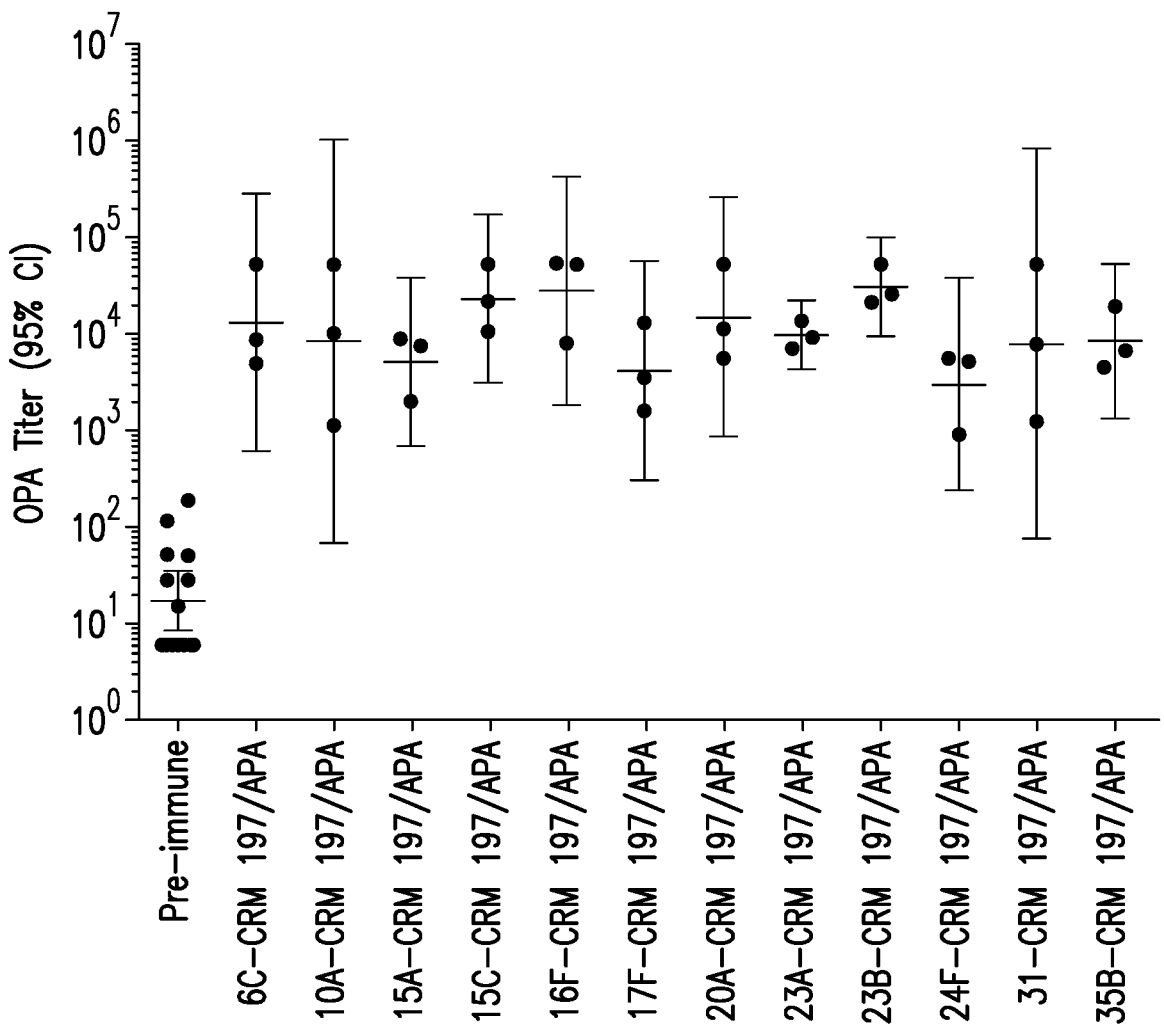
FIG. 16 provides serotype specific OPA dilution titers (post-dose 2) for rabbits immunized with S. pneumoniae monovalent serotypes conjugated to CRM197 and formulated with aluminum phosphate adjuvant (APA). Symbols indicate the individual titers and error bars represent the 95% confidence intervals (CIs) of the geometric mean titers (GMTs).

All monovalent pneumococcal conjugate vaccines were found to be immunogenic in rabbits (FIG. 15) and generate functional antibody which killed the respective bacterial strain (FIG. 16).

Example 42

Evaluation of Cross Protection of Serotypes 15A, 15B, 15C

Rabbits were immunized with 15A-CRM197/APA, 15B-CRM197/APA or 15C-CRM197/APA to evaluate cross-reactivity between each serotype.

Adult New Zealand White rabbits (NZWR, n=3/group) were intramuscularly (IM) immunized with 0.5 ml of respective monovalent conjugate vaccine on day 0 and day 14 (alternating sides). Monovalent pneumococcal conjugate vaccine, formulated in 20 mM L-Histidine, pH 5.8, 150 mM NaCl, and 0.2% (w/v) PS-20 and formulation process described in Example 38, was dosed at 2 μg PnPs (15A, 15B or 15C each conjugated to CRM197) with 125 μg APA per immunization. Sera were collected prior to study start (pre-immune) and on days 14 (post-dose 1, PD1) and 28 (post-dose 2, PD2). NZWRs were observed at least daily by trained animal care staff for any signs of illness or distress. The vaccine formulations in NZWRs were deemed to be safe and well tolerated, as no vaccine-related adverse events were noted. All animal experiments were performed in strict accordance with the recommendations in the Guide for Care and Use of Laboratory Animals of the National Institutes of Health. The NZWR experimental protocol was approved by the Institutional Animal Care and Use Committees at both Merck & Co., Inc and Covance (Denver, PA).

NZWR sera were tested in ELISA assays to evaluate IgG immunogenicity using a 1-2 mg/mL respective PnPs coating concentration. Functional antibody was determined through OPA based on previously described protocols available online at the Bacterial Respiratory Pathogen Reference Laboratory at the University of Alabama at Birmingham using Opsotiter® 3 software (UAB Research Foundation (Caro-Aguilar et al., 2017; Burton et al., 2006).

Figure 17:
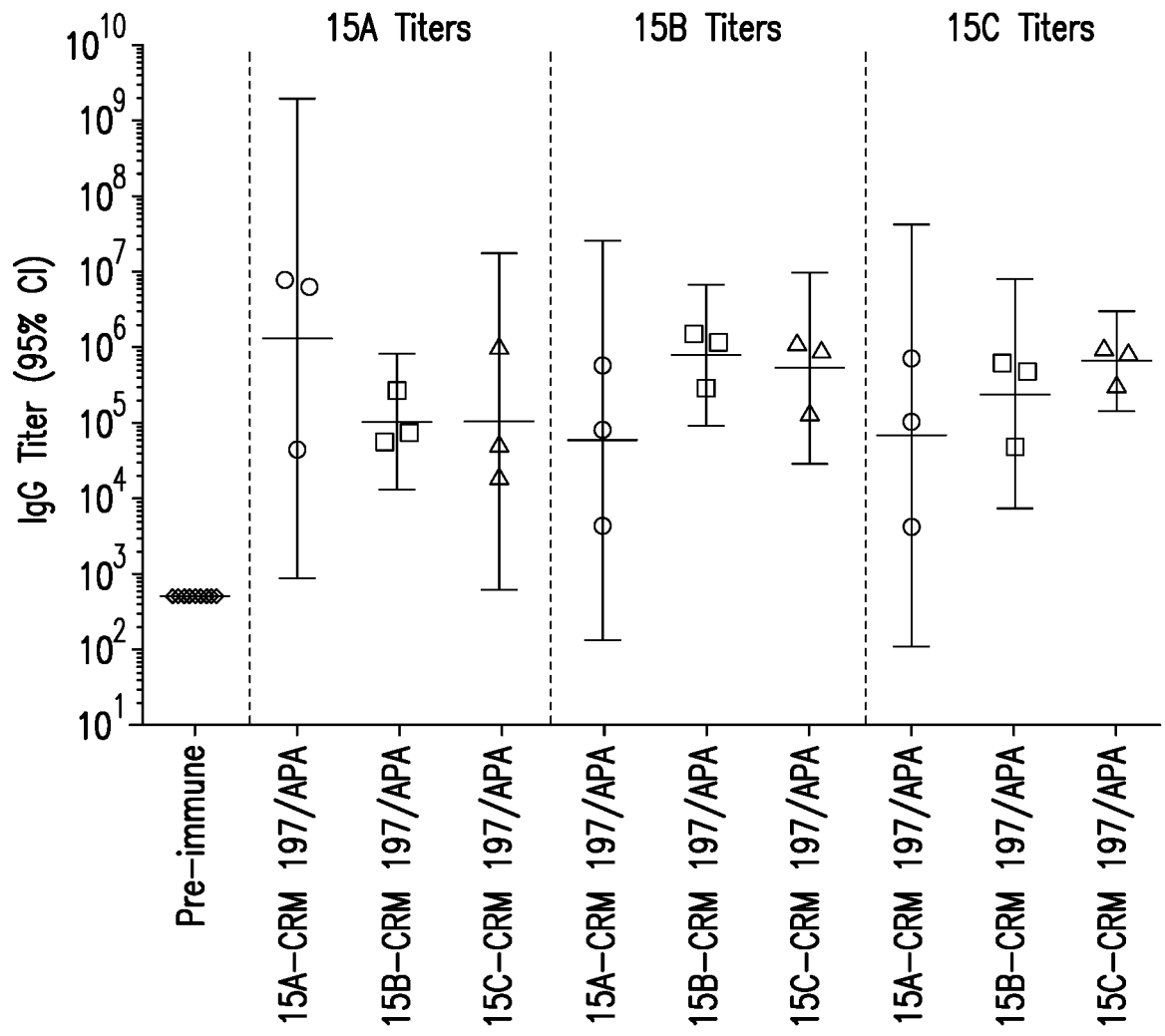
FIG. 17 provides ELISA IgG antibody dilution titers (post-dose 2) for rabbits immunized with S. pneumoniae serotype 15 monovalent conjugates. X-axis indicates the vaccine used to immunize rabbits. Dashed lines separate three separate ELISA assays using separate pneumococcal polysaccharide as a coating antigen. Symbols indicate the individual titers and error bars represent the 95% confidence intervals (CIs) of the geometric mean titers (GMTs).
Figure 18:
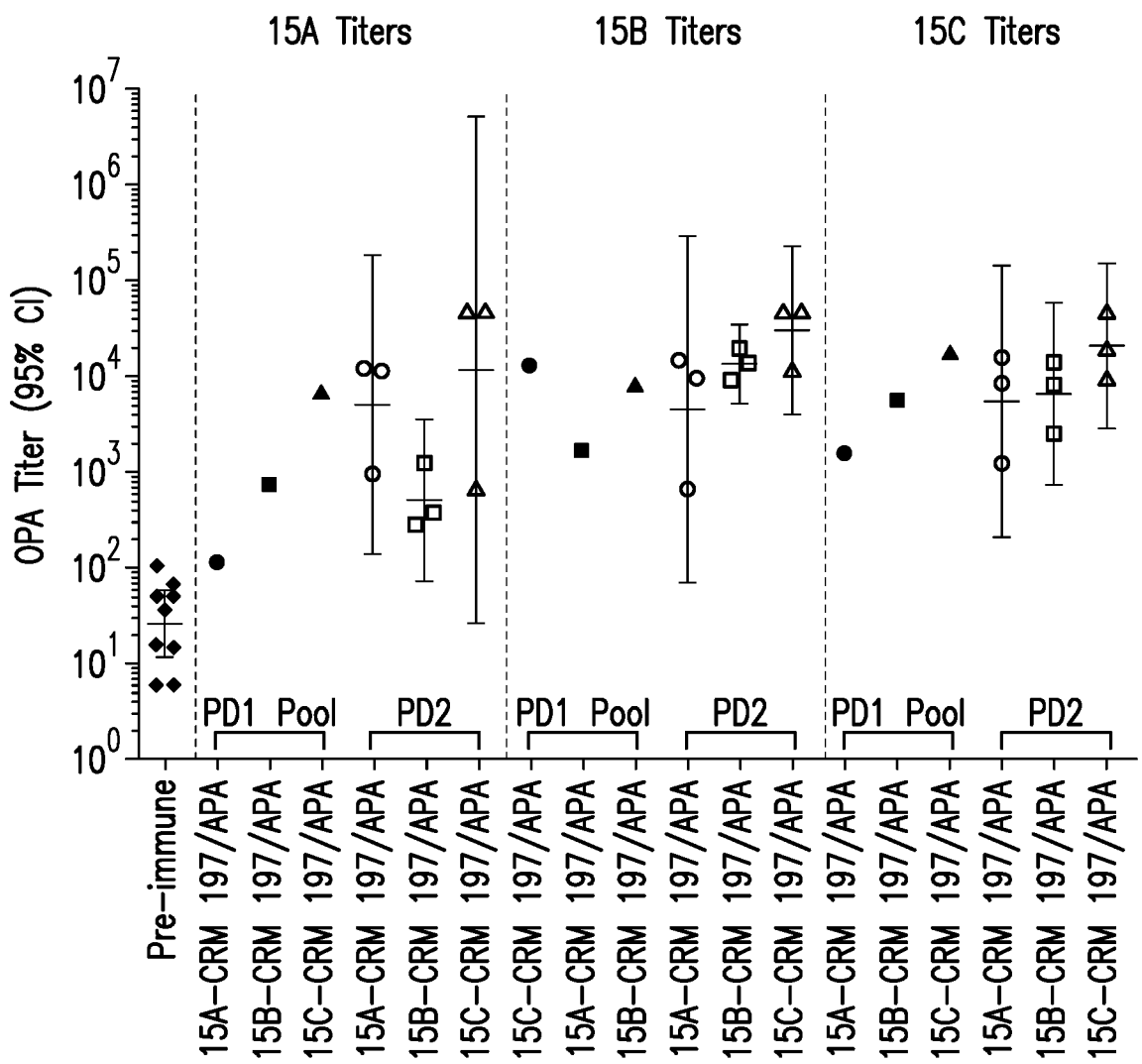
FIG. 18 shows serotype specific OPA dilution titers (pre-immune, post-dose 1 (PD1, pooled) and post-dose 2 (PD2)) for rabbits immunized with S. pneumoniae serotype 15 monovalent conjugates. X-axis indicates the vaccine used to immunize rabbits. Dashed lines separate three OPA assays using separate S. pneumoniae bacterial strains. Symbols indicate the individual titers and error bars represent the 95% confidence intervals (CIs) of the geometric mean titers (GMTs).

All three monovalent pneumococcal conjugate vaccines of serogroup 15 were found to be immunogenic in rabbits (FIG. 17) and generate functional antibody which killed the respective bacterial strain (FIG. 18). In addition, rabbits immunized with serogroup 15 monovalent pneumococcal conjugate vaccines had equivalent PD2 IgG and OPA titers to the homologous and heterologous polysaccharide and bacterial strain, respectively. Rabbits immunized with 15A-CRM197/APA, 15B-CRM197/APA or 15C-CRM197/APA all had cross reactivity to each pneumococcal polysaccharide (15A, 15B, 15C) (FIG. 17). Using post dose 2 (PD2) log transformed IgG data analyzed by One-way ANOVA with Tukey's multiple comparison test (P-value=0.354), there was no significant difference in the IgG titers across serogroup 15. In addition, rabbits immunized with 15A-CRM197/APA, 15B-CRM197/APA or 15C-CRM197/APA all had cross reactivity to each *S. pneumoniae* bacterial strain, (15A, 15B, 15C), as all rabbit hyper immune sera had functional antibody to each strain evaluated and killed the bacteria (FIG. 18). Similarly, using post dose 2 (PD2) log transformed OPA data analyzed by One-way ANOVA with Tukey's multiple comparison test (P-Value=0.054), there was no significant difference in OPA titers across the serogroup 15.

Example 43

Immunogenicity of PCV21 in New Zealand White Rabbits

Adult New Zealand White rabbits (NZWR, n=5/group) were intramuscularly (IM) immunized with 0.1-0.5 mL of pneumococcal conjugate vaccine on day 0 and day 14 (alternating sides). A PCV21 pneumococcal vaccine, formulated in 20 mM L-Histidine, pH 5.8, 150 mM NaCl, and 0.2% (w/v) PS-20 and formulation process described in Example 38, was dosed at 4, 2, 1, 0.4, 0.08 or 0.016 μg PnPs (3, 6C, 7F, 8, 9N, 10A, 11A, 12F, 15A, 15C, 16F, 17F, 19A, 20A, 22F, 23A, 23B, 24F, 31, 33F or 35B, each conjugated to CRM197) per immunization. Sera were collected prior to study start (pre-immune) and on days 14 (post-dose 1, PD1) and 28 (post-dose 2, PD2). NZWRs were observed at least daily by trained animal care staff for any signs of illness or distress. The vaccine formulations in NZWRs were deemed to be safe and well tolerated, as no vaccine-related adverse events were noted. All animal experiments were performed in strict accordance with the recommendations in the Guide for Care and Use of Laboratory Animals of the National Institutes of Health. The NZWR experimental protocol was approved by the Institutional Animal Care and Use Committees at both Merck & Co., Inc and Covance (Denver, PA).

NZWR sera were evaluated for IgG immunogenicity using a multiplexed electrochemiluminescence (ECL) assay. This assay was developed for use with rabbit serum based on the human assay described by Marchese et al. (Optimization and validation of a multiplex, electrochemiluminescence-based detection assay for the quantitation of immunoglobulin G serotype-specific antipneumococcal antibodies in human serum. *Clin Vaccine Immunol.* 16(3): 387-96 (2009)) using technology developed by MesoScale Discovery (a division of MesoScale Diagnostics, LLC, Gaithersburg, MD) which utilizes a SULFO-TAG™ label that emits light upon electrochemical stimulation. SULFO-TAG™-labeled anti-rabbit IgG was used as the secondary antibody for testing NZWR serum samples. Functional antibody was determined through multiplexed opsonophagocytic assays (MOPA) based on previously described protocols available online at the Bacterial Respiratory Pathogen Reference Laboratory at the University of Alabama at Birmingham using Opsotiter® 3 software (UAB Research Foundation, Caro-Aguilar et al, 2017, supra, Burton et al., 2006, supra).

PCV21 pneumococcal conjugate vaccines were found to be immunogenic in rabbits (FIGS. 19A, 19B, 20A, and 20B) and generate functional antibody which killed vaccine-type bacterial strains (FIGS. 21A and 21B) at all doses tested.

Figure 19A:
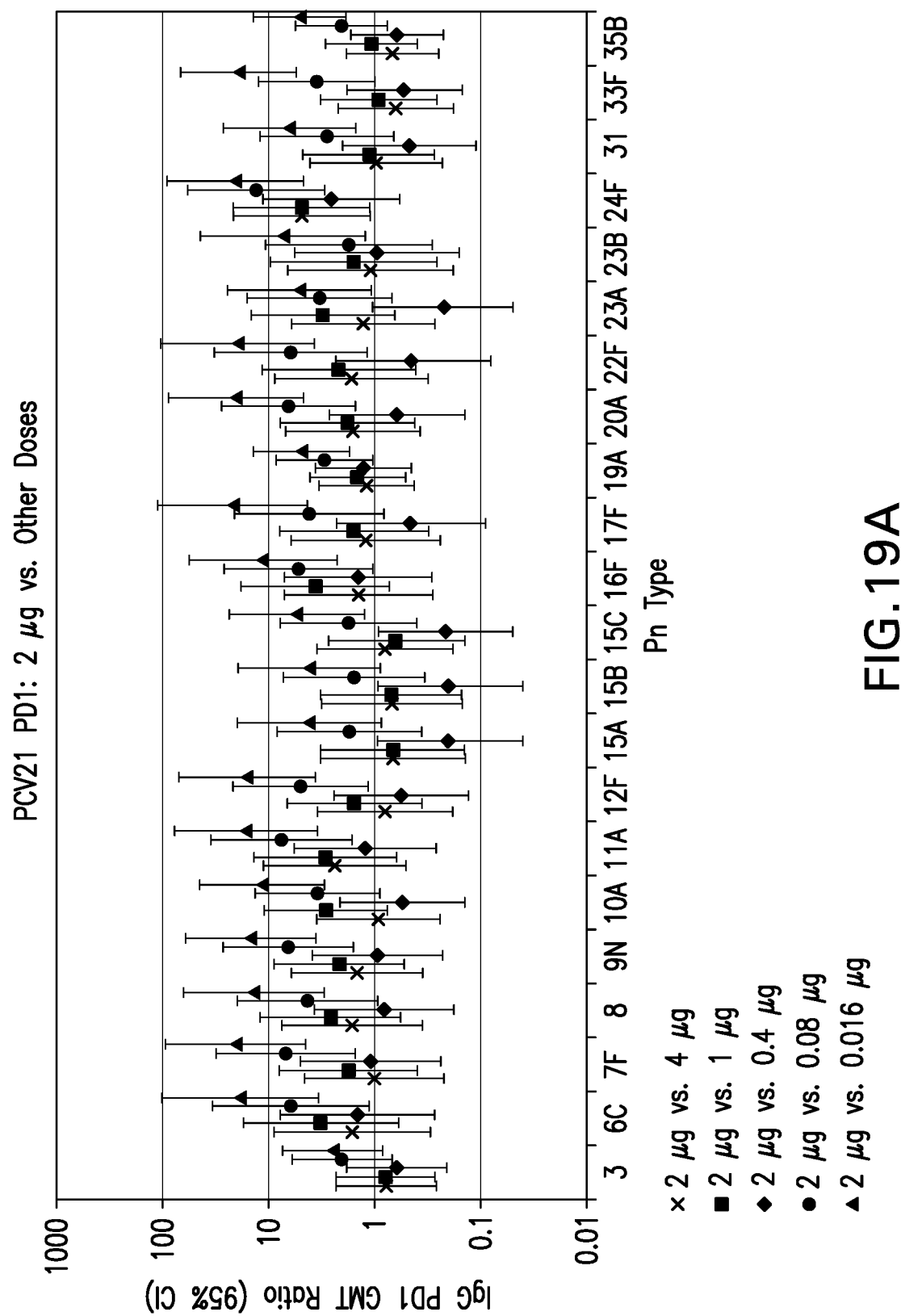
FIG. 19A provides a comparison of PD1 antibody responses in NZWR (5 per group) following vaccination with 4, 2, 1, 0.4, 0.08 or 0.016 μg/dose of PCV21. Symbols indicate PD1 geometric mean titer (GMT) ratios (Group 2 μg/dose vs. other dose groups) with error bars representing the 95% confidence interval (CI).

Comparable PD1 immunogenicity was observed for PCV21 dosed at 4, 2, 1 and 0.4 μg per PnPs, with the exception of 24F which had higher immunogenicity in the 2 μg dose compared to the 4 or 1 μg doses and 15A, 15B and 15C which had higher immunogenicity in the 0.4 μg dose compared to the 2 μg dose (FIGS. 19A and 19B). Therefore, there was not much of a vaccine dose response at the higher PnPs doses (0.4-4 μg/PnPs). Lower immunogenicity was observed at the 0.08 and 0.016 μg PnPs vaccine doses, as many serotypes were significantly lower when compared to the 2 μg vaccine dose.

Figure 20A:
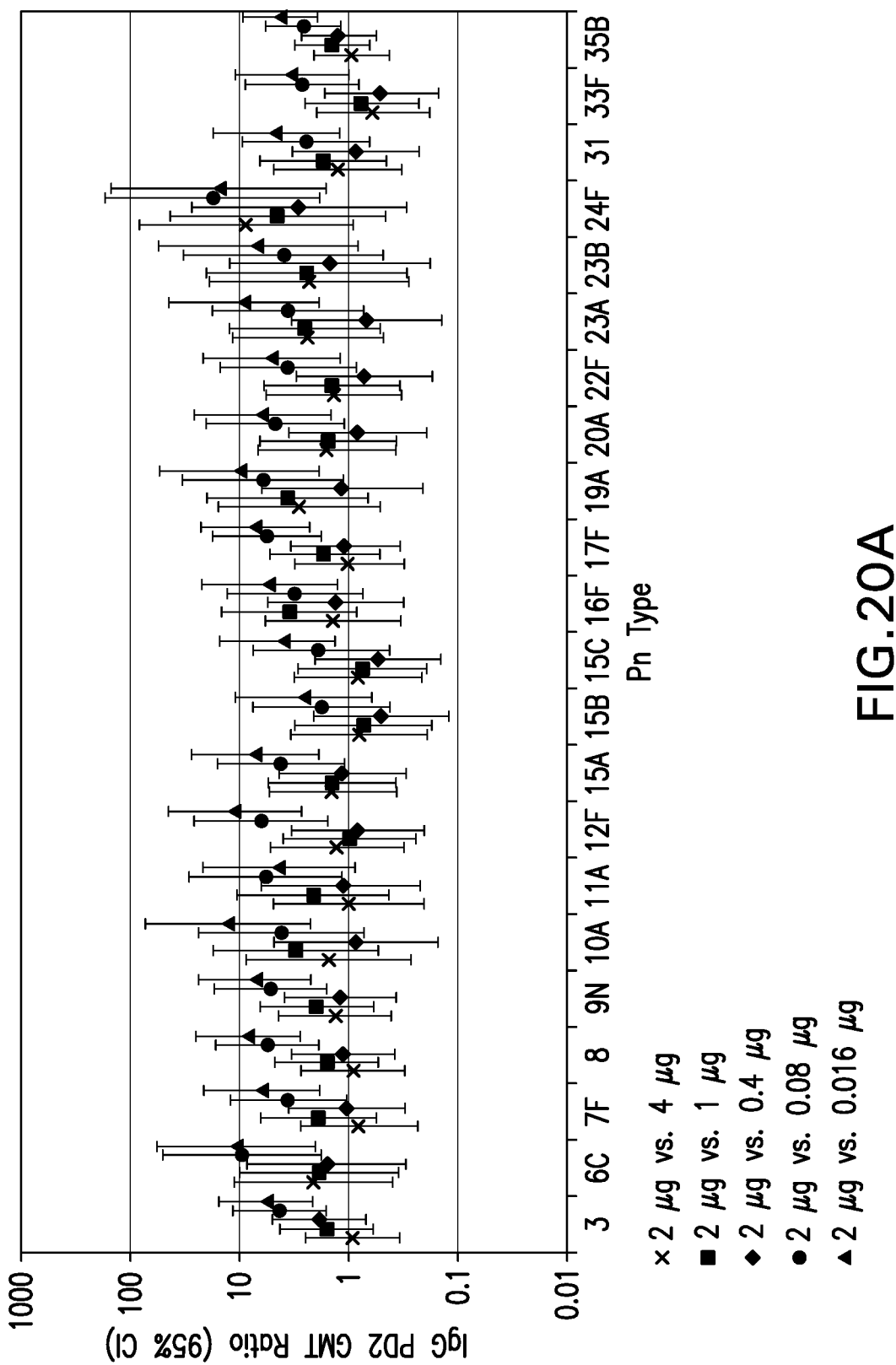
FIG. 20A provides a comparison of PD2 antibody responses in NZWR (5 per group) following vaccination with 4, 2, 1, 0.4, 0.08 or 0.016 μg/dose of PCV21. Symbols indicate PD2 GMT ratios (Group 2 μg/dose vs. other dose groups) with error bars representing the 95% CI.

Comparable PD2 immunogenicity was observed for PCV21 dosed at 4, 2, 1 and 0.4 μg per PnPs (FIGS. 20A and 20B).

Figure 21A:
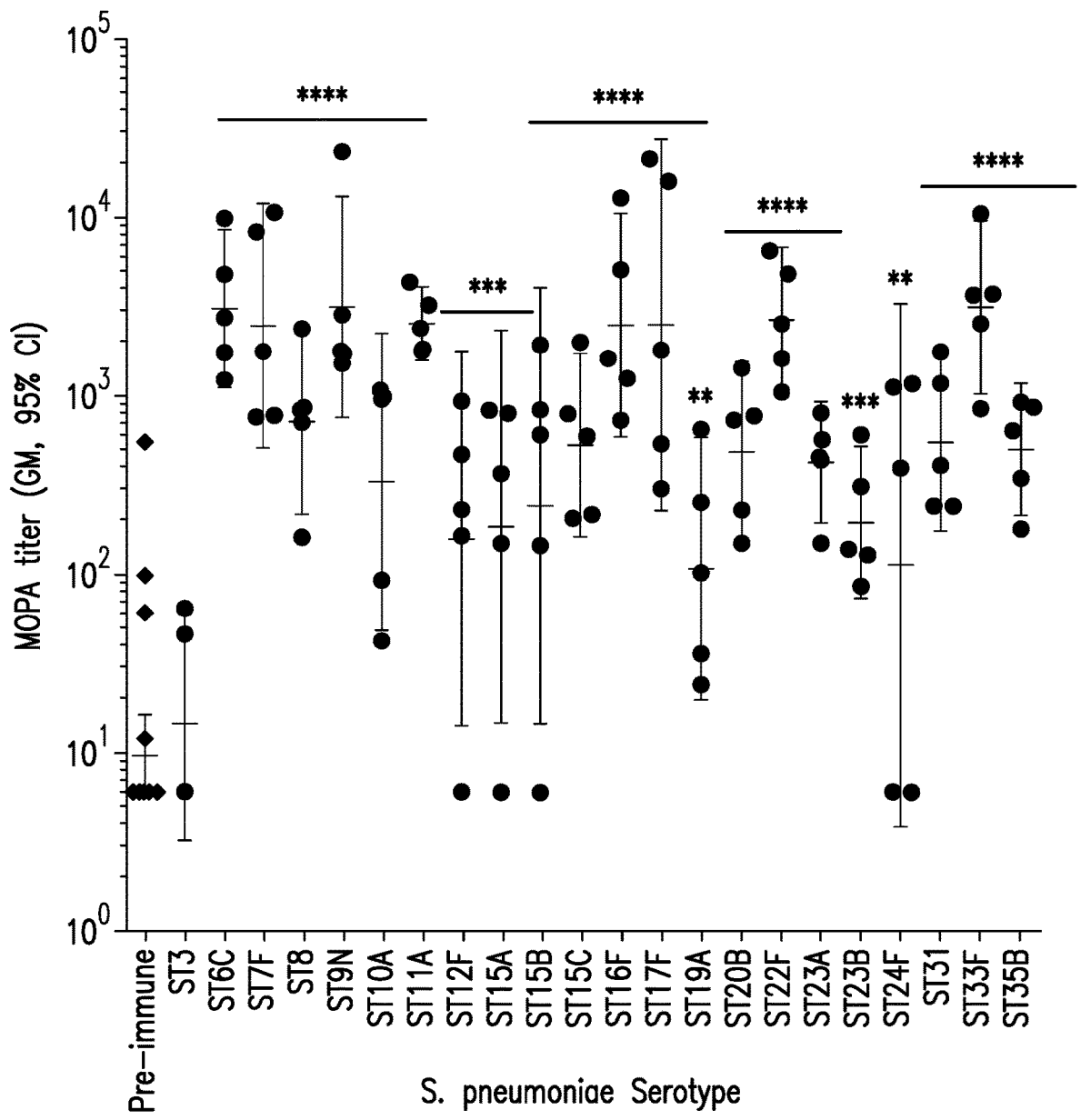
FIG. 21A shows the serotype specific PD1 OPA dilution titers for rabbits immunized with PCV21 (2 μg/PnPs). Symbols indicate the individual titers and error bars represent the 95% confidence intervals (CIs) of the geometric mean titers (GMTs).* p<0.05,  p<0.01, * p<0.001, ** p<0.0001.
Figure 21B:
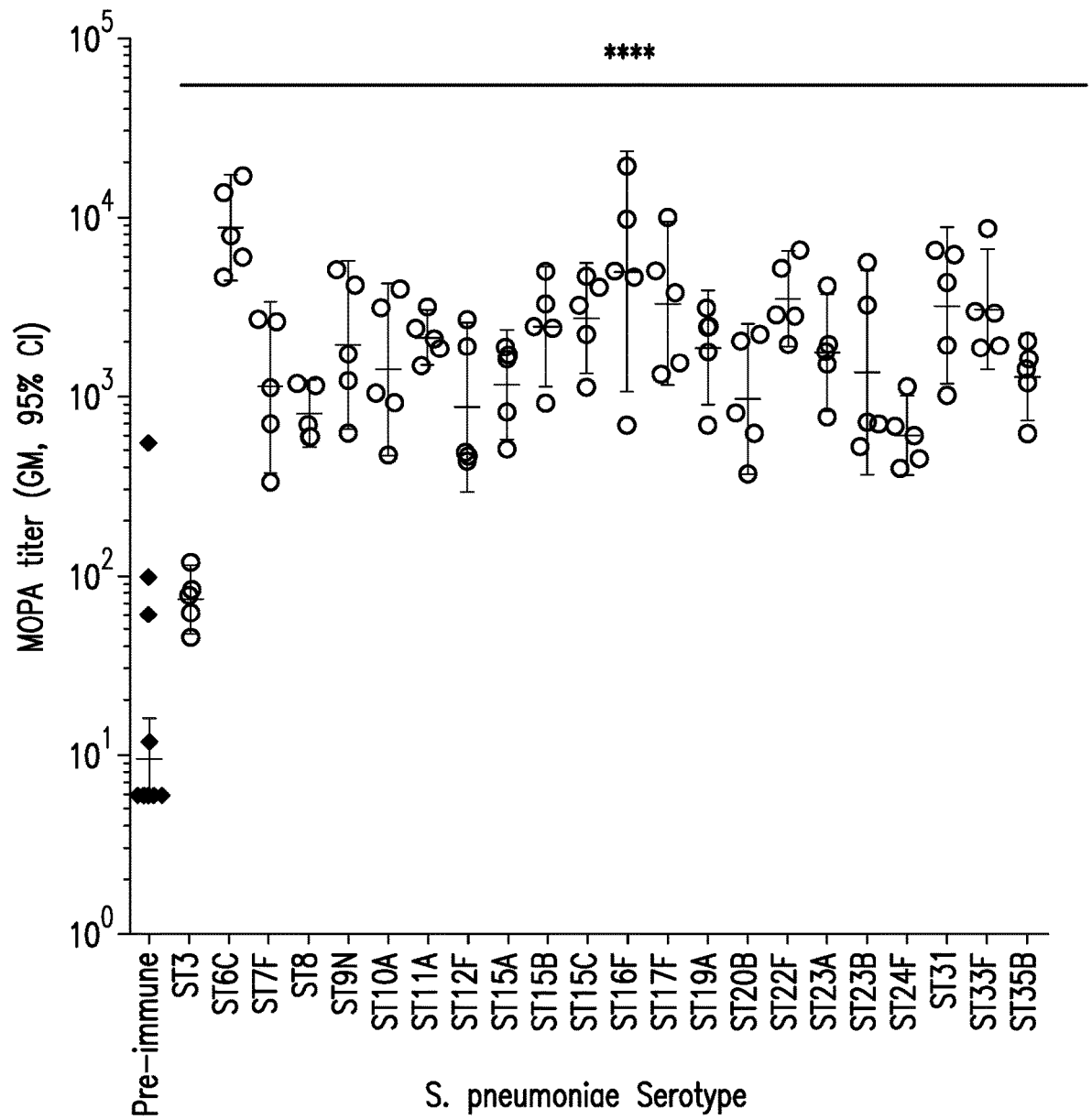
FIG. 21B shows serotype specific PD2 OPA dilution titers for rabbits immunized with PCV21 (2 μg/PnPs). Symbols indicate the individual titers and error bars represent the 95% confidence intervals (CIs) of the geometric mean titers (GMTs), ** p<0.0001. Serotype 15B data is included to evaluate cross protection.

In general comparable PD2 MOPA titers were observed for PCV21 dosed at 4, 2, 1 and 0.4 μg per PnPs with MOPA titers trending lower for the 0.08 and 0.016 μg PnPs vaccine doses, although many not reaching statistical significance (data not shown). PCV21 dosed at 2 μg per PnPs was selected as a representative data set for MOPA. Specifically, rabbits immunized with PCV21 at the 2 μg dose had significantly higher PD1 MOPA titers for all serotypes compared to pre-immune rabbit sera with the exception of serotype 3 (FIG. 21A). It should be noted that rabbit pre-immune sera from this study had higher background titers to serotypes 16F, 31 and 35B. Rabbits immunized with PCV21 at the 2 µg dose had significantly higher PD2 MOPA titers for all serotypes compared to pre-immune rabbit sera (FIG. 21B). Log Transformed data were analyzed by Oneway ANOVA with Dunnett's test to determine significance.

Example 44

Materials and Methods

Free Polysaccharide Testing

Free polysaccharide (polysaccharide that is not conjugated with CRM197) in conjugate sample is measured by first precipitating free protein and conjugates with deoxycholate (DOC) and hydrochloric acid. Precipitates are then filtered out and the filtrates are analyzed for free polysaccharide concentration by HPSEC/UV/MALS/RI. Free polysaccharide is calculated as a percentage of total polysaccharide measured by HPSEC/UV/MALS/RI.

Free Protein Testing

Free polysaccharide, polysaccharide-CRM197 conjugate, and free CRM197 in conjugate samples are separated by capillary electrophoresis in micellar electrokinetic chromatography (MEKC) mode. Briefly, samples are mixed with MEKC running buffer containing 25 mM borate, 100 mM SDS, pH 9.3, and are separated in a preconditioned barefused silica capillary. Separation is monitored at 200 nm and free CRM197 is quantified with a CRM197 standard curve. Free protein results are reported as a percentage of total protein content determined by the HPSEC/UV/MALS/RI procedure.

Molecular Weight and Concentration Analysis of Conjugates Using HPSEC/UV/MALS/RI Assay Conjugate samples were injected and separated by high performance size-exclusion chromatography (HPSEC). Detection was accomplished with ultraviolet (UV), multi-angle light scattering (MALS) and refractive index (RI) detectors in series. Protein concentration was calculated from UV280 using an extinction coefficient. Polysaccharide concentration was deconvoluted from the RI signal (contributed by both protein and polysaccharide) using the do/dc factors which are the change in a solution's refractive index with a change in the solute concentration reported in mL/g. Average molecular weight of the samples were calculated by Astra software (Wyatt Technology Corporation, Santa Barbara, CA) using the measured concentration and light scattering information across the entire sample peak. There are multiple form of average values of molecular weight for polydispersed molecules. For example number-average molecular weight Mn, weight-average molecular weight Mw, and z-average molecular weight Mz (Molecules, 2015, 20, 10313-10341). Unless specified, the molecular weights are weight-average molecular weight.

Determination of Lysine Consumption in Conjugated Protein as a Measure of the Number of Covalent Attachments Between Polysaccharide and Carrier Protein The Waters AccQ-Tag amino acid analysis (AAA) was used to measure the extent of conjugation in conjugate samples. Samples were hydrolyzed using vapor phase acid hydrolysis in the Eldex workstation, to break the carrier proteins down into their component amino acids. The free amino acids were derivatized using 6-aminoquinolyl-N-hydroxysuccinimidyl carbamate (AQC). The derivatized samples were then analyzed using UPLC with UV detection on a C18 column. The average protein concentration was obtained using representative amino acids other than lysine. Lysine consumption during conjugation (i.e., lysine loss) was determined by the difference between the average measured amount of lysine in the conjugate and the expected amount of lysine in the starting protein.

Example 45

Impact of Conjugation Process on Stability of a Pneumococcal Conjugate Vaccine

Individual pneumococcal polysaccharide-protein conjugates prepared utilizing different reductive amination solvents (aqueous or DMSO) as described in the Examples, supra, were used for the formulation of a 1-, 7-, 14-, and 21-valent pneumococcal conjugate vaccine drug product referred to as PCV1, PCV7, PCV14 and PCV21 at 84 µg/mL.

The drug product vaccine-filled containers were placed at 4° C. or 37° C. for up to 7 days. Intrinsic Protein Fluorescence Spectroscopy (IPFS) was used to assess the stability of pneumococcal polysaccharide-conjugated carrier protein, CRM197, in the PCV1, PCV7, PCV14 or PCV21 compositions upon storage for up to at 4° C. and 37° C. Fluorescence emission spectra (Em 290-400 nm) of undiluted samples were collected using a Jasco FP-6500 Spectrofluorometer at ambient room temperature in a 1 cm path length quartz cuvette. An Excitation wavelength of 280 nm was used with a scan speed of 100 nm/min and excitation and emission bandpass of 3 nm.

Figure 22A:
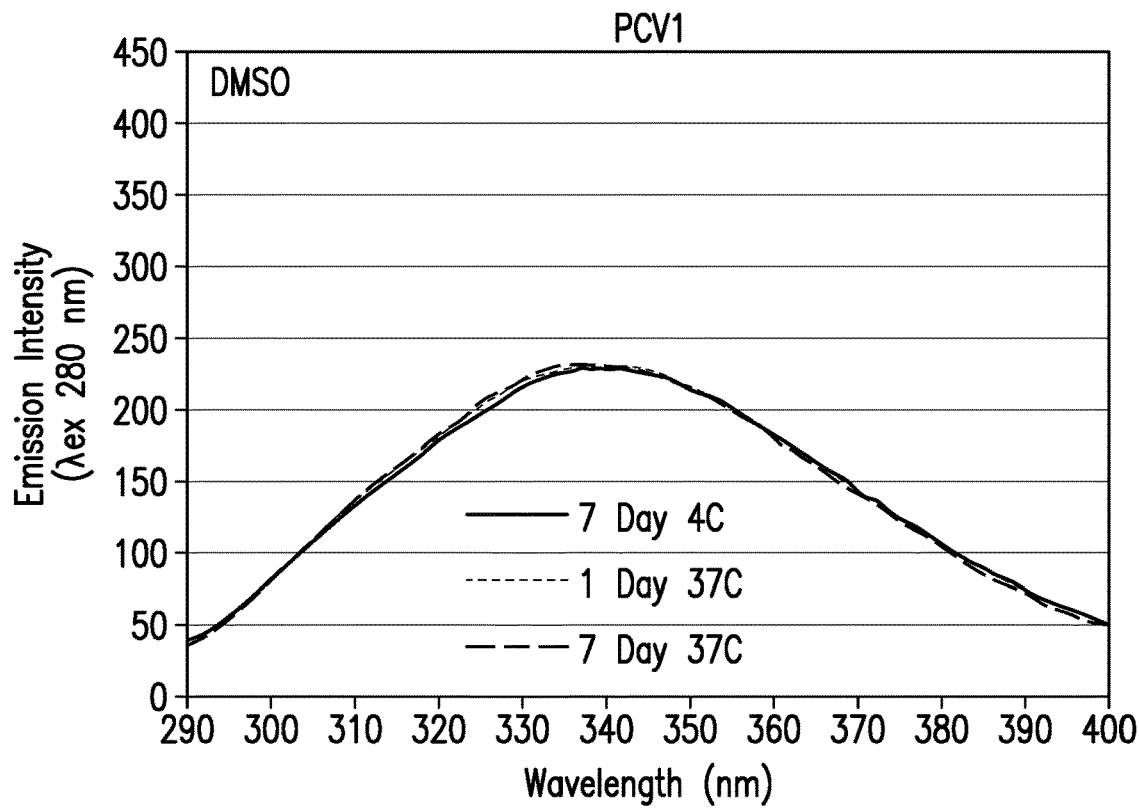
FIGS. 22A-22G show the impact of time and temperature (i.e. 7 Days at 4° C., 1 Day at 37° C. or 7 Days at 37° C.) on stability of three Pneumococcal Conjugate vaccines (PCV1 [FIG. 22A and FIG. 22B], PCV7 [FIG. 22C and FIG. 22D], and PCV14 [FIG. 22E and FIG. 22F]), prepared with all drug substances conjugated in either aqueous solvent or DMSO solvent, using intrinsic protein fluorescence spectroscopy with an excitation wavelength at 280 nm.
Figure 22B:
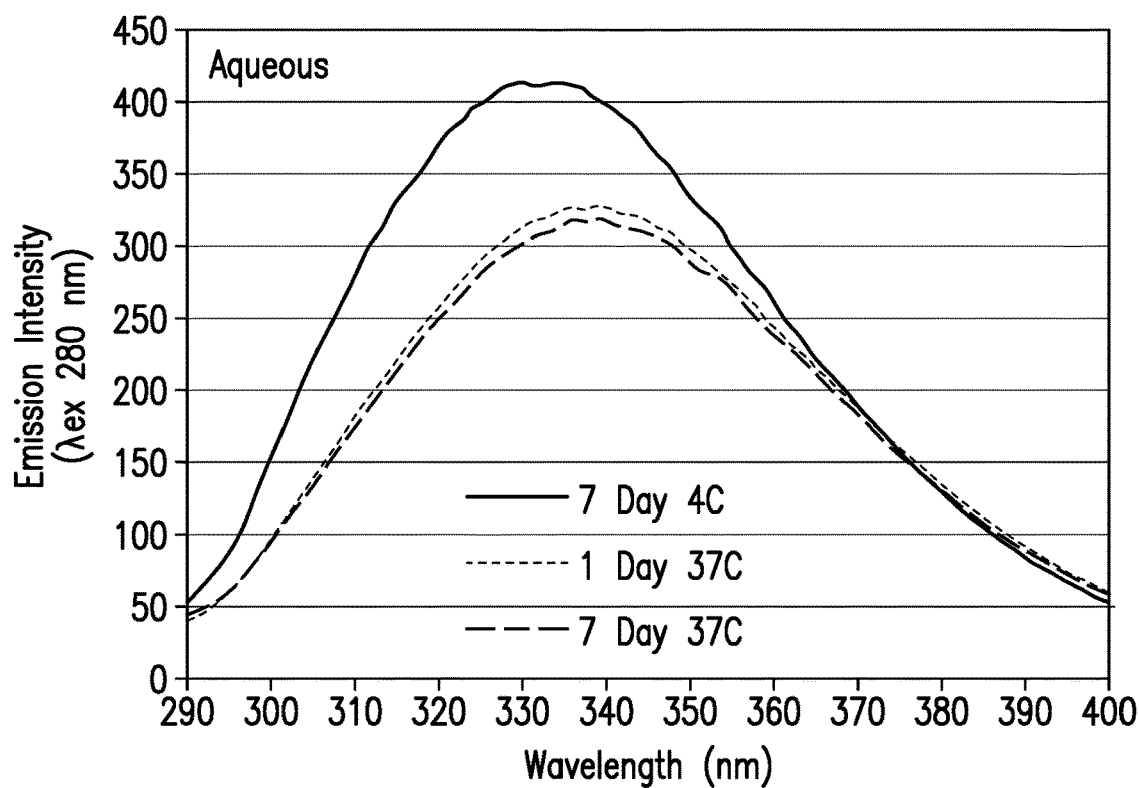
Figure 22C:
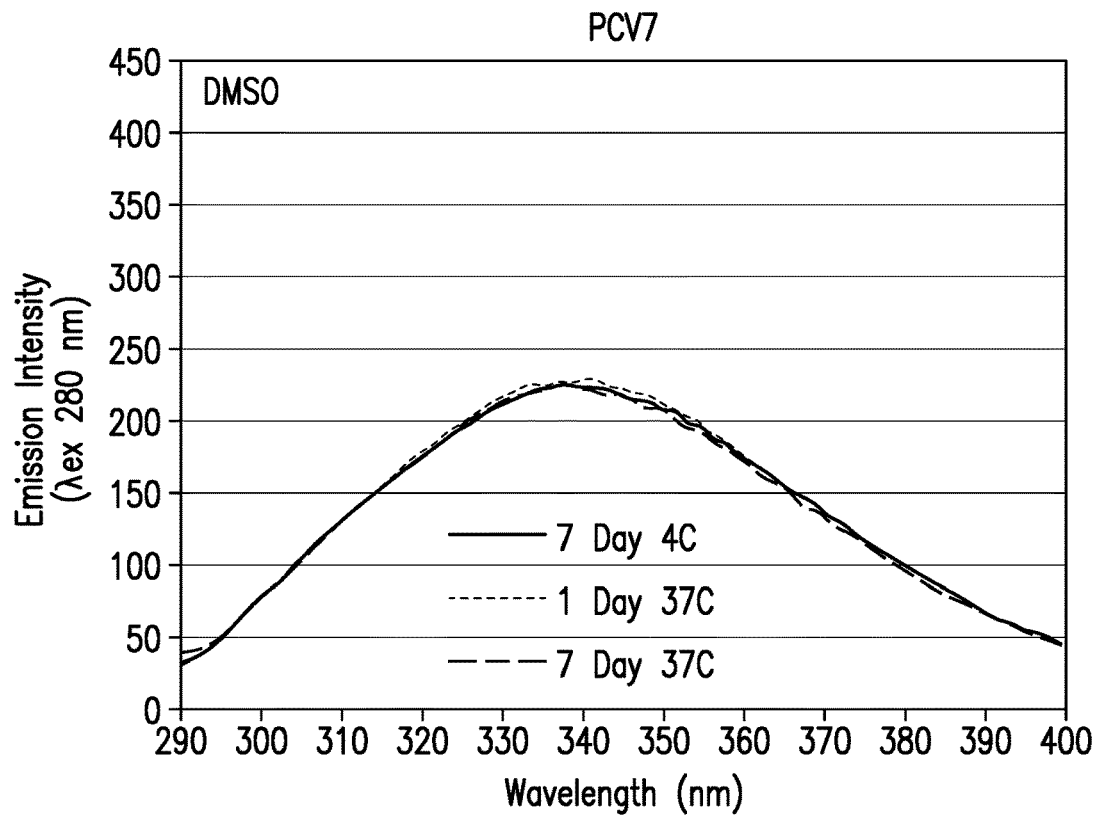
Figure 22D:
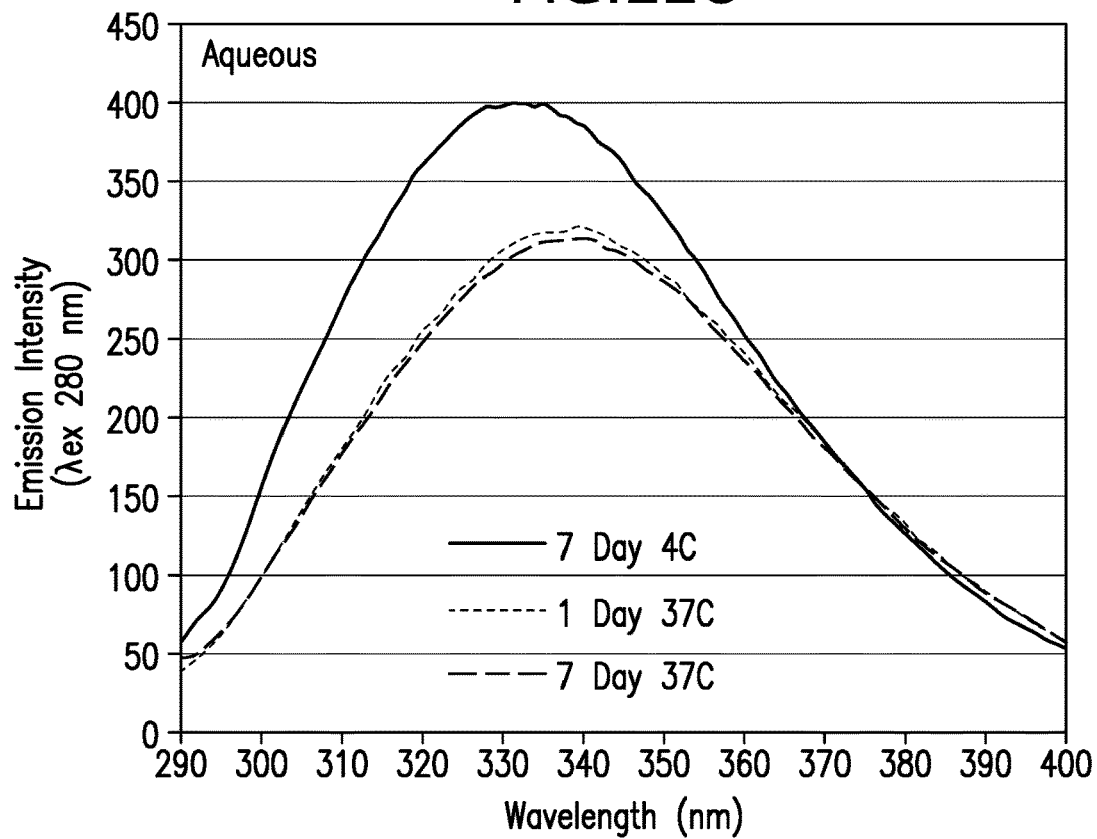
Figure 22E:
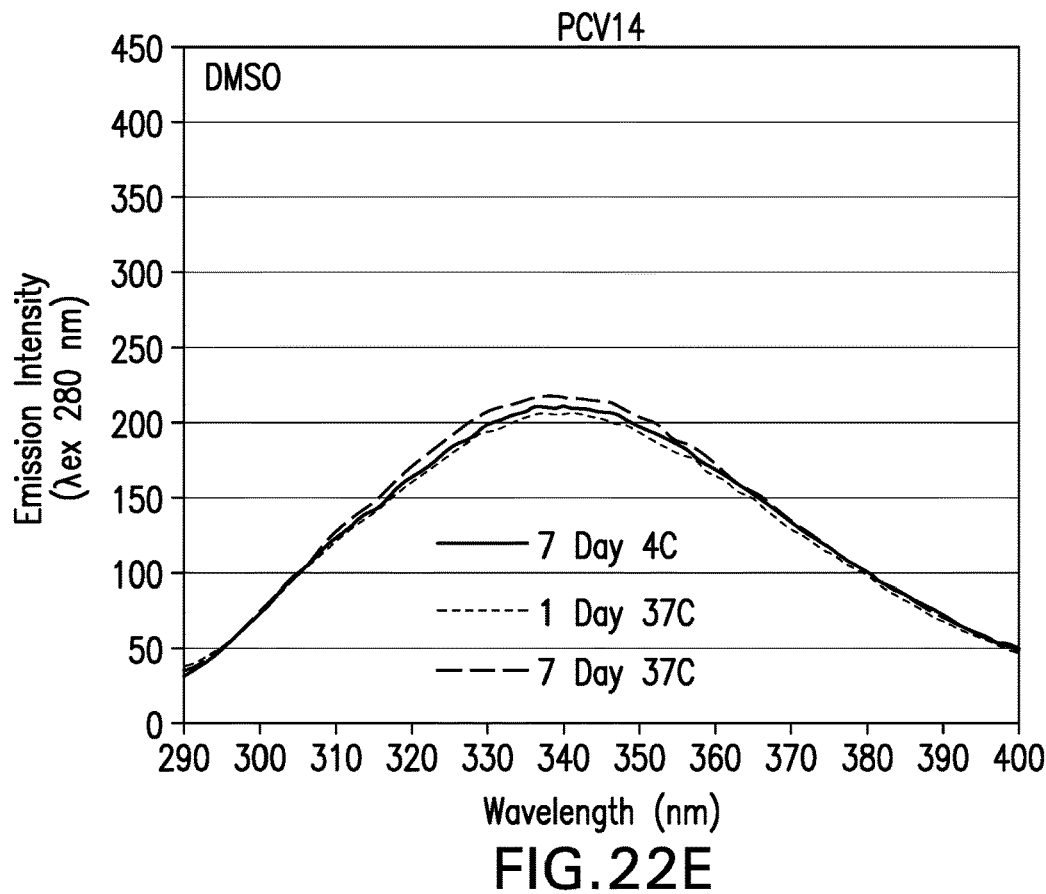
Figure 22F:
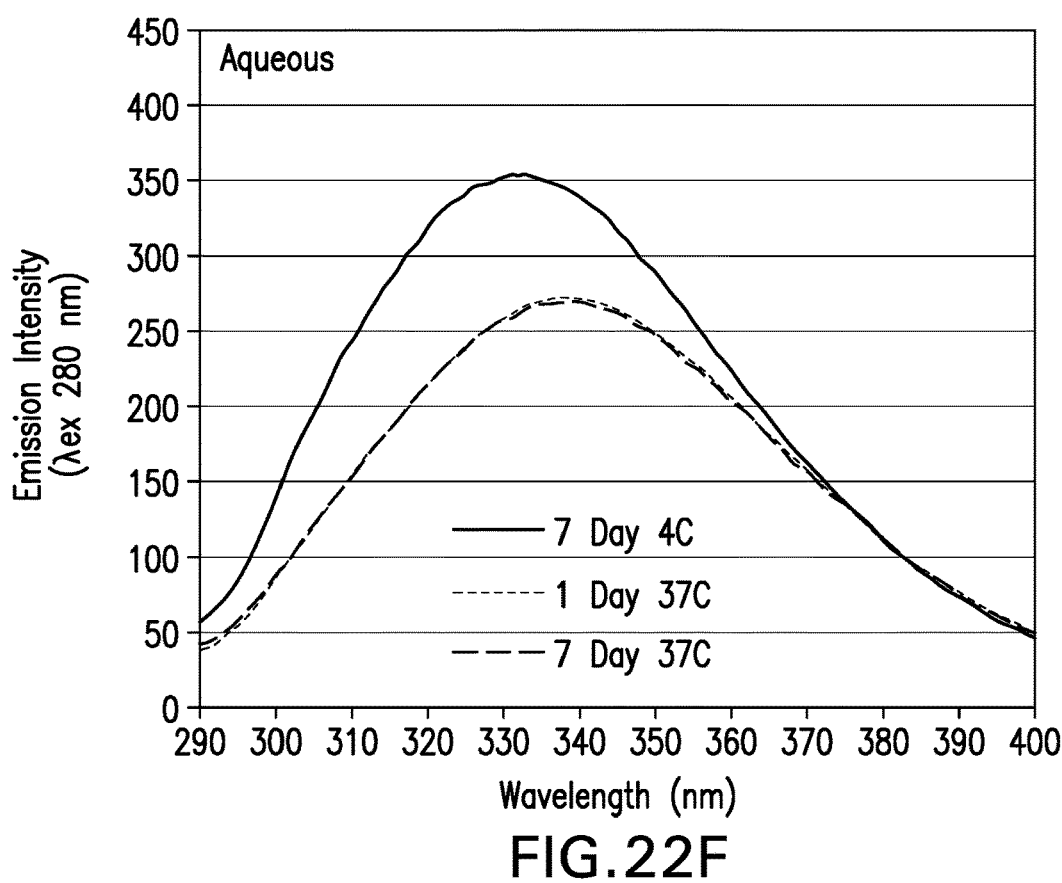
Figure 22G:
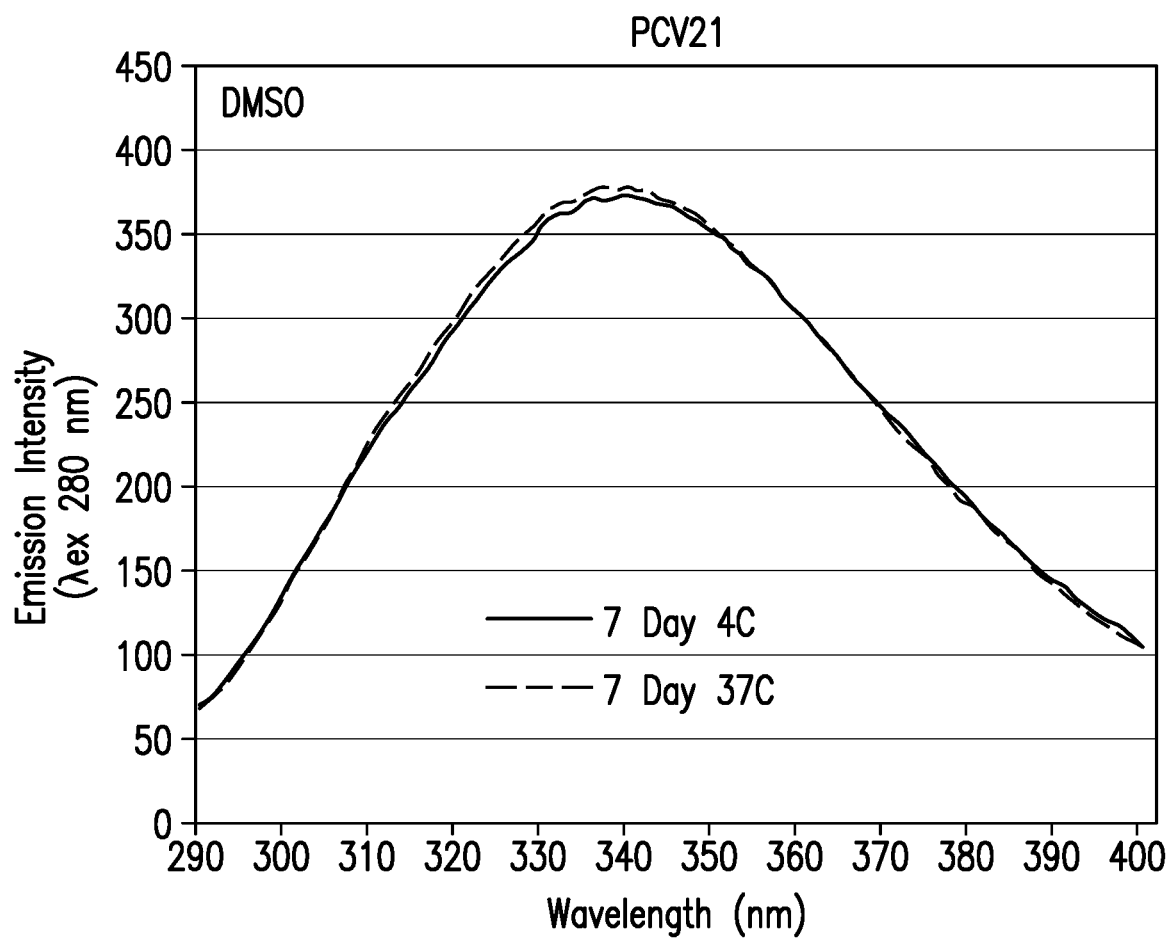

As shown in FIGS. 22A-F, the drug product formulations containing all polysaccharide-protein conjugates prepared using reductive amination in an aprotic solvent (e.g. DMSO) resulted in superior physical and chemical stability as compared to a vaccine utilizing all polysaccharide-protein conjugates prepared using aqueous solvent during reductive amination in the conjugation process (protic). In as little as 16 hours at 37° C., the fluorescence intensity of the PCV1, PCV7 and PCV14 drug products prepared using all polysaccharide-protein conjugates which were prepared using reductive amination in an aqueous solvent at 84 µg/mL PnPs was reduced and the emission maximum of the vaccine shifted from 332 nm to 338 nm. The PCV1, PCV7 and PCV14 vaccine drug products, at 84 µg/mL PnPs, utilizing drug substances prepared with reductive amination chemistry in an aprotic solvent (e.g. DMSO) did not show a change in fluorescence intensity or emission maximum at 338 nm. Moreover, a PCV21 drug product was also studied. It was formulated in 20 mM L-Histidine, pH 5.8, 150 mM NaCl, and 0.1% (w/v) PS-20 as described in Example 38, containing polysaccharide-protein conjugates prepared using reductive amination in an aprotic solvent (e.g. DMSO). The study showed superior physical and chemical stability after storage at 37° C. PCV21 did not show a change in fluorescence intensity or emission maximum 338 nm (FIG. 22G).

It should be understood that the resulting signal intensity and emission maximum acquired from the IPFS (EXAMPLE 40) measurement is due to the collective stability of the individual polysaccharide-protein conjugates in a multivalent complex drug product. We have shown that a vaccine drug product utilizing all polysaccharide-protein conjugates prepared in an aprotic solvent is stable while a vaccine drug product utilizing all drug substances prepared in a protic solvent is not stable under stressed conditions. If a vaccine drug product composition included a mixture of polysaccharide-protein conjugates using both protic and an aprotic conjugation process, the average emission maximum or intensity measured from the drug product would be weighted due to the contribution of each protic polysaccharide-protein conjugates emission at 332 nm and each aprotic of polysaccharide-protein conjugate emission at 338 nm. It would be expected that a weighted change would occur, in either intensity or emission maxima, upon elevated temperature for such a mixture due to the presence of the polysaccharide protein conjugates prepared using a protic conjugation process.

Figure 23:
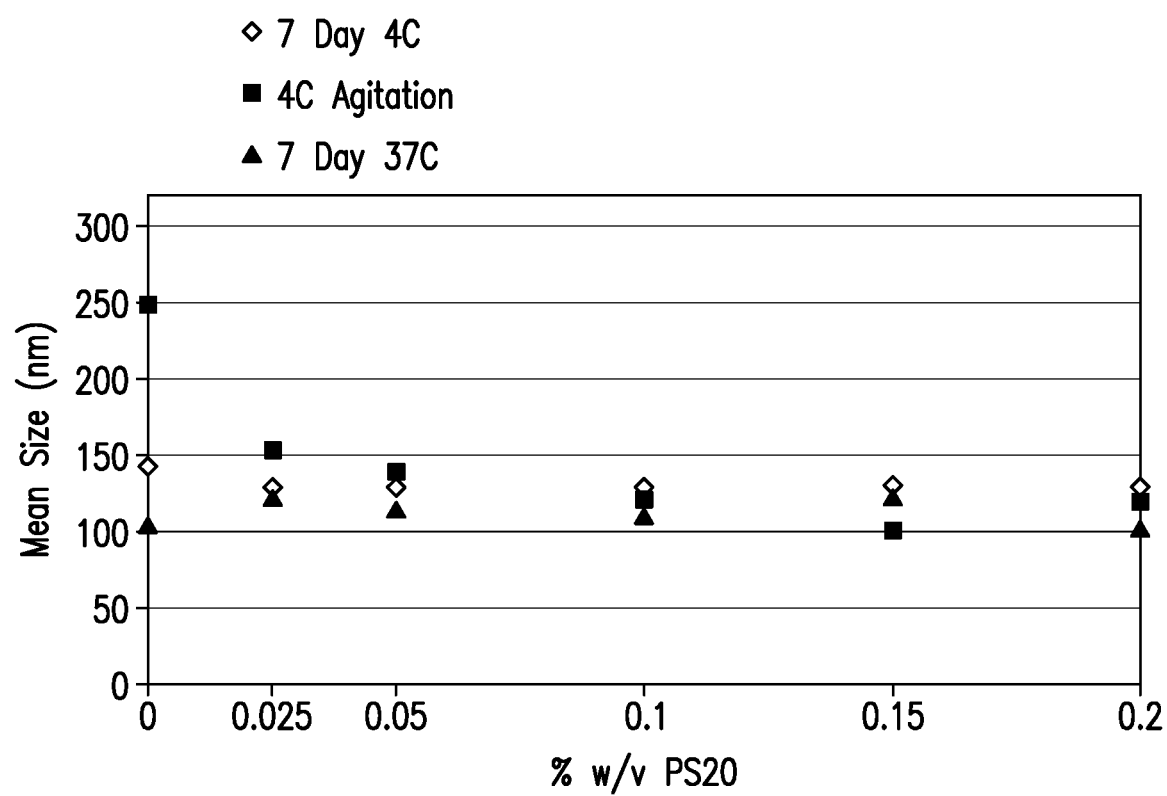
FIG. 23 shows the impact of temperature (7 Days at 4° C. or 37° C.) and agitation at 4° C. on the particle size distribution as analyzed by Nanoparticle Tracking Analysis (NTA) of six (6) PCV21 Pneumococcal Conjugate vaccine drug products formulated with PS-20 (0%, 0.025%, 0.05%, 0.1%, 0.15% or 0.2%; all w/v PS-20) at 0.084 mg/mL PnPs.

As shown in FIG. 23, to assess stability of the PCV21 drug product prepared at 0.084 mg/mL PnPs, Nanoparticle Tracking Analysis (NTA) was utilized. The technique collects videos of directly tracked nanoparticle populations as they move by Brownian motion to extrapolate particle size and concentration. A class 1, 635 nm laser focuses an 80 micron red laser beam through the liquid sample, illuminating particles as rapidly diffusing points of light. A CCD camera records a 30 frame per second video to track the movement of each individual illuminated particle over time. The system software identifies the center of each individual particle from the video and tracks the distance independently traversed to determine the mean square displacement. This tracking is performed simultaneously for every particle within the sample population in each frame until the raw data collected from the entire video is analyzed. By simultaneously measuring the mean square displacement of every individual particle tracked, its diffusion coefficient (Dt) and the spherical equivalent hydrodynamic radius (rh) are determined by applying the Stokes-Einstein equation. The software then represents this accumulated data as a particle size and concentration distribution. Raw data information on not only particle size and concentration, but also intensity, or brightness of the individual particle are gathered. Taken together the data are fitted and plotted individually as particle intensity relative to particle size, and particle concentration relative to particle size, and then on three dimensional contour plots comparing particle size, concentration, and intensity of all particle populations.

A conjugate vaccine comprised of carrier protein and polysaccharide antigen may together or separately be susceptible to aggregation within the 10-1000 nm particle size range, thereby making NTA a suitable stability indicating technique for assessing and quantitating aggregation phenomena. Upon exposure of drug product to 4° C. and 37° C. for 1 week, no significant aggregation of drug product was observed by NTA for formulations containing PS-20 at concentrations of 0.025% w/v, 0.05% w/v, 0.1% w/v, 0.15% w/v, and 0.2% w/v PS20 (as shown in FIG. 23). However, after subjecting formulations to agitation for 6 hr. at 4° C., the formulation lacking polysorbate 20 was ineffective at mitigating agitation induced aggregation of the drug product as evidenced by increased D90 particle size, broadened particle size distribution, and increased particle intensity as provided by NTA. Therefore it is preferred to keep polysorbate 20 at 0.025 to 0.2% or higher levels (w/v) to stabilize the drug product during routine manufacturing, storage, shipping and handling.

Figure 24:
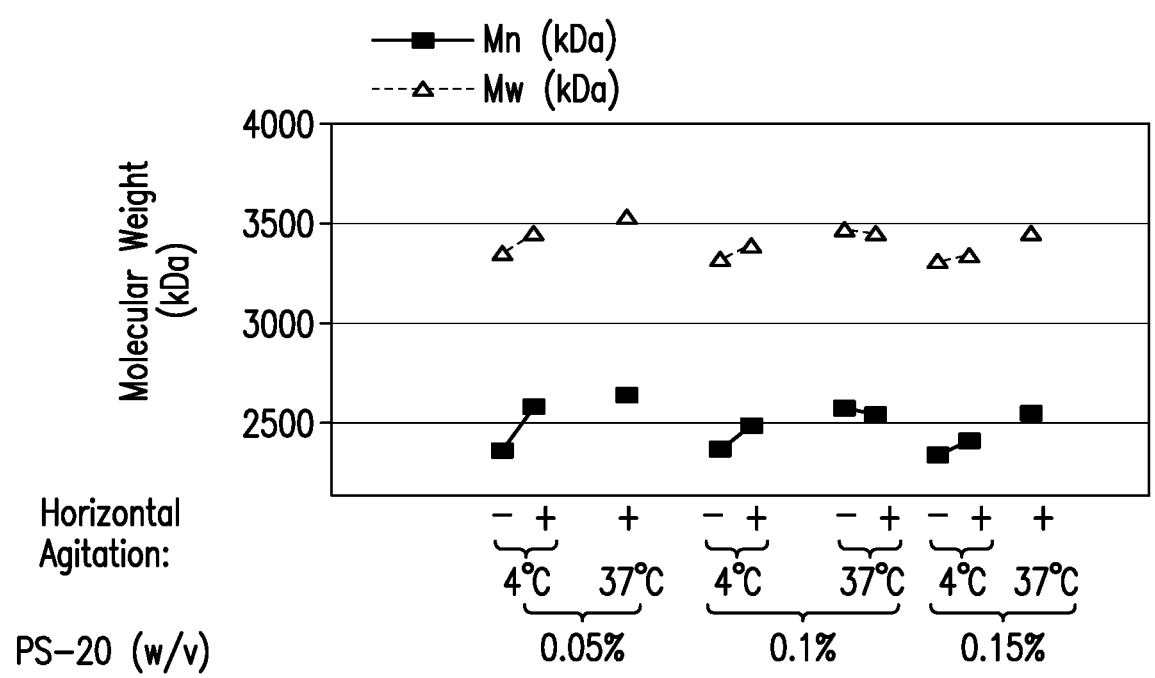
FIG. 24 shows the impact of temperature (4° C. and 37° C.) and agitation on the three PCV21 drug product average molecular weight as analyzed by HPSEC/UV/MALS/RI assay. Three PCV21 Pneumococcal Conjugate vaccine drug products were formulated with different concentrations of PS-20 (0.05%, 0.1%, and 0.15% w/v) at 0.084 mg/mL PnPs.

As described in Example 39, HPSEC UV/MALS/RI was used to measure the molecular weight of a 21-valent (PCV21) polysaccharide-protein conjugate drug product, formulated in 20 mM L-Histidine, pH 5.8, 150 mM NaCl, and 0 to 0.2% (w/v) PS-20 and formulation process described in Example 38. The formulations were placed at 4° C. or 37° C. for up to one week. In some cases, the syringes were placed on a horizontal rotation platform and shaken for up to 6 hours after storage for 1 week at 4° C. or 37° C. This was done to simulate the shipping and handling stresses that may accompany drug product manufacture and distribution. If the polysaccharide-protein conjugates in the drug products were degrading or depolymerizing, a decrease in molecular weight would be evident and if aggregation of the drug product formulation was occurring, an increase in molecular weight would occur. This measurement provides additional characterization on the quality of the vaccine drug product or polysaccharide-protein conjugates as a function of PS-20 concentration. As shown in FIG. 24, the PCV21 drug product formulations comprising all drug substances that were each prepared using reductive amination in an aprotic solvent (e.g. DMSO) were stable against depolymerization or chemical degradation of the carbohydrate and stable against aggregation of the protein in the drug product formulation due to heat treatment between 0.05% and 0.15% PS-20. Collectively, this indicates that a PCV21 drug product is stable through elevated temperature and physical stresses when formulated using PS-20 from 0.025% and 0.2% or higher levels.

Example 46

PCV21 Protection from Challenge in Mice

Young female Swiss Webster mice (6-8 weeks old, n=10/group) were intraperitoneally (IP) immunized with 0.1-0.5 mL of a 21-valent pneumococcal conjugate vaccine (PCV21) on days 0, day 14, and day 28. PCV21 pneumococcal vaccine was dosed at 4, 2, 0.4, 0.08 or 0.016 PnPs (3, 6C, 7F, 8, 9N, 10A, 11A, 12F, 15A, 15C, 16F, 17F, 19A, 20A, 22F, 23A, 23B, 24F, 31, 33F and 35B each conjugated to CRM197) per immunization. Mice were observed at least daily by trained animal care staff for any signs of illness or distress. The vaccine formulations in mice were deemed to be safe and well tolerated, as no vaccine-related adverse events were noted. On day 52 the mice were intratracheally challenged with *Streptococcus pneumoniae* serotype 24F. Exponential phase cultures of *S. pneumoniae* were centrifuged, washed, and suspended in sterile PBS. Mice were anesthetized with isoflurane prior to challenge. 105 cfu of *S. pneumoniae* in 0.1 mL of PBS was placed in the throat of mice hung upright by their incisors. Aspiration of the bacteria was induced by gently pulling the tongue outward and covering the nostrils. Mice were weighed daily and euthanized if weight loss exceeded 20% of starting weight. Blood was collected at 24 hours, 48 hours, and 72 hours to assess for bacteremia. Mice were observed at least twice daily by trained animal care staff for any signs of illness or distress. All animal experiments were performed in strict accordance with the recommendations in the Guide for Care and Use of Laboratory Animals of the National Institutes of Health. The mouse experimental protocol was approved by the Institutional Animal Care and Use Committee at Merck & Co., Inc.

Mouse sera were evaluated for IgG immunogenicity using a multiplexed electrochemiluminescence (ECL) assay. This assay was developed for use with mouse serum based on the human assay described by Marchese et al., Clin Vaccine Immunol. (2009) 16(3):387-96, using technology developed by MesoScale Discovery (a division of MesoScale Diagnostics, LLC, Gaithersburg, MD) which utilizes a SULFO-TAG™ label that emits light upon electrochemical stimulation. SULFO-TAG™-labeled anti-mouse IgG was used as the secondary antibody for testing mouse serum samples. Functional antibody was determined through multiplexed opsonophagocytic assays (MOPA) based on previously described protocols at www.vaccine.uab.edu and Opsotiter® 3 software owned by and licensed from University of Alabama (UAB) Research Foundation (See, Caro-Aguilar I. et al., Vaccine (2017) 35(6):865-72 and Burton R. L. and Nahm M. H. Clin. Vaccine Immunol. (2006) 13(9):1004-9).

Figure 25:
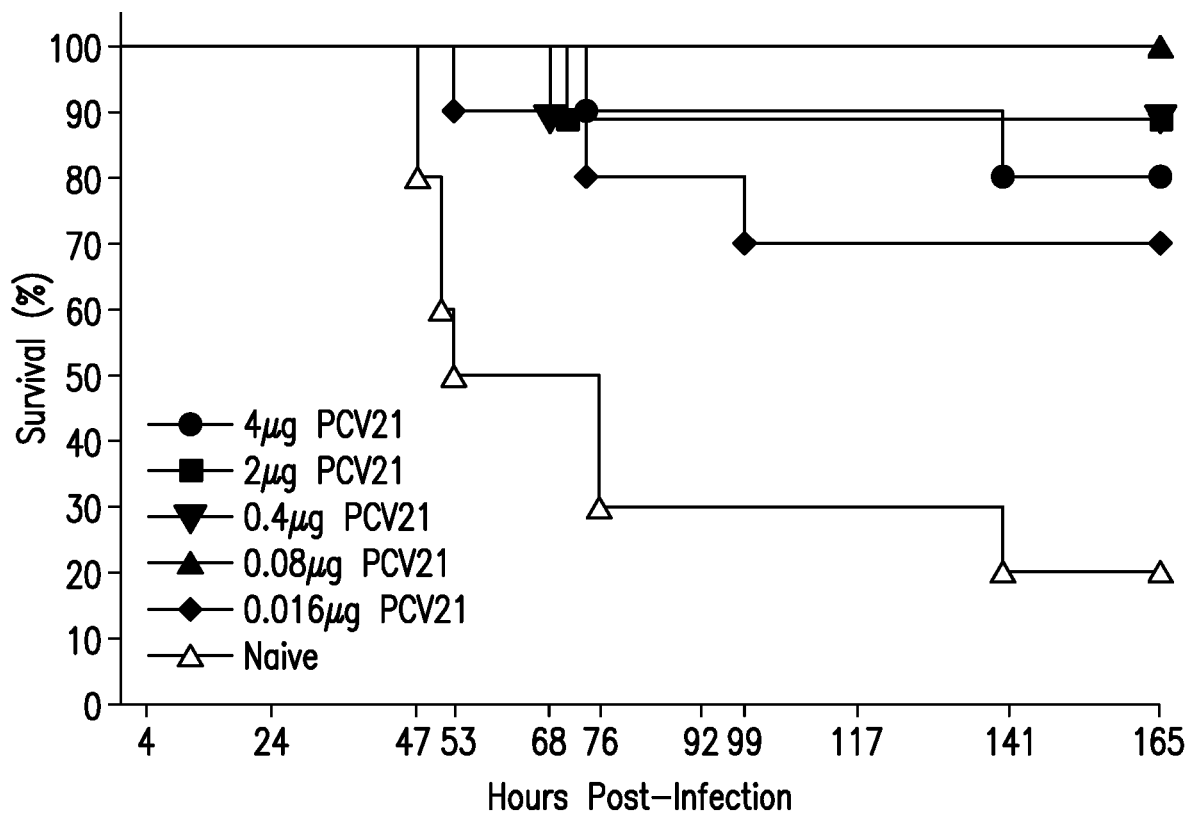
FIG. 25 shows that PCV21 immunized mice are protected from S. pneumoniae 24F intratracheal challenge.

PCV21 immunization generated antibody titers in Swiss Webster mice for all serotypes in the vaccine (data not shown). PCV21 was also immunogenic in Balb/c and CD1 mice (data not shown). PCV21 immunized Swiss Webster mice were also protected from challenge with *S. pneumoniae* serotype 24F (FIG. 25). Mantel Cox log-rank test indicates that all PCV21 immunized groups were significantly protected from challenge when compared to the naïve group (P<0.05). Likewise, PCV21 immunized mouse groups had little to no bacteremia, which was significantly less when compared to the naïve group (data not shown).

Example 47

PCV Immunogenicity and Functional Antibody in Rabbits

Adult New Zealand white rabbits (NZWR, n=5/group) were intramuscularly (IM) immunized with 0.1 mL of PCV on day 0 and day 14 (alternating sides). PCV was dosed at 0.4 µg PnPs per serotype per immunization with 25 µg [Al] in the form of Aluminum Phosphate Adjuvant (APA). In the case of PCV31, the dosing concentration of serotype 6B was doubled to 0.8 µg PnPs per immunization. PCV21 (as described in EXAMPLE 38) included purified polysaccharides from serotypes 3, 6C, 7F, 8, 9N, 10A, 11A, 12F, 15A, 15C, 16F, 17F, 19A, 20A, 22F, 23A, 23B, 24F, 31, 33F and 35B each conjugated to CRM197. Each polysaccharide-protein conjugate was prepared unadjuvanted or formulated with 250 µg [A1]/mL in the form of Aluminum Phosphate or APA to evaluate the effect of adjuvant (PCV21/APA). Lower valent PCVs were also formulated (as described in EXAMPLE 38) to include 8 novel STs (PCV8: 6C, 15A, 16F, 23A, 23B, 24F, 31 and 35B each conjugated to CRM197, unadjuvanted), the 16 STs not included in any licensed PCV (PCV16: 6C, 8, 9N, 10A, 11A, 12F, 15A, 15C, 16F, 17F, 20, 23A, 23B, 24F, 31 and 35B each conjugated to CRM197, unadjuvanted) or PCV31 (1, 3, 4, 5, 6A, 6B, 6C, 7F, 8, 9N, 9V, 10A, 11A, 12F, 14, 15A, 15C, 16F, 17F, 18C, 19A, 19F, 20A, 22F, 23A, 23B, 23F, 24F, 33F and 35B each conjugated to CRM197, formulated with 250 µg [A1]/mL in the form of Aluminum Phosphate) to evaluate carrier suppression as vaccine valency increased (PCV31/APA). Each vaccine used polysaccharide protein conjugates formulated at 4 µg/mL (w/v) Pneumococcal Polysaccharide (PnPs), except for 6B which was formulated at 8 µg/mL (w/v) Pneumococcal Polysaccharide (PnPs) in PCV31 or PCV31/APA. The final concentration of Pneumococcal Polysaccharide (PnPs) in each vaccine was 128 µg/mL PnPs in PCV31, 84 µg/mL PnPs in PCV21, 64 µg/mL in PCV16 and 32 µg/mL in PCV8.

Sera were collected prior to study start (pre-immune) and on days 14 (PD1) and 28 (PD2). NZWRs were observed at least daily by trained animal care staff for any signs of illness or distress. The vaccine formulations in NZWRs were deemed to be safe and well tolerated, as no vaccine-related adverse events were noted. All animal experiments were performed in strict accordance with the recommendations in the Guide for Care and Use of Laboratory Animals of the National Institutes of Health. The NZWR experimental protocol was approved by the Institutional Animal Care and Use Committees at both Merck & Co., Inc and Covance (Denver, PA).

Rabbit sera were evaluated for IgG immunogenicity using a multiplexed electrochemiluminescence (ECL) assay. This assay was developed for use with rabbit serum based on the human assay described by Marchese et al., Clin Vaccine Immunol. (2009) 16(3):387-96, using technology developed by MesoScale Discovery (a division of MesoScale Diagnostics, LLC, Gaithersburg, MD) which utilizes a SULFO-TAG™ label that emits light upon electrochemical stimulation. SULFO-TAGT™-labeled anti-rabbit IgG was used as the secondary antibody for testing NZWR serum samples. Functional antibody was determined through multiplexed opsonophagocytic assays (MOPA) based on previously described protocols at www.vaccine.uab.edu and Opsotiter® 3 software owned by and licensed from University of Alabama (UAB) Research Foundation (See, Caro-Aguilar I. et al., Vaccine (2017) 35(6):865-72 and Burton R. L. and Nahm M. H. Clin. Vaccine Immunol. (2006) 13(9):1004-9).

Rabbit sera were tested as a pool for pre-immune and PD1, and individually for PD2 in multiplexed electrochemiluminescent assays to determine antibody titers. PCVs generated antibody titers in rabbits for all serotypes following immunizations with the vaccine (data not shown). Serotype 15B polysaccharide was not included in PCV16, PCV21 or PCV31, however antibody titers to serotype 15B were observed following immunization with both PCV16, PCV21 and PCV31.

Figure 26A:
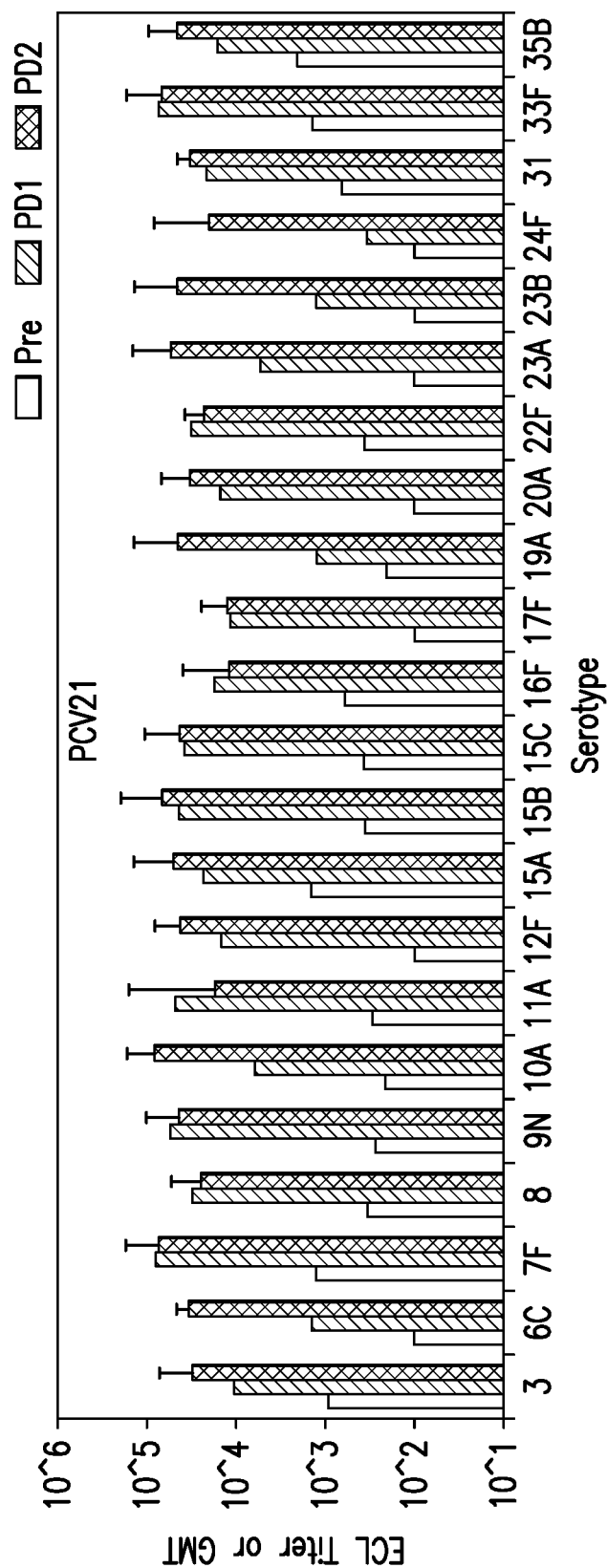
FIGS. 26A-26B shows pre (pooled), PD1 (pooled) and PD2 IgG antibody dilution titers as determined by ECL for rabbits immunized with PCV21 unadjuvanted (FIG. 26A) or formulated with APA (FIG. 26B). Error bars represent the 95% confidence intervals (CI) of the geometric mean titer (GMT). Serotype 15B data is included to evaluate cross protection.
Figure 26B:
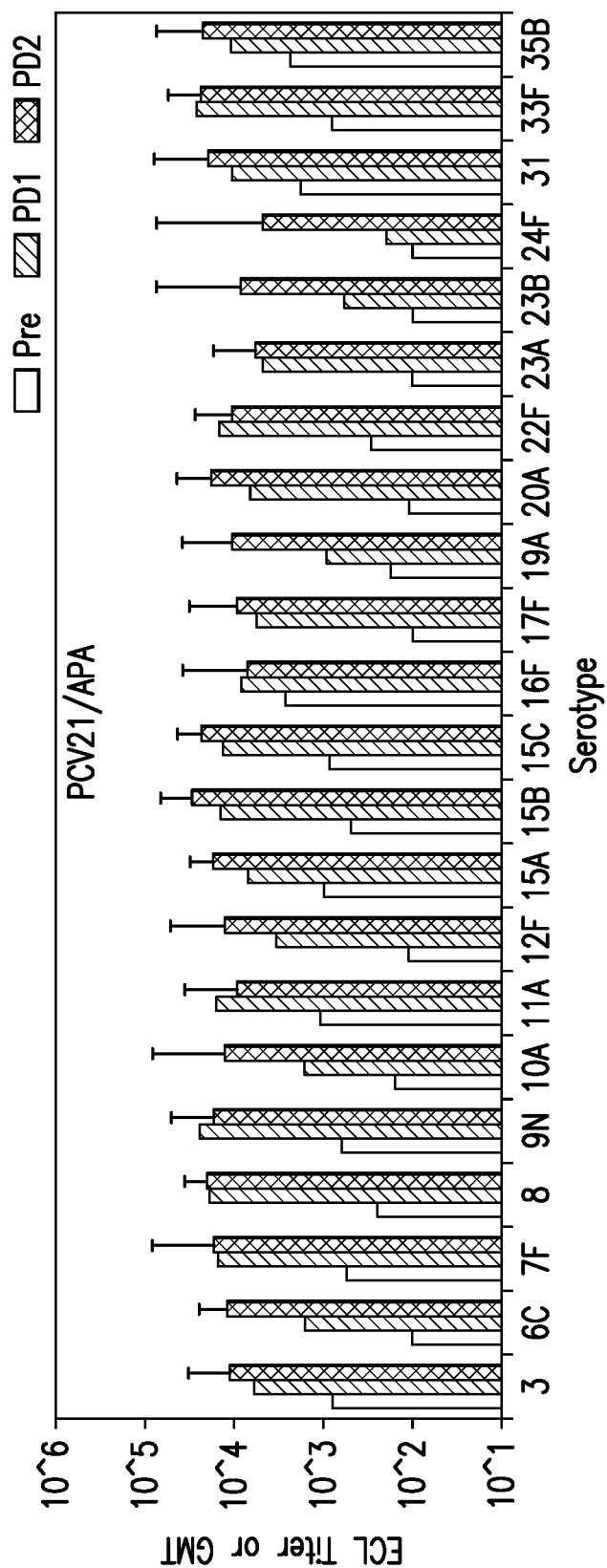
Figure 28:
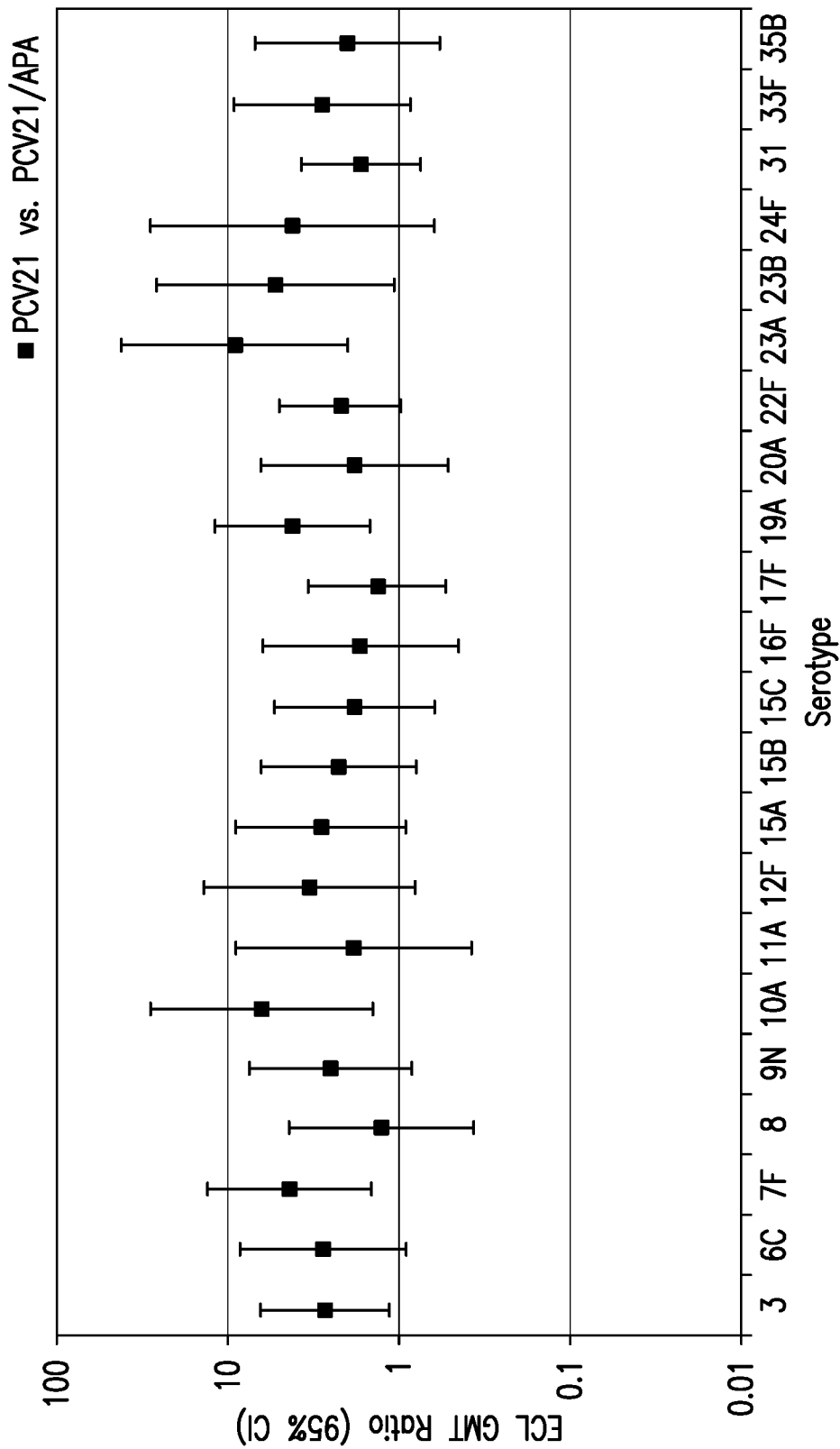
FIG. 28 shows the comparison of PD2 ECL antibody responses in NZWR (5 per group) following vaccination with PCV21 with or without APA. Symbols indicate PD2 GMT ratios with error bars representing the 95% CIs. Serotype 15B data is included to evaluate cross protection.

PCV21 without adjuvant had comparable to or significantly higher immunogenicity (serotypes 3, 7F, 10A, 19A, 23A and 23B) when compared to PCV21 with APA (FIG. 26A-B and FIG. 28), suggesting no additional immunogenicity benefit in rabbits with APA included in the vaccine.

Figure 27A:
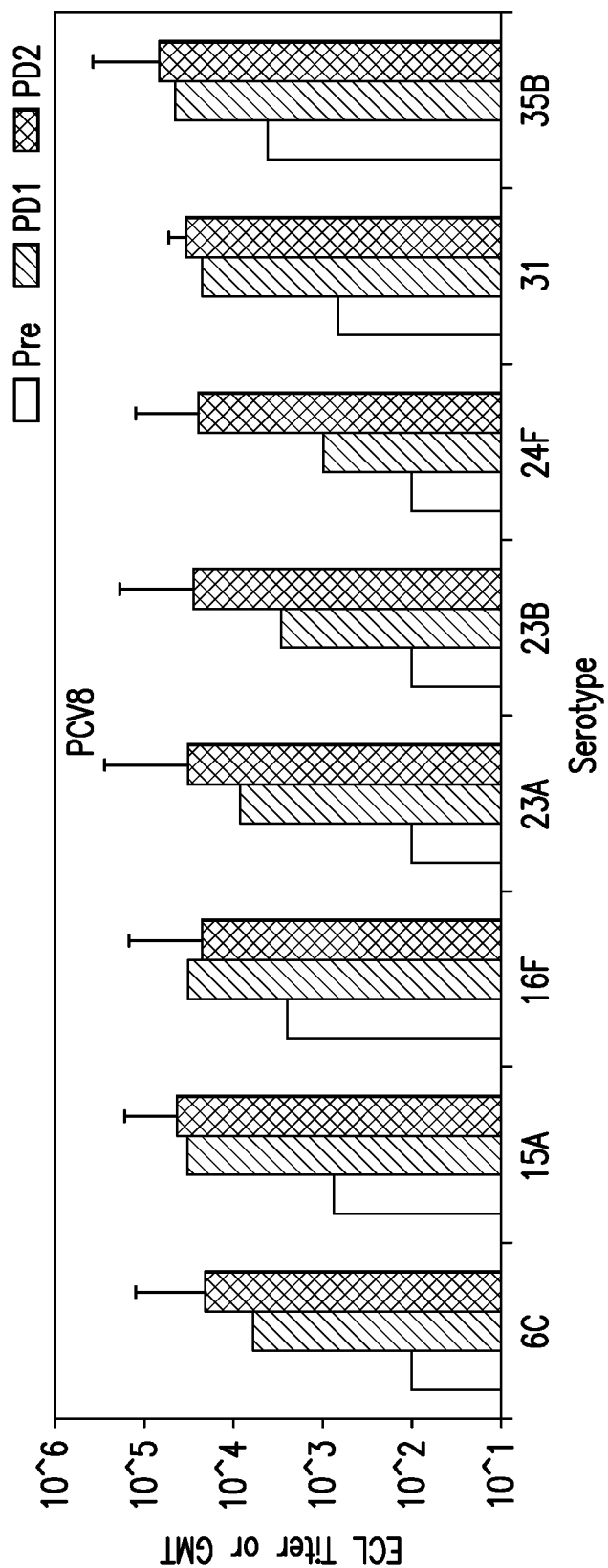
FIGS. 27A-27C shows pre (pooled), PD1 (pooled) and PD2 IgG antibody dilution titers as determined by ECL for rabbits immunized with PCV8 unadjuvanted (FIG. 27A), PCV16 unadjuvanted (FIG. 27B), and PCV31 with APA (FIG. 27C). Error bars represent the 95% confidence intervals (CI) of the geometric mean titer (GMT). Serotype 15B data is included to evaluate cross protection.
Figure 27B:
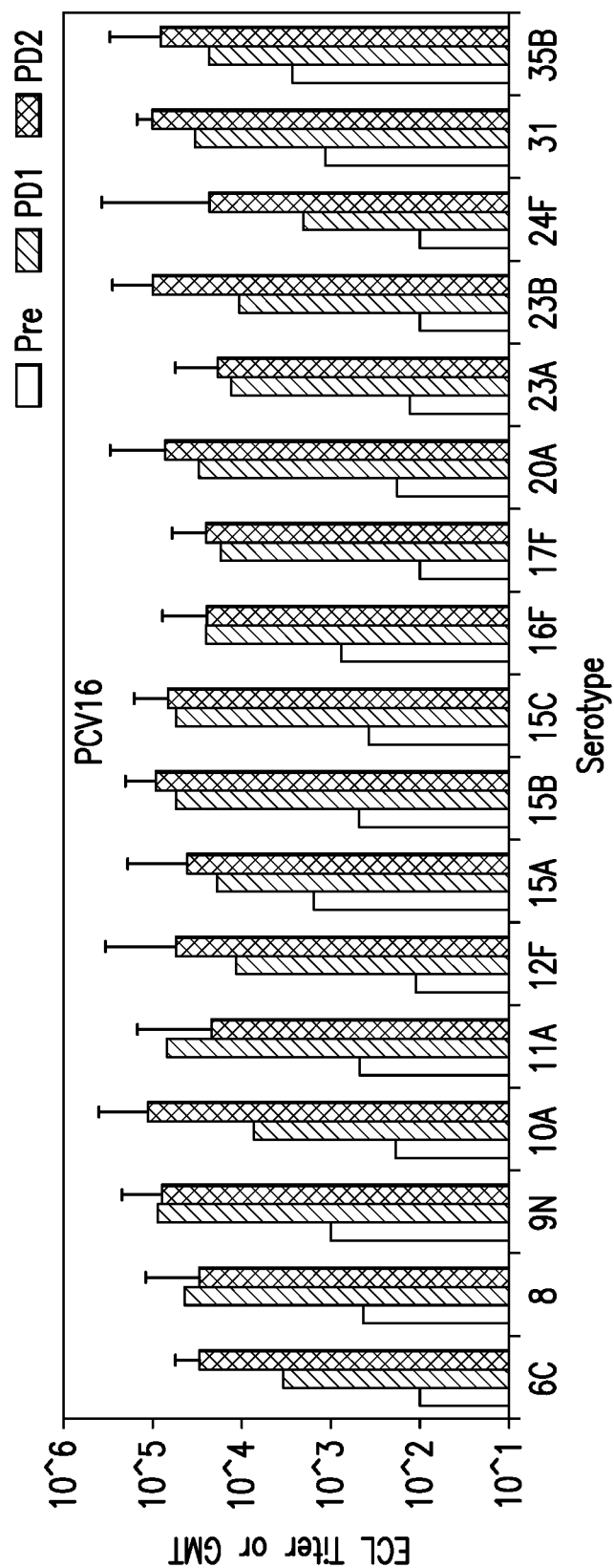
Figure 27C:
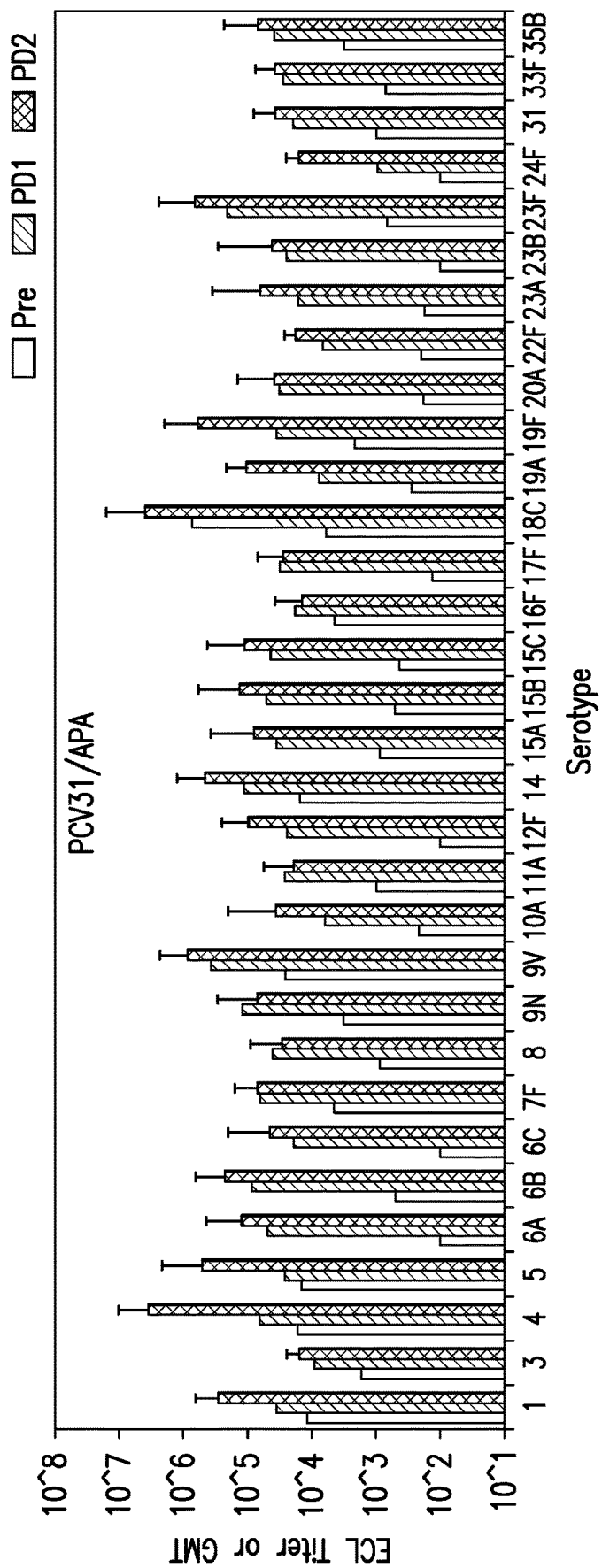
Figure 29:
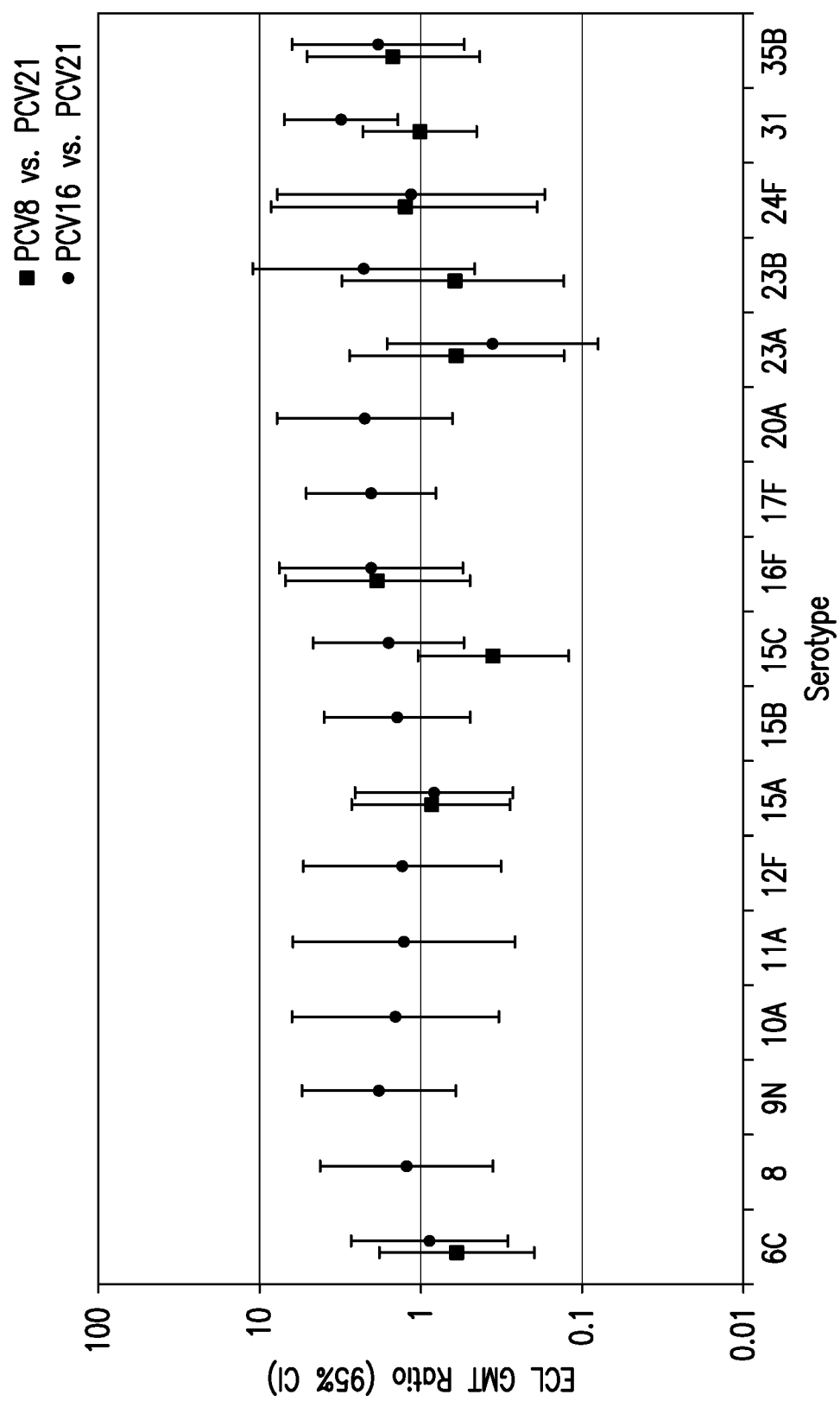
FIG. 29 shows the comparison of PD2 ECL antibody responses in NZWR (5 per group) for common serotypes and cross protected serotype 15B following vaccination with PCV21, PCV8 or PCV16. Symbols indicate PD2 ECL GMT ratios with error bars representing the 95% CIs.
Figure 30:
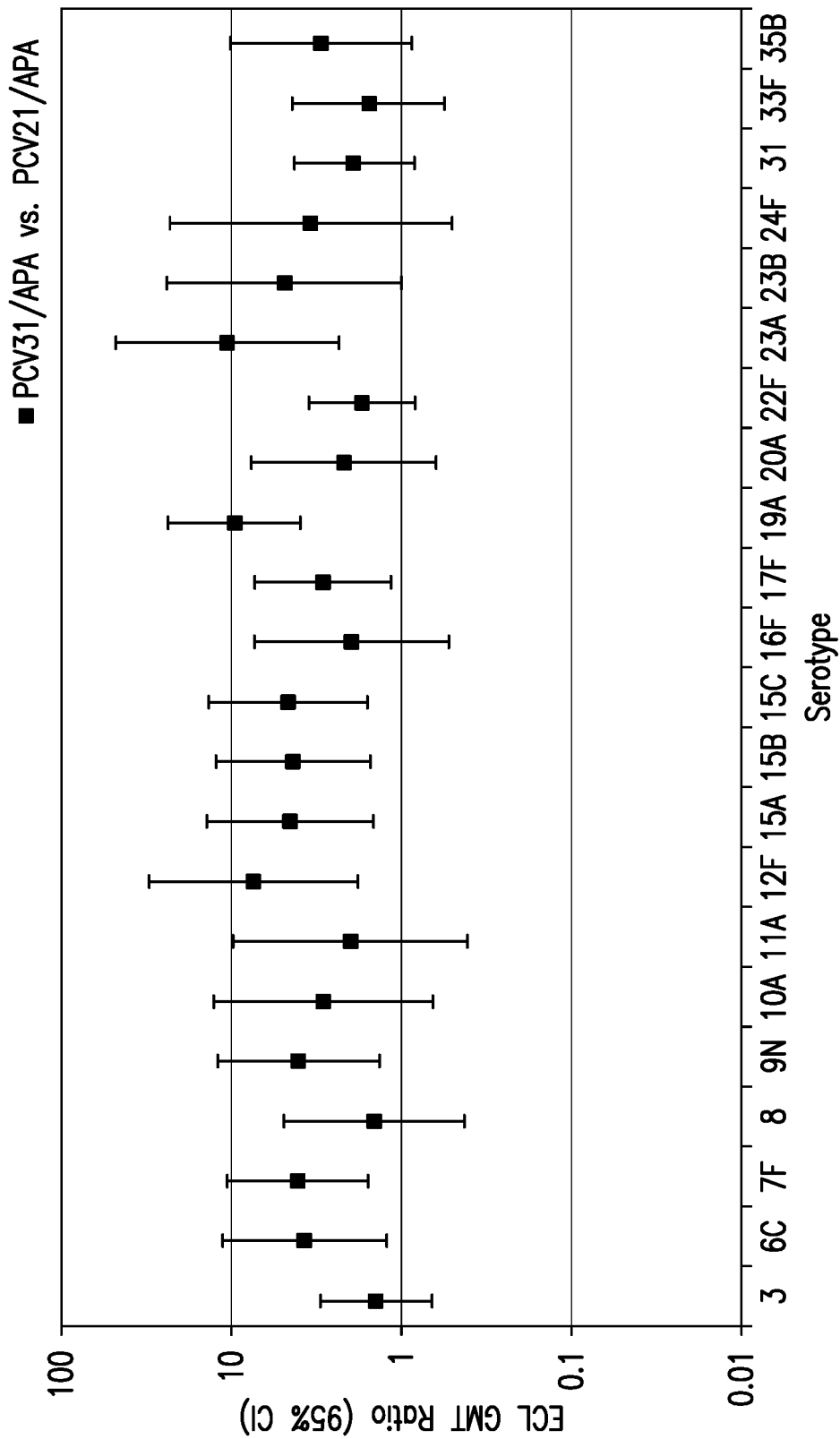
FIG. 30 shows the comparison of PD2 ECL antibody responses in NZWR (5 per group) for common serotypes and cross protected serotype 15B following vaccination with PCV21/APA or PCV31/APA. Symbols indicate PD2 ECL GMT ratios with error bars representing the 95% CIs.
Figure 31A:
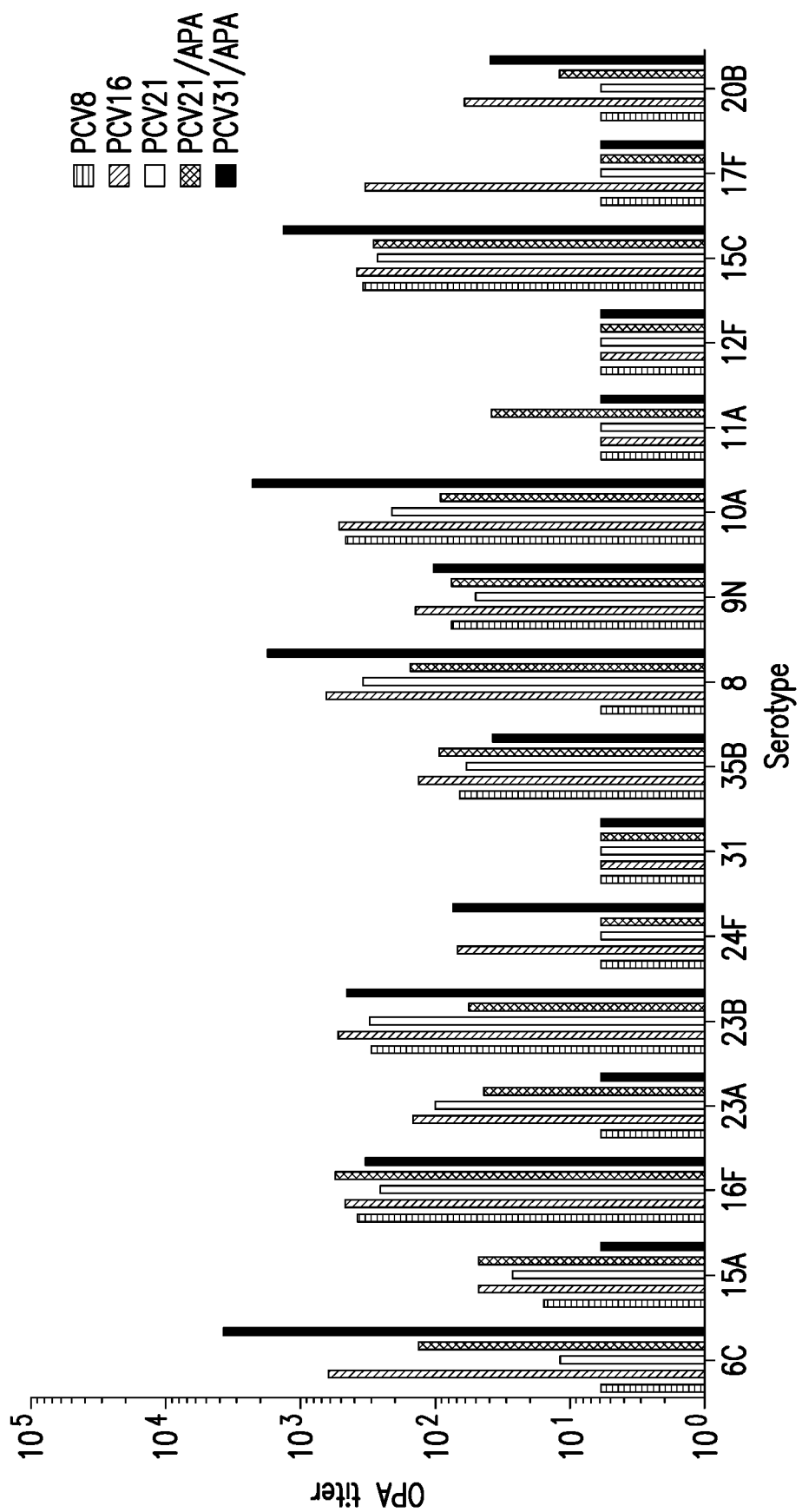
FIGS. 31A-31D shows serotype specific Pre (pooled) (FIG. 31A and FIG. 31B) and PD2 (FIG. 31C and FIG. 31D) OPA dilution titers for rabbits immunized with PCVs. Error bars represent the 95% CIs of the GMTs. PCV21 was used as the benchmark for statistical comparisons, * p<0.05.
Figure 31B:
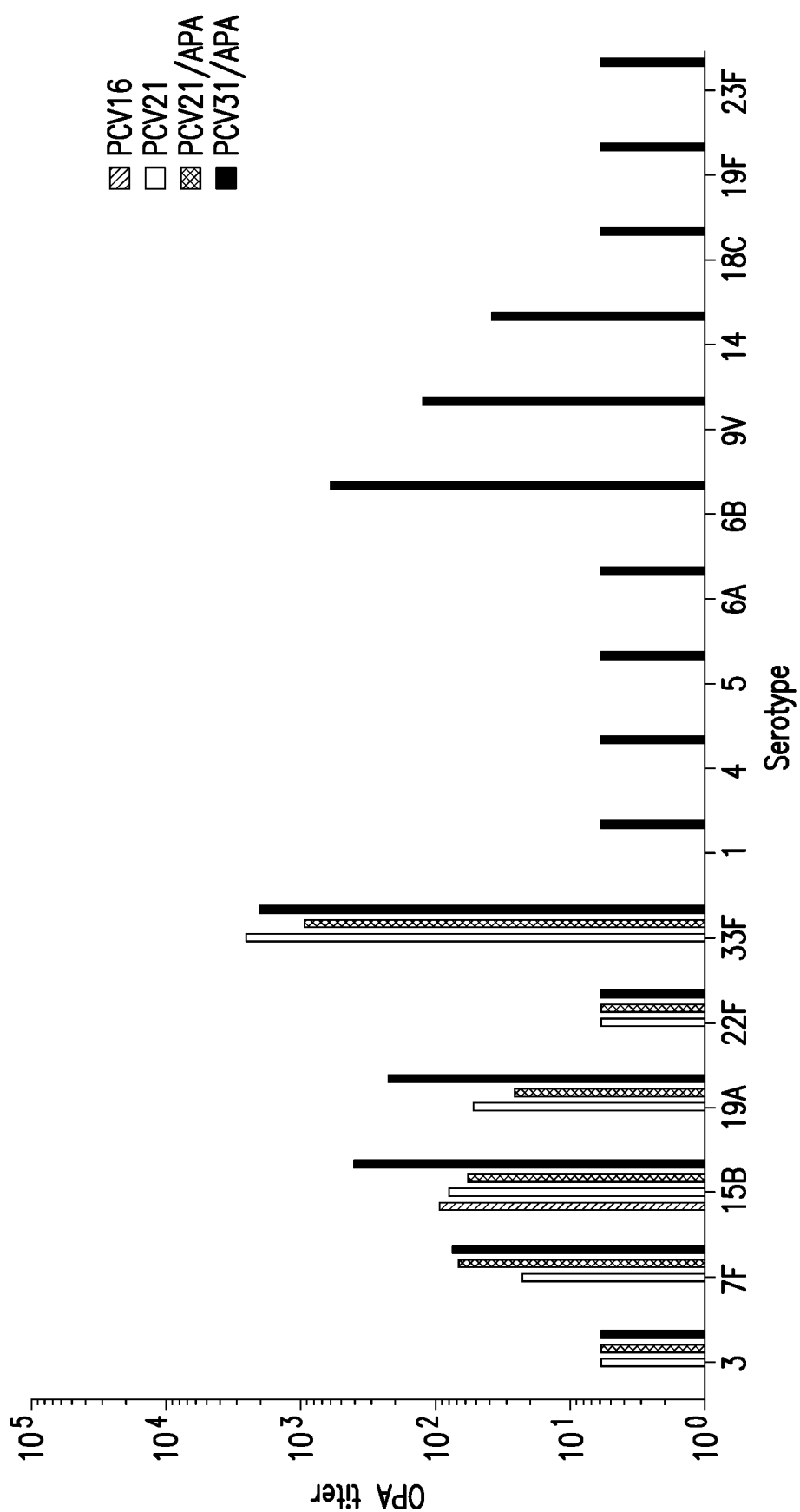
Figure 31C:
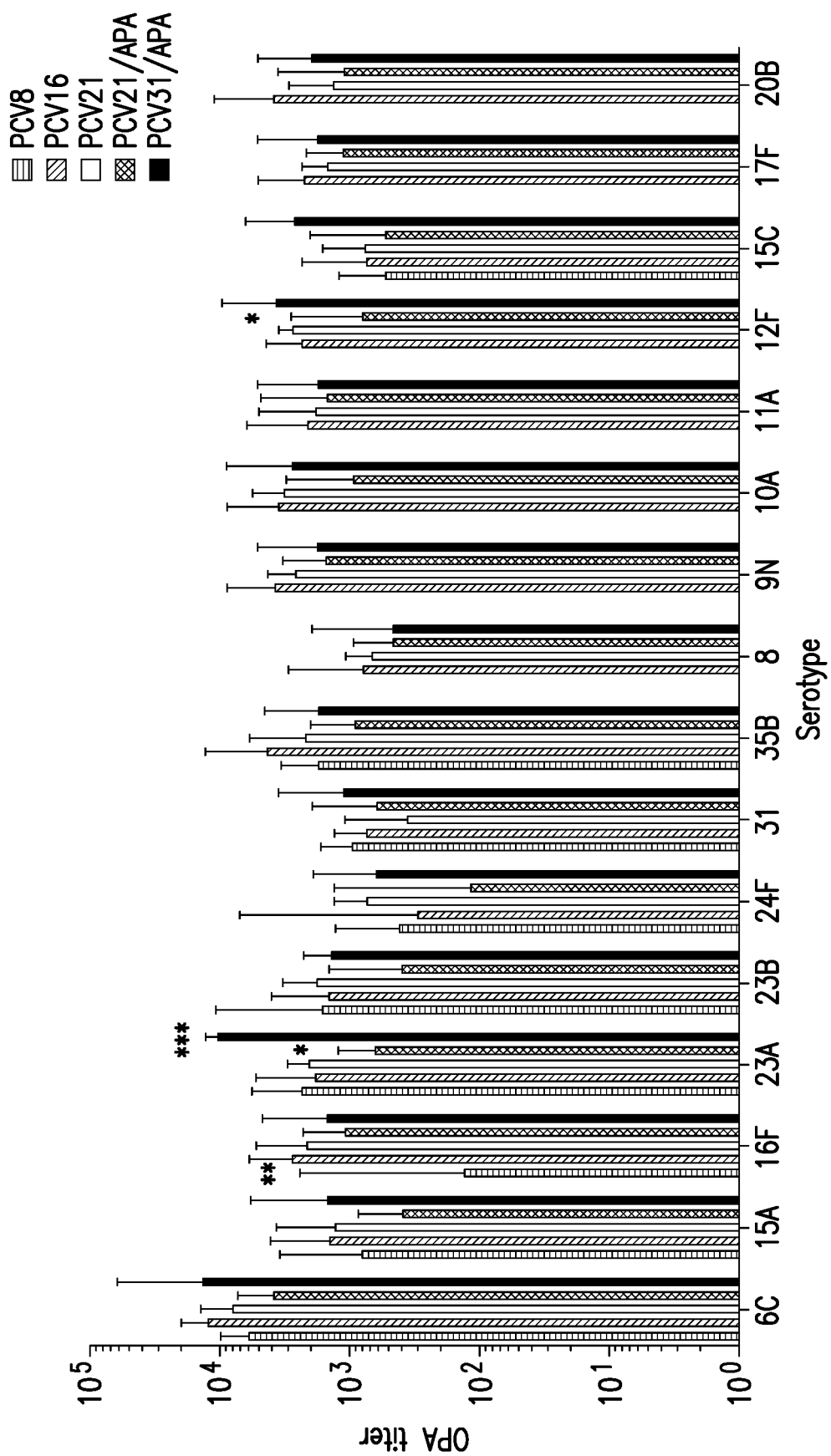
Figure 31D:
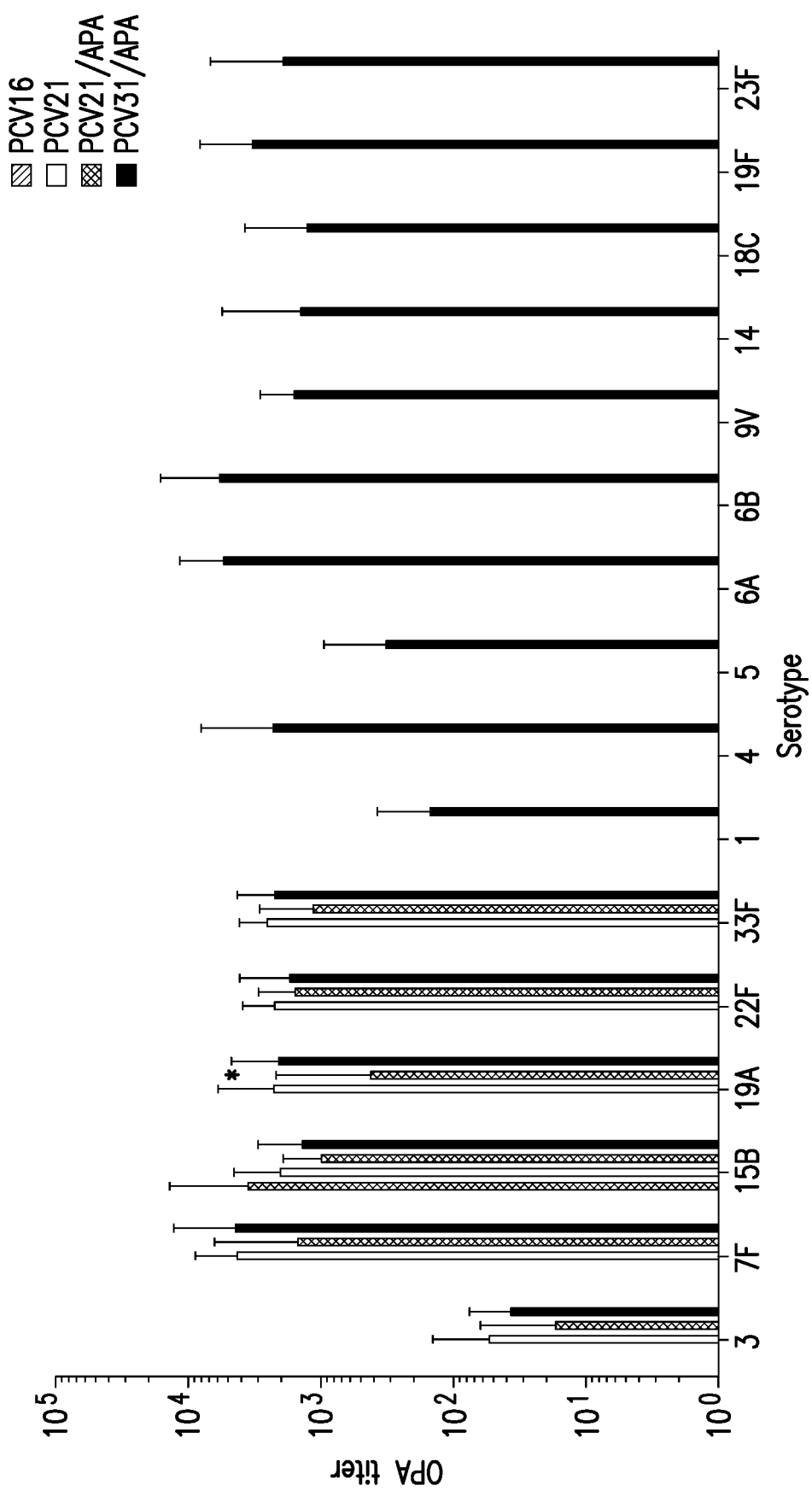

Carrier induced epitopic suppression refers to interference with the antibody response to an antigen (such as capsular polysaccharide) coupled to the same carrier protein (such as CRM197). Interference is thought to arise from competition for a limited number of carrier specific primed T helper cells. As a result, there may be a decrease in response to the capsular polysaccharide. Pfizer has observed a decrease in vaccine immunogenicity of shared serotypes as the vaccine valency increased from a 7-valent to 13-valent [Comparison of IgG antibody GMC of Prevnar (7 valent) vs Prevnar13. (table 9, page 29 of PCV13 monograph)]. Therefore, we sought to investigate the immunogenicity of lower valent PCVs compared to PCV21 (FIG. 27A-C). PCV8 (8 novel serotypes) had comparable immunogenicity relative to PCV21 for the 8 shared serotypes (FIG. 29). PCV16 (PCV21 minus 5 overlapping serotypes from PCV15) had comparable immunogenicity relative to PCV21 for 15 of the 16 shared serotypes (FIG. 29). Serotype 31 had higher immunogenicity in PCV16 (FIG. 29). Overall, there were no major trends of carrier suppression with PCV21 in NZWR. PCV31/APA had comparable immunogenicity relative to PCV21/APA for the 12 of the 21 shared serotypes. 10 serotypes (6C, 7F, 9N, 12F, 15A, 15B (not in PCV21), 15C, 17F, 19A, and 23A) had higher immunogenicity in PCV31, ranged between 2.9-fold and 11-fold (FIG. 30). Overall, there were no major trends of carrier suppression with PCV31 in NZWR.

PCVs were found to be immunogenic in rabbits and generated functional antibodies which killed vaccine-type bacterial strains. Rabbit sera were tested in multiplexed opsonophagocytic assays (MOPA) to determine functional antibody titers. PCV21 had comparable to or higher PD2 OPA titers when compared to PCV21/APA, PCV8 and PCV16 (FIGS. 31A-31D). Log Transformed data were analyzed by One-way ANOVA with Dunnett's test to determine significance. PCV21 had significantly higher OPA titers for serotype 16F compared to PCV8 and for serotypes 12F, 23A and 19A compared to PCV21/APA. PCV31 had significantly higher OPA titers for serotype 23A compared to PCV21.

Example 48

PCV21 Immunogenicity in Adult Rhesus Macaques

PCV21 was also assessed in adult Rhesus macaque immunogenicity models. Rhesus macaques were intramuscularly immunized with PCV21 on days 0, 28 and 56. PCV21 was dosed at 1 µg PnPs in a 0.25 mL volume (3, 6C, 7F, 8, 9N, 10A, 11A, 12F, 15A, 15C, 16F, 17F, 19A, 20A, 22F, 23A, 23B, 24F, 31, 33F and 35B each conjugated to CRM197) per immunization. Sera were collected prior to study start (pre-immune, day 0) and on days 14 (PD1), 28, 42 (PD2), 56, 70 (PD3) and 84.

Rhesus sera were evaluated for IgG immunogenicity using a multiplexed electrochemiluminescence (ECL) assay. This assay was developed for use with Rhesus serum based on the human assay described by Marchese et al. and Skinner et al. (Marchese R. D. et al., Clin. Vaccine Immunol. (2009) 16(3):387-96 and Skinner, J. M. et al., Vaccine (2011) 29(48):8870-8876) using technology developed by MesoScale Discovery (a division of MesoScale Diagnostics, LLC, Gaithersburg, MD) which utilizes a SULFO-TAG™ label that emits light upon electrochemical stimulation. SULFO-TAG™-labeled anti-human IgG was used as the secondary antibody for testing Rhesus serum samples. Functional antibody was determined through multiplexed opsonophagocytic assays (MOPA) based on previously described protocols at www.vaccine.uab.edu and Opsotiter® 3 software owned by and licensed from University of Alabama (UAB) Research Foundation (See, Caro-Aguilar I. et al., Vaccine (2017) 35(6):865-72 and Burton R. L. and Nahm M. H. Clin. Vaccine Immunol. (2006) 13(9):1004-9).

Figure 32:
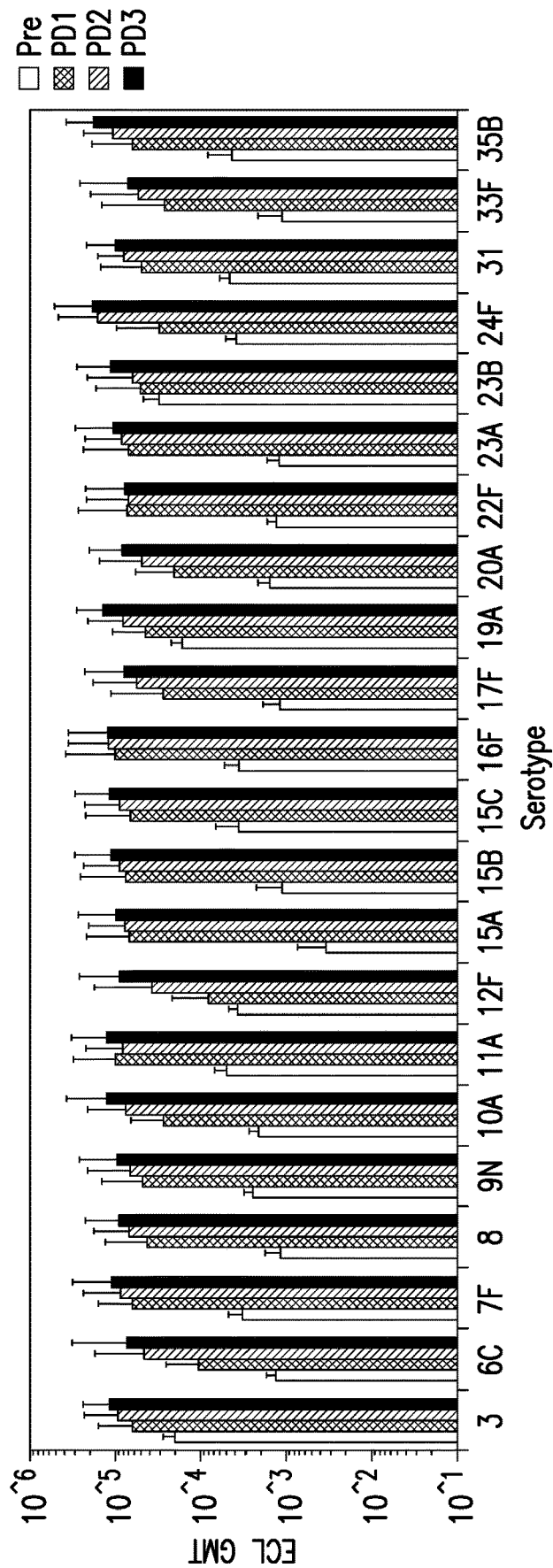
FIG. 32 shows pre, PD1, PD2 and PD3 IgG antibody dilution titers as determined by ECL for adult Rhesus macaques (n=8) immunized with PCV21. Error bars represent the 95% CIs of the GMTs. Serotype 15B data is included to evaluate cross protection.
Figure 33:
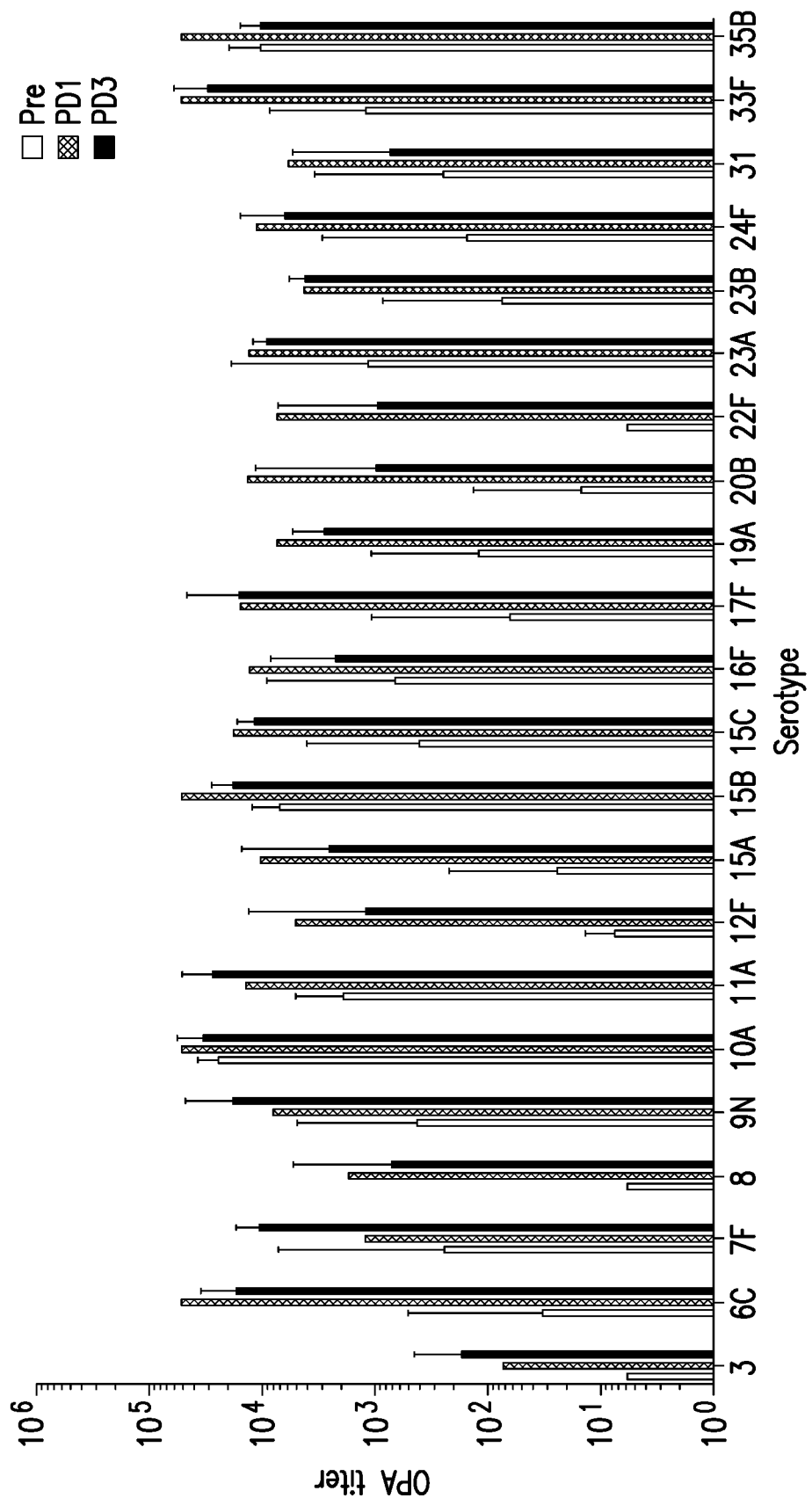
FIG. 33 shows pre, PD1 (pooled) and PD3 OPA dilution titers of PCV21 immunized adult Rhesus macaques (n=8). Error bars represent the 95% CIs of the GMTs. Serotype 15B data is included to evaluate cross protection.

PCV21 was found to be immunogenic in adult monkeys and generated functional antibodies which killed vaccine-type bacterial strains at all time points tested (FIGS. 32 and 33). It is also of note that PCV21, which contains polysaccharide conjugates 15A-CRM197 and 15C-CRM197, also provides cross-reactivity to 15B, as evidenced in ECL. PCV21 was immunogenic with one dose of vaccine in the monkeys (FIG. 32). Most serotypes reached their maximum titer at PD1, with the exception of STs 6C, 12F and 24F, which benefited from additional immunizations. The adult Rhesus monkeys had higher pre-existing antibody titers as compared to former PCV studies in infant Rhesus monkeys. The pre-existing antibody titers were most apparent when testing the sera samples in MOPA, which made determining the opsonophagocytic titer difficult. All study time points were tested in MOPA as pooled or individual samples, but for easier viewing, only pre-immune, PD1 and PD3 are shown (FIG. 33), as there was not much difference in the OPA titers between PD1 and PD3.

Figure 34:
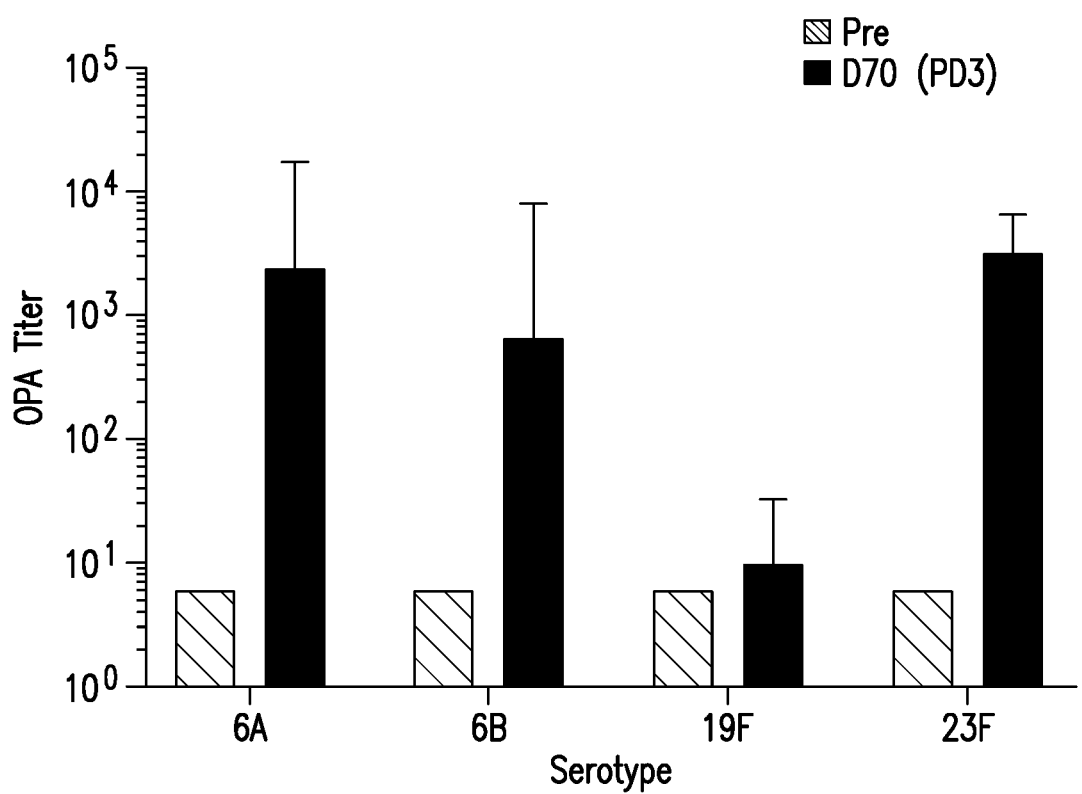
FIG. 34 shows pre and PD3 (day 70) OPA titers to four serotypes not contained in the PCV21 vaccine for adult Rhesus macaques immunized with PCV21.

PCV21 immunized adult Rhesus macaque sera were evaluated for cross protection to other *S. pneumoniae* bacteria (FIG. 34). PCV21 immunized macaque sera had cross protection with serotypes 6A, 6B and 23F but not 19F. The cross protection to 6A and 6B is likely due to immunization with polysaccharide conjugate 6C-CRM197 as part of a multivalent PCV21. Similarly, immunization with polysaccharide conjugates 23A-CRM197 and 23B-CRM197 as part of a multivalent PCV resulted in cross protection to serotype 23F. Immunization with PCV21 including polysaccharide conjugate 19A-CRM197 did not provide cross protection to 19F.

Example 49

PCV21 Immunogenicity in Adult Rhesus Macaques—Evaluation of Adjuvant and Carrier Suppression Another monkey study included evaluation of PCV21 with and without APA and comparison of shared serotype immunogenicity to evaluate carrier suppression. Adult Rhesus macaques (n=5/group) were intramuscularly immunized with vaccines at a half human dose on day 0 of the study. PCV21 was dosed at 1 µg PnPs in a 0.25 mL volume (3, 6C, 7F, 8, 9N, 10A, 11A, 12F, 15A, 15C, 16F, 17F, 19A, 20, 22F, 23A, 23B, 24F, 31, 33F and 35B each conjugated to CRM197) per immunization. One group included PCV21, adjuvanted with 62.5 µg [Al] in the form of Aluminum Phosphate. Another group included PCV15 dosed at 1 µg PnPs in a 0.25 mL volume (1, 3, 4, 5, 6A, 7F, 9V, 14, 18C, 19A, 19F, 22F, 23F and 33F each conjugated to CRM197 with 6B dosed at 2 µg) per immunization and adjuvanted with 62.5 µg [Al] in the form of Aluminum Phosphate. Another group included Prevnar13® (PCV13) dosed at 1.1 µg PnPs in a 0.25 mL volume (1, 3, 4, 5, 6A, 7F, 9V, 14, 18C, 19A, 19F and 23F each conjugated to CRM197 with 6B dosed at 2.2 µg) per immunization. Sera were collected prior to study start (pre-immune, day 0) and on day 28.

Figure 35:
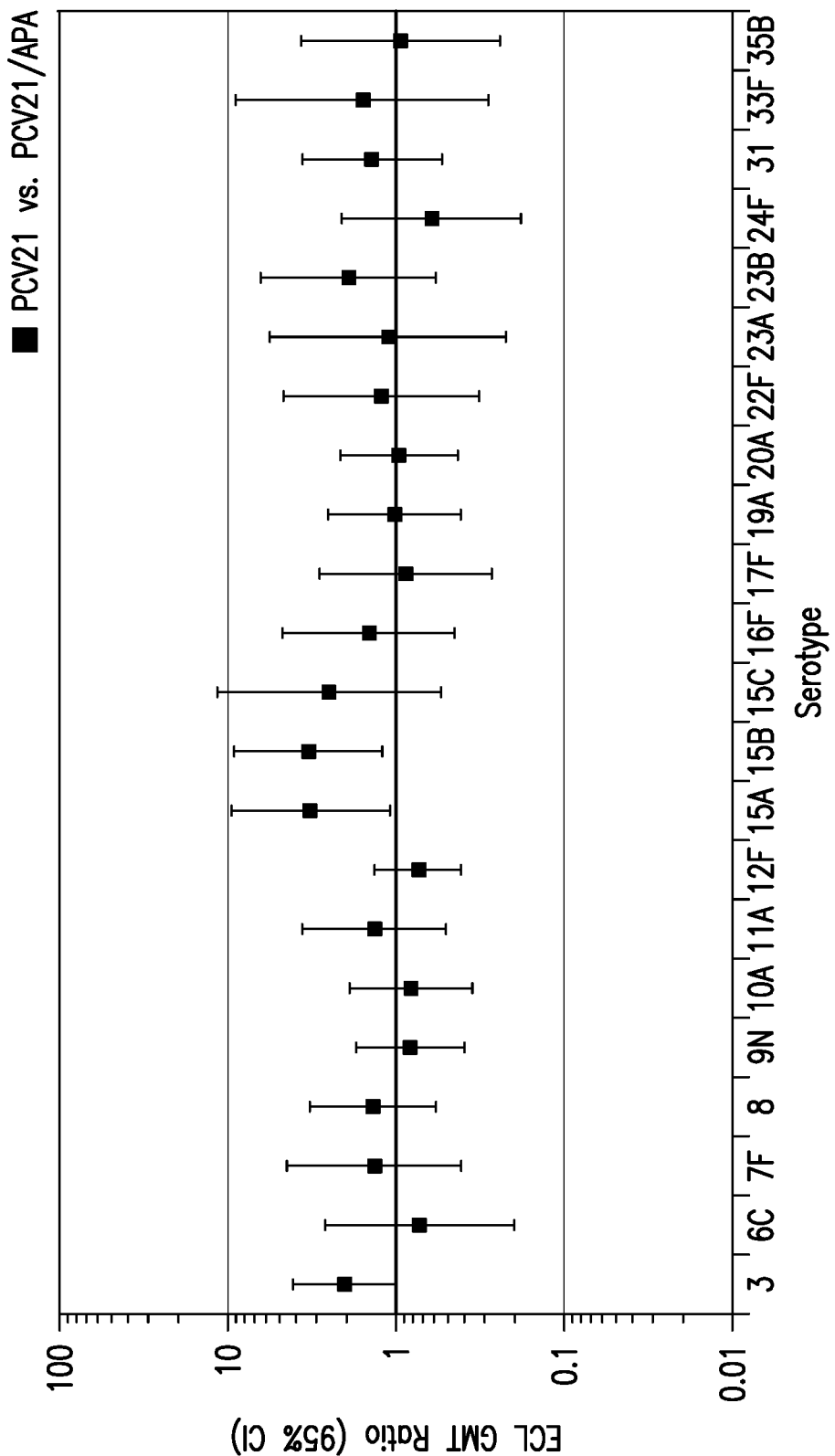
FIG. 35 shows the comparison of PD1 ECL antibody responses in adult Rhesus macaques (5 per group) following vaccination with PCV21 with or without APA. Symbols indicate PD1 ECL GMT ratios (PCV21 vs. PCV21/APA) with error bars representing the 95% CIs. Serotype 15B data is included to evaluate cross protection.

PCV21 was found to be immunogenic in adult monkeys and generated functional antibodies which killed vaccine-type bacterial strains. PCV21 without adjuvant had comparable to or significantly higher immunogenicity (serotypes 15A and 15B) when compared to PCV21 with APA (FIG. 35). PCV21 did not include serotype 15B.

Figure 36:
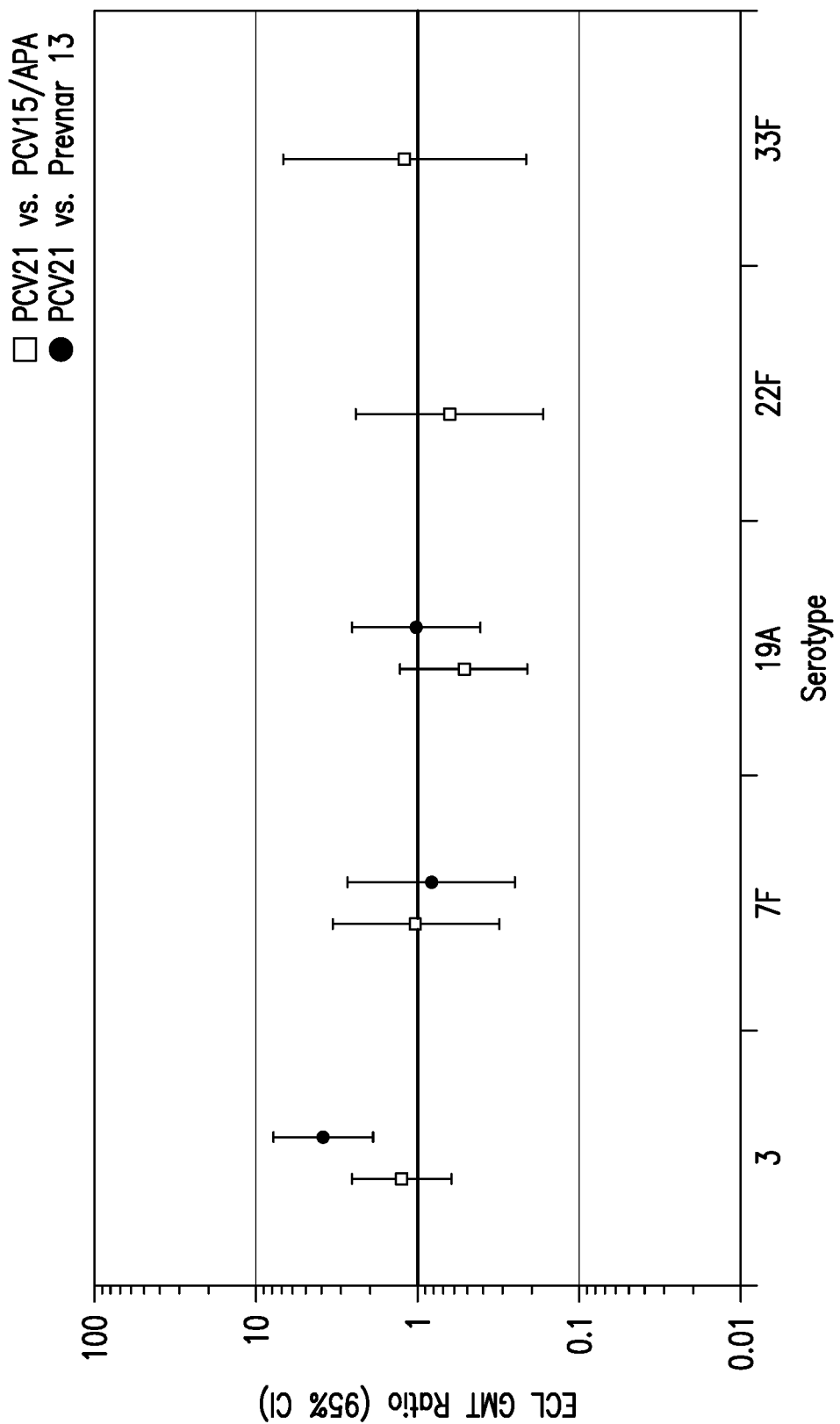
FIG. 36 shows PD1 IgG antibody responses to serotype 3, 7F, 19A, 22F, and 33F in adult Rhesus macaques (2-5 per group) following vaccination with PCV21 compared to PCV15 or Prevnar13. Symbols indicate PD1 ECL GMT ratios with error bars representing the 95% CIs.

PCV21 immunized monkeys were compared to those immunized with PCV15 and Prevnar13. PCV21 and PCV15 have 5 shared serotypes (3, 7F, 19A, 22F, 33F); there was no difference in immunogenicity of those 5 serotypes between monkeys immunized with PCV21 or PCV15 (FIG. 36). PCV21 and Prevnar13 have 3 shared serotypes (3, 7F, 19A); there was no difference in immunogenicity for serotypes 7F and 19A. Prevnar13 immunized monkeys had lower antibody titers for serotype 3 compared to PCV21 (FIG. 36). This finding is consistent with the PCV15 human clinical data, showing serotype 3 to be more immunogenic in Merck's PCV15 vaccine. Taken together, these results suggest that carrier suppression was not observed in adult Rhesus macaques immunized with PCV21 when compared to Prevnar13 or PCV15.

Example 50

Serotype 6A, 6B and 6C Cross Reactivity—Monovalent Study

The monovalent drug product was prepared using Pneumococcal polysaccharide 6A-CRM197 conjugate or Pneumococcal polysaccharide 6B-CRM197 conjugate and was formulated in 20 mM histidine pH 5.8 and 150 mM sodium chloride and 0.1% w/v polysorbate-20 (PS-20) at a target total polysaccharide concentration of 4.0 µg/mL of either serotype. The conjugates were prepared by individually conjugating the CRM197 protein to Pneumococcal polysaccharide (PnPs) types (either –6A or –6B). The required volume of bulk conjugates needed to obtain the target concentration of individual serotypes were calculated based on batch volume and concentration of individual bulk polysaccharide concentrations. The individual conjugates were added to a solution of histidine, sodium chloride and PS-20 to create a 2× conjugate blend. The formulation vessel containing the 2× conjugate blend were mixed using a magnetic stir bar, and sterile filtered into another vessel. The sterile filtered 2× blend was then diluted with saline to achieve the desired target total polysaccharide and excipient concentrations. The formulations were then filled into vials and stored at 2-8° C.

Rabbits were immunized with 6A-CRM197 or 6B-CRM197 to evaluate cross-reactivity within serogroup 6. Adult New Zealand White rabbits (NZWR, n=3/group) were intramuscularly (IM) immunized with 0.25 mL of respective monovalent conjugate vaccine on day 0 and day 14 (alternating sides). Monovalent pneumococcal conjugate vaccine, formulated in 20 mM L-Histidine pH 5.8 150 mM NaCl and 0.1% (w/v) PS-20 with a formulation process described in Example 38, was dosed at 1 µg PnPs (6A or 6B each conjugated to CRM197). Sera were collected prior to study start (pre-immune) and on days 14 (post-dose 1, PD1) and 28 (post-dose 2, PD2). NZWRs were observed at least daily by trained animal care staff for any signs of illness or distress. The vaccine formulations in NZWRs were deemed to be safe and well tolerated, as no vaccine-related adverse events were noted. All animal experiments were performed in strict accordance with the recommendations in the Guide for Care and Use of Laboratory Animals of the National Institutes of Health. The NZWR experimental protocol was approved by the Institutional Animal Care and Use Committees at both Merck & Co., Inc and Covance (Denver, PA).

NZWR sera were tested in ELISA assays to evaluate IgG immunogenicity using a 2 µg/mL respective PnPs coating concentration. Functional antibody was determined through opsonophagocytosis assays (OPA) based on previously described protocols at www.vaccine.uab.edu and Opsotiter® 3 software owned by and licensed from UAB Research Foundation (See, Caro-Aguilar I. et al., Vaccine (2017) 35(6):865-72 and Burton R. L. and Nahm M. H. Clin. Vaccine Immunol. (2006) 13(9):1004-9).

Figure 37A:
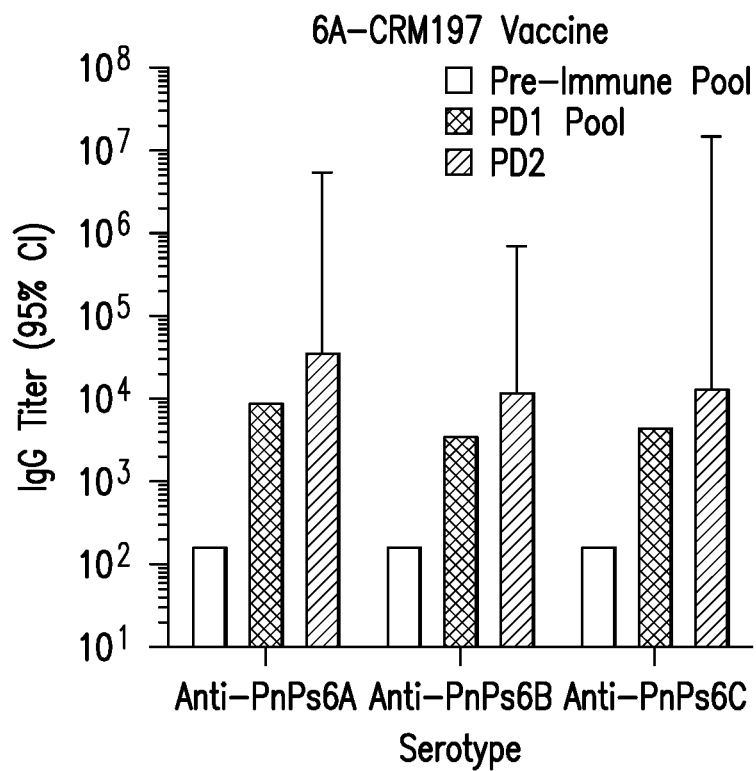
FIGS. 37A and 37B show ELISA IgG antibody dilution titers to 6A, 6B, and 6C ((pre-immune and PD1, pooled) and PD2) for rabbits immunized with 6A-CRM197 (FIG. 37A) or 6B-CRM197 (FIG. 37B) monovalent drug products. Bars indicate geometric mean titers (GMTs) and error bars represent the 95% confidence intervals (CIs) of the GMTs.
Figure 37B:
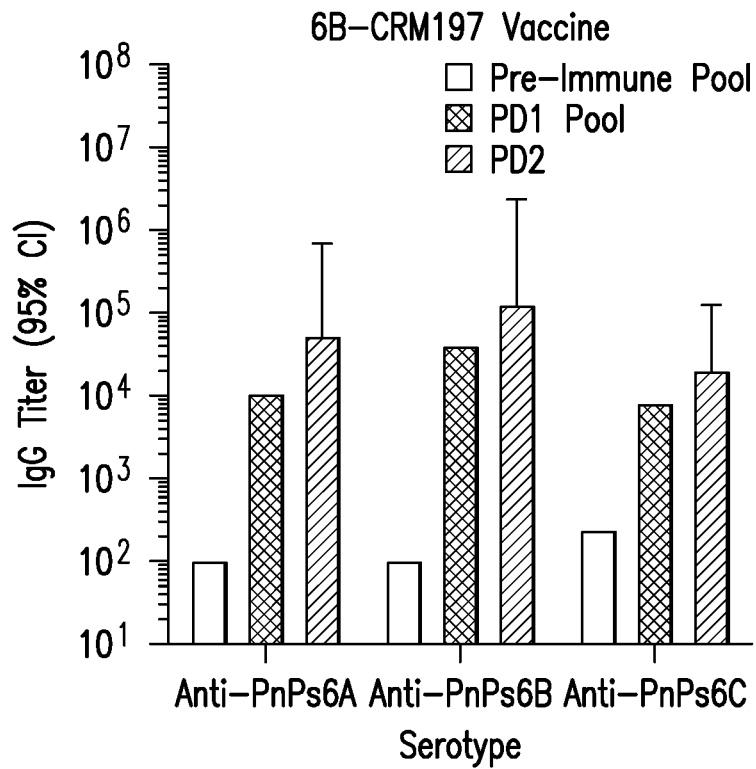
Figure 38A:
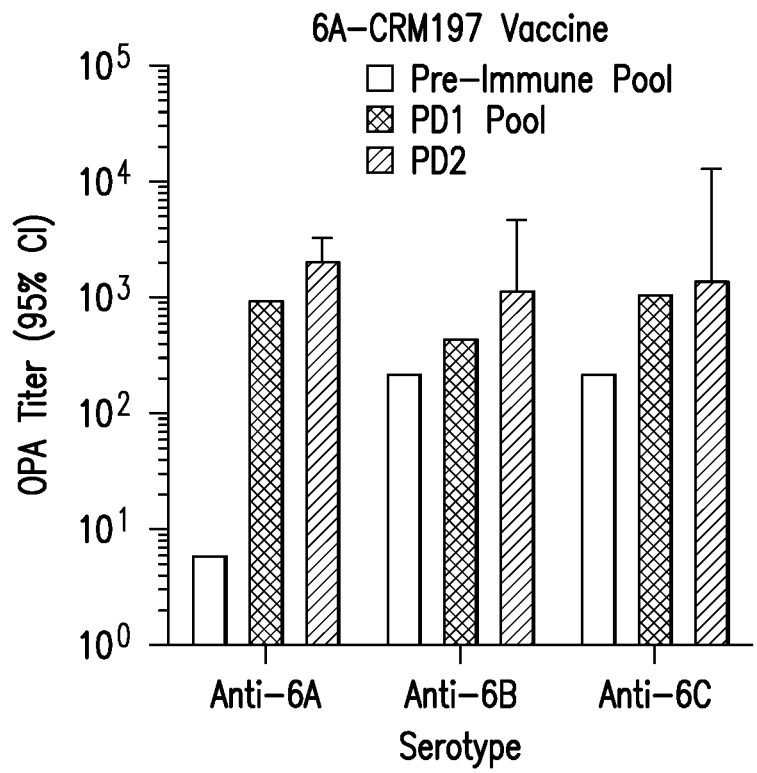
FIGS. 38A and 38B show serotype specific OPA dilution titers to 6A, 6B, and 6C ((pre-immune and PD1 pooled) and PD2) for rabbits immunized with 6A-CRM197 (FIG. 38A) or 6B-CRM197 (FIG. 38B) monovalent drug products. Bars indicate geometric mean titers (GMTs) and error bars represent the 95% confidence intervals (CIs) of the GMTs.
Figure 38B:
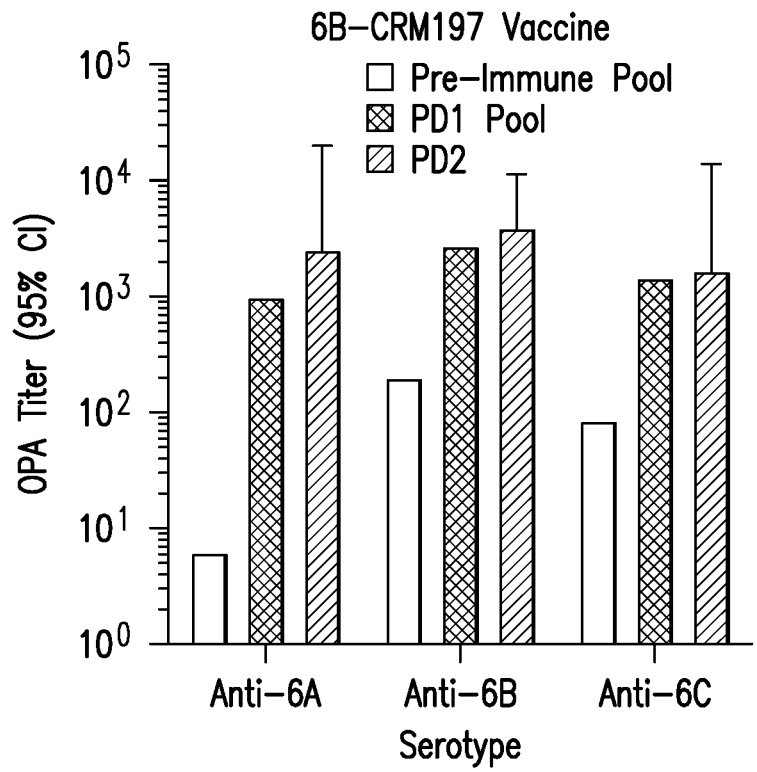

Both 6A-CRM197 and 6B-CRM197 were found to be immunogenic in rabbits (FIGS. 37A-37B) and generate functional antibody which killed the respective bacterial strain (FIGS. 38A-38B). In addition, rabbits immunized with serogroup 6 monovalent pneumococcal conjugate vaccines had equivalent PD2 IgG and OPA titers to the homologous and heterologous polysaccharide and bacterial strain, respectively. Rabbits immunized with 6A-CRM197 or 6B-CRM197 all had cross reactivity to each pneumococcal polysaccharide (PnPs 6A, PnPs 6B and PnPs 6C) (FIGS. 37A-37B). Using post-dose 2 (PD2) log transformed IgG data analyzed by One-way ANOVA, there was no significant difference in the IgG titers across serogroup 6. In addition, rabbits immunized with 6A-CRM197 or 6B-CRM197 all had cross reactivity to each *S. pneumoniae* bacterial strain (6A, 6B and 6C), as all rabbit hyper immune sera had functional antibody to each strain evaluated and killed the bacteria (FIGS. 38A-38B). Similarly, using post-dose 2 (PD2) log transformed OPA data analyzed by One-way ANOVA, there was no significant difference in OPA titers across the serogroup 6.

Example 51

Serotype 20A and 20B Cross Reactivity—Monvalent Study

The monovalent drug product was prepared using Pneumococcal polysaccharide 20A-CRM197 conjugate and was formulated in 20 mM histidine pH 5.8 and 150 mM sodium chloride and 0.2% w/v Polysorbate-20 (PS-20) at 4.0 µg/mL. The formulation was prepared with 250.0 µg [Al]/mL in the form of Aluminum Phosphate as the adjuvant (20A-CRM197/APA). The conjugate was prepared by individually conjugating the CRM197 protein to Pneumococcal polysaccharide (PnPs) type 20. The required volume of bulk conjugate needed to obtain the target concentration of individual serotype was calculated based on batch volume and concentration of individual bulk polysaccharide concentration. The single conjugate was added to a solution of histidine, sodium chloride and PS-20 to produce a 4× conjugate blend at 16.0 µg/mL. The formulation vessel containing the conjugate blend was mixed using a magnetic stir bar and the sterile was filtered into another vessel. The sterile filtered 4× blend was then added to another vessel containing Aluminum Phosphate Adjuvant to achieve the desired target total polysaccharide, excipient and adjuvant concentrations. The formulations were then filled into glass vials and stored at 2-8° C.

Rabbits were immunized with 20A-CRM197/APA or PCV21 to evaluate cross-reactivity within serogroup 20. Adult New Zealand White rabbits (NZWR, n=3/group) were intramuscularly (IM) immunized with pneumococcal conjugate vaccine on day 0 and day 14 (alternating sides). Monovalent pneumococcal conjugate vaccine, formulated as described above, was dosed at 1 µg PnPs in 0.25 ml (ST20A conjugated to CRM197 and 62.5 µg [Al] in the form of Aluminum Phosphate was used as the adjuvant), a PCV21 multivalent pneumococcal conjugate vaccine (84 µg/mL PnPs), formulated in 20 mM L-Histidine pH 5.8 150 mM NaCl and 0.2% (w/v) PS-20 with a formulation process described in Example 38, was dosed at 0.4 µg PnPs in 0.1 ml (serotypes 3, 6C, 7F, 8, 9N, 10A, 11A, 12F, 15A, 15C, 16F, 17F, 19A, 20, 22F, 23A, 23B, 24F, 31, 33F and 35B each conjugated to CRM197). Sera were collected prior to study start (pre-immune) and on days 14 (post-dose 1, PD1) and 28 (post-dose 2, PD2). NZWRs were observed at least daily by trained animal care staff for any signs of illness or distress. The vaccine formulations in NZWRs were deemed to be safe and well tolerated, as no vaccine-related adverse events were noted. All animal experiments were performed in strict accordance with the recommendations in the Guide for Care and Use of Laboratory Animals of the National Institutes of Health. The NZWR experimental protocol was approved by the Institutional Animal Care and Use Committees at both Merck & Co., Inc and Covance (Denver, PA).

NZWR sera were tested in opsonophagocytosis assays (OPA) to evaluate functional antibody based on previously described protocols at www.vaccine.uab.edu and Opsotiter® 3 software owned by and licensed from UAB Research Foundation (See, Caro-Aguilar I. et al., Vaccine (2017) 35(6):865-72 and Burton R. L. and Nahm M. H. Clin. Vaccine Immunol. (2006) 13(9):1004-9).

Figure 39A:
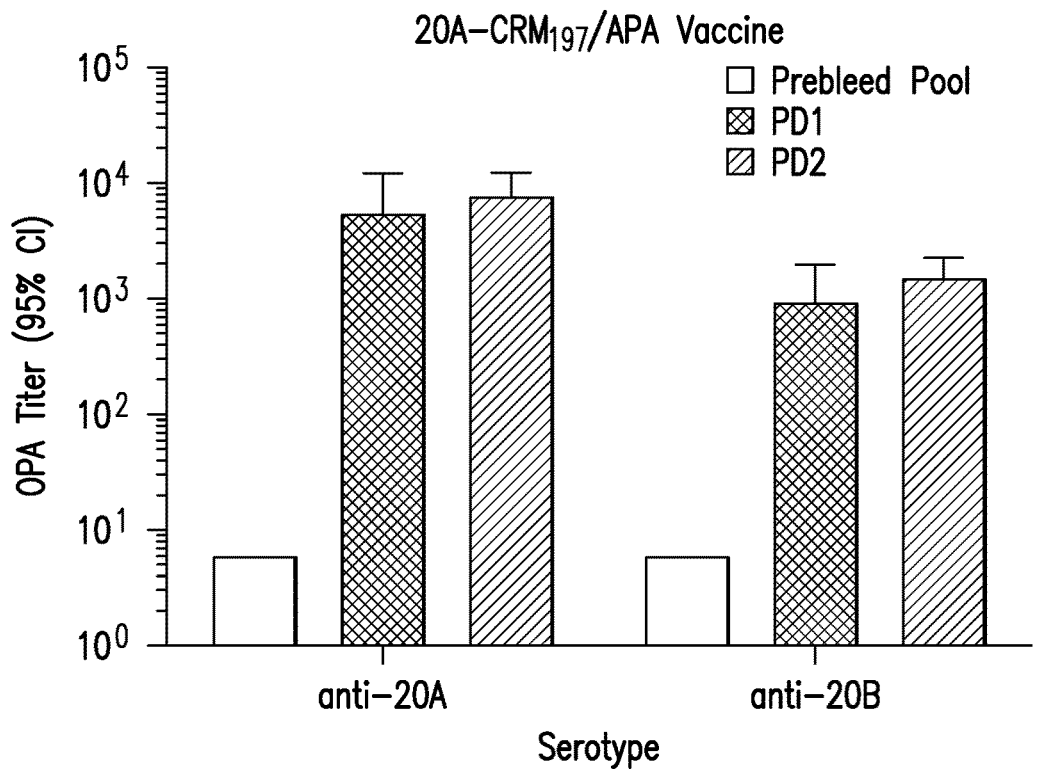
FIGS. 39A and 39B show serotype specific OPA dilution titers to 20A and 20B (pre-immune (pooled), PD1 and PD2) for rabbits immunized with 20A-CRM197/APA (FIG. 39A) or PCV21 (FIG. 39B). Bars indicate geometric mean titers (GMTs) and error bars represent the 95% confidence intervals (CIs) of the GMTs.
Figure 39B:
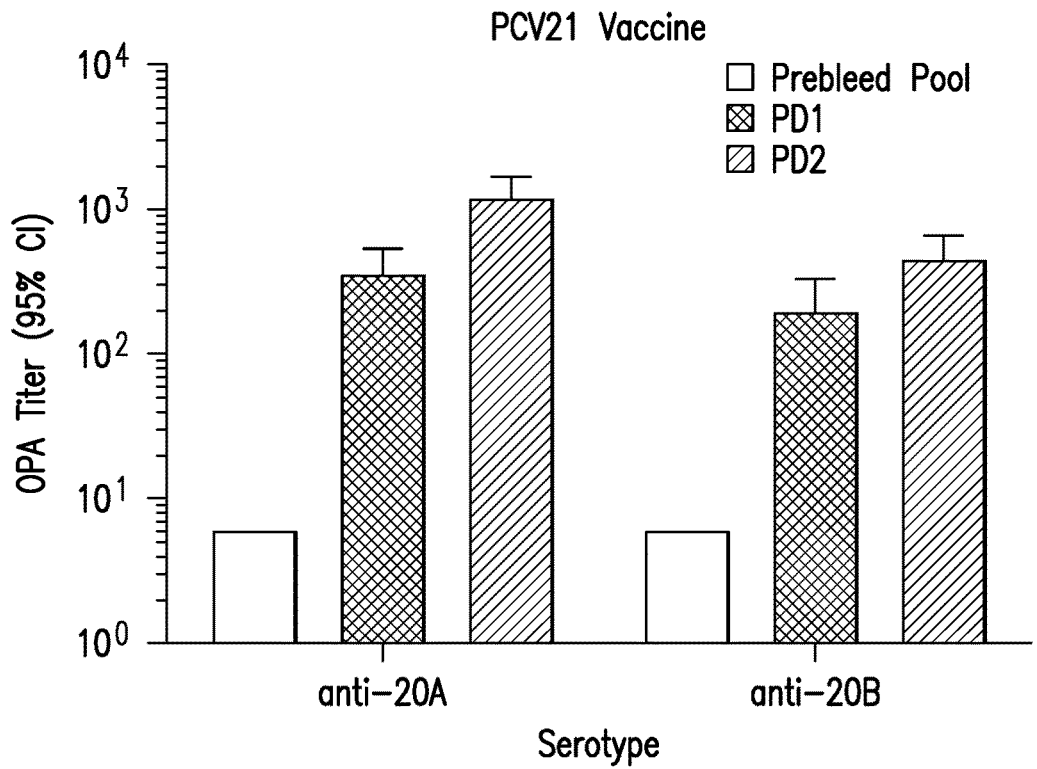

Rabbits immunized with both monovalent 20A-CRM197/APA and multivalent PCV21 vaccines generated functional antibody which killed both *S. pneumoniae* serotypes 20A and 20B (FIGS. 39A-39B). This suggests that serotype 20A and 20B share structural similarity, resulting in cross-reactivity within the serogroup.

What is claimed is:

1. An immunogenic composition comprising *S. pneumoniae* polysaccharide carrier protein conjugates, wherein each of the conjugates comprises a polysaccharide of a particular *S. pneumoniae* serotype conjugated to a carrier protein wherein:
   1) the *S. pneumoniae* serotypes consist of 3, 7F, 19A, 22F, 33F, 6A, 15A, 16F, 23A, 23B, 24F, 31, 35B, 8, 9N, 10A 11A 12F, de-O-acetylated 15B, 17F, and 20A;
   2) the carrier protein is CRM197; and
   3) the concentration of each polysaccharide is 8 μg/mL (w/v).

2. The immunogenic composition of claim 1 further comprising an adjuvant.

3. The immunogenic composition of claim 2 wherein the adjuvant is an aluminum phosphate adjuvant.

4. An immunogenic composition comprising *S. pneumoniae* polysaccharide carrier protein conjugates, wherein each of the conjugates comprises a polysaccharide of a particular *S. pneumoniae* serotype conjugated to a carrier protein wherein:
   1) the *S. pneumoniae* serotypes consist of 3, 7F, 19A, 22F, 33F, 6A, 15A, 16F, 23A, 23B, 24F, 31, 35B, 8, 9N, 10A 11A 12F, 15C, 17F, and 20A;
   2) the carrier protein is CRM197; and
   3) the concentration of each polysaccharide is 8 μg/mL (w/v).

5. The immunogenic composition of claim 4 further comprising an adjuvant.

6. The immunogenic composition of claim 5 wherein the adjuvant is an aluminum phosphate adjuvant.

7. An immunogenic composition comprising *S. pneumoniae* polysaccharide carrier protein conjugates, wherein each of the conjugates comprises a polysaccharide of a particular *S. pneumoniae* serotype conjugated to a carrier protein wherein:
   1) the *S. pneumoniae* serotypes consist of 3, 7F, 19A, 22F, 33F, 6A, 15A, 16F, 23A, 23B, 24F, 31, 35B, 8, 9N, 10A, 11A, 12F, 15B, 17F, and 20A;
   2) the carrier protein is CRM197; and
   3) the concentration of each polysaccharide is 8 μg/mL (w/v).

8. The immunogenic composition of claim 7 further comprising an adjuvant.

9. The immunogenic composition of claim 8 wherein the adjuvant is an aluminum phosphate adjuvant.

* * * * *

SEQUENCE LISTING

Sequence total quantity: 1
SEQ ID NO: 1          moltype = AA  length = 535
FEATURE               Location/Qualifiers -continued

```
REGION                 1..535
                       note = CRM197 variant of diphtheria toxin
source                 1..535
                       mol_type = protein
                       organism = synthetic construct
SEQUENCE: 1
GADDVVDSSK SFVMENFSSY HGTKPGYVDS IQKGIQKPKS GTQGNYDDDW KEFYSTDNKY  60
DAAGYSVDNE NPLSGKAGGV VKVTYPGLTK VLALKVDNAE TIKKELGLSL TEPLMEQVGT  120
EEFIKRFGDG ASRVVLSLPF AEGSSSVEYI NNWEQAKALS VELEINFETR GKRGQDAMYE  180
YMAQACAGNR VRRSVGSSLS CINLDWDVIR DKTKTKIESL KEHGPIKNKM SESPNKTVSE  240
EKAKQYLEEF HQTALEHPEL SELKTVTGTN PVFAGANYAA WAVNVAQVID SETADNLEKT  300
TAALSILPGI GSVMGIADGA VHHNTEEIVA QSIALSSLMV AQAIPLVGEL VDIGFAAYNF  360
VESIINLFQV VHNSYNRPAY SPGHKTQPFL HDGYAVSWNT VEDSIIRTGF QGESGHDIKI  420
TAENTPLPIA GVLLPTIPGK LDVNKSKTHI SVNGRKIRMR CRAIDGDVTF CRPKSPVYVG  480
NGVHANLHVA FHRSSSEKIH SNEISSDSIG VLGYQKTVDH TKVNSKLSLF FEIKS       535
```